US008088618B2

(12) United States Patent
Fung et al.

(10) Patent No.: US 8,088,618 B2
(45) Date of Patent: Jan. 3, 2012

(54) ANTI-IL 13 ANTIBODIES AND USES THEREOF

(75) Inventors: Sek Chung Fung, Gaithersburg, MD (US); Matthew Moyle, Redmond, WA (US); Mason Lu, Houston, TX (US); Changning Yan, Houston, TX (US); Sanjaya Singh, Sandy Hook, CT (US); Dan Huang, Short Hills, NJ (US)

(73) Assignee: Genentech, Inc., South San Francisco, CA (US)

( * ) Notice: Subject to any disclaimer, the term of this patent is extended or adjusted under 35 U.S.C. 154(b) by 433 days.

(21) Appl. No.: 12/240,604

(22) Filed: Sep. 29, 2008

(65) Prior Publication Data
US 2011/0014199 A1    Jan. 20, 2011

Related U.S. Application Data

(62) Division of application No. 10/583,927, filed as application No. PCT/US2004/043501 on Dec. 23, 2004.

(60) Provisional application No. 60/532,130, filed on Dec. 23, 2003.

(51) Int. Cl.
C12N 5/10      (2006.01)
C07K 16/24     (2006.01)

(52) U.S. Cl. ............... 435/335; 530/350; 530/387.1; 530/387.3; 530/388.23; 530/389.1; 530/389.2; 530/391.3

(58) Field of Classification Search .......... 530/350, 530/387.1, 387.3, 388.23, 389.1, 389.2, 391.3; 435/335

See application file for complete search history.

(56) References Cited

U.S. PATENT DOCUMENTS

| 5,011,778 | A | 4/1991 | Newman et al. |
| 5,359,037 | A | 10/1994 | Wallach et al. |
| 5,596,072 | A | 1/1997 | Culpepper et al. |
| 5,652,123 | A | 7/1997 | Caput et al. |
| 5,677,165 | A | 10/1997 | De Boer et al. |
| 5,705,154 | A | 1/1998 | Dalie et al. |
| 5,710,023 | A | 1/1998 | Collins et al. |
| 5,717,072 | A | 2/1998 | Mosley et al. |
| 5,747,037 | A | 5/1998 | Noelle et al. |
| 5,783,181 | A | 7/1998 | Browne et al. |
| 5,965,709 | A | 10/1999 | Presta et al. |
| 5,994,514 | A | 11/1999 | Jardieu et al. |
| 6,037,453 | A | 3/2000 | Jardieu et al. |
| 6,143,871 | A | 11/2000 | Bonnefoy et al. |
| 6,156,321 | A | 12/2000 | Thorpe et al. |
| 6,299,875 | B1 | 10/2001 | Caplan et al. |
| 6,329,509 | B1 | 12/2001 | Jardieu et al. |
| 6,468,528 | B1 | 10/2002 | Mak et al. |
| 6,576,232 | B1 | 6/2003 | Debinski et al. |
| 6,664,227 | B1 | 12/2003 | Wynn et al. |
| 6,743,604 | B1 | 6/2004 | Bonnefoy et al. |
| 6,911,530 | B1 | 6/2005 | Willson et al. |
| 7,078,494 | B1 | 7/2006 | Collins et al. |
| 7,078,496 | B2 | 7/2006 | Roberts et al. |
| 7,312,024 | B2 | 12/2007 | Mak et al. |
| 7,553,487 | B2 | 6/2009 | Collins et al. |
| 7,615,213 | B2 | 11/2009 | Kasaian et al. |
| 7,674,459 | B2 | 3/2010 | Fung et al. |
| 2003/0049257 | A1 | 3/2003 | Mak et al. |
| 2003/0235555 | A1 | 12/2003 | Shealey et al. |
| 2005/0277126 | A1 | 12/2005 | Collins et al. |
| 2008/0008648 | A1 | 1/2008 | Fung et al. |
| 2009/0214523 | A1 | 8/2009 | Fung et al. |
| 2010/0266494 | A1 | 10/2010 | Fung et al. |
| 2011/0123530 | A1 | 5/2011 | Arron et al. |

FOREIGN PATENT DOCUMENTS

| EP | 1 270 595 A1 | 1/2003 |
| EP | 0876482 (B1) | 3/2003 |
| EP | 1 327 681 A1 | 7/2003 |
| EP | 1 646 656 A2 | 1/2005 |
| EP | 1141286 (B1) | 10/2006 |
| JP | 2007-161724 | 6/2007 |
| JP | 2008-500024 | 1/2008 |
| WO | WO 89/04838 | 6/1989 |
| WO | WO 91/09059 | 6/1991 |
| WO | WO 93/15766 | 8/1993 |
| WO | WO 94/04680 | 3/1994 |
| WO | WO 94/14975 | 7/1994 |
| WO | WO 95/14780 | 6/1995 |
| WO | WO 97/15663 | 5/1997 |
| WO | WO 97/20926 (A1) | 6/1997 |
| WO | WO 97/29131 | 8/1997 |
| WO | WO 97/31946 | 9/1997 |
| WO | WO 97/47742 | 12/1997 |
| WO | WO 98/10638 | 3/1998 |
| WO | WO 98/30240 | 7/1998 |
| WO | WO 00/15663 | 3/2000 |
| WO | WO 00/23410 A2 | 4/2000 |

(Continued)

OTHER PUBLICATIONS

Rasmussen et al. (Biotechnol. Lett. Jun. 2007; 29 (6): 845-852).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*

(Continued)

Primary Examiner — Stephen Rawlings
(74) Attorney, Agent, or Firm — Jones Day

(57) ABSTRACT

The present invention relates to anti-IL13 antibodies that bind specifically and with high affinity to both glycosylated and non-glycosylated human IL13, does not bind mouse IL13, and neutralize human IL13 activity at an approximate molar ratio of 1:2 (MAb:IL13). The invention also relates to the use of these antibodies in the treatment of IL13-mediated diseases, such as allergic disease, including asthma, allergic asthma, non-allergic (intrinsic) asthma, allergic rhinitis, atopic dermatitis, allergic conjunctivitis, eczema, urticaria, food allergies, chronic obstructive pulmonary disease, ulcerative colitis, RSV infection, uveitis, scleroderma, and osteoporosis.

37 Claims, 44 Drawing Sheets

FOREIGN PATENT DOCUMENTS

| | | |
|---|---|---|
| WO | WO 00/36103 | 6/2000 |
| WO | WO 00/44407 A2 | 8/2000 |
| WO | WO 01/34645 A2 | 5/2001 |
| WO | WO 01/92514 A1 | 6/2001 |
| WO | WO 02/055100 | 7/2002 |
| WO | WO 03/018635 A1 | 3/2003 |
| WO | WO 03/035847 A2 | 5/2003 |
| WO | WO 03/040164 A2 | 5/2003 |
| WO | WO 03/086451 A1 | 10/2003 |
| WO | WO 04/001655 A1 | 12/2003 |
| WO | WO 2004/019974 A2 | 3/2004 |
| WO | WO 2004/019975 A2 | 3/2004 |
| WO | WO 2004/019979 A2 | 3/2004 |
| WO | WO 2005/007699 A2 | 1/2005 |
| WO | WO 2005/062967 A2 | 7/2005 |
| WO | WO 2005/062972 A2 | 7/2005 |
| WO | WO 2005/121177 A2 | 12/2005 |
| WO | WO 2005/123126 A2 | 12/2005 |
| WO | WO 2007/036745 A2 | 4/2007 |
| WO | WO 2007/036745 A3 | 4/2007 |
| WO | WO 2007/045477 A2 | 4/2007 |
| WO | WO 2007/045477 A3 | 4/2007 |
| WO | WO 2008/140455 A1 | 11/2008 |
| WO | WO 2009/124090 A1 | 10/2009 |

OTHER PUBLICATIONS

Chien et al. (Proc. Natl. Acad. Sci. USA. Jul. 1989; 86 (14): 5532-5536).*
Caldas et al. (Mol. Immunol. May 2003; 39 (15): 941-952).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Rudikoff et al. (Proc. Natl. Acad. Sci. USA. 1982; 79 (6): 1979-1983).*
Winkler et al. (J. Immunol. Oct. 15, 2000; 165 (8): 4505-4514).*
Iba et al. (Protein Eng. May 1998; 11 (5): 361-70).*
Kettleborough et al. (Protein Eng. Oct. 1991; 4 (7): 773-83).*
Andrews et al., 2002, "Kinetic analysis of the interleukin-13 receptor complex." J. Biol. Chem., vol. 277(48):46073-46078.
Bellanti, 1998, "Cytokines and allergic diseases: Clinical aspects," Allergy and Asthma, Proc., vol. 19(6):337-340.
Blanchard et al., 2005, "Inhibition of human interleukin-13-induced respiratory and oesophageal inflammation by anti-human-interleukin-13 antibody (CAT-354)," Clin. Exp. Allergy, vol. 35:1096-1103.
Bost et al., 1996, "In vivo treatment with anti-interleukin-13 antibodies significantly reduces the humoral immune response against an oral immunogen in mice," Immunology, vol. 87(4):633-641.
Bree et al., 2007, "IL-13 blockade reduces lung inflammation after Ascaris suum challenge in cynomolgus monkeys," J. Allergy Clin. Immunol., vol. 119(5)1251-1257.
Brinkmann et al., 1995, "TCR-stimulated naive human CD4+45R0− T cells develop into effector cells that secrete IL-13, IL-5, and IFN-γ, but No. IL-4, and help efficient IgE production by B cells," J. Immunol., vol. 154(7):3078-3087.
Campbell et al., 2003, "Allergic humans are hypo-responsive to CXCR3 chemokines in a ThI immunity-promoting loop," FASEB J., vol. 18(2):329-331.
Caput et al., 1996, "Cloning and characterization of a specific interleukin (IL)-13 binding protein structurally related to the IL-5 receptor α chain," J. Biol. Chem., vol. 271(28):16921-16926.
Carballido et al., 1995, "IL-4 induces human B cell maturation and IgE synthesis in SCID-hu mice," J. Immunol., vol. 155(9):4162-4170.
Casolaro et al., 1996, "Biology and genetics of atopic disease," Curr. Opin. Immunol., vol. 8:796-803.
De Vries et al., 1996, "Modulation of the human IgE response," Eur. Respir. J., Suppl. 22:58s-62s.
De Vries, 1994, "Novel fundamental approaches to intervening in IgE-mediated allergic diseases," J. Invest. Dematol., vol. 102:141-144.
Debinski et al., 1995, "A novel chimeric protein composed on interleukin 13 and pseudomonas exotoxin is highly cytotoxic to human carcinoma cells expressing receptors for interleukin 13 and interleukin 4," J. of Biological Chemistry, vol. 270(28):16775-16780.
Debinski et al., 1995, "Human glioma cells overexpress receptors for interleukin 13 and are extremely sensitivity to a novel chimeric protein composed of interleukin 13 and pseudomonas exotoxin," Clinical Cancer Research, vol. 1:1253-258.
Donaldson et al., 1998, "The murine IL-13 receptor alpha 2: molecular cloning, characterization, and comparison with murine IL-13 receptor alpha 1," J. Immunol., vol. 161:2317-2324.
Doucet et al., 1998, "Interleukin (IL) 4 and IL-13 act on human lung fibroblasts," J. Clin. Invest., vol. 101:2129-2139.
Economides, et al., 1995, "Designer cytokines: Targeting actions to cells of choice," Science, vol. 270:1351-1353.
Enomoto et al., 2002, "High-throughput miniaturized immunoassay for human interleukin-13 secreted from NK3.3 cells using homogenous time-resolved fluorescence," J of Pharm and Biomedical Analysis, vol. 28:73-79.
Fauci et al., 1998, "Harrison's Principles of Internal Medicine," $14^{th}$ Edition, Mc Graw-Hill Companies, Inc., New York, pp. 1419-1420, 1760-1761.
Fichtner-Feigl et al., 2005, "IL-13 signaling through the IL-13$\alpha_2$ receptor is involved in induction of TGF-$\beta^1$production and fibrosis," Nature Medicine, vol. 12:99-106.
Gabrielsson et al., 1998, "Increased frequencies of allergen-induced interleukin-13 producing cells in atopic individuals during the pollen season," Scand. J. Immunol., vol. 48:429-435.
Ghaffar et al., 1997, "IL-13 mRNA and immunoreactivity in allergen-induced rhinitis: Comparison with IL-4 expression and modulation by topical glucocorticoid therapy," Am. J. Respir. Cell Mol. Biol., vol. 17:17-24.
Ghamdi et al., 1997, "IL-4 and IL-3 expression in chronic sinusitis: Relationship with cellular infiltrate and effect of topical corticosteroid treatment," J. of Otolaryngology, vol. 26(3):160-166.
Grünig et al., 1998, "Requirement for IL-13 independently of IL-4 in experimental asthma," Science, vol. 282:2261-2263.
Hamid et al., 1996, "In vivo expression of IL-12 and IL-13 in atopic dermatitis," J. Allergy Clin. Immunol., vol. 98:225-231.
Huang et al., 1995, "IL-13 expression at the sites of allergen challenge in patients with asthma," J. Immunol., vol. 155:2688-2694.
Humbert et al., 1997, "Elevated expression of messenger ribonucleic acid encoding IL-13 in the bronchial mucosa of atopic and nonatopic subjects with asthma," J. Allergy Clin. Immunol., vol. 99:657-665.
Janeway and Travers, 1997, "Immunobiology: The Immune System in Health and Disease," $3^{rd}$ Edition, Garland Publishing Inc., pp. 12:8-12:11.
Kapp et al., 1999, "Interleukin 13 is secreted by and stimulated the growth of Hodgkin and Reed-Sternberg Cells," J. Exp. Med., vol. 189(12):1939-1945.
Kasaian et al., 2007, "Efficacy of IL-13 neutralization in a sheep model of experimental asthma," Am. J. Respir. Cell Mol. Biol., vol. 36:368-376.
Kawakami et al., 2001, "Interleukin-13 receptor-targeted cancer therapy in an immunodeficient animal model of human head and neck cancer," Cancer Research, vol. 61:6194-6200.
Kimata et al., 1995, "Involvement of interleukin (IL)-13, but not IL-4, in spontaneous IgE and IgG4 production in nephritic syndrome," Eur. J. Immunol., vol. 25:1497-1501.
Kotsimbos et al., 1996, "Interleukin-13 and interleukin-4 are coexpressed in atopic asthma," Proceedings of the Assoc. of American Physicians, vol. 108(5):368-373.
Kroegel et al., 1996, "Endobronchial secretion of interleukin-13 following local allergen challenge in atopic asthma: relationship to interleukin-4 and eosinophil counts," Eur. Respir. J., vol. 9:899-904.
Levy et al., 1997, "Role of IL-13 in CD4 T cell-dependent IgE production in atopy," Int. Arch. Allergy Immunol., vol. 112:49-58.

Maini et al., 1997, "Interleukin-I3 receptors on human prostate carcinoma cell lines represent a novel target for a chimeric protein composed of IL-13 and a mutated form of pseudomonas exotoxin," J. Urology, vol. 158:948-953.

Marsh et al., 1994, "Linkage analysis of IL4 and other chromosome 5q31.1 markers and total serum immunoglobulin E concentrations," Science, vol. 264:1152-1156.

McKenzie et al., 1993, "Interleukin 13, a T-cell-derived cytokine that regulates human monocyte and B-cell function," Proc. Natl. Acad. Sci. U.S.A., vol. 90(8):3735-3739.

McKenzie et al., 1994, "Measurement of interleukin-13," Current Protocols in Immunology, Unit 6.18, Suppl. 10:6.18.1-6.18.5, Coligan et al. eds., John Wiley & Sons, New York.

McKenzie et al., 1998, "Impaired development of Th2 cells in IL-13 deficient mice," Immunity, vol. 9:423-432.

Mentink-Kane et al., 2004, "Opposing roles for IL-13 and IL-13 receptor α2 in health and disease," Immunological Reviews, vol. 202:191-202.

Naseer et al.. 1997, "Expression of IL-12 and IL-13 mRNA in asthma and their modulation in response to steroid therapy," Am. J. Respir. Crit. Care Med., vol. 155:845-851.

Ohno et al., 1985, "Antigen-binding specificities of antibodies are primarily determined by seven residues of VH," Proc. Natl. Acad. Sci. U S A.. vol. 82(9):2945-2949.

Oshima et al.. 2001, "Characterization of a powerful high affinity antagonist that inhibits biological activities of human interleukin-13," J. Biol. Chem.. vol. 276(18):15185-15191.

Pawankar et al., 1997, "Nasal mast cells in perennial allergic rhinitics exhibit increased expression of the $F_{C_E}$RI. CDR401., IL-4, and IL-13, and can induce IgE synthesis in B cells." J. Clin. Invest., vol. 99(7):1492-1499.

Postma et al., 1995, "Genetic susceptibility to asthma—Bronchial hyperresponsiveness coinherited with a major gene for atopy." N. Engl. J. Med., vol. 333(14):894-900.

Punnonen et al., "Cytokines and IgE regulation," Allergy and Allergic Diseases: The New Mechanisms and Therapeutics, pp. 13-40, Edited by J.A. Denburg, Human Press Inc., Totowa, NJ 1998.

Roitt et al., 1996, Immunology, Fourth Edition, Published by Mosby, London, pp. 22-1-22.5 and glossary.

Roitt et al., Immunology, 2000, Publisher "Mir", Moscow, pp. 110-111.

Roitt, I.M., 1988, Essential Immunology, Sixth Edition, Blackwell Scientific Publications, Oxford, pp. 195-196.

Schildbach et al., 1993. "Modulation of antibody affinity by a non-contact residue," Protein Sci. vol. 2(2):206-14.

Skinnider et al., 2002, "Signal transducer and activator of transcription 6 is frequently activated in Hodgkin and Reed-Sternberg cells of Hodgkin lymphoma," Blood, vol. 99(2):618-626.

Skinnider et al., 2002,"The role of interleukin 13 in classical Hodgkin lymphoma," Leuk. Lymphoma, vol. 43(6):1203-1210.

Tekkanat et al., 2001, "IL-13-induced airway hyperreactivity during respiratory syncytial virus infection is STAT6 dependent," J. Immunol., vol. 166:3542-3548.

Terabe et al., 2000, "NKT cell-mediated repression of tumor immunosurveillance by IL-13 and the IL-4R-STAT6 pathway," Nat. Immunol., vol. 1(6):515-520.

Terabe et al., 2004, "Role of IL-13 in regulation of anti-tumor immunity and tumor growth," Cancer Immunol. Immunother., vol. 53:79-85.

Trieu et al., "Inhibition of Hodgkin lymphoma cell line growth using an adenovirus expressing the soluble IL-13 decoy receptor (sIL-13Ralpha2)," Blood vol. 100(11):Abstract No. 2272 & 44 Annual meeting of the American Society of Hematology; Philadelphia, PA, USA, Dec. 6-10, 2002.

Trieu et al.. 2004, "Soluble interleukin-13Rα2 decoy receptor inhibits Hodgkin'slymphoma growth in vitro and invivo," Cancer Research, vol. 64:3271-3275.

Van Der Pouw Kraan et al., 1996, "Human IL-13 production is negatively influenced by CD3 engagement—enhancement of IL-13 production by cyclosporine A," J. Immunol., vol. 156(5):1818-1823.

Van Der Pouw Kraan et al., 1998, "The role of IL-13 in IgE synthesis by allergic asthma patients," Clin. Exp. Immunol., vol. 111:129-135.

Vugmeyster et al., 2008, "Preclinical pharmacokenetics, interspecies scaling, and tissue distribution of humanized monoclonal anti-IL-13 antibodies with different IL-13 neutralization mechanisms," Intl. Immunopharmacol., vol. 8:477-483.

Warner, 1998, "Bronchial hyperresponsivenes, atopy, airway inflammation, and asthma," Pediatr. Allergy Immunol., vol. 9:56-60.

Wills-Karp et al., 1998, "Interleukin-13: central mediator of allergic asthma," Science, vol. 282:2258-2261.

Wood et al., 2003, "Enhanced interleukin (IL)-13 responses in mice lacking IL-13 receptor α 2," J. Exp. Med., vol. 197(6):703-709.

World Health Organization, 1992, "International statistical classification of diseases and related health problems," $10^{TH}$ Revision, vol. 1, pp. 536-537.

Wynn, T. A., 2003, "IL-I3 effector functions," Annual Review of Immunol., vol. 21:425-456.

Yang et al., 2004, "Anti-IL-13 monoclonal antibody inhibits airway hyperresponsiveness, inflammation and airway remodeling," Cytokine, vol. 28:224-232.

Yang et al.. 2005, "Therapeutic dosing with anti-interleukin-13 monoclonal antibody inhibits asthma progression in mice," J. Pharmacol. Exp. Ther., vol. 312:8-15.

Yssel et al., 1998, "The role of IgE in asthma," Clin. Exp. Allergy. vol. 28, Supp. 5:104-109.

Zhang et al. 1997, "Identification, purification, and characterization of a soluble interleukin (IL)—3-binding protein," J. of Biol. Chem., vol. 272(14):9474-9480.

Zhang et al., 2003, "Identification and application of monoclonal antibodies against IL-6," Molecular Cardiology of China, vol. 3(3):152-156.

Office Action, dated Feb. 28, 2011, of U.S. Appl. No. 10/583,927, filed Dec. 23, 2004.

Rader et al., 1998, "A phage display approach for rapid antibody humanization: Designed combinatorial V gene libraries," Proc. Natl. Acad. Sci. USA, 95:8910-8915.

Venkayya et al.., 2002, "The Th2 Lymphocyte Products IL-4 and IL-13 Rapidly Induce Airway Hyperresponsiveness Through Direct Effects on Resident Airway Cells" Am J. Resp. Cell. Mol. Biol. 26: 202-208.

"Monoclonal Anti-Human IL 13 Antibody," R&D Systems, Inc. Catalog [on-line], Oct. 2002 [retrieved on Oct. 14, 2002], Retrieved from the Internet:< URL: http://www.rndsystems.com/asp/c_search.asp?ucategory=3&factors=IL%2D13>.

Ahlers et al., 2002, "A push-pull approach to maximize vaccine efficacy: abrogating suppression with an IL-13 inhibitor while augmenting help with granulocyte/macrophage colony-stimulating factor and CD40L." Proc Natl Acad Sci U S A; 99(20):13020-5.

Akbari et al., 2003, "Essential role of NKT cells producing IL-4 and IL-13 in the development of allergen-induced airway hyperreactivity." Nat Med. 9(5):582-8.

Alberts et al., 1994, "An antibody molecule is composed of two identical light chains and two identical heavy chains," Molecular Biology of the Cell, Third Edition, Garland Publishing, Inc., New York, pp. 1208-1209.

Amrad Corporation, Ltd. "IL-13 Receptor Antibody Porject." Aug. 17. 2005.

Arima et al., 2002, "Upregulation of IL-13 concentration in vivo by the IL13 variant associated with bronchial asthma" J Allergy Clin Immunol. 109(6):980-7.

Arima et al., 2005, "Characterization of the interaction between interleukin-13 and interleukin-13 receptors". J. Biol. Chem. vol. 280(26):24915-24922.

Asthma and Allergy Foundation of America and The National Pharmaceutical Council, "A Closer Look at Asthma" A joint publication of AAFA and NPC, pp. 1-6, Oct. 2001.

Blease et al., 2001, "Therapeutic effect of IL-13 immunoneutralization during chronic experimental fungal asthma," J. Immunol., vol. 165:5219-5224.

Brewer et al., 2004, "Inhibition of key cytokines by tetrathiomolybdate in the bleomycin model of pulmonary fibrosis." J. Inorg. Biochem. 98(12):2160-7.

Brown et al., 1989, "A family of small inducible proteins secreted by leukocytes are members of a new superfamily that includes leukocyte and fibroblast-derived inflammatory agents, growth factors, and indicators of various activation processes." J. Immunol. 142(2):679-87.
Carrington, B., "BIAcore analysis of hIL-13Rα2 binding/blocking to hIL-13 pre-bound to antibody JES10-5A2 or antibody 213," Jun. 7, 2007, UCB Celltech, pp. 1-3.
Cohn et al. 1998, "Cutting Edge: IL-4-independent induction of airway hyperresponsiveness by Th2, but not Th1, cells," J. Immunol. vol. 161:3813-3816.
Cohn et al., 1997, "Induction of airway mucus production By T helper 2 (Th2) cells: a critical role for interleukin 4 in cell recruitment but not mucus production." J. Exp. Med. vol. 186(10):1737-1747.
Daniels et al., 2004, "Imatinib mesylate inhibits the profibrogenic activity of TGF-beta and prevents bleomycin-mediated lung fibrosis." J. Clin. Invest. 114(9):1308-16.
De Swart et al., 2002, Immunization of macaques with formalin-inactivated respiratory syncytial virus (RSV) induces interleukin-13-associated hypersensitivity to subsequent RSV infection. J. Virol. 76(22):11561-9.
Dorland's Illustrated Medical Dictionary, $28^{th}$ ed., 1994, p. 151.
Encyclopedia Britannica'S Guide to the Nobel Prizes, 2007, "Immune system disorders," [on-line], Jun. 27, 2007 [retrieved on Jun. 27, 2007], pp. 1-4, Retrieved from the Internet:< URL: http://www.britannica.com/nobelprize/article-215507>.
Hasegawa et al., 2003, "Serum levels of tumor necrosis factor and interleukin-13 are elevated in patients with localized scleroderma." Dermatology. 207(2):141-7.
Heller et al., 2002, "Oxazolone colitis, a Th2 colitis model resembling ulcerative colitis, is mediated by IL-13-producing NK-T cells." Immunity. 17(5):629-38.
Heller et al., 2005, "Interleukin-13 is the key effector Th2 cytokine in ulcerative colitis that affects epithelial tight junctions, apoptosis, and cell restitution." Gastroenterology. 129(2):550-64.
Hershey GK., 2003, "IL-I3 receptors and signaling pathways: an evolving web." J. Allergy Clin. Immunol. 111 (4):677-90.
Jakubzick et al., 2003, "Therapeutic attenuation of pulmonary fibrosis via targeting of IL-4- and IL-13-responsive cells." J Immunol. 171(5):2684-93.
Janeway et al., Chapter 11, $3^{rd}$ ed. of Immunobiology, 1997.
Janeway et al., Chapter 12, $3^{rd}$ ed. of Immunobiology, 1997.
Janeway et al., Section 9:18, $3^{rd}$ ed. of Immunobiology, 1997.
Kawakami et al., 2002, "Intratumor administration of interleukin 13 receptor-targeted cytotoxin induces apoptotic cell death in human malignant glioma tumor xenografts." Mol Cancer Ther. 1(12):999-1007.
Keane et al., 1999, "IFN-gamma-inducible protein-10 attenuates bleomycin-induced pulmonary fibrosis via inhibition of angiogenesis." J Immunol. 163(10):5686-92.
Keane et al., 1999, "Neutralization of the CXC chemokine, macrophage inflammatory protein-2, attenuates bleomycin-induced pulmonary fibrosis." J Immunol. 162(9):5511-8.
Kim et al., 2002, "IL-13-induced Clara cell secretory protein expression in airway epithelium: role of EGFR signaling pathway." Am. J. Physiol. Lung Cell Mol. Physiol 283:L67-L75.
Kuperman et al., 2002, "Direct effects of interleukin-13 on epithelial cells cause airway hyperreactivity and mucus overproduction in asthma." Nat. Med. 8(8):885-9.
Laporte et al., 2008, "Molecular and structural basis of cytokine receptor plciotropy in the interleukin-4/13 system," Cell. vol. 132(2):259-272 (HHMI Author Manuscript).
Lauder & McKenzie, 2001, "Measurement of Interleukin-13," Current Protocols in Immunology, Unit 6.18, Supplement 46, 6.18.1-6.18.6, John Wiley & Sons, Inc., New York.
Lee et al., 2001, "Serum levels of interleukins (IL)-4, IL-5, IL-13, and interferon-gamma in acute asthma." J. Asthma, 38(8):665-71.
Liu et al., 2004, "Regulation of found in inflammatory zone 1 expression in bleomycin-induced lung fibrosis: role of IL-4/1L-13 and mediation via STAT-6." J. Immunol. 173(5):3425-31.

Lukacs et al., 2001, "Respiratory syncytial virus predisposes mice to augmented allergic airway responses via IL-13-mediated mechanisms." J. Immunol. 167(2):1060-5.
Madhankumar et al., 2002, "Alanine-scanning mutagenesis of alpha-helix D segment of interleukin-13 reveals new functionally important residues of the cytokine." J Biol Chem. 277(45):43194-205.
Matsushita et al., 2004, "Upregulation of interleukin-13 and its receptor in a murine model of bleomycin-induced scleroderma." Int. Arch. Allergy Immunol. 135(4):348-56.
Merck Manual—Online Medical Dictionary, "Hyperimmunoglobulinemia E Syndrome" [on-line], Jul. 7, 2007 [Retrieved on Jul. 7, 2007], Retrieved from the Internet:< URL: http://.www.merck.com/mmhe/sec16/ch184k.html>, pp. 1-2.
Miloux et al., 1997, "Cloning of the human IL-13R alphal chain and reconstitution with the IL4R alpha of a functional IL-4/1L-13 receptor complex." FEBS Lett. 401(2-3):163-6.
Mueller et al., 2002, "Structure, binding, and antagonists in the IL-4/IL-13 receptor system," Biochimica et Biophysica Acta. vol. 1592(3):237-250.
Okuma et al., 2004, "C-C chemokine receptor 2 (CCR2) deficiency improves bleomycin-induced pulmonary fibrosis by attenuation of both macrophage infiltration and production of macrophage-derived matrix metalloproteinases." J. Pathol. 204(5):594-604.
Oxford Concise Medical Dictionary, "Atopy," Fourth Edition 1994, Oxford University Press, Great Britain, pp. 54-55.
Peebles et al., 2001, "Immune interaction between respiratory syncytial virus infection and allergen sensitization critically depends on timing of challenges." J Infect Dis. 184(11)1374-9.
Reeck et al.. 1987, "Homology" In Proteins and Nucleic Acids: a Terminology Muddle and a Way Out of It. Cell. 50(5):667.
Roberge et al.. 1998, "Treatment of uveitis with recombinant human interleukin-13." Br J Ophthalmol. 82(10):1195-8.
Rudikoff et al., 1982, "Single amino acid substitution altering antigen-binding specificity," Proc. Nat'l Acad. Sci. U.S.A., vol. 79(6): 1979-1983.
Schacker et al, 2002, "Collagen deposition in HIV-1 infected lymphatic tissues and T cell homeostasis." J. Clin. Invest. 110(8):1133-9.
Singer et al., 1998, "Gens and Genoms", Moscow, Mir. 1988, vol. I, p. 63 (in Russian with English translation).
Taber's Cyclopedic Medical Dictionary, "Atopy," 18th Edition, F.A. Davis Company, Philadelphia, 1993. p. 170.
Teplyakov et al., 2009, "Epitope mapping of anti-interleukin-13 neutralizing antibody CNTO607," J. Mol. Biol. vol. 389(1):115-123.
Teplyakov et al., 2010, "On the domain pairing in chimeric antibodies," Mol. Immunol. vol. 47(14):2422-2426.
Thompson et al., 1999, "Mutants of interleukin 13 with altered reactivity toward interleukin 13 receptors," J. Biol. Chem., vol. 274(42):29944-29950.
Tsarbopoulos et al., 2000, "Mass spectrometric mapping of disulfide bonds in recombinant human interleukin-13," J. Mass. Spectrom., vol. 35(3):446-453.
Vita et al., 1995, "Characterization and comparison of the interleukin 13 receptor with the interleukin 4 receptor on several cell types," J. Biol. Chem. 270(8):3512-3517.
Wardemann et al., 2003, "Predominant autoantibody production by early human B cell precursors," Science vol. 301(5638):1374-1377.
Wikipedia entry for "Hypersensitivity" [on-line], [Retrieved on Jul. 2, 2007], pp. 1-4, Retrieved from the Internet:< URL: http://en.wikipedia.org/wiki/Hypersensitivity>.
Wills-Karp M., 2004, "Interleukin-13 in asthma pathogenesis." Curr. Allergy Asthma Rep. 4(2):123-31.
Zuegg et al., 2001, "Structural model of human IL-13 defines the spatial interactions with the IL-13Rα/IL-4Rα receptor," Immunol. Cell Biol. vol. 79(4):332-339.

* cited by examiner

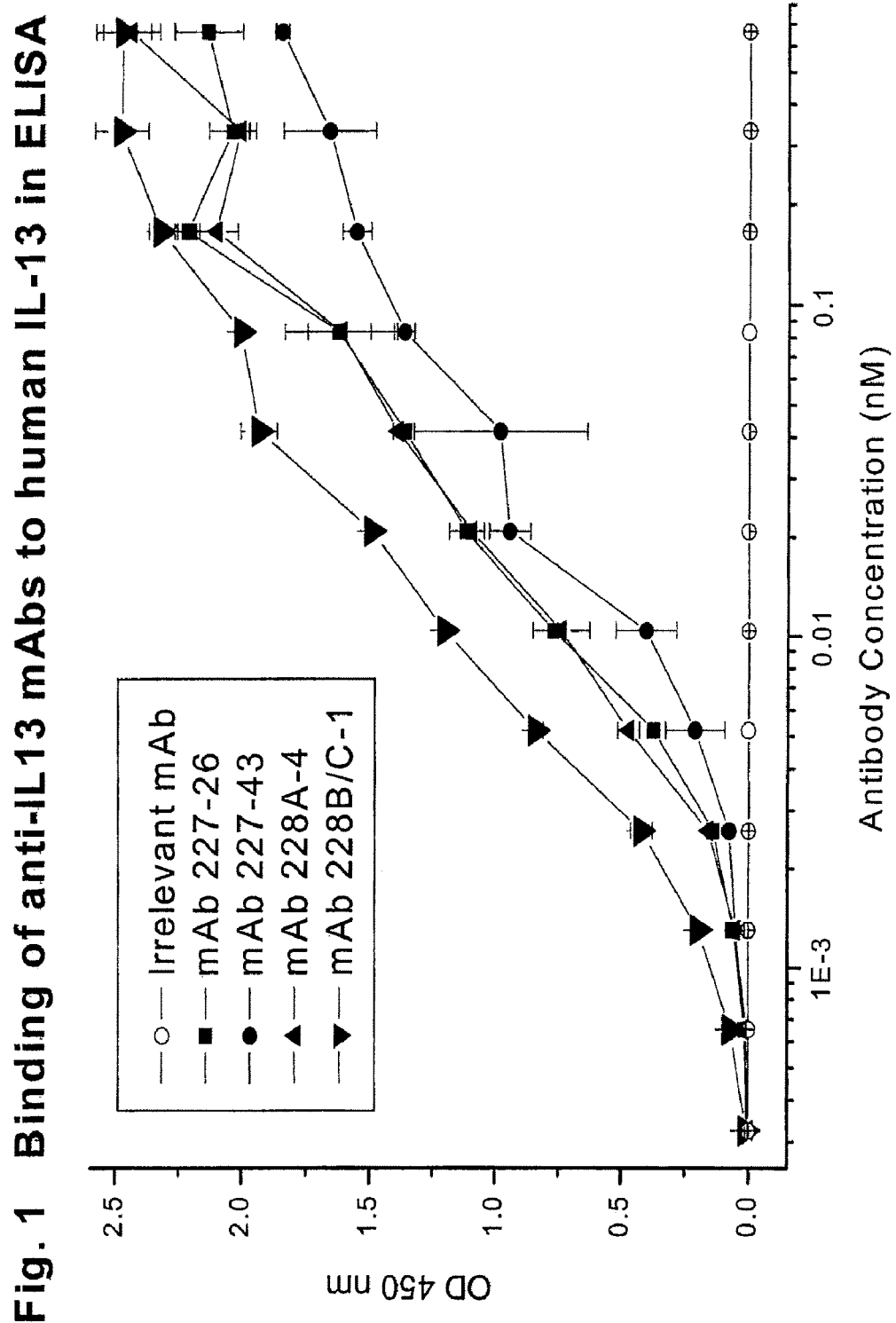
Fig. 1 Binding of anti-IL13 mAbs to human IL-13 in ELISA

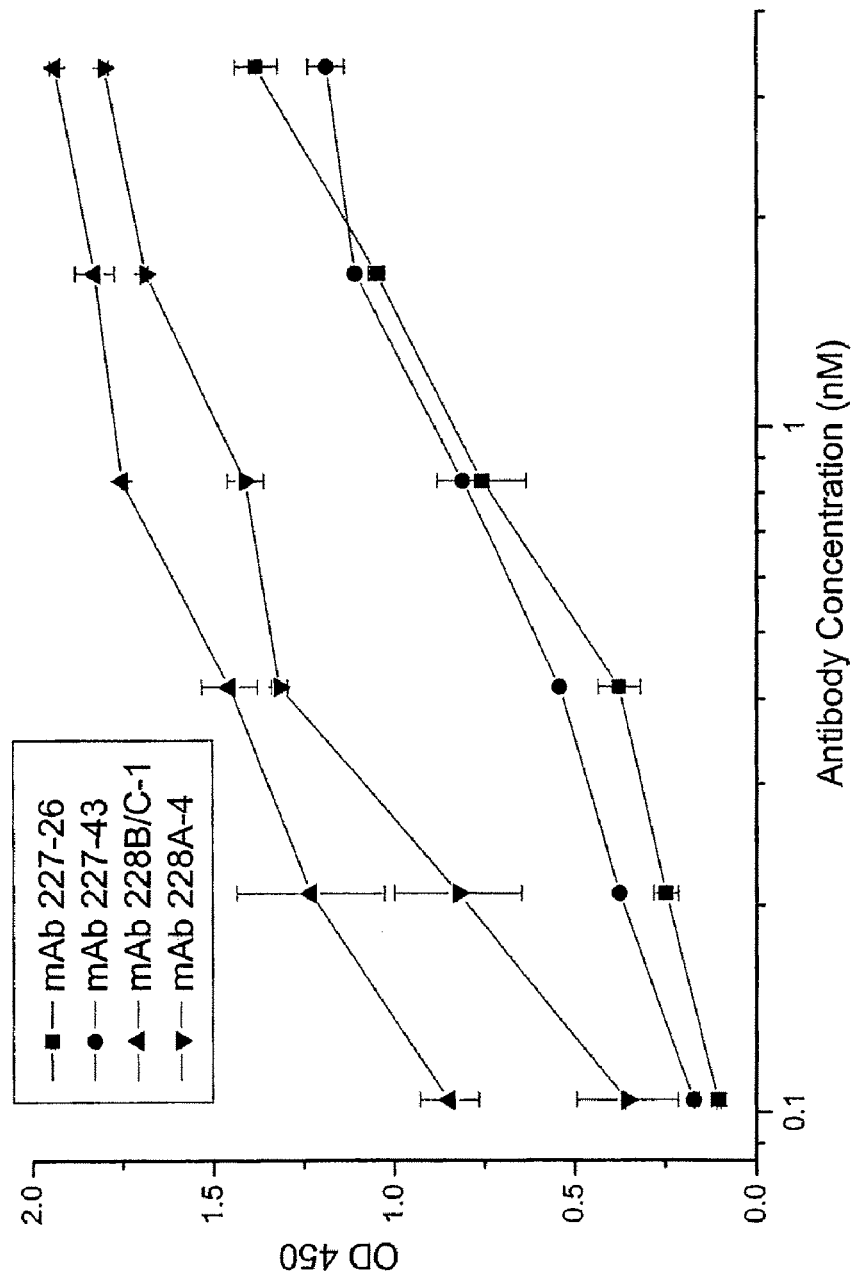
Fig. 2 Binding of anti-IL13 mAbs to MT-IL13/Fc

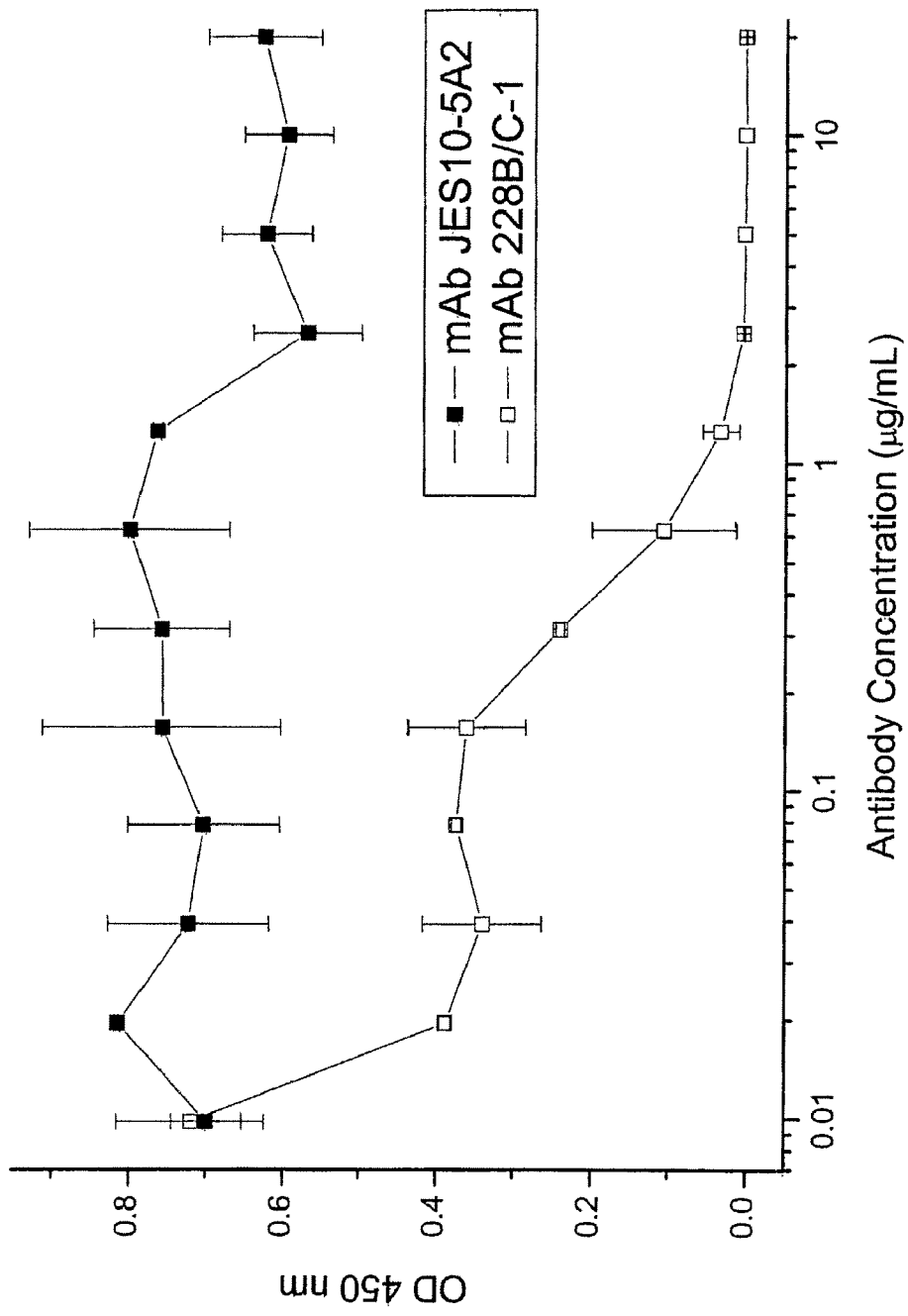
Fig. 3 Anti-IL13 mAb JES10-5A2 does not compete with the binding of mAb 228B/C-1-HRP to Human IL-13 in ELISA

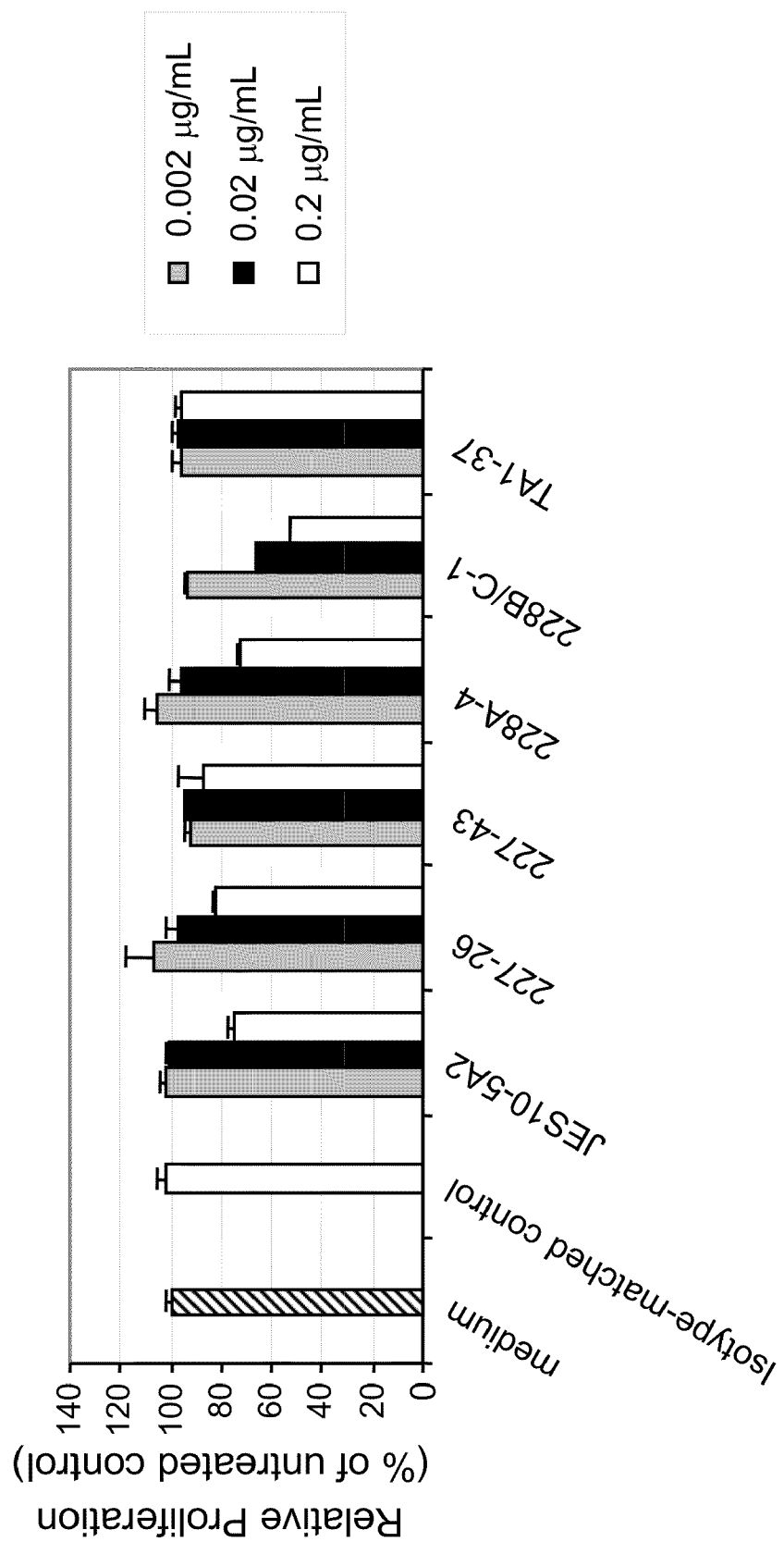
Fig. 4 Effect of anti-IL13 mAbs on the proliferation of L-1236 cells

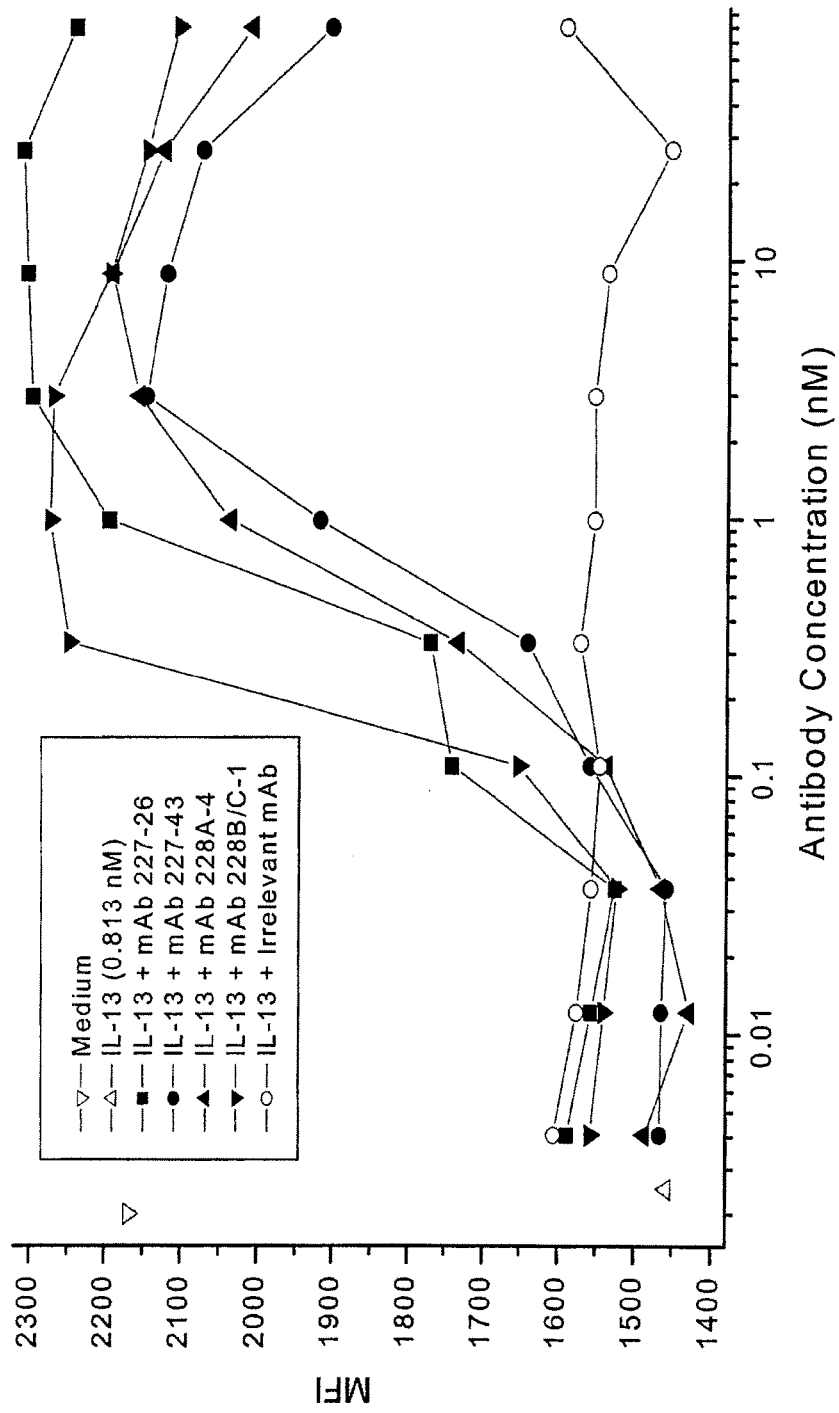
Fig. 5  Effect of anti-IL13 mAbs on IL13-induced suppression of CD14 expression in human monocytes

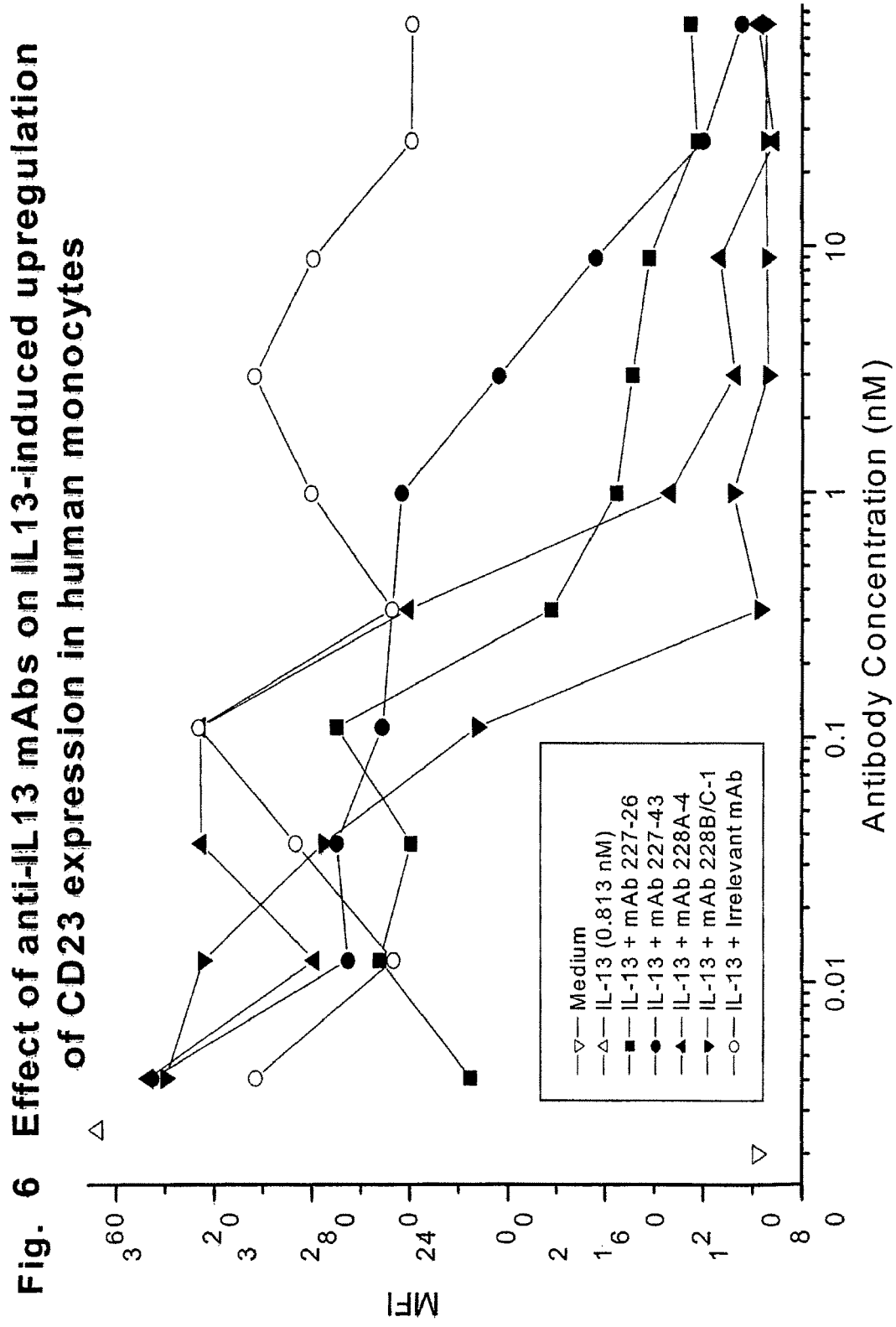

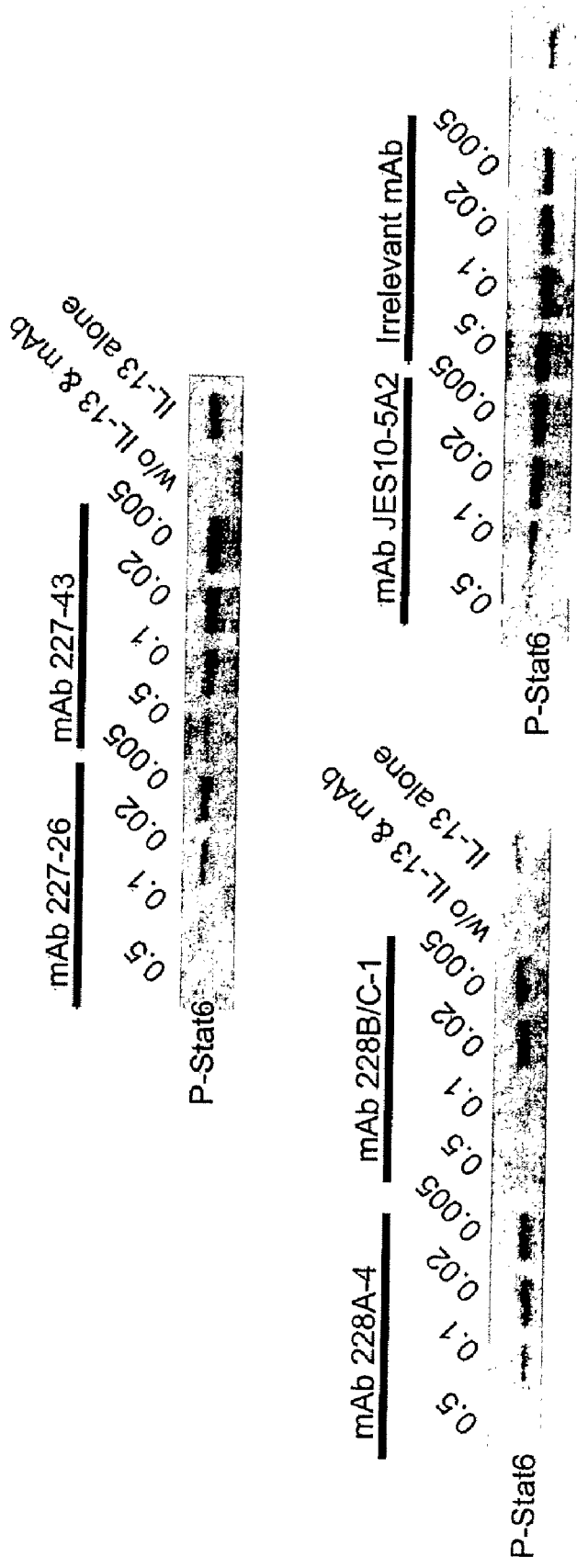
Fig. 7 Anti-IL13 mAbs Inhibit IL13-Induced Stat6 Phosphorylation in THP-1 Cells

FIGURE 8

228B/C-1 Antibody
Heavy Chain (VH)

```
  1                   10                  20                         30
QVQLQESGPGLVAPSQSLSITCTVSGFSLNAYSVNWV 40                   50 52a 53            60           65        70
RQPPGKGLEWLGMIWGDGKIVYNSALKSRLNISKDSS 80 82                90               95            100 b c d e f 101
KSQVFLKMSSLQSDDTARYYCAGDGYYPPYAMDNWGHGT

118
SVTVSS                (SEQ ID NO 4)
```

Light Chain (VK)

```
  1                   10                  20                         30
NIVLTQSPASLAVSLGQRATISCRASKSVDSYGNSFMHW 40                  50                60              70
YQQKPGQPPKLLIYLASNLESGVPARFSGSGSRTDFTLTI 80                 90             100                    113
DPVEADDAASYYCQQNNEDPRTFGGGTKLEIKRA            (SEQ ID NO 3)
```

Underlined: Kabat CDR. Bold/Italic: Chothia CDR1.

FIGURE 9
228A-4 Antibody
Heavy Chain (VH)

```
         1                    10                   20                   30
         Q V Q L K E S G P G L V A P S Q S L S I T C T V S G F S L T  T D Y N I N W I R Q
         40                          50   52a53              60                   65         70
         P P G K G L E W L G M I W G D G S T A Y N S A L K S R L S I S K D N S K S Q I F
         80  82ab c 83                90                      95         100 b c d e f 101         110
         L K M N S L Q T E D T A R Y Y C A R D G Y F P Y A M A Y W G Q G T
                    118
         S V T V S S         (SEQ ID NO 6)
```

Light Chain (VK)

```
         1                    10                   20                   30
         N I V L T Q S P T S L A V S L G Q R A T I S C R A S E S V D S Y G N G F I H W
         40                          50                    60                             70
         Y Q Q K P G Q P P K L L I Y L A S N L E S G V P A R F S G S G S R T D F T L T I
         80                     90                     100                      113
         D P M E A D D A A T Y Y C Q Q N N E D P R T F G G G T K L E I K R A   (SEQ ID NO 5)
```

Underlined: Kabat CDR. Bold/Italic: Chothia CDR1.

FIGURE 10
227-26 Antibody
Heavy Chain (VH)

```
         1                   10                  20                  30
         Q V Q L Q Q S G D D L V L P G A S V K L S C K A S G Y T F T S Y W I N W I
                         40             50 52a 53        60              65            70
         K Q R P G Q G L E W I G H I A P G S G S T Y F N E M F K G K A T L T V D T
                         80                  90              95          100 b c d e f
         S S S T A Y I Q L S S L S S E D S A V Y F C A R S D I F L S Y A M D Y W G Q
                 118
         G T S V T V S S      (SEQ ID NO 8)
```

Light Chain (VK)

```
         1                   10                  20                  30
         D V L M T Q T P L S L P V S L G D Q A S I S C R S S Q S I V H S N G N T Y L Q
                         40             50              60              70
         W Y L Q K P G Q S P K L L I Y K V S N R F S G V P D R F S G S G S G T D F T L K
                         80                  90              100             114
         I S R V E A E D L G V Y Y C F Q G S H V P Y T F G G G T K L E I K R A    (SEQ ID NO 7)
```

Underlined: Kabat CDR. Bold/Italic: Chothia CDR1.

FIGURE 11 A -1

VK CHAIN

| | FR1 | | | | | | | | | | | | | | | | | | | | | | | SEQ ID NO | CDR1 |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | | |
| Murine 228B/C-1 | N | I | V | L | T | Q | S | P | A | S | L | A | V | S | L | G | Q | R | A | T | I | S | C | 20 | |
| Human Template | D | I | V | M | T | Q | S | P | D | S | L | S | V | S | L | G | E | R | A | T | I | N | C | 21 | |
| | | | | | | | | | | | | | | | | | | | | | | | | | |
| Clone B | D | I | V | M | T | Q | S | P | A | S | L | A | V | S | L | G | E | R | A | T | I | N | C | 22 | |
| Clone J | D | I | V | L | T | Q | S | P | D | S | L | A | V | S | L | G | E | R | A | T | I | N | C | 23 | |
| Clone L | D | I | V | L | T | Q | S | P | A | S | L | S | V | S | L | G | E | R | A | T | I | N | C | 24 | |
| Clone N | D | I | V | L | T | Q | S | P | A | S | L | A | V | S | L | G | E | R | A | T | I | N | C | 153 | |
| Clone P | D | I | V | L | T | Q | S | P | A | S | L | A | V | S | L | G | E | R | A | T | I | N | C | 153 | |
| Clone R | D | I | V | L | T | Q | S | P | D | S | L | A | V | S | L | G | E | R | A | T | I | N | C | 23 | |
| | | | | | | | | | | | | | | | | | | | | | | | | | |
| HT2-NEW #1 | D | I | V | M | T | Q | S | P | D | S | L | S | V | S | L | G | E | R | A | T | I | N | C | 21 | |
| HT2-NEW #9 | D | I | V | M | T | Q | S | P | D | S | L | S | V | S | L | G | E | R | A | T | I | N | C | 21 | |
| HT2-NEW #14 | D | I | V | L | T | Q | S | P | A | S | L | S | V | S | L | G | E | R | A | T | I | N | C | 24 | |
| HT2-NEW #17 | D | I | V | L | T | Q | S | P | D | S | L | A | V | S | L | G | E | R | A | T | I | N | C | 23 | |
| HT2-NEW #21 | D | I | V | M | T | Q | S | P | D | S | L | S | V | S | L | G | E | R | A | T | I | N | C | 21 | |
| HT2-NEW #36 | D | I | V | L | T | Q | S | P | D | S | L | A | V | S | L | G | E | R | A | T | I | N | C | 23 | |
| HT2-NEW #65 | D | I | V | L | T | Q | S | P | D | S | L | A | V | S | L | G | E | R | A | T | I | N | C | 23 | |
| HT2-NEW #67 | D | I | V | L | T | Q | S | P | A | S | L | A | V | S | L | G | E | R | A | T | I | N | C | 153 | |
| HT2-NEW #70 | D | I | V | M | T | Q | S | P | D | S | L | S | V | S | L | G | E | R | A | T | I | N | C | 21 | |
| HT2-NEW #73 | D | I | V | L | T | Q | S | P | A | S | L | A | V | S | L | G | E | R | A | T | I | N | C | 153 | |
| HT2-NEW #74 | D | I | V | L | T | Q | S | P | A | S | L | A | V | S | L | G | E | R | A | T | I | N | C | 153 | |
| HT2-NEW #78 | D | I | V | L | T | Q | S | P | A | S | L | A | V | S | L | G | E | R | A | T | I | N | C | 153 | |
| HT2-NEW #79 | D | I | V | L | T | Q | S | P | A | S | L | A | V | S | L | G | E | R | A | T | I | N | C | 153 | |
| HT2-NEW #80 | D | I | V | M | T | Q | S | P | D | S | L | S | V | S | L | G | E | R | A | T | I | N | C | 21 | |
| HT2-NEW #87 | D | I | V | M | T | Q | S | P | D | S | L | S | V | S | L | G | E | R | A | T | I | N | C | 21 | |
| HT2-NEW #275 | D | I | V | L | T | Q | S | P | D | S | L | A | V | S | L | G | E | R | A | T | I | N | C | 23 | |
| HT2-NEW #284 | D | I | V | M | T | Q | S | P | A | S | L | A | V | S | L | G | E | R | A | T | I | N | C | 22 | |
| HT2-NEW #291 | D | I | V | L | T | Q | S | P | A | S | L | S | V | S | L | G | E | R | A | T | I | N | C | 24 | |
| HT2-NEW #300 | D | I | V | L | T | Q | S | P | D | S | L | S | V | S | L | G | E | R | A | T | I | N | C | 25 | |
| HT2-NEW #302 | D | I | V | M | T | Q | S | P | A | S | L | A | V | S | L | G | E | R | A | T | I | N | C | 22 | |
| HT2-NEW #322 | D | I | V | L | T | Q | S | P | D | S | L | A | V | S | L | G | E | R | A | T | I | N | C | 23 | |
| HT2-NEW #111 | D | I | V | L | T | Q | S | P | A | S | L | A | V | S | L | G | E | R | A | T | I | N | C | 153 | |
| HT2-NEW #115 | D | I | V | M | T | Q | S | P | D | S | L | S | V | S | L | G | E | R | A | T | I | N | C | 21 | |
| HT2-NEW #116 | D | I | V | M | T | Q | S | P | D | S | L | S | V | S | L | G | E | R | A | T | I | N | C | 21 | |
| HT2-NEW #117 | D | I | V | M | T | Q | S | P | D | S | L | S | V | S | L | G | E | R | A | T | I | N | C | 21 | |
| HT2-NEW #143 | D | I | V | L | T | Q | S | P | A | S | L | S | V | S | L | G | E | R | A | T | I | N | C | 24 | |
| HT2-NEW #162 | D | I | V | L | T | Q | S | P | D | S | L | S | V | S | L | G | E | R | A | T | I | N | C | 25 | |
| HT2-NEW #139 | D | I | V | M | T | Q | S | P | A | S | L | A | V | S | L | G | E | R | A | T | I | N | C | 22 | |
| HT2-NEW #177 | D | I | V | L | T | Q | S | P | A | S | L | S | V | S | L | G | E | R | A | T | I | N | C | 24 | |
| HT2-NEW #313 | D | I | V | L | T | Q | S | P | D | S | L | S | V | S | L | G | E | R | A | T | I | N | C | 25 | |

FIGURE 11 A - 2

VK CHAIN

| | FR2 | | | | | | | | | | | | | | | SEQ ID NO | CDR2 |
|---|---|---|---|---|---|---|---|---|---|---|---|---|---|---|---|---|---|
| | 40 | 41 | 42 | 43 | 44 | 45 | 46 | 47 | 48 | 49 | 50 | 51 | 52 | 53 | 54 | | |
| Murine 228B/C-1 | W | Y | Q | Q | K | P | G | Q | P | P | K | L | L | I | Y | 29 | |
| Human Template | W | Y | Q | Q | K | P | G | Q | P | P | K | L | L | I | Y | 29 | |
| | | | | | | | | | | | | | | | | 29 | |
| Clone B | W | Y | Q | Q | K | P | G | Q | P | P | K | L | L | I | Y | 29 | |
| Clone J | W | Y | Q | Q | K | P | G | Q | P | P | K | L | L | I | Y | 29 | |
| Clone L | W | Y | Q | Q | K | P | G | Q | P | P | K | L | L | I | Y | 29 | |
| Clone N | W | Y | Q | Q | K | P | G | Q | P | P | K | L | L | I | Y | 29 | |
| Clone P | W | Y | Q | Q | K | P | G | Q | P | P | K | L | L | I | Y | 29 | |
| Clone R | W | Y | Q | Q | K | P | G | Q | P | P | K | L | L | I | Y | 29 | |
| HT2-NEW #1 | W | Y | Q | Q | K | P | G | Q | P | P | K | L | L | I | Y | 29 | |
| HT2-NEW #9 | W | Y | Q | Q | K | P | G | Q | P | P | K | L | L | I | Y | 29 | |
| HT2-NEW #14 | W | Y | Q | Q | K | P | G | Q | P | P | K | L | L | I | Y | 29 | |
| HT2-NEW #17 | W | Y | Q | Q | K | P | G | Q | P | P | K | L | L | I | Y | 29 | |
| HT2-NEW #21 | W | Y | Q | Q | K | P | G | Q | P | P | K | L | L | I | Y | 29 | |
| HT2-NEW #36 | W | Y | Q | Q | K | P | G | Q | P | P | K | L | L | I | Y | 29 | |
| HT2-NEW #65 | W | Y | Q | Q | K | P | G | Q | P | P | K | L | L | I | Y | 29 | |
| HT2-NEW #67 | W | Y | Q | Q | K | P | G | Q | P | P | K | L | L | I | Y | 29 | |
| HT2-NEW #70 | W | Y | Q | Q | K | P | G | Q | P | P | K | L | L | I | Y | 29 | |
| HT2-NEW #73 | W | Y | Q | Q | K | P | G | Q | P | P | K | L | L | I | Y | 29 | |
| HT2-NEW #74 | W | Y | Q | Q | K | P | G | Q | P | P | K | L | L | I | Y | 29 | |
| HT2-NEW #78 | W | Y | Q | Q | K | P | G | Q | P | P | K | L | L | I | Y | 29 | |
| HT2-NEW #79 | W | Y | Q | Q | K | P | G | Q | P | P | K | L | L | I | Y | 29 | |
| HT2-NEW #80 | W | Y | Q | Q | K | P | G | Q | P | P | K | L | L | I | Y | 29 | |
| HT2-NEW #87 | W | Y | Q | Q | K | P | G | Q | P | P | K | L | L | I | Y | 29 | |
| HT2-NEW #275 | W | Y | Q | Q | K | P | G | Q | P | P | K | L | L | I | Y | 29 | |
| HT2-NEW #284 | W | Y | Q | Q | K | P | G | Q | P | P | K | L | L | I | Y | 29 | |
| HT2-NEW #291 | W | Y | Q | Q | K | P | G | Q | P | P | K | L | L | I | Y | 29 | |
| HT2-NEW #300 | W | Y | Q | Q | K | P | G | Q | P | P | K | L | L | I | Y | 29 | |
| HT2-NEW #302 | W | Y | Q | Q | K | P | G | Q | P | P | K | L | L | I | Y | 29 | |
| HT2-NEW #322 | W | Y | Q | Q | K | P | G | Q | P | P | K | L | L | I | Y | 29 | |
| HT2-NEW #111 | W | Y | Q | Q | K | P | G | Q | P | P | K | L | L | I | Y | 29 | |
| HT2-NEW #115 | W | Y | Q | Q | K | P | G | Q | P | P | K | L | L | I | Y | 29 | |
| HT2-NEW #116 | W | Y | Q | Q | K | P | G | Q | P | P | K | L | L | I | Y | 29 | |
| HT2-NEW #117 | W | Y | Q | Q | K | P | G | Q | P | P | K | L | L | I | Y | 29 | |
| HT2-NEW #143 | W | Y | Q | Q | K | P | G | Q | P | P | K | L | L | I | Y | 29 | |
| HT2-NEW #162 | W | Y | Q | Q | K | P | G | Q | P | P | K | L | L | I | Y | 29 | |
| HT2-NEW #139 | W | Y | Q | Q | K | P | G | Q | P | P | K | L | L | I | Y | 29 | |
| HT2-NEW #177 | W | Y | Q | Q | K | P | G | Q | P | P | K | L | L | I | Y | 29 | |
| HT2-NEW #313 | W | Y | Q | Q | K | P | G | Q | P | P | K | L | L | I | Y | 29 | |

FIGURE 11 B-1

VK CHAIN

FR3

| | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | SEQ ID NO | CDR3 |
|---|---|---|---|---|---|---|---|---|---|---|---|---|---|---|---|---|---|---|---|---|---|---|---|---|---|---|---|---|---|---|---|---|---|---|
| Murine 228B/C-1 | G | V | P | A | R | F | S | G | S | G | S | R | T | D | F | T | L | T | I | D | P | V | E | A | D | D | A | A | S | Y | Y | C | 30 | |
| Human Template | G | V | P | D | R | F | S | G | S | G | S | G | T | D | F | T | L | T | I | S | S | L | Q | A | E | D | V | A | V | Y | Y | C | 31 | |
| Clone B | G | V | P | D | R | F | S | G | S | G | S | G | T | D | F | T | L | T | I | D | P | L | Q | A | E | D | V | A | V | Y | Y | C | 32 | |
| Clone J | G | V | P | D | R | F | S | G | S | G | S | G | T | D | F | T | L | T | I | D | S | L | Q | A | E | D | V | A | V | Y | Y | C | 33 | |
| Clone L | G | V | P | D | R | F | S | G | S | G | S | R | T | D | F | T | L | T | I | D | P | L | Q | A | E | D | V | A | V | Y | Y | C | 34 | |
| Clone N | G | V | P | D | R | F | S | G | S | G | S | R | T | D | F | T | L | T | I | D | P | V | Q | A | E | D | V | A | V | Y | Y | C | 35 | |
| Clone P | G | V | P | D | R | F | S | G | S | G | S | R | T | D | F | T | L | T | I | D | S | V | Q | A | E | D | V | A | V | Y | Y | C | 36 | |
| Clone R | G | V | P | D | R | F | S | G | S | G | S | R | T | D | F | T | L | T | I | S | S | V | Q | A | E | D | V | A | V | Y | Y | C | 37 | |
| HT2-NEW #1 | G | V | P | D | R | F | S | G | S | G | S | R | T | D | F | T | L | T | I | S | P | V | Q | A | E | D | V | A | V | Y | Y | C | 38 | |
| HT2-NEW #9 | G | V | P | D | R | F | S | G | S | G | S | R | T | D | F | T | L | T | I | S | S | V | E | A | E | D | V | A | V | Y | Y | C | 39 | |
| HT2-NEW #14 | G | V | P | D | R | F | S | G | S | G | S | R | T | D | F | T | L | T | I | S | P | V | E | A | E | D | V | A | V | Y | Y | C | 40 | |
| HT2-NEW #17 | G | V | P | D | R | F | S | G | S | G | S | R | T | D | F | T | L | T | I | S | S | V | Q | A | E | D | V | A | V | Y | Y | C | 37 | |
| HT2-NEW #21 | G | V | P | D | R | F | S | G | S | G | S | G | T | D | F | T | L | T | I | S | S | V | E | A | E | D | V | A | V | Y | Y | C | 41 | |
| HT2-NEW #36 | G | V | P | D | R | F | S | G | S | G | S | R | T | D | F | T | L | T | I | S | S | V | Q | A | E | D | V | A | V | Y | Y | C | 37 | |
| HT2-NEW #65 | G | V | P | D | R | F | S | G | S | G | S | G | T | D | F | T | L | T | I | S | S | L | Q | A | E | D | V | A | V | Y | Y | C | 31 | |
| HT2-NEW #67 | G | V | P | D | R | F | S | G | S | G | S | G | T | D | F | T | L | T | I | D | P | L | E | A | E | D | V | A | V | Y | Y | C | 42 | |
| HT2-NEW #70 | G | V | P | D | R | F | S | G | S | G | S | G | T | D | F | T | L | T | I | S | S | V | E | A | E | D | V | A | V | Y | Y | C | 39 | |
| HT2-NEW #73 | G | V | P | D | R | F | S | G | S | G | S | R | T | D | F | T | L | T | I | D | S | V | Q | A | E | D | V | A | V | Y | Y | C | 36 | |
| HT2-NEW #74 | G | V | P | D | R | F | S | G | S | G | S | G | T | D | F | T | L | T | I | S | P | V | Q | A | E | D | V | A | V | Y | Y | C | 43 | |
| HT2-NEW #78 | G | V | P | D | R | F | S | G | S | G | S | G | T | D | F | T | L | T | I | D | S | V | E | A | E | D | V | A | V | Y | Y | C | 44 | |
| HT2-NEW #79 | G | V | P | D | R | F | S | G | S | G | S | G | T | D | F | T | L | T | I | S | P | V | Q | A | E | D | V | A | V | Y | Y | C | 39 | |
| HT2-NEW #80 | G | V | P | D | R | F | S | G | S | G | S | G | T | D | F | T | L | T | I | S | S | V | E | A | E | D | V | A | V | Y | Y | C | 39 | |
| HT2-NEW #87 | G | V | P | D | R | F | S | G | S | G | S | G | T | D | F | T | L | T | I | S | S | V | E | A | E | D | V | A | V | Y | Y | C | 39 | |
| HT2-NEW #275 | G | V | P | D | R | F | S | G | S | G | S | G | T | D | F | T | L | T | I | D | S | L | Q | A | E | D | V | A | V | Y | Y | C | 33 | |
| HT2-NEW #284 | G | V | P | D | R | F | S | G | S | G | S | G | T | D | F | T | L | T | I | D | S | L | Q | A | E | D | V | A | V | Y | Y | C | 33 | |
| HT2-NEW #291 | G | V | P | D | R | F | S | G | S | G | S | G | T | D | F | T | L | T | I | S | P | V | Q | A | E | D | V | A | V | Y | Y | C | 43 | |
| HT2-NEW #300 | G | V | P | D | R | F | S | G | S | G | S | R | T | D | F | T | L | T | I | D | S | V | Q | A | E | D | V | A | V | Y | Y | C | 36 | |
| HT2-NEW #302 | G | V | P | D | R | F | S | G | S | G | S | G | T | D | F | T | L | T | I | S | S | V | E | A | E | D | V | A | V | Y | Y | C | 39 | |
| HT2-NEW #322 | G | V | P | D | R | F | S | G | S | G | S | R | T | D | F | T | L | T | I | D | S | L | E | A | E | D | V | A | V | Y | Y | C | 45 | |
| HT2-NEW #111 | G | V | P | D | R | F | S | G | S | G | S | G | T | D | F | T | L | T | I | D | P | L | Q | A | E | D | V | A | V | Y | Y | C | 32 | |
| HT2-NEW #115 | G | V | P | D | R | F | S | G | S | G | S | G | T | D | F | T | L | T | I | S | S | V | E | A | E | D | V | A | V | Y | Y | C | 39 | |
| HT2-NEW #116 | G | V | P | D | R | F | S | G | S | G | S | G | T | D | F | T | L | T | I | S | S | V | E | A | E | D | V | A | V | Y | Y | C | 39 | |
| HT2-NEW #117 | G | V | P | D | R | F | S | G | S | G | S | G | T | D | F | T | L | T | I | S | S | V | E | A | E | D | V | A | V | Y | Y | C | 39 | |
| HT2-NEW #143 | G | V | P | D | R | F | S | G | S | G | S | R | T | D | F | T | L | T | I | D | S | V | Q | A | E | D | V | A | V | Y | Y | C | 36 | |
| HT2-NEW #162 | G | V | P | D | R | F | S | G | S | G | S | G | T | D | F | T | L | T | I | D | P | V | Q | A | E | D | V | A | V | Y | Y | C | 46 | |
| HT2-NEW #139 | G | V | P | D | R | F | S | G | S | G | S | G | T | D | F | T | L | T | I | D | P | V | Q | A | E | D | V | A | V | Y | Y | C | 46 | |
| HT2-NEW #177 | G | V | P | D | R | F | S | G | S | G | S | G | T | D | F | T | L | T | I | D | S | V | E | A | E | D | V | A | V | Y | Y | C | 44 | |
| HT2-NEW #313 | G | V | P | D | R | F | S | G | S | G | S | G | T | D | F | T | L | T | I | S | S | V | E | A | E | D | V | A | V | Y | Y | C | 39 | |

FIGURE 11 B-2

VK CHAIN

| | FR4 | | | | | | | | | | | | |
|---|---|---|---|---|---|---|---|---|---|---|---|---|---|
| | 103 | 104 | 105 | 106 | 107 | 108 | 109 | 110 | 111 | 112 | 113 | 114 | SEQ ID NO |
| Murine 228B/C-1 | F | G | G | G | T | K | L | E | I | K | R | A | 57 |
| Human Template | F | G | G | G | T | K | V | E | I | K | R | | 58 |
| | | | | | | | | | | | | | |
| Clone B | F | G | G | G | T | K | L | E | I | K | R | | 59 |
| Clone J | F | G | G | G | T | K | L | E | I | K | R | | 59 |
| Clone L | F | G | G | G | T | K | L | E | I | K | R | | 59 |
| Clone N | F | G | G | G | T | K | V | E | I | K | R | | 58 |
| Clone P | F | G | G | G | T | K | L | E | I | K | R | | 58 |
| Clone R | F | G | G | G | T | K | V | E | I | K | R | | 58 |
| | | | | | | | | | | | | | |
| HT2-NEW #1 | F | G | G | G | T | K | V | E | I | K | R | | 58 |
| HT2-NEW #9 | F | G | G | G | T | K | V | E | I | K | R | | 58 |
| HT2-NEW #14 | F | G | G | G | T | K | V | E | I | K | R | | 58 |
| HT2-NEW #17 | F | G | G | G | T | K | V | E | I | K | R | | 58 |
| HT2-NEW #21 | F | G | G | G | T | K | V | E | I | K | R | | 58 |
| HT2-NEW #36 | F | G | G | G | T | K | V | E | I | K | R | | 58 |
| HT2-NEW #65 | F | G | G | G | T | K | V | E | I | K | R | | 58 |
| HT2-NEW #67 | F | G | G | G | T | K | V | E | I | K | R | | 58 |
| HT2-NEW #70 | F | G | G | G | T | K | V | E | I | K | R | | 58 |
| HT2-NEW #73 | F | G | G | G | T | K | L | E | I | K | R | | 59 |
| HT2-NEW #74 | F | G | G | G | T | K | V | E | I | K | R | | 58 |
| HT2-NEW #78 | F | G | G | G | T | K | V | E | I | K | R | | 58 |
| HT2-NEW #79 | F | G | G | G | T | K | V | E | I | K | R | | 58 |
| HT2-NEW #80 | F | G | G | G | T | K | V | E | I | K | R | | 58 |
| HT2-NEW #87 | F | G | G | G | T | K | V | E | I | K | R | | 58 |
| HT2-NEW #275 | F | G | G | G | T | K | V | E | I | K | R | | 58 |
| HT2-NEW #284 | F | G | G | G | T | K | V | E | I | K | R | | 58 |
| HT2-NEW #291 | F | G | G | G | T | K | L | E | I | K | R | | 59 |
| HT2-NEW #300 | F | G | G | G | T | K | V | E | I | K | R | | 58 |
| HT2-NEW #302 | F | G | G | G | T | K | L | E | I | K | R | | 59 |
| HT2-NEW #322 | F | G | G | G | T | K | V | E | I | K | R | | 58 |
| HT2-NEW #111 | F | G | G | G | T | K | L | E | I | K | R | | 59 |
| HT2-NEW #115 | F | G | G | G | T | K | V | E | I | K | R | | 58 |
| HT2-NEW #116 | F | G | G | G | T | K | V | E | I | K | R | | 58 |
| HT2-NEW #117 | F | G | G | G | T | K | V | E | I | K | R | | 58 |
| HT2-NEW #143 | F | G | G | G | T | K | L | E | I | K | R | | 59 |
| HT2-NEW #162 | F | G | G | G | T | K | V | E | I | K | R | | 58 |
| HT2-NEW #139 | F | G | G | G | T | K | V | E | I | K | R | | 58 |
| HT2-NEW #177 | F | G | G | G | T | K | V | E | I | K | R | | 58 |
| HT2-NEW #313 | F | G | G | G | T | K | V | E | I | K | R | | 58 |

FIGURE 11 C - 1

VK CHAIN    FR1

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | SEQ ID NO | CDR1 |
|---|---|---|---|---|---|---|---|---|---|---|---|---|---|---|---|---|---|---|---|---|---|---|---|---|---|
| HT2-dp27 #7 | D | I | V | M | T | Q | S | P | D | S | L | S | V | S | L | G | E | R | A | T | I | N | C | 21 | |
| HT2-dp27 #13 | D | I | V | M | T | Q | S | P | D | S | L | S | V | S | L | G | E | R | A | T | I | N | C | 21 | |
| HT2-dp27 #19 | D | I | V | M | T | Q | S | P | A | S | L | A | V | S | L | G | E | R | A | T | I | N | C | 22 | |
| HT2-dp27 #29 | D | I | V | L | T | Q | S | P | V | S | L | A | V | S | L | G | E | R | A | T | I | N | C | 26 | |
| HT2-dp27 #34 | D | I | V | L | T | Q | S | P | A | S | L | S | V | S | L | G | E | R | A | T | I | N | C | 24 | |
| HT2-dp27 #40 | D | I | V | L | T | Q | S | P | A | S | L | S | V | S | L | G | E | R | A | T | I | N | C | 24 | |
| HT2-dp27 #43 | D | I | V | M | T | Q | S | P | D | S | L | A | V | S | L | G | E | R | A | T | I | N | C | 28 | |
| HT2-dp27 #50 | D | I | V | M | T | Q | S | P | A | S | L | A | V | S | L | G | E | R | A | T | I | N | C | 22 | |
| HT2-dp27 #53 | D | I | V | M | T | Q | S | P | A | S | L | S | V | S | L | G | E | R | A | T | I | N | C | 27 | |
| HT2-dp27 #57 | D | I | V | M | T | Q | S | P | A | S | L | S | V | S | L | G | E | R | A | T | I | N | C | 27 | |
| HT2-dp27 #66 | D | I | V | M | T | Q | S | P | D | S | L | A | V | S | L | G | E | R | A | T | I | N | C | 28 | |
| HT2-dp27 #67 | D | I | V | M | T | Q | S | P | A | S | L | A | V | S | L | G | E | R | A | T | I | N | C | 22 | |
| HT2-dp27 #73 | D | I | V | M | T | Q | S | P | A | S | L | S | V | S | L | G | E | R | A | T | I | N | C | 24 | |
| HT2-dp27 #74 | D | I | V | M | T | Q | S | P | D | S | L | S | V | S | L | G | E | R | A | T | I | N | C | 21 | |
| HT2-dp27 #89 | D | I | V | M | T | Q | S | P | D | S | L | S | V | S | L | G | E | R | A | T | I | N | C | 21 | |
| HT2-dp27 #92 | D | I | V | L | T | Q | S | P | A | S | L | A | V | S | L | G | E | R | A | T | I | N | C | 153 | |
| HT2-dp27 #100 | D | I | V | M | T | Q | S | P | A | S | L | S | V | S | L | G | E | R | A | T | I | N | C | 27 | |
| HT2-dp27 #111 | D | I | V | L | T | Q | S | P | A | S | L | S | V | S | L | G | E | R | A | T | I | N | C | 24 | |
| HT2-dp27 #112 | D | I | V | M | T | Q | S | P | A | S | L | A | V | S | L | G | E | R | A | T | I | N | C | 22 | |
| HT2-dp27 #118 | D | I | V | L | T | Q | S | P | A | S | L | A | V | S | L | G | E | R | A | T | I | N | C | 154 | |
| HT2-dp27 #123 | D | I | V | L | T | Q | S | P | A | S | L | A | V | S | L | G | E | R | A | T | I | N | C | 153 | |
| HT2-dp27-#136 | D | I | V | M | T | Q | S | P | A | S | L | S | V | S | L | G | E | R | A | T | I | N | C | 27 | |
| HT2-dp27 #144 | D | I | V | M | T | Q | S | P | D | S | L | S | V | S | L | G | E | R | A | T | I | N | C | 21 | |
| HT2-dp27 #146 | D | I | V | M | T | Q | S | P | A | S | L | A | V | S | L | G | E | R | A | T | I | N | C | 22 | |
| HT2-dp27 #15 | D | I | V | M | T | Q | S | P | A | S | L | S | V | S | L | G | E | R | A | T | I | N | C | 27 | |
| HT2-dp27 #26 | D | I | V | M | T | Q | S | P | A | S | L | S | V | S | L | G | E | R | A | T | I | N | C | 27 | |
| HT2-dp27 #83 | D | I | V | M | T | Q | S | P | A | S | L | S | V | S | L | G | E | R | A | T | I | N | C | 27 | |
| HT2-dp27 #164 | D | I | V | L | T | Q | S | P | A | S | L | A | V | S | L | G | E | R | A | T | I | N | C | 153 | |
| HT2-dp27 #177 | D | I | V | L | T | Q | S | P | D | S | L | S | V | S | L | G | E | R | A | T | I | N | C | 25 | |
| HT2-dp27 #195 | D | I | V | M | T | Q | S | P | A | S | L | A | V | S | L | G | E | R | A | T | I | N | C | 22 | |
| HT2-dp27 #198 | D | I | V | M | T | Q | S | P | A | S | L | S | V | S | L | G | E | R | A | T | I | N | C | 27 | |
| HT2-dp27 #150 | D | I | V | M | T | Q | S | P | D | S | L | S | V | S | L | G | E | R | A | T | I | N | C | 21 | |
| HT2-dp27 #268 | D | I | V | M | T | Q | S | P | A | S | L | A | V | S | L | G | E | R | A | T | I | N | C | 22 | |
| HT2-dp27 #270 | D | I | V | M | T | Q | S | P | A | S | L | S | V | S | L | G | E | R | A | T | I | N | C | 27 | |
| HT2-dp27 #199 | D | I | V | M | T | Q | S | P | A | S | L | S | V | S | L | G | E | R | A | T | I | N | C | 27 | |
| HT2-dp27 #273 | D | I | V | L | T | Q | S | P | A | S | L | A | V | S | L | G | E | R | A | T | I | N | C | 153 | |
| HT2-dp27 #282 | D | I | V | L | T | Q | S | P | D | S | L | S | V | S | L | G | E | R | A | T | I | N | C | 25 | |
| HT2-dp27 #304 | D | I | V | L | T | Q | S | P | D | S | L | A | V | S | L | G | E | R | A | T | I | N | C | 23 | |
| HT2-dp27 #155B | D | I | V | L | T | Q | S | P | D | S | L | A | V | S | L | G | E | R | A | T | I | N | C | 23 | |
| HT2-dp27 #274 | D | I | V | M | T | Q | S | P | A | S | L | S | V | S | L | G | E | R | A | T | I | N | C | 27 | |
| HT2-dp27 #275 | D | I | V | L | T | Q | S | P | A | S | L | A | V | S | L | G | E | R | A | T | I | N | C | 153 | |
| HT2-dp27 #276 | D | I | V | L | T | Q | S | P | D | S | L | S | V | S | L | G | E | R | A | T | I | N | C | 25 | |
| HT2-dp27 #299 | D | I | V | L | T | Q | S | P | A | S | L | S | V | S | L | G | E | R | A | T | I | N | C | 24 | |
| HT2-dp27 #301 | D | I | V | L | T | Q | S | P | D | S | L | S | V | S | L | G | E | R | A | T | I | N | C | 25 | |
| HT2-dp27 #308 | D | I | V | M | T | Q | S | P | D | S | L | S | V | S | L | G | E | R | A | T | I | N | C | 21 | |
| HT2-dp27 #467 | D | I | V | M | T | Q | S | P | D | S | L | S | V | S | L | G | E | R | A | T | I | N | C | 21 | |
| HT2-dp27 #530 | D | I | V | M | T | Q | S | P | A | S | L | S | V | S | L | G | E | R | A | T | I | N | C | 27 | |
| HT2-dp27 #580 | D | I | V | M | T | Q | S | P | A | S | L | A | V | S | L | G | E | R | A | T | I | N | C | 22 | |
| HT2-dp27 #345 | D | I | V | L | T | Q | S | P | A | S | L | S | V | S | L | G | E | R | A | T | I | N | C | 24 | |
| HT2-dp27 #374 | D | I | V | L | T | Q | S | P | A | S | L | A | V | S | L | G | E | R | A | T | I | N | C | 153 | |
| HT2-dp27 #443 | D | I | V | L | T | Q | S | P | D | S | L | A | V | S | L | G | E | R | A | T | I | N | C | 23 | |
| HT2-dp27 #459 | D | I | V | M | T | Q | S | P | A | S | L | A | V | S | L | G | E | R | A | T | I | N | C | 22 | |
| HT2-dp27 #470 | D | I | V | L | T | Q | S | P | D | S | L | S | V | S | L | G | E | R | A | T | I | N | C | 25 | |
| HT2-dp27 #471 | D | I | V | L | T | Q | S | P | A | S | L | A | V | S | L | G | E | R | A | T | I | N | C | 153 | |
| HT2-dp27 #486 | D | I | V | M | T | Q | S | P | D | S | L | A | V | S | L | G | E | R | A | T | I | N | C | 28 | |
| HT2-dp27 #610 | D | I | V | M | T | Q | S | P | D | S | L | A | V | S | L | G | E | R | A | T | I | N | C | 28 | |
| HT2-dp27 #624 | D | I | V | M | T | Q | S | P | D | S | L | S | V | S | L | G | E | R | A | T | I | N | C | 21 | |
| HT2-dp27 #634 | D | I | V | L | T | Q | S | P | A | S | L | A | V | S | L | G | E | R | A | T | I | N | C | 153 | |

FIGURE 11 C - 2

VK CHAIN    FR2

| | 40 | 41 | 42 | 43 | 44 | 45 | 46 | 47 | 48 | 49 | 50 | 51 | 52 | 53 | 54 | SEQ ID NO | CDR2 |
|---|---|---|---|---|---|---|---|---|---|---|---|---|---|---|---|---|---|
| HT2-dp27 #7 | W | Y | Q | Q | K | P | G | Q | P | P | K | L | L | I | Y | 29 | |
| HT2-dp27 #13 | W | Y | Q | Q | K | P | G | Q | P | P | K | L | L | I | Y | 29 | |
| HT2-dp27 #19 | W | Y | Q | Q | K | P | G | Q | P | P | K | L | L | I | Y | 29 | |
| HT2-dp27 #29 | W | Y | Q | Q | K | P | G | Q | P | P | K | L | L | I | Y | 29 | |
| HT2-dp27 #34 | W | Y | Q | Q | K | P | G | Q | P | P | K | L | L | I | Y | 29 | |
| HT2-dp27 #40 | W | Y | Q | Q | K | P | G | Q | P | P | K | L | L | I | Y | 29 | |
| HT2-dp27 #43 | W | Y | Q | Q | K | P | G | Q | P | P | K | L | L | I | Y | 29 | |
| HT2-dp27 #50 | W | Y | Q | Q | K | P | G | Q | P | P | K | L | L | I | Y | 29 | |
| HT2-dp27 #53 | W | Y | Q | Q | K | P | G | Q | P | P | K | L | L | I | Y | 29 | |
| HT2-dp27 #57 | W | Y | Q | Q | K | P | G | Q | P | P | K | L | L | I | Y | 29 | |
| HT2-dp27 #66 | W | Y | Q | Q | K | P | G | Q | P | P | K | L | L | I | Y | 29 | |
| HT2-dp27 #67 | W | Y | Q | Q | K | P | G | Q | P | P | K | L | L | I | Y | 29 | |
| HT2-dp27 #73 | W | Y | Q | Q | K | P | G | Q | P | P | K | L | L | I | Y | 29 | |
| HT2-dp27 #74 | W | Y | Q | Q | K | P | G | Q | P | P | K | L | L | I | Y | 29 | |
| HT2-dp27 #89 | W | Y | Q | Q | K | P | G | Q | P | P | K | L | L | I | Y | 29 | |
| HT2-dp27 #92 | W | Y | Q | Q | K | P | G | Q | P | P | K | L | L | I | Y | 29 | |
| HT2-dp27 #100 | W | Y | Q | Q | K | P | G | Q | P | P | K | L | L | I | Y | 29 | |
| HT2-dp27 #111 | W | Y | Q | Q | K | P | G | Q | P | P | K | L | L | I | Y | 29 | |
| HT2-dp27 #112 | W | Y | Q | Q | K | P | G | Q | P | P | K | L | L | I | Y | 29 | |
| HT2-dp27 #118 | W | Y | Q | Q | K | P | G | Q | P | P | K | L | L | I | Y | 29 | |
| HT2-dp27 #123 | W | Y | Q | Q | K | P | G | Q | P | P | K | L | L | I | Y | 29 | |
| HT2-dp27-#136 | W | Y | Q | Q | K | P | G | Q | P | P | K | L | L | I | Y | 29 | |
| HT2-dp27 #144 | W | Y | Q | Q | K | P | G | Q | P | P | K | L | L | I | Y | 29 | |
| HT2-dp27 #146 | W | Y | Q | Q | K | P | G | Q | P | P | K | L | L | I | Y | 29 | |
| HT2-dp27 #15 | W | Y | Q | Q | K | P | G | Q | P | P | K | L | L | I | Y | 29 | |
| HT2-dp27 #26 | W | Y | Q | Q | K | P | G | Q | P | P | K | L | L | I | Y | 29 | |
| HT2-dp27 #83 | W | Y | Q | Q | K | P | G | Q | P | P | K | L | L | I | Y | 29 | |
| HT2-dp27 #164 | W | Y | Q | Q | K | P | G | Q | P | P | K | L | L | I | Y | 29 | |
| HT2-dp27 #177 | W | Y | Q | Q | K | P | G | Q | P | P | K | L | L | I | Y | 29 | |
| HT2-dp27 #195 | W | Y | Q | Q | K | P | G | Q | P | P | K | L | L | I | Y | 29 | |
| HT2-dp27 #198 | W | Y | Q | Q | K | P | G | Q | P | P | K | L | L | I | Y | 29 | |
| HT2-dp27 #150 | W | Y | Q | Q | K | P | G | Q | P | P | K | L | L | I | Y | 29 | |
| HT2-dp27 #268 | W | Y | Q | Q | K | P | G | Q | P | P | K | L | L | I | Y | 29 | |
| HT2-dp27 #270 | W | Y | Q | Q | K | P | G | Q | P | P | K | L | L | I | Y | 29 | |
| HT2-dp27 #199 | W | Y | Q | Q | K | P | G | Q | P | P | K | L | L | I | Y | 29 | |
| HT2-dp27 #273 | W | Y | Q | Q | K | P | G | Q | P | P | K | L | L | I | Y | 29 | |
| HT2-dp27 #282 | W | Y | Q | Q | K | P | G | Q | P | P | K | L | L | I | Y | 29 | |
| HT2-dp27 #304 | W | Y | Q | Q | K | P | G | Q | P | P | K | L | L | I | Y | 29 | |
| HT2-dp27 #155B | W | Y | Q | Q | K | P | G | Q | P | P | K | L | L | I | Y | 29 | |
| HT2-dp27 #274 | W | Y | Q | Q | K | P | G | Q | P | P | K | L | L | I | Y | 29 | |
| HT2-dp27 #275 | W | Y | Q | Q | K | P | G | Q | P | P | K | L | L | I | Y | 29 | |
| HT2-dp27 #276 | W | Y | Q | Q | K | P | G | Q | P | P | K | L | L | I | Y | 29 | |
| HT2-dp27 #299 | W | Y | Q | Q | K | P | G | Q | P | P | K | L | L | I | Y | 29 | |
| HT2-dp27 #301 | W | Y | Q | Q | K | P | G | Q | P | P | K | L | L | I | Y | 29 | |
| HT2-dp27 #308 | W | Y | Q | Q | K | P | G | Q | P | P | K | L | L | I | Y | 29 | |
| HT2-dp27 #467 | W | Y | Q | Q | K | P | G | Q | P | P | K | L | L | I | Y | 29 | |
| HT2-dp27 #530 | W | Y | Q | Q | K | P | G | Q | P | P | K | L | L | I | Y | 29 | |
| HT2-dp27 #580 | W | Y | Q | Q | K | P | G | Q | P | P | K | L | L | I | Y | 29 | |
| HT2-dp27 #345 | W | Y | Q | Q | K | P | G | Q | P | P | K | L | L | I | Y | 29 | |
| HT2-dp27 #374 | W | Y | Q | Q | K | P | G | Q | P | P | K | L | L | I | Y | 29 | |
| HT2-dp27 #443 | W | Y | Q | Q | K | P | G | Q | P | P | K | L | L | I | Y | 29 | |
| HT2-dp27 #459 | W | Y | Q | Q | K | P | G | Q | P | P | K | L | L | I | Y | 29 | |
| HT2-dp27 #470 | W | Y | Q | Q | K | P | G | Q | P | P | K | L | L | I | Y | 29 | |
| HT2-dp27 #471 | W | Y | Q | Q | K | P | G | Q | P | P | K | L | L | I | Y | 29 | |
| HT2-dp27 #486 | W | Y | Q | Q | K | P | G | Q | P | P | K | L | L | I | Y | 29 | |
| HT2-dp27 #610 | W | Y | Q | Q | K | P | G | Q | P | P | K | L | L | I | Y | 29 | |
| HT2-dp27 #624 | W | Y | Q | Q | K | P | G | Q | P | P | K | L | L | I | Y | 29 | |
| HT2-dp27 #634 | W | Y | Q | Q | K | P | G | Q | P | P | K | L | L | I | Y | 29 | |

FIGURE 11 D -1
VK CHAIN    FR3

| | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | SEQ ID NO | CDR3 |
|---|---|---|---|---|---|---|---|---|---|---|---|---|---|---|---|---|---|---|---|---|---|---|---|---|---|---|---|---|---|---|---|---|---|---|
| HT2-dp27 #7 | G | V | P | D | R | F | S | G | S | G | S | G | T | D | F | T | L | T | I | D | S | V | Q | A | E | D | V | A | V | Y | Y | C | 47 | |
| HT2-dp27 #13 | G | V | P | D | R | F | S | G | S | G | S | G | T | D | F | T | L | T | I | D | S | V | Q | A | E | D | V | A | V | Y | Y | C | 47 | |
| HT2-dp27 #19 | G | V | P | D | R | F | S | G | S | G | S | R | T | D | F | T | L | T | I | D | S | L | E | A | E | D | V | A | V | Y | Y | C | 45 | |
| HT2-dp27 #29 | G | V | P | D | R | F | S | G | S | G | S | R | T | D | F | T | L | T | I | D | P | V | Q | A | E | D | V | A | V | Y | Y | C | 35 | |
| HT2-dp27 #34 | G | V | P | D | R | F | S | G | S | G | S | G | T | D | F | T | L | T | I | S | P | V | Q | A | E | D | V | A | V | Y | Y | C | 43 | |
| HT2-dp27 #40 | G | V | P | D | R | F | S | G | S | G | S | R | T | D | F | T | L | T | I | D | S | V | E | A | E | D | V | A | V | Y | Y | C | 155 | |
| HT2-dp27 #43 | G | V | P | D | R | F | S | G | S | G | S | G | T | D | F | T | L | T | I | D | S | V | Q | A | E | D | V | A | V | Y | Y | C | 47 | |
| HT2-dp27 #50 | G | V | P | D | R | F | S | G | S | G | S | G | T | D | F | T | L | T | I | D | P | V | E | A | E | D | V | A | V | Y | Y | C | 49 | |
| HT2-dp27 #53 | G | V | P | D | R | F | S | G | S | G | S | G | T | D | F | T | L | T | I | D | S | V | Q | A | E | D | V | A | V | Y | Y | C | 47 | |
| HT2-dp27 #57 | G | V | P | D | R | F | S | G | S | G | S | G | T | D | F | T | L | T | I | S | P | V | E | A | E | D | V | A | V | Y | Y | C | 48 | |
| HT2-dp27 #66 | G | V | P | D | R | F | S | G | S | G | S | R | T | D | F | T | L | T | I | D | S | V | E | A | E | D | V | A | V | Y | Y | C | 155 | |
| HT2-dp27 #67 | G | V | P | D | R | F | S | G | S | G | S | G | T | D | F | T | L | T | I | D | S | L | Q | A | E | D | V | A | V | Y | Y | C | 33 | |
| HT2-dp27 #73 | G | V | P | D | R | F | S | G | S | G | S | G | T | D | F | T | L | T | I | D | P | V | E | A | E | D | V | A | V | Y | Y | C | 49 | |
| HT2-dp27 #74 | G | V | P | D | R | F | S | G | S | G | S | G | T | D | F | T | L | T | I | D | S | V | E | A | E | D | V | A | V | Y | Y | C | 44 | |
| HT2-dp27 #89 | G | V | P | D | R | F | S | G | S | G | S | G | T | D | F | T | L | T | I | S | S | L | Q | A | E | D | V | A | V | Y | Y | C | 31 | |
| HT2-dp27 #92 | G | V | P | D | R | F | S | G | S | G | S | G | T | D | F | T | L | T | I | D | (T) | V | Q | A | E | D | V | A | V | Y | Y | C | 50 | |
| HT2-dp27 #100 | G | V | P | D | R | F | S | G | S | G | S | G | T | D | F | T | L | T | I | D | P | V | E | A | E | D | V | A | V | Y | Y | C | 49 | |
| HT2-dp27 #111 | G | V | P | D | R | F | S | G | S | G | S | G | T | D | F | T | L | T | I | D | S | V | E | A | E | D | V | A | V | Y | Y | C | 44 | |
| HT2-dp27 #112 | G | V | P | D | R | F | S | G | S | G | S | G | T | D | F | T | L | T | I | D | P | L | E | A | E | D | V | A | V | Y | Y | C | 42 | |
| HT2-dp27 #118 | G | V | P | D | R | F | S | G | S | G | S | R | T | D | F | T | L | T | I | S | P | L | Q | A | E | D | V | A | V | Y | Y | C | 51 | |
| HT2-dp27 #123 | G | V | P | D | R | F | S | G | S | G | S | R | T | D | F | T | L | T | I | S | S | L | E | A | E | D | V | A | V | Y | Y | C | 52 | |
| HT2-dp27-#136 | G | V | P | D | R | F | S | G | S | G | S | R | T | D | F | T | L | T | I | D | S | V | E | A | E | D | V | A | V | Y | Y | C | 155 | |
| HT2-dp27 #144 | G | V | P | D | R | F | S | G | S | G | S | G | T | D | F | T | L | T | I | S | S | V | Q | A | E | D | V | A | V | Y | Y | C | 55 | |
| HT2-dp27 #146 | G | V | P | D | R | F | S | G | S | G | S | G | T | D | F | T | L | T | I | S | S | V | Q | A | E | D | V | A | V | Y | Y | C | 55 | |
| HT2-dp27 #15 | G | V | P | D | R | F | S | G | S | G | S | G | T | D | F | T | L | T | I | D | P | L | E | A | E | D | V | A | V | Y | Y | C | 42 | |
| HT2-dp27 #26 | G | V | P | D | R | F | S | G | S | G | S | R | T | D | F | T | L | T | I | D | P | V | E | A | E | D | V | A | V | Y | Y | C | 156 | |
| HT2-dp27 #83 | G | V | P | D | R | F | S | G | S | G | S | R | T | D | F | T | L | T | I | D | P | L | E | A | E | D | V | A | V | Y | Y | C | 53 | |
| HT2-dp27 #164 | G | V | P | D | R | F | S | G | S | G | S | R | T | D | F | T | L | T | I | S | P | L | E | A | E | D | V | A | V | Y | Y | C | 157 | |
| HT2-dp27 #177 | G | V | P | D | R | F | S | G | S | G | S | R | T | D | F | T | L | T | I | S | S | V | Q | A | E | D | V | A | V | Y | Y | C | 37 | |
| HT2-dp27 #195 | G | V | P | D | R | F | S | G | S | G | S | G | T | D | F | T | L | T | I | S | S | L | E | A | E | D | V | A | V | Y | Y | C | 54 | |
| HT2-dp27 #198 | G | V | P | D | R | F | S | G | S | G | S | G | T | D | F | T | L | T | I | D | S | V | Q | A | E | D | V | A | V | Y | Y | C | 47 | |
| HT2-dp27 #150 | G | V | P | D | R | F | S | G | S | G | S | G | T | D | F | T | L | T | I | D | P | V | E | A | E | D | V | A | V | Y | Y | C | 49 | |
| HT2-dp27 #268 | G | V | P | D | R | F | S | G | S | G | S | G | T | D | F | T | L | T | I | D | S | L | Q | A | E | D | V | A | V | Y | Y | C | 33 | |
| HT2-dp27 #270 | G | V | P | D | R | F | S | G | S | G | S | G | T | D | F | T | L | T | I | D | S | L | Q | A | E | D | V | A | V | Y | Y | C | 33 | |
| HT2-dp27 #199 | G | V | P | D | R | F | S | G | S | G | S | G | T | D | F | T | L | T | I | D | S | V | Q | A | E | D | V | A | V | Y | Y | C | 47 | |
| HT2-dp27 #273 | G | V | P | D | R | F | S | G | S | G | S | G | T | D | F | T | L | T | I | S | S | V | Q | A | E | D | V | A | V | Y | Y | C | 55 | |
| HT2-dp27 #282 | G | V | P | D | R | F | S | G | S | G | S | R | T | D | F | T | L | T | I | S | P | V | E | A | E | D | V | A | V | Y | Y | C | 40 | |
| HT2-dp27 #304 | G | V | P | D | R | F | S | G | S | G | S | R | T | D | F | T | L | T | I | D | S | V | E | A | E | D | V | A | V | Y | Y | C | 158 | |
| HT2-dp27 #155B | G | V | P | D | R | F | S | G | S | G | S | G | T | D | F | T | L | T | I | S | S | V | Q | A | E | D | V | A | V | Y | Y | C | 35 | |
| HT2-dp27 #274 | G | V | P | D | R | F | S | G | S | G | S | R | T | D | F | T | L | T | I | D | P | V | Q | A | E | D | V | A | V | Y | Y | C | 159 | |
| HT2-dp27 #275 | G | V | P | D | R | F | S | G | S | G | S | R | T | D | F | T | L | T | I | S | P | L | Q | A | E | D | V | A | V | Y | Y | C | 51 | |
| HT2-dp27 #276 | G | V | P | D | R | F | S | G | S | G | S | G | T | D | F | T | L | T | I | D | S | V | Q | A | E | D | V | A | V | Y | Y | C | 47 | |
| HT2-dp27 #299 | G | V | P | D | R | F | S | G | S | G | S | G | T | D | F | T | L | T | I | S | P | V | Q | A | E | D | V | A | V | Y | Y | C | 43 | |
| HT2-dp27 #301 | G | V | P | D | R | F | S | G | S | G | S | G | T | D | F | T | L | T | I | S | P | L | Q | A | E | D | V | A | V | Y | Y | C | 56 | |
| HT2-dp27 #308 | G | V | P | D | R | F | S | G | S | G | S | R | T | D | F | T | L | T | I | D | P | V | E | A | E | D | V | A | V | Y | Y | C | 156 | |
| HT2-dp27 #467 | G | V | P | D | R | F | S | G | S | G | S | G | T | D | F | T | L | T | I | S | P | V | Q | A | E | D | V | A | V | Y | Y | C | 43 | |
| HT2-dp27 #530 | G | V | P | D | R | F | S | G | S | G | S | G | T | D | F | T | L | T | I | S | S | L | Q | A | E | D | V | A | V | Y | Y | C | 160 | |
| HT2-dp27 #580 | G | V | P | D | R | F | S | G | S | G | S | G | T | D | F | T | L | T | I | D | P | L | E | A | E | D | V | A | V | Y | Y | C | 53 | |
| HT2-dp27 #345 | G | V | P | D | R | F | S | G | S | G | S | G | T | D | F | T | L | T | I | S | S | L | E | A | E | D | V | A | V | Y | Y | C | 52 | |
| HT2-dp27 #374 | G | V | P | D | R | F | S | G | S | G | S | G | T | D | F | T | L | T | I | D | S | L | Q | A | E | D | V | A | V | Y | Y | C | 161 | |
| HT2-dp27 #443 | G | V | P | D | R | F | S | G | S | G | S | R | T | D | F | T | L | T | I | S | S | L | E | A | E | D | V | A | V | Y | Y | C | 52 | |
| HT2-dp27 #459 | G | V | P | D | R | F | S | G | S | G | S | G | T | D | F | T | L | T | I | D | S | L | Q | A | E | D | V | A | V | Y | Y | C | 161 | |
| HT2-dp27 #470 | G | V | P | D | R | F | S | G | S | G | S | G | T | D | F | T | L | T | I | S | S | V | Q | A | E | D | V | A | V | Y | Y | C | 55 | |
| HT2-dp27 #471 | G | V | P | D | R | F | S | G | S | G | S | G | T | D | F | T | L | T | I | D | S | V | E | A | E | D | V | A | V | Y | Y | C | 44 | |
| HT2-dp27 #486 | G | V | P | D | R | F | S | G | S | G | S | R | T | D | F | T | L | T | I | S | S | L | E | A | E | D | V | A | V | Y | Y | C | 52 | |
| HT2-dp27 #610 | G | V | P | D | R | F | S | G | S | G | S | G | T | D | F | T | L | T | I | D | S | L | E | A | E | D | V | A | V | Y | Y | C | 162 | |
| HT2-dp27 #624 | G | V | P | D | R | F | S | G | S | G | S | R | T | D | F | T | L | T | I | D | S | L | Q | A | E | D | V | A | V | Y | Y | C | 161 | |
| HT2-dp27 #634 | G | V | P | D | R | F | S | G | S | G | S | R | T | D | F | T | L | T | I | S | S | L | E | A | E | D | V | A | V | Y | Y | C | 52 | |

FIGURE 11 D -2

VK CHAIN FR4

| | 103 | 104 | 105 | 106 | 107 | 108 | 109 | 110 | 111 | 112 | 113 | 114 | SEQ ID NO |
|---|---|---|---|---|---|---|---|---|---|---|---|---|---|
| HT2-dp27 #7 | F | G | G | G | T | K | V | E | I | K | R | | 58 |
| HT2-dp27 #13 | F | G | G | G | T | K | V | E | I | K | R | | 58 |
| HT2-dp27 #19 | F | G | G | G | T | K | V | E | I | K | R | | 58 |
| HT2-dp27 #29 | F | G | G | G | T | K | L | E | I | K | R | | 59 |
| HT2-dp27 #34 | F | G | G | G | T | K | V | E | I | K | R | | 58 |
| HT2-dp27 #40 | F | G | G | G | T | K | V | E | I | K | R | | 58 |
| HT2-dp27 #43 | F | G | G | G | T | K | V | E | I | K | R | | 59 |
| HT2-dp27 #50 | F | G | G | G | T | K | L | E | I | K | R | | 58 |
| HT2-dp27 #53 | F | G | G | G | T | K | L | E | I | K | R | | 59 |
| HT2-dp27 #57 | F | G | G | G | T | K | V | E | I | K | R | | 58 |
| HT2-dp27 #66 | F | G | G | G | T | K | V | E | I | K | R | | 58 |
| HT2-dp27 #67 | F | G | G | G | T | K | V | E | I | K | R | | 58 |
| HT2-dp27 #73 | F | G | G | G | T | K | V | E | I | K | R | | 58 |
| HT2-dp27 #74 | F | G | G | G | T | K | V | E | I | K | R | | 58 |
| HT2-dp27 #89 | F | G | G | G | T | K | L | E | I | K | R | | 59 |
| HT2-dp27 #92 | F | G | G | G | T | K | V | E | I | K | R | | 58 |
| HT2-dp27 #100 | F | G | G | G | T | K | V | E | I | K | R | | 58 |
| HT2-dp27 #111 | F | G | G | G | T | K | V | E | I | K | R | | 58 |
| HT2-dp27 #112 | F | G | G | G | T | K | V | E | I | K | R | | 58 |
| HT2-dp27 #118 | F | G | G | G | T | K | L | E | I | K | R | | 59 |
| HT2-dp27 #123 | F | G | G | G | T | K | L | E | I | K | R | | 59 |
| HT2-dp27-#136 | F | G | G | G | T | K | V | E | I | K | R | | 58 |
| HT2-dp27 #144 | F | G | G | G | T | K | V | E | I | K | R | | 58 |
| HT2-dp27 #146 | F | G | G | G | T | K | V | E | I | K | R | | 58 |
| HT2-dp27 #15 | F | G | G | G | T | K | V | E | I | K | R | | 58 |
| HT2-dp27 #26 | F | G | G | G | T | K | L | E | I | K | R | | 59 |
| HT2-dp27 #83 | F | G | G | G | T | K | V | E | I | K | R | | 58 |
| HT2-dp27 #164 | F | G | G | G | T | K | V | E | I | K | R | | 58 |
| HT2-dp27 #177 | F | G | G | G | T | K | V | E | I | K | R | | 58 |
| HT2-dp27 #195 | F | G | G | G | T | K | V | E | I | K | R | | 58 |
| HT2-dp27 #198 | F | G | G | G | T | K | L | E | I | K | R | | 59 |
| HT2-dp27 #150 | F | G | G | G | T | K | V | E | I | K | R | | 58 |
| HT2-dp27 #268 | F | G | G | G | T | K | L | E | I | K | R | | 59 |
| HT2-dp27 #270 | F | G | G | G | T | K | V | E | I | K | R | | 58 |
| HT2-dp27 #199 | F | G | G | G | T | K | L | E | I | K | R | | 59 |
| HT2-dp27 #273 | F | G | G | G | T | K | L | E | I | K | R | | 59 |
| HT2-dp27 #282 | F | G | G | G | T | K | L | E | I | K | R | | 59 |
| HT2-dp27 #304 | F | G | G | G | T | K | L | E | I | K | R | | 59 |
| HT2-dp27 #155B | F | G | G | G | T | K | L | E | I | K | R | | 59 |
| HT2-dp27 #274 | F | G | G | G | T | K | V | E | I | K | R | | 58 |
| HT2-dp27 #275 | F | G | G | G | T | K | L | E | I | K | R | | 59 |
| HT2-dp27 #276 | F | G | G | G | T | K | L | E | I | K | R | | 59 |
| HT2-dp27 #299 | F | G | G | G | T | K | V | E | I | K | R | | 58 |
| HT2-dp27 #301 | F | G | G | G | T | K | V | E | I | K | R | | 58 |
| HT2-dp27 #308 | F | G | G | G | T | K | L | E | I | K | R | | 59 |
| HT2-dp27 #467 | F | G | G | G | T | K | L | E | I | K | R | | 59 |
| HT2-dp27 #530 | F | G | G | G | T | K | V | E | I | K | R | | 59 |
| HT2-dp27 #580 | F | G | G | G | T | K | V | E | I | K | R | | 58 |
| HT2-dp27 #345 | F | G | G | G | T | K | V | E | I | K | R | | 58 |
| HT2-dp27 #374 | F | G | G | G | T | K | V | E | I | K | R | | 58 |
| HT2-dp27 #443 | F | G | G | G | T | K | V | E | I | K | R | | 58 |
| HT2-dp27 #459 | F | G | G | G | T | K | V | E | I | K | R | | 58 |
| HT2-dp27 #470 | F | G | G | G | T | K | V | E | I | K | R | | 58 |
| HT2-dp27 #471 | F | G | G | G | T | K | L | E | I | K | R | | 59 |
| HT2-dp27 #486 | F | G | G | G | T | K | L | E | I | K | R | | 59 |
| HT2-dp27 #610 | F | G | G | G | T | K | V | E | I | K | R | | 58 |
| HT2-dp27 #624 | F | G | G | G | T | K | V | E | I | K | R | | 58 |
| HT2-dp27 #634 | F | G | G | G | T | K | V | E | I | K | R | | 58 |

FIGURE 12A - 1

VH CHAIN

| | FR1 | | | | | | | | | | | | | | | | | | | | | | | | | | | | | | SEQ ID NO | CDR1 |
|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | | |
| Murine 288B/C | Q | V | Q | L | Q | E | S | G | P | G | L | V | A | P | S | Q | S | L | S | I | T | C | T | V | S | G | F | S | L | N | 60 | |
| DP27 | Q | V | T | L | R | E | S | G | P | A | L | V | K | P | T | Q | T | L | T | L | T | C | T | F | S | G | F | S | L | S | 61 | |
| NEW | Q | V | Q | L | Q | E | S | G | P | G | L | V | R | P | S | Q | T | L | S | L | T | C | T | V | S | G | S | T | F | S | 62 | |
| Clone 1 | Q | V | T | L | R | E | S | G | P | A | L | V | K | P | T | Q | T | L | T | L | T | C | T | V | S | G | F | S | L | N | 64 | |
| Clone 2 | Q | V | T | L | R | E | S | G | P | A | L | V | K | P | T | Q | T | L | T | L | T | C | T | V | S | G | F | S | L | N | 64 | |
| Clone 3 | Q | V | T | L | R | E | S | G | P | A | L | V | K | P | T | Q | T | L | T | L | T | C | T | V | S | G | F | S | L | S | 65 | |
| Clone 4 | Q | V | T | L | R | E | S | G | P | A | L | V | K | P | T | Q | T | L | T | L | T | C | T | V | S | G | F | S | L | N | 64 | |
| Clone 5 | Q | V | T | L | R | E | S | G | P | A | L | V | K | P | T | Q | T | L | T | L | T | C | T | V | S | G | F | S | L | N | 64 | |
| HT2-NEW #1 | Q | V | Q | L | Q | E | S | G | P | G | L | V | R | P | S | Q | T | L | S | L | T | C | T | V | S | G | S | T | F | S | 62 | |
| HT2-NEW #9 | Q | V | Q | L | Q | E | S | G | P | G | L | V | R | P | S | Q | T | L | S | L | T | C | T | V | S | G | S | T | F | S | 62 | |
| HT2-NEW #14 | Q | V | Q | L | Q | E | S | G | P | G | L | V | R | P | S | Q | T | L | S | L | T | C | T | V | S | G | S | T | F | S | 62 | |
| HT2-NEW #17 | Q | V | Q | L | Q | E | S | G | P | G | L | V | R | P | S | Q | T | L | S | L | T | C | T | V | S | G | S | T | F | S | 62 | |
| HT2-NEW #21 | Q | V | Q | L | Q | E | S | G | P | G | L | V | R | P | S | Q | T | L | S | L | T | C | T | V | S | G | S | T | F | S | 62 | |
| HT2-NEW #36 | Q | V | Q | L | Q | E | S | G | P | G | L | V | R | P | S | Q | T | L | S | L | T | C | T | V | S | G | S | T | F | S | 62 | |
| HT2-NEW #65 | Q | V | Q | L | Q | E | S | G | P | G | L | V | R | P | S | Q | T | L | S | L | T | C | T | V | S | G | S | T | F | S | 62 | |
| HT2-NEW #67 | Q | V | Q | L | Q | E | S | G | P | G | L | V | R | P | S | Q | T | L | S | L | T | C | T | V | S | G | S | T | F | S | 62 | |
| HT2-NEW #70 | Q | V | Q | L | Q | E | S | G | P | G | L | V | R | P | S | Q | T | L | S | L | T | C | T | V | S | G | S | T | F | S | 62 | |
| HT2-NEW #73 | Q | V | Q | L | Q | E | S | G | P | G | L | V | R | P | S | Q | T | L | S | L | T | C | T | V | S | G | S | T | F | S | 63 | |
| HT2-NEW #74 | Q | V | Q | L | Q | E | S | G | P | G | L | V | R | P | S | Q | T | L | S | L | T | C | T | V | S | G | S | T | F | S | 62 | |
| HT2-NEW #78 | Q | V | Q | L | Q | E | S | G | P | G | L | V | R | P | S | Q | T | L | S | L | T | C | T | V | S | G | S | T | F | S | 62 | |
| HT2-NEW #79 | Q | V | Q | L | Q | E | S | G | P | G | L | V | R | P | S | Q | T | L | S | L | T | C | T | V | S | G | S | T | F | S | 62 | |
| HT2-NEW #80 | Q | V | Q | L | Q | E | S | G | P | G | L | V | R | P | S | Q | T | L | S | L | T | C | T | V | S | G | S | T | F | S | 62 | |
| HT2-NEW #87 | Q | V | Q | L | Q | E | S | G | P | G | L | V | R | P | S | Q | T | L | S | L | T | C | T | V | S | G | S | T | F | S | 62 | |
| HT2-NEW #275 | Q | V | Q | L | Q | E | S | G | P | G | L | V | R | P | S | Q | T | L | S | L | T | C | T | V | S | G | S | T | F | S | 62 | |
| HT2-NEW #284 | Q | V | Q | L | Q | E | S | G | P | G | L | V | R | P | S | Q | T | L | S | L | T | C | T | V | S | G | S | T | F | S | 62 | |
| HT2-NEW #291 | Q | V | Q | L | Q | E | S | G | P | G | L | V | R | P | S | Q | T | L | S | L | T | C | T | V | S | G | S | T | F | S | 62 | |
| HT2-NEW #300 | Q | V | Q | L | Q | E | S | G | P | G | L | V | R | P | S | Q | T | L | S | L | T | C | T | V | S | G | S | T | F | S | 62 | |
| HT2-NEW #302 | Q | V | Q | L | Q | E | S | G | P | G | L | V | R | P | S | Q | T | L | S | L | T | C | T | V | S | G | S | T | F | S | 62 | |
| HT2-NEW #322 | Q | V | Q | L | Q | E | S | G | P | G | L | V | R | P | S | Q | T | L | S | L | T | C | T | V | S | G | S | T | F | S | 62 | |
| HT2-NEW #111 | Q | V | Q | L | Q | E | S | G | P | G | L | V | R | P | S | Q | T | L | S | L | T | C | T | V | S | G | S | T | F | S | 62 | |
| HT2-NEW #115 | Q | V | Q | L | Q | E | S | G | P | G | L | V | R | P | S | Q | T | L | S | L | T | C | T | V | S | G | S | T | F | S | 62 | |
| HT2-NEW #116 | Q | V | Q | L | Q | E | S | G | P | G | L | V | R | P | S | Q | T | L | S | L | T | C | T | V | S | G | S | T | F | S | 62 | |
| HT2-NEW #117 | Q | V | Q | L | Q | E | S | G | P | G | L | V | R | P | S | Q | T | L | S | L | T | C | T | V | S | G | S | T | F | S | 62 | |
| HT2-NEW #143 | Q | V | Q | L | Q | E | S | G | P | G | L | V | R | P | S | Q | T | L | S | L | T | C | T | V | S | G | S | T | F | S | 62 | |
| HT2-NEW #162 | Q | V | Q | L | Q | E | S | G | P | G | L | V | R | P | S | Q | T | L | S | L | T | C | T | V | S | G | S | T | F | S | 62 | |
| HT2-NEW #139 | Q | V | Q | L | Q | E | S | G | P | G | L | V | R | P | S | Q | T | L | S | L | T | C | T | V | S | G | S | T | F | S | 62 | |
| HT2-NEW #177 | Q | V | Q | L | Q | E | S | G | P | G | L | V | R | P | S | Q | T | L | S | L | T | C | T | V | S | G | S | T | F | S | 62 | |
| HT2-NEW #313 | Q | V | Q | L | Q | E | S | G | P | G | L | V | R | P | S | Q | T | L | S | L | T | C | T | V | S | G | S | T | F | S | 62 | |

FIGURE 12A - 2

VH CHAIN

| | FR2 | | | | | | | | | | | | | | SEQ ID NO | CDR2 |
|---|---|---|---|---|---|---|---|---|---|---|---|---|---|---|---|---|
| | 36 | 37 | 38 | 39 | 40 | 41 | 42 | 43 | 44 | 45 | 46 | 47 | 48 | 49 | | |
| Murine 288B/C | W | V | R | Q | P | P | G | K | G | L | E | W | L | G | 67 | |
| DP27 | W | I | R | Q | P | P | G | K | A | L | E | W | L | A | 68 | |
| NEW | W | V | R | Q | P | P | G | R | G | L | E | W | I | G | 69 | |
| | | | | | | | | | | | | | | | | |
| Clone 1 | W | V | R | Q | P | P | G | K | A | L | E | W | L | G | 70 | |
| Clone 2 | W | I | R | Q | P | P | G | K | A | L | E | W | L | A | 68 | |
| Clone 3 | W | I | R | Q | P | P | G | K | G | L | E | W | L | G | 71 | |
| Clone 4 | W | V | R | Q | P | P | G | K | A | L | E | W | L | G | 70 | |
| Clone 5 | W | V | R | Q | P | P | G | K | A | L | E | W | L | G | 70 | |
| | | | | | | | | | | | | | | | | |
| HT2-NEW #1 | W | V | R | Q | P | P | G | K | G | L | E | W | L | G | 67 | |
| HT2-NEW #9 | W | V | R | Q | P | P | G | K | G | L | E | W | L | G | 67 | |
| HT2-NEW #14 | W | V | R | Q | P | P | G | K | G | L | E | W | I | G | 163 | |
| HT2-NEW #17 | W | V | R | Q | P | P | G | K | G | L | E | W | L | G | 67 | |
| HT2-NEW #21 | W | V | R | Q | P | P | G | K | G | L | E | W | L | G | 67 | |
| HT2-NEW #36 | W | V | R | Q | P | P | G | K | G | L | E | W | L | G | 67 | |
| HT2-NEW #65 | W | V | R | Q | P | P | G | R | G | L | E | W | I | G | 69 | |
| HT2-NEW #67 | W | V | R | Q | P | P | G | R | G | L | E | W | L | G | 164 | |
| HT2-NEW #70 | W | V | R | Q | P | P | G | K | G | L | E | W | L | G | 67 | |
| HT2-NEW #73 | W | V | R | Q | P | P | G | R | G | L | E | W | I | G | 69 | |
| HT2-NEW #74 | W | V | R | Q | P | P | G | R | G | L | E | W | I | G | 69 | |
| HT2-NEW #78 | W | V | R | Q | P | P | G | K | G | L | E | W | I | G | 163 | |
| HT2-NEW #79 | W | V | R | Q | P | P | G | R | G | L | E | W | I | G | 69 | |
| HT2-NEW #80 | W | V | R | Q | P | P | G | K | G | L | E | W | L | G | 67 | |
| HT2-NEW #87 | W | V | R | Q | P | P | G | K | G | L | E | W | L | G | 67 | |
| HT2-NEW #275 | W | V | R | Q | P | P | G | K | G | L | E | W | L | G | 67 | |
| HT2-NEW #284 | W | V | R | Q | P | P | G | K | G | L | E | W | L | G | 67 | |
| HT2-NEW #291 | W | V | R | Q | P | P | G | K | G | L | E | W | L | G | 67 | |
| HT2-NEW #300 | W | V | R | Q | P | P | G | R | G | L | E | W | L | G | 164 | |
| HT2-NEW #302 | W | V | R | Q | P | P | G | R | G | L | E | W | L | G | 164 | |
| HT2-NEW #322 | W | V | R | Q | P | P | G | R | G | L | E | W | L | G | 164 | |
| HT2-NEW #111 | W | V | R | Q | P | P | G | R | G | L | E | W | I | G | 69 | |
| HT2-NEW #115 | W | V | R | Q | P | P | G | K | G | L | E | W | L | G | 67 | |
| HT2-NEW #116 | W | V | R | Q | P | P | G | K | G | L | E | W | L | G | 67 | |
| HT2-NEW #117 | W | V | R | Q | P | P | G | K | G | L | E | W | L | G | 67 | |
| HT2-NEW #143 | W | V | R | Q | P | P | G | K | G | L | E | W | I | G | 163 | |
| HT2-NEW #162 | W | V | R | Q | P | P | G | R | G | L | E | W | I | G | 69 | |
| HT2-NEW #139 | W | V | R | Q | P | P | G | K | G | L | E | W | L | G | 67 | |
| HT2-NEW #177 | W | V | R | Q | P | P | G | K | G | L | E | W | I | G | 163 | |
| HT2-NEW #313 | W | V | R | Q | P | P | G | K | G | L | E | W | I | G | 163 | |

FIGURE 12 B - 1

VH CHAIN

FR3

| | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 | SEQ ID NO | CDR3 |
|---|---|---|---|---|---|---|---|---|---|---|---|---|---|---|---|---|---|---|---|---|---|---|---|---|---|---|---|---|---|---|---|---|---|---|
| Murine 288B/C | R | L | N | I | S | K | D | S | S | K | S | Q | V | F | L | K | M | S | S | L | Q | S | D | D | T | A | R | Y | Y | C | A | G | 76 | |
| DP27 | R | L | T | I | S | K | D | T | S | K | N | Q | V | V | L | T | M | T | N | M | D | P | V | D | T | A | T | Y | Y | C | A | R | 77 | |
| NEW | R | V | T | M | L | K | D | T | S | K | N | Q | F | S | L | R | L | S | S | V | T | A | A | D | T | A | V | Y | Y | C | A | R | 78 | |
| Clone 1 | R | L | T | I | S | K | D | S | S | K | N | Q | V | V | L | T | M | T | N | M | D | P | V | D | T | A | T | Y | Y | C | A | G | 79 | |
| Clone 2 | R | L | T | I | S | K | D | S | S | K | N | Q | V | V | L | T | M | T | N | M | D | P | V | D | T | A | T | Y | Y | C | A | G | 79 | |
| Clone 3 | R | L | T | I | S | K | D | T | S | K | N | Q | V | V | L | T | M | T | N | M | D | P | V | D | T | A | T | Y | Y | C | A | G | 80 | |
| Clone 4 | R | L | T | I | S | K | D | T | S | K | N | Q | V | V | L | T | M | T | N | M | D | P | V | D | T | A | R | Y | Y | C | A | G | 81 | |
| Clone 5 | R | L | T | I | S | K | D | T | S | K | N | Q | V | V | L | T | M | T | N | M | D | P | V | D | T | A | R | Y | Y | C | A | G | 81 | |
| HT2-NEW #1 | R | L | N | M | S | K | D | T | S | K | N | Q | F | F | L | R | L | S | S | V | T | A | A | D | T | A | V | Y | Y | C | A | G | 82 | |
| HT2-NEW #9 | R | L | N | M | S | K | D | T | S | K | N | Q | F | F | L | R | L | S | S | V | T | A | A | D | T | A | R | Y | Y | C | A | G | 83 | |
| HT2-NEW #14 | R | V | N | M | S | K | D | T | S | K | N | Q | F | S | L | R | L | S | S | V | T | A | A | D | T | A | V | Y | Y | C | A | R | 84 | |
| HT2-NEW #17 | R | L | N | M | S | K | D | T | S | K | N | Q | F | S | L | R | L | S | S | V | T | A | A | D | T | A | V | Y | Y | C | A | G | 165 | |
| HT2-NEW #21 | R | L | N | M | S | K | D | T | S | K | N | Q | F | F | L | R | L | S | S | V | T | A | A | D | T | A | R | Y | Y | C | A | G | 83 | |
| HT2-NEW #36 | R | L | N | M | S | K | D | T | S | K | N | Q | F | S | L | R | L | S | S | V | T | A | A | D | T | A | V | Y | Y | C | A | G | 165 | |
| HT2-NEW #65 | R | L | T | I | S | K | D | T | S | K | N | Q | F | S | L | R | L | S | S | V | T | A | A | D | T | A | R | Y | Y | C | A | G | 166 | |
| HT2-NEW #67 | R | V | N | M | S | K | D | T | S | K | N | Q | F | S | L | R | L | S | S | V | T | A | A | D | T | A | R | Y | Y | C | A | G | 167 | |
| HT2-NEW #70 | R | L | N | M | S | K | D | T | S | K | N | Q | F | F | L | R | L | S | S | V | T | A | A | D | T | A | R | Y | Y | C | A | G | 83 | |
| HT2-NEW #73 | R | V | T | M | L | K | D | T | S | K | N | Q | F | S | L | R | L | S | S | V | T | A | A | D | T | A | V | Y | Y | C | A | G | 168 | |
| HT2-NEW #74 | R | V | T | I | L | K | D | T | S | K | N | Q | F | S | L | R | L | S | S | V | T | A | A | D | T | A | R | Y | Y | C | A | G | 169 | |
| HT2-NEW #78 | R | V | N | I | L | K | D | T | S | K | N | Q | F | S | L | R | L | S | S | V | T | A | A | D | T | A | V | Y | Y | C | A | G | 170 | |
| HT2-NEW #79 | R | V | T | I | L | K | D | T | S | K | N | Q | F | S | L | R | L | S | S | V | T | A | A | D | T | A | R | Y | Y | C | A | G | 169 | |
| HT2-NEW #80 | R | L | N | M | S | K | D | T | S | K | N | Q | F | F | L | R | L | S | S | V | T | A | A | D | T | A | R | Y | Y | C | A | G | 83 | |
| HT2-NEW #87 | R | L | N | M | S | K | D | T | S | K | N | Q | F | F | L | R | L | S | S | V | T | A | A | D | T | A | R | Y | Y | C | A | G | 83 | |
| HT2-NEW #275 | R | V | N | I | L | K | D | T | S | K | N | Q | F | F | L | R | L | S | S | V | T | A | A | D | T | A | R | Y | Y | C | A | G | 171 | |
| HT2-NEW #284 | R | L | I | I | S | K | D | T | S | K | N | Q | F | S | L | R | L | S | S | V | T | A | A | D | T | A | V | Y | Y | C | A | G | 172 | |
| HT2-NEW #291 | R | L | T | I | L | K | D | T | S | K | N | Q | F | F | L | R | L | S | S | V | T | A | A | D | T | A | V | Y | Y | C | A | G | 173 | |
| HT2-NEW #300 | R | V | T | I | S | K | D | T | S | K | N | Q | F | S | L | R | L | S | S | V | T | A | A | D | T | A | V | Y | Y | C | A | G | 174 | |
| HT2-NEW #302 | R | V | N | M | S | K | D | T | S | K | N | Q | F | S | L | R | L | S | S | V | T | A | A | D | T | A | V | Y | Y | C | A | G | 175 | |
| HT2-NEW #322 | R | V | N | I | S | K | D | T | S | K | N | Q | F | F | L | R | L | S | S | V | T | A | A | D | T | A | R | Y | Y | C | A | G | 176 | |
| HT2-NEW #111 | R | L | T | I | S | K | D | T | S | K | N | Q | F | F | L | R | L | S | S | V | T | A | A | D | T | A | R | Y | Y | C | A | G | 177 | |
| HT2-NEW #115 | R | L | N | M | S | K | D | T | S | K | N | Q | F | F | L | R | L | S | S | V | T | A | A | D | T | A | R | Y | Y | C | A | G | 83 | |
| HT2-NEW #116 | R | L | N | M | S | K | D | T | S | K | N | Q | F | F | L | R | L | S | S | V | T | A | A | D | T | A | R | Y | Y | C | A | G | 83 | |
| HT2-NEW #117 | R | L | N | M | S | K | D | T | S | K | N | Q | F | F | L | R | L | S | S | V | T | A | A | D | T | A | R | Y | Y | C | A | G | 83 | |
| HT2-NEW #143 | R | V | N | M | S | K | D | T | S | K | N | Q | F | S | L | R | L | S | S | V | T | A | A | D | T | A | R | Y | Y | C | A | G | 167 | |
| HT2-NEW #162 | R | L | T | M | S | K | D | T | S | K | N | Q | F | S | L | R | L | S | S | V | T | A | A | D | T | A | V | Y | Y | C | A | G | 178 | |
| HT2-NEW #139 | R | V | T | M | S | K | D | T | S | K | N | Q | F | F | L | R | L | S | S | V | T | A | A | D | T | A | R | Y | Y | C | A | G | 179 | |
| HT2-NEW #177 | R | V | T | M | S | K | D | T | S | K | N | Q | F | S | L | R | L | S | S | V | T | A | A | D | T | A | V | Y | Y | C | A | G | 180 | |
| HT2-NEW #313 | R | V | N | M | S | K | D | T | S | K | N | Q | F | S | L | R | L | S | S | V | T | A | A | D | T | A | R | Y | Y | C | A | G | 167 | |

FIGURE 12 B - 2

VH CHAIN

FR4

| | 103 | 104 | 105 | 106 | 107 | 108 | 109 | 110 | 111 | 112 | 113 | SEQ ID NO |
|---|---|---|---|---|---|---|---|---|---|---|---|---|
| Murine 288B/C | W | G | H | G | T | S | V | T | V | S | S | 91 |
| DP27 | W | G | Q | G | S | L | V | T | V | S | S | 92 |
| NEW | W | G | Q | G | S | L | V | T | V | S | S | 92 |
| Clone 1 | W | G | H | G | S | L | V | T | V | S | S | 181 |
| Clone 2 | W | G | H | G | S | L | V | T | V | S | S | 181 |
| Clone 3 | W | G | H | G | S | L | V | T | V | S | S | 181 |
| Clone 4 | W | G | Q | G | S | L | V | T | V | S | S | 92 |
| Clone 5 | W | G | Q | G | S | L | V | T | V | S | S | 92 |
| HT2-NEW #1 | W | G | Q | G | S | L | V | T | V | S | S | 92 |
| HT2-NEW #9 | W | G | Q | G | S | L | V | T | V | S | S | 92 |
| HT2-NEW #14 | W | G | Q | G | S | L | V | T | V | S | S | 92 |
| HT2-NEW #17 | W | G | Q | G | S | L | V | T | V | S | S | 92 |
| HT2-NEW #21 | W | G | Q | G | S | L | V | T | V | S | S | 92 |
| HT2-NEW #36 | W | G | Q | G | S | L | V | T | V | S | S | 92 |
| HT2-NEW #65 | W | G | Q | G | S | L | V | T | V | S | S | 92 |
| HT2-NEW #67 | W | G | Q | G | S | L | V | T | V | S | S | 92 |
| HT2-NEW #70 | W | G | Q | G | S | L | V | T | V | S | S | 92 |
| HT2-NEW #73 | W | G | Q | G | S | L | V | T | V | S | S | 92 |
| HT2-NEW #74 | W | G | Q | G | S | L | V | T | V | S | S | 92 |
| HT2-NEW #78 | W | G | Q | G | S | L | V | T | V | S | S | 92 |
| HT2-NEW #79 | W | G | Q | G | S | L | V | T | V | S | S | 92 |
| HT2-NEW #80 | W | G | Q | G | S | L | V | T | V | S | S | 92 |
| HT2-NEW #87 | W | G | Q | G | S | L | V | T | V | S | S | 92 |
| HT2-NEW #275 | W | G | Q | G | S | L | V | T | V | S | S | 92 |
| HT2-NEW #284 | W | G | Q | G | S | L | V | T | V | S | S | 92 |
| HT2-NEW #291 | W | G | Q | G | S | L | V | T | V | S | S | 92 |
| HT2-NEW #300 | W | G | Q | G | S | L | V | T | V | S | S | 92 |
| HT2-NEW #302 | W | G | Q | G | S | L | V | T | V | S | S | 92 |
| HT2-NEW #322 | W | G | Q | G | S | L | V | T | V | S | S | 92 |
| HT2-NEW #111 | W | G | Q | G | S | L | V | T | V | S | S | 92 |
| HT2-NEW #115 | W | G | Q | G | S | L | V | T | V | S | S | 92 |
| HT2-NEW #116 | W | G | Q | G | S | L | V | T | V | S | S | 92 |
| HT2-NEW #117 | W | G | Q | G | S | L | V | T | V | S | S | 92 |
| HT2-NEW #143 | W | G | Q | G | S | L | V | T | V | S | S | 92 |
| HT2-NEW #162 | W | G | Q | G | S | L | V | T | V | S | S | 92 |
| HT2-NEW #139 | W | G | Q | G | S | L | V | T | V | S | S | 92 |
| HT2-NEW #177 | W | G | Q | G | S | L | V | T | V | S | S | 92 |
| HT2-NEW #313 | W | G | Q | G | S | L | V | T | V | S | S | 92 |

FIGURE 12C - 1

VH CHAIN

| | FR1 | | | | | | | | | | | | | | | | | | | | | | | | | | | | | | SEQ ID NO | CDR1 |
|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | | |
| HT2-dp27 #7 | Q | V | T | L | R | E | S | G | P | A | L | V | K | P | T | Q | T | L | T | L | T | C | T | V | S | G | F | S | L | N | 64 | |
| HT2-dp27 #13 | Q | V | T | L | R | E | S | G | P | A | L | V | K | P | T | Q | T | L | T | L | T | C | T | V | S | G | F | S | L | N | 64 | |
| HT2-dp27 #19 | Q | V | T | L | R | E | S | G | P | A | L | V | K | P | T | Q | T | L | T | L | T | C | T | V | S | G | F | S | L | N | 64 | |
| HT2-dp27 #29 | Q | V | T | L | R | E | S | G | P | A | L | V | K | P | T | Q | T | L | T | L | T | C | T | V | S | G | F | S | L | N | 64 | |
| HT2-dp27 #34 | Q | V | T | L | R | E | S | G | P | A | L | V | K | P | T | Q | T | L | T | L | T | C | T | V | S | G | F | S | L | N | 64 | |
| HT2-dp27 #40 | Q | V | T | L | R | E | S | G | P | A | L | V | K | P | T | Q | T | L | T | L | T | C | T | V | S | G | F | S | L | S | 65 | |
| HT2-dp27 #43 | Q | V | T | L | R | E | S | G | P | A | L | V | K | P | T | Q | T | L | T | L | T | C | T | V | S | G | F | S | L | S | 65 | |
| HT2-dp27 #50 | Q | V | T | L | R | E | S | G | P | A | L | V | K | P | T | Q | T | L | T | L | T | C | T | V | S | G | F | S | L | N | 64 | |
| HT2-dp27 #53 | Q | V | T | L | R | E | S | G | P | A | L | V | K | P | T | Q | T | L | T | L | T | C | T | V | S | G | F | S | L | S | 65 | |
| HT2-dp27 #57 | Q | V | T | L | R | E | S | G | P | A | L | V | K | P | T | Q | T | L | T | L | T | C | T | V | S | G | F | S | L | N | 64 | |
| HT2-dp27 #66 | Q | V | T | L | R | E | S | G | P | A | L | V | K | P | T | Q | T | L | T | L | T | C | T | V | S | G | F | S | L | N | 64 | |
| HT2-dp27 #67 | Q | V | T | L | R | E | S | G | P | A | L | V | K | P | T | Q | T | L | T | L | T | C | T | V | S | G | F | S | L | N | 64 | |
| HT2-dp27 #73 | Q | V | T | L | R | E | S | G | P | A | L | V | K | P | T | Q | T | L | T | L | T | C | T | V | S | G | F | S | L | S | 65 | |
| HT2-dp27 #74 | Q | V | T | L | R | E | S | G | P | A | L | V | K | P | T | Q | T | L | T | L | T | C | T | V | S | G | F | S | L | N | 64 | |
| HT2-dp27 #89 | Q | V | T | L | R | E | S | G | P | A | L | V | K | P | T | Q | T | L | T | L | T | C | T | V | S | G | F | S | L | N | 64 | |
| HT2-dp27 #92 | Q | V | T | L | R | E | S | G | P | A | L | V | K | P | T | Q | T | L | T | L | T | C | T | V | S | G | F | S | L | S | 65 | |
| HT2-dp27 #100 | Q | V | T | L | R | E | S | G | P | A | L | V | K | P | T | Q | T | L | T | L | T | C | T | V | S | G | F | S | L | N | 64 | |
| HT2-dp27 #111 | Q | V | T | L | R | E | S | G | P | A | L | V | K | P | T | Q | T | L | T | L | T | C | T | V | S | G | F | S | L | N | 64 | |
| HT2-dp27 #112 | Q | V | T | L | R | E | S | G | P | A | L | V | K | P | T | Q | T | L | T | L | T | C | T | V | S | G | F | S | L | N | 64 | |
| HT2-dp27 #118 | Q | V | T | L | R | E | S | G | P | A | L | V | K | P | T | Q | T | L | T | L | T | C | T | V | S | G | F | S | L | N | 64 | |
| HT2-dp27 #123 | Q | V | T | L | R | E | S | G | P | A | L | V | K | P | T | Q | T | L | T | L | T | C | T | V | S | G | F | S | L | N | 64 | |
| HT2-dp27-#136 | Q | V | T | L | R | E | S | G | P | A | L | V | K | P | T | Q | T | L | T | L | T | C | T | V | S | G | F | S | L | N | 64 | |
| HT2-dp27 #144 | Q | V | T | L | R | E | S | G | P | A | L | V | K | P | T | Q | T | L | T | L | T | C | T | V | S | G | F | S | L | S | 65 | |
| HT2-dp27 #146 | Q | V | T | L | R | E | S | G | P | A | L | V | K | P | T | Q | T | L | T | L | T | C | T | V | S | G | F | S | L | S | 65 | |
| HT2-dp27 #15 | Q | V | T | L | R | E | S | G | P | A | L | V | K | P | T | Q | T | L | T | L | T | C | T | V | S | G | F | S | L | S | 65 | |
| HT2-dp27 #26 | Q | V | T | L | R | E | S | G | P | A | L | V | K | P | T | Q | T | L | T | L | T | C | T | V | S | G | F | S | L | S | 65 | |
| HT2-dp27 #83 | Q | V | T | L | R | E | S | G | P | A | L | V | K | P | T | Q | T | L | T | L | T | C | T | V | S | G | F | S | L | N | 64 | |
| HT2-dp27 #164 | Q | V | T | L | R | E | S | G | P | A | L | V | K | P | T | Q | T | L | T | L | T | C | T | V | S | G | F | S | L | S | 65 | |
| HT2-dp27 #177 | Q | V | T | L | R | E | S | G | P | A | L | V | K | P | T | Q | T | L | T | L | T | C | T | V | S | G | F | S | L | N | 64 | |
| HT2-dp27 #195 | Q | V | T | L | R | E | S | G | P | A | L | V | K | P | T | Q | T | L | T | L | T | C | T | V | S | G | F | S | L | N | 64 | |
| HT2-dp27 #198 | Q | V | T | L | R | E | S | G | P | A | L | V | K | P | T | Q | T | L | T | L | T | C | T | V | S | G | F | S | L | S | 65 | |
| HT2-dp27 #150 | Q | V | T | L | R | E | S | G | P | A | L | V | K | P | T | Q | T | L | T | L | T | C | T | V | S | G | F | S | L | N | 64 | |
| HT2-dp27 #268 | Q | V | T | L | R | E | S | G | P | A | L | V | K | P | T | Q | T | L | T | L | T | C | T | F | S | G | F | S | L | N | 66 | |
| HT2-dp27 #270 | Q | V | T | L | R | E | S | G | P | A | L | V | K | P | T | Q | T | L | T | L | T | C | T | V | S | G | F | S | L | N | 64 | |
| HT2-dp27 #199 | Q | V | T | L | R | E | S | G | P | A | L | V | K | P | T | Q | T | L | T | L | T | C | T | V | S | G | F | S | L | S | 65 | |
| HT2-dp27 #273 | Q | V | T | L | R | E | S | G | P | A | L | V | K | P | T | Q | T | L | T | L | T | C | T | V | S | G | F | S | L | N | 64 | |
| HT2-dp27 #282 | Q | V | T | L | R | E | S | G | P | A | L | V | K | P | T | Q | T | L | T | L | T | C | T | V | S | G | F | S | L | N | 64 | |
| HT2-dp27 #304 | Q | V | T | L | R | E | S | G | P | A | L | V | K | P | T | Q | T | L | T | L | T | C | T | V | S | G | F | S | L | N | 64 | |
| HT2-dp27 #155B | Q | V | T | L | R | E | S | G | P | A | L | V | K | P | T | Q | T | L | T | L | T | C | T | V | S | G | F | S | L | N | 64 | |
| HT2-dp27 #274 | Q | V | T | L | R | E | S | G | P | A | L | V | K | P | T | Q | T | L | T | L | T | C | T | V | S | G | F | S | L | S | 65 | |
| HT2-dp27 #275 | Q | V | T | L | R | E | S | G | P | A | L | V | K | P | T | Q | T | L | T | L | T | C | T | V | S | G | F | S | L | N | 64 | |
| HT2-dp27 #276 | Q | V | T | L | R | E | S | G | P | A | L | V | K | P | T | Q | T | L | T | L | T | C | T | V | S | G | F | S | L | S | 65 | |
| HT2-dp27 #299 | Q | V | T | L | R | E | S | G | P | A | L | V | K | P | T | Q | T | L | T | L | T | C | T | V | S | G | F | S | L | N | 64 | |
| HT2-dp27 #301 | Q | V | T | L | R | E | S | G | P | A | L | V | K | P | T | Q | T | L | T | L | T | C | T | V | S | G | F | S | L | N | 64 | |
| HT2-dp27 #308 | Q | V | T | L | R | E | S | G | P | A | L | V | K | P | T | Q | T | L | T | L | T | C | T | V | S | G | F | S | L | N | 64 | |

FIGURE 12C - 2

VH CHAIN

| | FR1 | | | | | | | | | | | | | | | | | | | | | | | | | | | | | | SEQ ID NO | CDR1 |
|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | | |
| HT2-dp27 #530 | Q | V | T | L | R | E | S | G | P | A | L | V | K | P | T | Q | T | L | T | L | T | C | T | V | S | G | F | S | L | S | 65 | |
| HT2-dp27 #580 | Q | V | T | L | R | E | S | G | P | A | L | V | K | P | T | Q | T | L | T | L | T | C | T | V | S | G | F | S | L | S | 65 | |
| HT2-dp27 #345 | Q | V | T | L | R | E | S | G | P | A | L | V | K | P | T | Q | T | L | T | L | T | C | T | V | S | G | F | S | L | N | 64 | |
| HT2-dp27 #374 | Q | V | T | L | R | E | S | G | P | A | L | V | K | P | T | Q | T | L | T | L | T | C | T | V | S | G | F | S | L | S | 65 | |
| HT2-dp27 #443 | Q | V | T | L | R | E | S | G | P | A | L | V | K | P | T | Q | T | L | T | L | T | C | T | V | S | G | F | S | L | S | 65 | |
| HT2-dp27 #459 | Q | V | T | L | R | E | S | G | P | A | L | V | K | P | T | Q | T | L | T | L | T | C | T | V | S | G | F | S | L | N | 64 | |
| HT2-dp27 #470 | Q | V | T | L | R | E | S | G | P | A | L | V | K | P | T | Q | T | L | T | L | T | C | T | V | S | G | F | S | L | S | 65 | |
| HT2-dp27 #471 | Q | V | T | L | R | E | S | G | P | A | L | V | K | P | T | Q | T | L | T | L | T | C | T | V | S | G | F | S | L | N | 64 | |
| HT2-dp27 #486 | Q | V | T | L | R | E | S | G | P | A | L | V | K | P | T | Q | T | L | T | L | T | C | T | V | S | G | F | S | L | N | 64 | |
| HT2-dp27 #610 | Q | V | T | L | R | E | S | G | P | A | L | V | K | P | T | Q | T | L | T | L | T | C | T | V | S | G | F | S | L | S | 65 | |
| HT2-dp27 #624 | Q | V | T | L | R | E | S | G | P | A | L | V | K | P | T | Q | T | L | T | L | T | C | T | V | S | G | F | S | L | N | 64 | |
| HT2-dp27 #634 | Q | V | T | L | R | E | S | G | P | A | L | V | K | P | T | Q | T | L | T | L | T | C | T | V | S | G | F | S | L | N | 64 | |

FIGURE 12C - 3

VH CHAIN

| | FR2 | | | | | | | | | | | | | | SEQ ID NO | CDR2 |
|---|---|---|---|---|---|---|---|---|---|---|---|---|---|---|---|---|
| | 36 | 37 | 38 | 39 | 40 | 41 | 42 | 43 | 44 | 45 | 46 | 47 | 48 | 49 | | |
| HT2-dp27 #7 | W | I | R | Q | P | P | G | K | A | L | E | W | L | G | 72 | |
| HT2-dp27 #13 | W | I | R | Q | P | P | G | K | A | L | E | W | L | G | 72 | |
| HT2-dp27 #19 | W | I | R | Q | P | P | G | K | G | L | E | W | L | G | 71 | |
| HT2-dp27 #29 | W | V | R | Q | P | P | G | K | G | L | E | W | L | G | 67 | |
| HT2-dp27 #34 | W | V | R | Q | P | P | G | K | G | L | E | W | L | G | 67 | |
| HT2-dp27 #40 | W | I | R | Q | P | P | G | K | G | L | E | W | L | G | 71 | |
| HT2-dp27 #43 | W | I | R | Q | P | P | G | K | G | L | E | W | L | A | 73 | |
| HT2-dp27 #50 | W | V | R | Q | P | P | G | K | G | L | E | W | L | A | 74 | |
| HT2-dp27 #53 | W | V | R | Q | P | P | G | K | G | L | E | W | L | G | 67 | |
| HT2-dp27 #57 | W | I | R | Q | P | P | G | K | A | L | E | W | L | G | 72 | |
| HT2-dp27 #66 | W | V | R | Q | P | P | G | K | G | L | E | W | L | G | 67 | |
| HT2-dp27 #67 | W | I | R | Q | P | P | G | K | A | L | E | W | L | G | 72 | |
| HT2-dp27 #73 | W | V | R | Q | P | P | G | K | G | L | E | W | L | G | 67 | |
| HT2-dp27 #74 | W | V | R | Q | P | P | G | K | G | L | E | W | L | G | 67 | |
| HT2-dp27 #89 | W | I | R | Q | P | P | G | K | A | L | E | W | L | G | 72 | |
| HT2-dp27 #92 | W | I | R | Q | P | P | G | K | G | L | E | W | L | A | 73 | |
| HT2-dp27 #100 | W | V | R | Q | P | P | G | K | A | L | E | W | L | A | 75 | |
| HT2-dp27 #111 | W | I | R | Q | P | P | G | K | G | L | E | W | L | A | 73 | |
| HT2-dp27 #112 | W | I | R | Q | P | P | G | K | G | L | E | W | L | A | 73 | |
| HT2-dp27 #118 | W | I | R | Q | P | P | G | K | G | L | E | W | L | G | 71 | |
| HT2-dp27 #123 | W | V | R | Q | P | P | G | K | A | L | E | W | L | A | 75 | |
| HT2-dp27-#136 | W | V | R | Q | P | P | G | K | G | L | E | W | L | A | 74 | |
| HT2-dp27 #144 | W | V | R | Q | P | P | G | K | G | L | E | W | L | A | 74 | |
| HT2-dp27 #146 | W | V | R | Q | P | P | G | K | G | L | E | W | L | G | 67 | |
| HT2-dp27 #15 | W | V | R | Q | P | P | G | K | A | L | E | W | L | G | 70 | |
| HT2-dp27 #26 | W | V | R | Q | P | P | G | K | G | L | E | W | L | A | 74 | |
| HT2-dp27 #83 | W | V | R | Q | P | P | G | K | G | L | E | W | L | G | 67 | |
| HT2-dp27 #164 | W | V | R | Q | P | P | G | K | G | L | E | W | L | G | 67 | |
| HT2-dp27 #177 | W | V | R | Q | P | P | G | K | G | L | E | W | L | G | 67 | |
| HT2-dp27 #195 | W | I | R | Q | P | P | G | K | A | L | E | W | L | G | 72 | |
| HT2-dp27 #198 | W | V | R | Q | P | P | G | K | G | L | E | W | L | G | 67 | |
| HT2-dp27 #150 | W | I | R | Q | P | P | G | K | G | L | E | W | L | G | 71 | |
| HT2-dp27 #268 | W | V | R | Q | P | P | G | K | G | L | E | W | L | G | 67 | |
| HT2-dp27 #270 | W | I | R | Q | P | P | G | K | G | L | E | W | L | G | 71 | |
| HT2-dp27 #199 | W | V | R | Q | P | P | G | K | G | L | E | W | L | G | 67 | |
| HT2-dp27 #273 | W | I | R | Q | P | P | G | K | A | L | E | W | L | G | 72 | |
| HT2-dp27 #282 | W | V | R | Q | P | P | G | K | A | L | E | W | L | A | 75 | |
| HT2-dp27 #304 | W | V | R | Q | P | P | G | K | G | L | E | W | L | A | 74 | |
| HT2-dp27 #155E | W | V | R | Q | P | P | G | K | G | L | E | W | L | G | 67 | |
| HT2-dp27 #274 | W | V | R | Q | P | P | G | K | G | L | E | W | L | G | 67 | |
| HT2-dp27 #275 | W | I | R | Q | P | P | G | K | G | L | E | W | L | G | 71 | |
| HT2-dp27 #276 | W | I | R | Q | P | P | G | K | A | L | E | W | L | A | 68 | |
| HT2-dp27 #299 | W | V | R | Q | P | P | G | K | G | L | E | W | L | A | 74 | |
| HT2-dp27 #301 | W | I | R | Q | P | P | G | K | G | L | E | W | L | G | 71 | |
| HT2-dp27 #308 | W | V | R | Q | P | P | G | K | G | L | E | W | L | G | 67 | |

FIGURE 12C - 4

VH CHAIN

FR2

| | 36 | 37 | 38 | 39 | 40 | 41 | 42 | 43 | 44 | 45 | 46 | 47 | 48 | 49 | SEQ ID NO | CDR2 |
|---|---|---|---|---|---|---|---|---|---|---|---|---|---|---|---|---|
| HT2-dp27 #530 | W | V | R | Q | P | P | G | K | A | L | E | W | L | G | 70 | |
| HT2-dp27 #580 | W | I | R | Q | P | P | G | K | G | L | E | W | L | G | 71 | |
| HT2-dp27 #345 | W | V | R | Q | P | P | G | K | G | L | E | W | L | G | 67 | |
| HT2-dp27 #374 | W | I | R | Q | P | P | G | K | G | L | E | W | L | G | 71 | |
| HT2-dp27 #443 | W | I | R | Q | P | P | G | K | G | L | E | W | L | G | 71 | |
| HT2-dp27 #459 | W | I | R | Q | P | P | G | K | A | L | E | W | L | G | 72 | |
| HT2-dp27 #470 | W | V | R | Q | P | P | G | K | A | L | E | W | L | A | 75 | |
| HT2-dp27 #471 | W | I | R | Q | P | P | G | K | G | L | E | W | L | G | 71 | |
| HT2-dp27 #486 | W | I | R | Q | P | P | G | K | A | L | E | W | L | G | 72 | |
| HT2-dp27 #610 | W | V | R | Q | P | P | G | K | G | L | E | W | L | A | 74 | |
| HT2-dp27 #624 | W | I | R | Q | P | P | G | K | G | L | E | W | L | A | 73 | |
| HT2-dp27 #634 | W | V | R | Q | P | P | G | K | G | L | E | W | L | G | 67 | |

FIGURE 12D - 1

VH CHAIN

FR3

| | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 | SEQ ID NO | CDR3 |
|---|---|---|---|---|---|---|---|---|---|---|---|---|---|---|---|---|---|---|---|---|---|---|---|---|---|---|---|---|---|---|---|---|---|---|
| HT2-dp27 #7 | R | L | N | I | S | K | D | S | S | K | N | Q | V | V | L | T | M | T | N | M | D | P | V | D | T | A | T | Y | Y | C | A | G | 88 | |
| HT2-dp27 #13 | R | L | N | I | S | K | D | S | S | K | N | Q | V | V | L | T | M | T | N | M | D | P | V | D | T | A | T | Y | Y | C | A | G | 88 | |
| HT2-dp27 #19 | R | L | N | I | S | K | D | S | S | K | N | Q | V | V | L | T | M | T | N | M | D | P | V | D | T | A | R | Y | Y | C | A | G | 182 | |
| HT2-dp27 #29 | R | L | N | I | S | K | D | S | S | K | N | Q | V | V | L | T | M | T | N | M | D | P | V | D | T | A | T | Y | Y | C | A | G | 88 | |
| HT2-dp27 #34 | R | L | N | I | S | K | D | S | S | K | N | Q | V | V | L | T | M | T | N | M | D | P | V | D | T | A | R | Y | Y | C | A | G | 182 | |
| HT2-dp27 #40 | R | L | N | I | S | K | D | T | S | K | N | Q | V | V | L | T | M | T | N | M | D | P | V | D | T | A | T | Y | Y | C | A | G | 87 | |
| HT2-dp27 #43 | R | L | N | I | S | K | D | T | S | K | N | Q | V | V | L | T | M | T | N | M | D | P | V | D | T | A | R | Y | Y | C | A | G | 183 | |
| HT2-dp27 #50 | R | L | N | I | S | K | D | T | S | K | N | Q | V | V | L | T | M | T | N | M | D | P | V | D | T | A | R | Y | Y | C | A | G | 183 | |
| HT2-dp27 #53 | R | L | T | I | S | K | D | T | S | K | N | Q | V | V | L | T | M | T | N | M | D | P | V | D | T | A | R | Y | Y | C | A | G | 81 | |
| HT2-dp27 #57 | R | L | N | I | S | K | D | S | S | K | N | Q | V | V | L | T | M | T | N | M | D | P | V | D | T | A | T | Y | Y | C | A | G | 88 | |
| HT2-dp27 #66 | R | L | N | I | S | K | D | T | S | K | N | Q | V | V | L | T | M | T | N | M | D | P | V | D | T | A | T | Y | Y | C | A | G | 87 | |
| HT2-dp27 #67 | R | L | N | I | S | K | D | S | S | K | N | Q | V | V | L | T | M | T | N | M | D | P | V | D | T | A | T | Y | Y | C | A | G | 88 | |
| HT2-dp27 #73 | R | L | N | I | S | K | D | T | S | K | N | Q | V | V | L | T | M | T | N | M | D | P | V | D | T | A | T | Y | Y | C | A | G | 87 | |
| HT2-dp27 #74 | R | L | N | I | S | K | D | S | S | K | N | Q | V | V | L | T | M | T | N | M | D | P | V | D | T | A | T | Y | Y | C | A | G | 88 | |
| HT2-dp27 #89 | R | L | N | I | S | K | D | T | S | K | N | Q | V | V | L | T | M | T | N | M | D | P | V | D | T | A | T | Y | Y | C | A | G | 87 | |
| HT2-dp27 #92 | R | L | N | I | S | K | D | T | S | K | N | Q | V | V | L | T | M | T | N | M | D | P | V | D | T | A | T | Y | Y | C | A | G | 87 | |
| HT2-dp27 #100 | R | L | T | I | S | K | D | S | S | K | N | Q | V | V | L | T | M | T | N | M | D | P | V | D | T | A | R | Y | Y | C | A | G | 90 | |
| HT2-dp27 #111 | R | L | N | I | S | K | D | T | S | K | N | Q | V | V | L | T | M | T | N | M | D | P | V | D | T | A | T | Y | Y | C | A | G | 87 | |
| HT2-dp27 #112 | R | L | N | I | S | K | D | T | S | K | N | Q | V | V | L | T | M | T | N | M | D | P | V | D | T | A | T | Y | Y | C | A | G | 87 | |
| HT2-dp27 #118 | R | L | T | I | S | K | D | I | S | K | N | Q | V | V | L | T | M | T | N | M | D | P | V | D | T | A | R | Y | Y | C | A | G | 184 | |
| HT2-dp27 #123 | R | L | T | I | S | K | D | T | S | K | N | Q | V | V | L | T | M | T | N | M | D | P | V | D | T | A | T | Y | Y | C | A | G | 80 | |
| HT2-dp27-#136 | R | L | T | I | S | K | D | T | S | K | N | Q | V | V | L | T | M | T | N | M | D | P | V | D | T | A | R | Y | Y | C | A | G | 81 | |
| HT2-dp27 #144 | R | L | N | I | S | K | D | T | S | K | N | Q | V | V | L | T | M | T | N | M | D | P | V | D | T | A | T | Y | Y | C | A | G | 87 | |
| HT2-dp27 #146 | R | L | N | I | S | K | D | S | S | K | N | Q | V | V | L | T | M | T | N | M | D | P | V | D | T | A | T | Y | Y | C | A | G | 88 | |
| HT2-dp27 #15 | R | L | N | I | S | K | D | T | S | K | N | Q | V | V | L | T | M | T | N | M | D | P | V | D | T | A | R | Y | Y | C | A | G | 183 | |
| HT2-dp27 #26 | R | L | N | I | S | K | D | T | S | K | N | Q | V | V | L | T | M | T | N | M | D | P | V | D | T | A | R | Y | Y | C | A | R | 85 | |
| HT2-dp27 #83 | R | L | N | I | S | K | D | S | S | K | N | Q | V | V | L | T | M | T | N | M | D | P | V | D | T | A | R | Y | Y | C | A | G | 182 | |
| HT2-dp27 #164 | R | L | N | I | S | K | D | T | S | K | N | Q | V | V | L | T | M | T | N | M | D | P | V | D | T | A | T | Y | Y | C | A | G | 87 | |
| HT2-dp27 #177 | R | L | N | I | S | K | D | T | S | K | N | Q | V | V | L | T | M | T | N | M | D | P | V | D | T | A | T | Y | Y | C | A | G | 87 | |
| HT2-dp27 #195 | R | L | N | I | S | K | D | S | S | K | N | Q | V | V | L | T | M | T | N | M | D | P | V | D | T | A | R | Y | Y | C | A | G | 182 | |
| HT2-dp27 #198 | R | L | T | I | S | K | D | T | S | K | N | Q | V | V | L | T | M | T | N | M | D | P | V | D | T | A | R | Y | Y | C | A | G | 81 | |
| HT2-dp27 #150 | R | L | T | I | S | K | D | T | S | K | N | Q | V | V | L | T | M | T | N | M | D | P | V | D | T | A | R | Y | Y | C | A | G | 81 | |
| HT2-dp27 #268 | R | L | N | I | S | K | D | T | S | K | N | Q | V | V | L | T | M | T | N | M | D | P | V | D | T | A | R | Y | Y | C | A | G | 183 | |
| HT2-dp27 #270 | R | L | N | I | S | K | D | T | S | K | N | Q | V | V | L | T | M | T | N | M | D | P | V | D | T | A | R | Y | Y | C | A | G | 183 | |
| HT2-dp27 #199 | R | L | T | I | S | K | D | T | S | K | N | Q | V | V | L | T | M | T | N | M | D | P | V | D | T | A | R | Y | Y | C | A | G | 81 | |
| HT2-dp27 #273 | R | L | N | I | S | K | D | S | S | K | N | Q | V | V | L | T | M | T | N | M | D | P | V | D | T | A | T | Y | Y | C | A | G | 79 | |
| HT2-dp27 #282 | R | L | N | I | S | K | D | S | S | K | N | Q | V | V | L | T | M | T | N | M | D | P | V | D | T | A | T | Y | Y | C | A | G | 88 | |
| HT2-dp27 #304 | R | L | T | I | S | K | D | T | S | K | N | Q | V | V | L | T | M | T | N | M | D | P | V | D | T | A | T | Y | Y | C | A | G | 80 | |
| HT2-dp27 #155E | R | L | N | I | S | K | D | T | S | K | N | Q | V | V | L | T | M | T | N | M | D | P | V | D | T | A | R | Y | Y | C | A | G | 183 | |
| HT2-dp27 #274 | R | L | N | I | S | K | D | T | S | K | N | Q | V | V | L | T | M | T | N | M | D | P | V | D | T | A | T | Y | Y | C | A | G | 87 | |
| HT2-dp27 #275 | R | L | T | I | S | K | D | (I) | S | K | N | Q | V | V | L | T | M | T | N | M | D | P | V | D | T | A | R | Y | Y | C | A | G | 86 | |
| HT2-dp27 #276 | R | L | T | I | S | K | D | S | S | K | N | Q | V | V | L | T | M | T | N | M | D | P | V | D | T | A | T | Y | Y | C | A | G | 79 | |
| HT2-dp27 #299 | R | L | N | I | S | K | D | S | S | K | N | Q | V | V | L | T | M | T | N | M | D | P | V | D | T | A | R | Y | Y | C | A | G | 182 | |
| HT2-dp27 #301 | R | L | N | I | S | K | D | T | S | K | N | Q | V | V | L | T | M | T | N | M | D | P | V | D | T | A | T | Y | Y | C | A | G | 87 | |
| HT2-dp27 #308 | R | L | N | I | S | K | D | S | S | K | N | Q | V | V | L | T | M | T | N | M | D | P | V | D | T | A | R | Y | Y | C | A | G | 182 | |

FIGURE 12D - 2

VH CHAIN

| | FR3 | | | | | | | | | | | | | | | | | | | | | | | | | | | | | SEQ ID NO | CDR3 |
|---|---|---|---|---|---|---|---|---|---|---|---|---|---|---|---|---|---|---|---|---|---|---|---|---|---|---|---|---|---|---|---|
| | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 | | |
| HT2-dp27 #530 | R | L | N | I | S | K | D | T | S | K | N | Q | V | V | L | T | M | T | N | M | D | P | V | D | T | A | R | Y | Y | C | A | G | 183 |
| HT2-dp27 #580 | R | L | N | I | S | K | D | S | S | K | N | Q | V | V | L | T | M | T | N | M | D | P | V | D | T | A | T | Y | Y | C | A | G | 88 |
| HT2-dp27 #345 | R | L | N | I | S | K | D | T | S | K | N | Q | V | V | L | T | M | T | N | M | D | P | V | D | T | A | T | Y | Y | C | A | R | 89 |
| HT2-dp27 #374 | R | L | N | I | S | K | D | S | S | K | N | Q | V | V | L | T | M | T | N | M | D | P | V | D | T | A | T | Y | Y | C | A | G | 88 |
| HT2-dp27 #443 | R | L | T | I | S | K | D | T | S | K | N | Q | V | V | L | T | M | T | N | M | D | P | V | D | T | A | T | Y | Y | C | A | G | 80 |
| HT2-dp27 #459 | R | L | N | I | S | K | D | S | S | K | N | Q | V | V | L | T | M | T | N | M | D | P | V | D | T | A | T | Y | Y | C | A | G | 88 |
| HT2-dp27 #470 | R | L | N | I | S | K | D | T | S | K | N | Q | V | V | L | T | M | T | N | M | D | P | V | D | T | A | T | Y | Y | C | A | G | 87 |
| HT2-dp27 #471 | R | L | N | I | S | K | D | S | S | K | N | Q | V | V | L | T | M | T | N | M | D | P | V | D | T | A | T | Y | Y | C | A | G | 88 |
| HT2-dp27 #486 | R | L | N | I | S | K | D | T | S | K | N | Q | V | V | L | T | M | T | N | M | D | P | V | D | T | A | T | Y | Y | C | A | G | 87 |
| HT2-dp27 #610 | R | L | N | I | S | K | D | T | S | K | N | Q | V | V | L | T | M | T | N | M | D | P | V | D | T | A | T | Y | Y | C | A | G | 87 |
| HT2-dp27 #624 | R | L | T | I | S | K | D | S | S | K | N | Q | V | V | L | T | M | T | N | M | D | P | V | D | T | A | T | Y | Y | C | A | G | 79 |
| HT2-dp27 #634 | R | L | T | I | S | K | D | S | S | K | N | Q | V | V | L | T | M | T | N | M | D | P | V | D | T | A | R | Y | Y | C | A | G | 90 |

FIGURE 12D - 3

VH CHAIN

| | FR4 | | | | | | | | | | | |
|---|---|---|---|---|---|---|---|---|---|---|---|---|
| | 103 | 104 | 105 | 106 | 107 | 108 | 109 | 110 | 111 | 112 | 113 | SEQ ID NO |
| HT2-dp27 #7 | W | G | Q | G | S | L | V | T | V | S | S | 92 |
| HT2-dp27 #13 | W | G | Q | G | S | L | V | T | V | S | S | 92 |
| HT2-dp27 #19 | W | G | H | G | S | L | V | T | V | S | S | 181 |
| HT2-dp27 #29 | W | G | Q | G | S | L | V | T | V | S | S | 92 |
| HT2-dp27 #34 | W | G | Q | G | S | L | V | T | V | S | S | 92 |
| HT2-dp27 #40 | W | G | H | G | S | L | V | T | V | S | S | 181 |
| HT2-dp27 #43 | W | G | H | G | S | L | V | T | V | S | S | 181 |
| HT2-dp27 #50 | W | G | Q | G | S | L | V | T | V | S | S | 92 |
| HT2-dp27 #53 | W | G | H | G | S | L | V | T | V | S | S | 181 |
| HT2-dp27 #57 | W | G | H | G | S | L | V | T | V | S | S | 181 |
| HT2-dp27 #66 | W | G | Q | G | S | L | V | T | V | S | S | 92 |
| HT2-dp27 #67 | W | G | Q | G | S | L | V | T | V | S | S | 92 |
| HT2-dp27 #73 | W | G | H | G | S | L | V | T | V | S | S | 181 |
| HT2-dp27 #74 | W | G | Q | G | S | L | V | T | V | S | S | 92 |
| HT2-dp27 #89 | W | G | H | G | S | L | V | T | V | S | S | 181 |
| HT2-dp27 #92 | W | G | Q | G | S | L | V | T | V | S | S | 92 |
| HT2-dp27 #100 | W | G | Q | G | S | L | V | T | V | S | S | 92 |
| HT2-dp27 #111 | W | G | H | G | S | L | V | T | V | S | S | 181 |
| HT2-dp27 #112 | W | G | H | G | S | L | V | T | V | S | S | 181 |
| HT2-dp27 #118 | W | G | Q | G | S | L | V | T | V | S | S | 92 |
| HT2-dp27 #123 | W | G | Q | G | S | L | V | T | V | S | S | 92 |
| HT2-dp27-#136 | W | G | H | G | S | L | V | T | V | S | S | 181 |
| HT2-dp27 #144 | W | G | H | G | S | L | V | T | V | S | S | 181 |
| HT2-dp27 #146 | W | G | H | G | S | L | V | T | V | S | S | 181 |
| HT2-dp27 #15 | W | G | Q | G | S | L | V | T | V | S | S | 92 |
| HT2-dp27 #26 | W | G | Q | G | S | L | V | T | V | S | S | 92 |
| HT2-dp27 #83 | W | G | Q | G | S | L | V | T | V | S | S | 92 |
| HT2-dp27 #164 | W | G | Q | G | S | L | V | T | V | S | S | 92 |
| HT2-dp27 #177 | W | G | H | G | S | L | V | T | V | S | S | 181 |
| HT2-dp27 #195 | W | G | Q | G | S | L | V | T | V | S | S | 92 |
| HT2-dp27 #198 | W | G | Q | G | S | L | V | T | V | S | S | 92 |
| HT2-dp27 #150 | W | G | Q | G | S | L | V | T | V | S | S | 92 |
| HT2-dp27 #268 | W | G | H | G | S | L | V | T | V | S | S | 181 |
| HT2-dp27 #270 | W | G | H | G | S | L | V | T | V | S | S | 181 |
| HT2-dp27 #199 | W | G | Q | G | S | L | V | T | V | S | S | 92 |
| HT2-dp27 #273 | W | G | H | G | S | L | V | T | V | S | S | 181 |
| HT2-dp27 #282 | W | G | H | G | S | L | V | T | V | S | S | 181 |
| HT2-dp27 #304 | W | G | Q | G | S | L | V | T | V | S | S | 92 |
| HT2-dp27 #155E | W | G | H | G | S | L | V | T | V | S | S | 181 |
| HT2-dp27 #274 | W | G | H | G | S | L | V | T | V | S | S | 181 |
| HT2-dp27 #275 | W | G | Q | G | S | L | V | T | V | S | S | 92 |
| HT2-dp27 #276 | W | G | Q | G | S | L | V | T | V | S | S | 92 |
| HT2-dp27 #299 | W | G | Q | G | S | L | V | T | V | S | S | 92 |
| HT2-dp27 #301 | W | G | Q | G | S | L | V | T | V | S | S | 92 |
| HT2-dp27 #308 | W | G | H | G | S | L | V | T | V | S | S | 181 |

FIGURE 12D - 4

VH CHAIN

FR4

| | 103 | 104 | 105 | 106 | 107 | 108 | 109 | 110 | 111 | 112 | 113 | SEQ ID NO |
|---|---|---|---|---|---|---|---|---|---|---|---|---|
| HT2-dp27 #530 | W | G | Q | G | S | L | V | T | V | S | S | 92 |
| HT2-dp27 #580 | W | G | Q | G | S | L | V | T | V | S | S | 92 |
| HT2-dp27 #345 | W | G | Q | G | S | L | V | T | V | S | S | 92 |
| HT2-dp27 #374 | W | G | H | G | S | L | V | T | V | S | S | 181 |
| HT2-dp27 #443 | W | G | Q | G | S | L | V | T | V | S | S | 92 |
| HT2-dp27 #459 | W | G | Q | G | S | L | V | T | V | S | S | 92 |
| HT2-dp27 #470 | W | G | Q | G | S | L | V | T | V | S | S | 92 |
| HT2-dp27 #471 | W | G | Q | G | S | L | V | T | V | S | S | 92 |
| HT2-dp27 #486 | W | G | H | G | S | L | V | T | V | S | S | 181 |
| HT2-dp27 #610 | W | G | Q | G | S | L | V | T | V | S | S | 92 |
| HT2-dp27 #624 | W | G | Q | G | S | L | V | T | V | S | S | 92 |
| HT2-dp27 #634 | W | G | H | G | S | L | V | T | V | S | S | 181 |

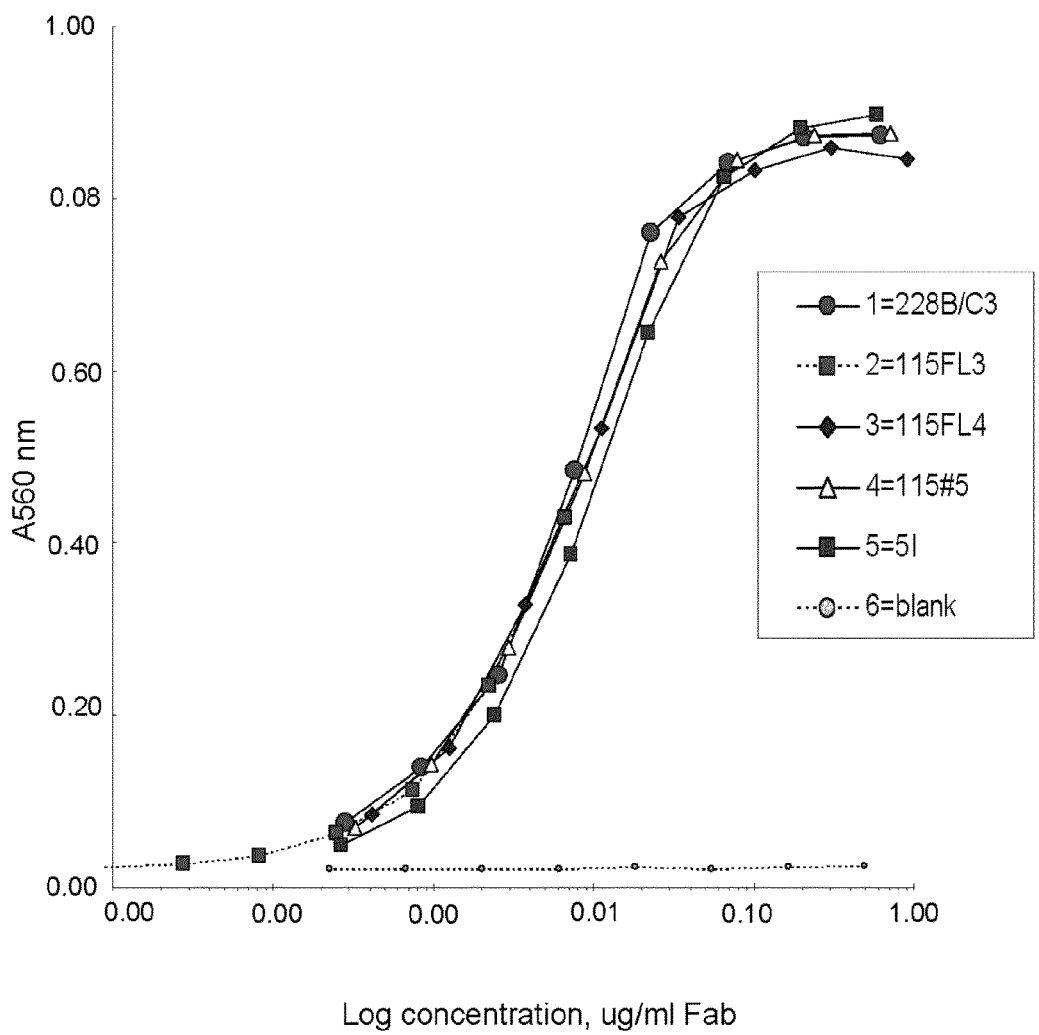

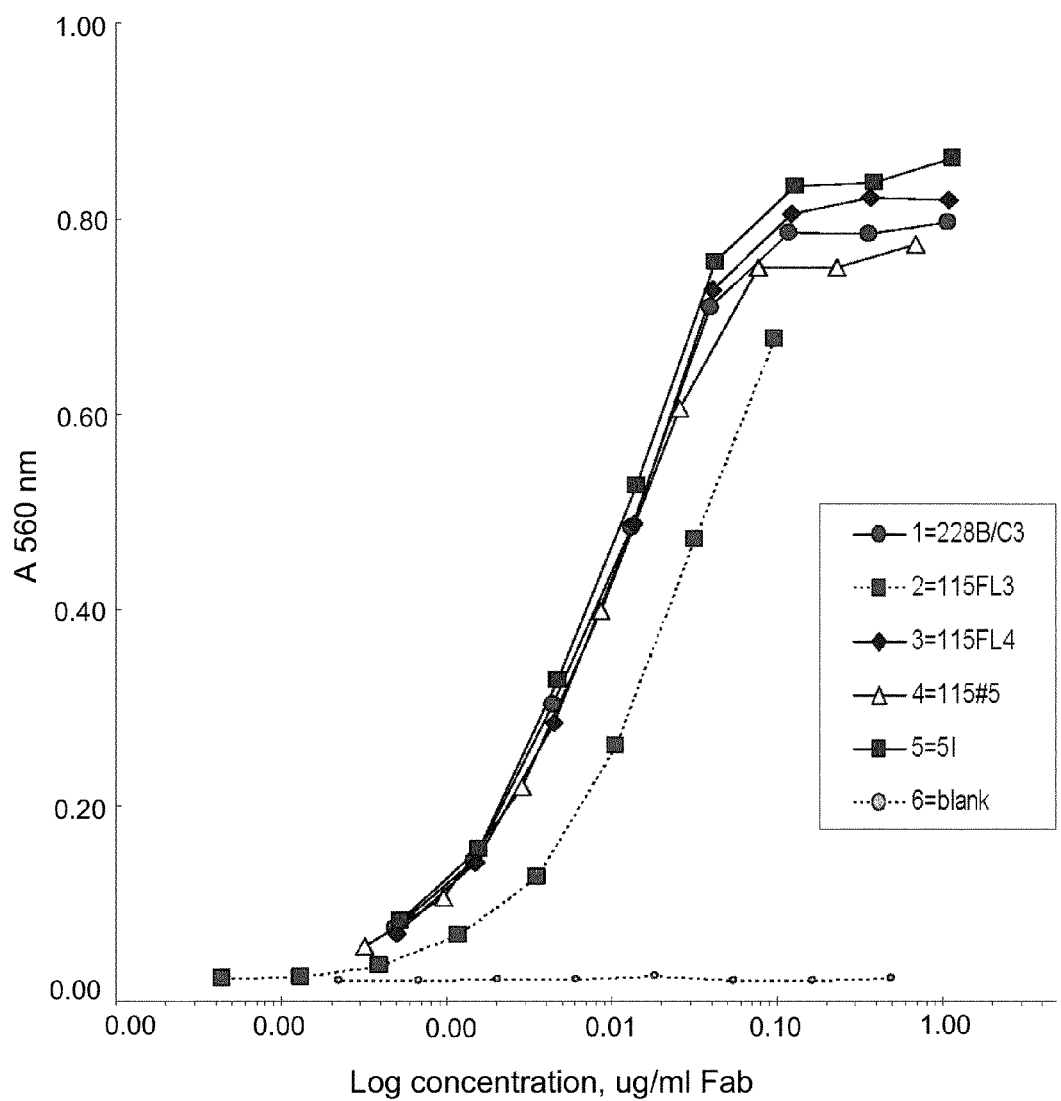

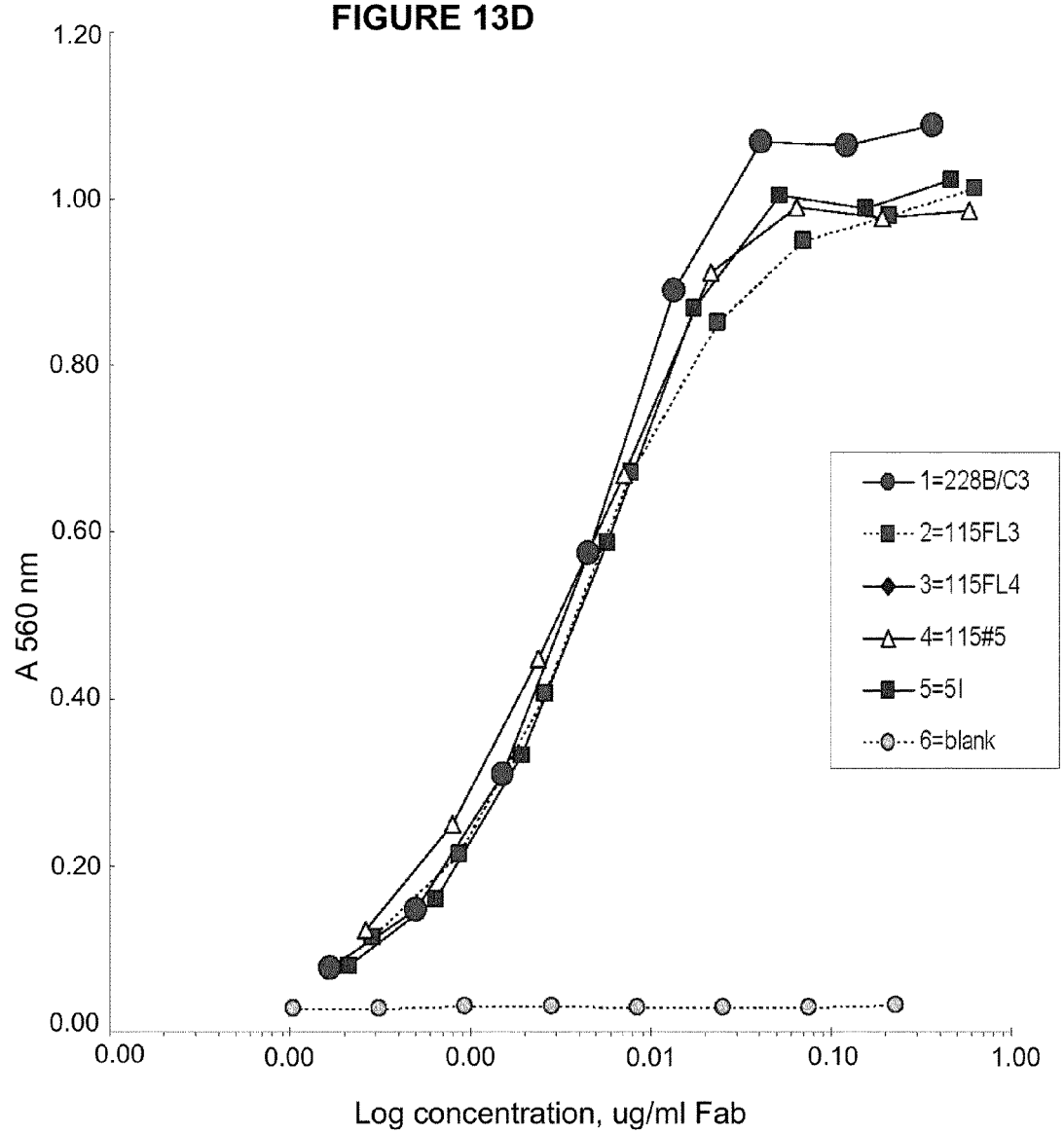

FIGURE 15

| | | | | | | | | | | | | | | SEQ ID NO: |
|---|---|---|---|---|---|---|---|---|---|---|---|---|---|---|
| CDR-L1 L1-59 (parent) | R | A | S | K | S | V | D | S | Y | G | Q | S | F | M | H | 100 |
| CL-5 | R | A | S | K | S | V | D | S | Y | G | Q | S | F | M | H | 100 |
| CL-13 | R | A | S | K | S | V | D | S | Y | G | Q | S | F | M | H | 100 |
| CL-42 | R | A | S | K | S | V | D | S | Y | G | Q | S | F | M | H | 100 |
| CL-48 | R | A | S | K | S | V | D | S | Y | G | Q | S | F | M | H | 100 |
| CL-50 | R | A | S | K | S | V | D | S | Y | G | Q | S | F | M | H | 100 |
| CL-56 | R | A | S | K | S | V | D | S | Y | G | Q | S | F | M | H | 100 |
| CL-65 | R | A | S | K | S | V | D | S | Y | G | Q | S | F | M | H | 100 |
| CL-69 | R | A | S | K | S | V | D | S | Y | G | Q | S | F | M | H | 100 |
| CL-82 | R | A | S | K | S | V | D | S | Y | G | Q | S | F | M | H | 100 |
| CL-94 | R | A | S | K | S | V | D | S | Y | G | Q | S | F | M | H | 100 |

| | | | | | | | | | SEQ ID NO: |
|---|---|---|---|---|---|---|---|---|---|
| CDR-L3 L1-59 (parent) | Q | Q | N | N | E | D | P | R | T | 115 |
| CL-5 | Q | Q | N | A | E | D | P | R | T | 116 |
| CL-13 | Q | Q | N | N | E | D | P | R | T | 115 |
| CL-42 | Q | Q | N | A | E | D | P | R | T | 116 |
| CL-48 | Q | Q | N | N | E | D | P | R | T | 115 |
| CL-50 | Q | Q | N | A | E | D | P | R | T | 116 |
| CL-56 | Q | Q | N | A | E | D | P | R | T | 116 |
| CL-65 | Q | Q | N | N | E | D | P | R | T | 115 |
| CL-69 | Q | Q | N | A | E | D | P | R | T | 116 |
| CL-82 | Q | Q | N | N | E | D | P | R | T | 115 |
| CL-94 | Q | Q | N | A | E | D | P | R | T | 116 |

| | | | | | | SEQ ID NO: |
|---|---|---|---|---|---|---|
| CDR-H1 L1-59 (parent) | A | Y | S | V | N | 117 |
| CL-5 | A | Y | S | V | N | 117 |
| CL-13 | A | K | S | V | N | 118 |
| CL-42 | A | N | S | V | N | 119 |
| CL-48 | A | N | S | V | N | 119 |
| CL-50 | A | K | S | V | N | 118 |
| CL-56 | A | K | S | V | N | 118 |
| CL-65 | A | S | S | V | N | 185 |
| CL-69 | A | N | S | V | N | 119 |
| CL-82 | A | N | S | V | N | 119 |
| CL-94 | A | N | S | V | N | 119 |

| | | | | | | | | | | SEQ ID NO: |
|---|---|---|---|---|---|---|---|---|---|---|
| CDR-H3 L1-59 (parent) | D | G | Y | Y | P | Y | A | M | D | N | 135 |
| CL-5 | D | G | Y | Y | P | Y | A | M | K | N | 137 |
| CL-13 | D | G | Y | Y | P | Y | A | M | S | N | 139 |
| CL-42 | D | G | Y | Y | P | Y | A | M | K | N | 137 |
| CL-48 | D | G | Y | Y | P | Y | A | M | K | N | 137 |
| CL-50 | D | G | Y | Y | P | Y | A | M | K | N | 137 |
| CL-56 | D | G | Y | Y | P | Y | A | M | S | N | 139 |
| CL-65 | D | G | R | Y | P | Y | A | M | K | N | 138 |
| CL-69 | D | G | Y | Y | P | Y | A | M | D | N | 135 |
| CL-82 | D | G | Y | Y | P | Y | A | M | K | N | 137 |
| CL-94 | D | G | Y | Y | P | Y | A | M | K | N | 137 |

Figure 17  Variable Region Amino Acid Sequences for anti-IL13 Candidates

CL-5 (Affinity Matured Candidate) Vk:

DIVMTQSPDSLSVSLGERATINCRASKSVDSYGQSFMHWYQQKPGQPPKLLIYLASNLESGVPDRFSGSGSGTDFT
LTISSLQAEDVAVYYCQQNAEDPRTFGGGTKVEIKR    (SEQ ID NO 93)

CL-5 (Affinity Matured Candidate) Vh:

QVTLRESGPALVKPTQTLTLTCTGSGFSLSAYSVNWIRQPPGKALEWLAMIWGDGKIVYNSALKSRLTISKDTSKN
QVVLTMTNMDPVDTATYYCAVDGYYPYAMKNWGQGSLVTVSS    (SEQ ID NO 94)

CL-13 (Affinity Matured Candidate) Vk:

DIVMTQSPDSLSVSLGERATINCRASKSVDSYGQSFMHWYQQKPGQPPKLLIYLASNLESGVPDRFSGSGSGTDFT
LTISSLQAEDVAVYYCQQNEDPRTFGGGTKVEIKR    (SEQ ID NO 95)

CL-13 (Affinity Matured Candidate) Vh:

QVTLRESGPALVKPTQTLTLTCTGSGFSLSAKSVNWIRQPPGKALEWLAMIWGDGKIVYNSALKSRLTISKDTSKN
QVVLTMTNMDPVDTATYYCAVDGYYPYAMSNWGQGSLVTVSS    (SEQ ID NO 96)

CL-50 (Affinity Matured Candidate) Vk:

DIVMTQSPDSLSVSLGERATINCRASKSVDSYGQSFMHWYQQKPGQPPKLLIYLASNLESGVPDRFSGSGSGTDFT
LTISSLQAEDVAVYYCQQNAEDPRTFGGGTKVEIKR    (SEQ ID NO 97)

CL-50 (Affinity Matured Candidate) Vh:

QVTLRESGPALVKPTQTLTLTCTGSGFSLSAKSVNWIRQPPGKALEWLAMIWGDGKIVYNSALKSRLTISKDTSKN
QVVLTMTNMDPVDTATYYCAVDGYYPYAMKNWGQGSLVTVSS    (SEQ ID NO 98)

FIGURE 18

Alignment of IL13 protein sequences

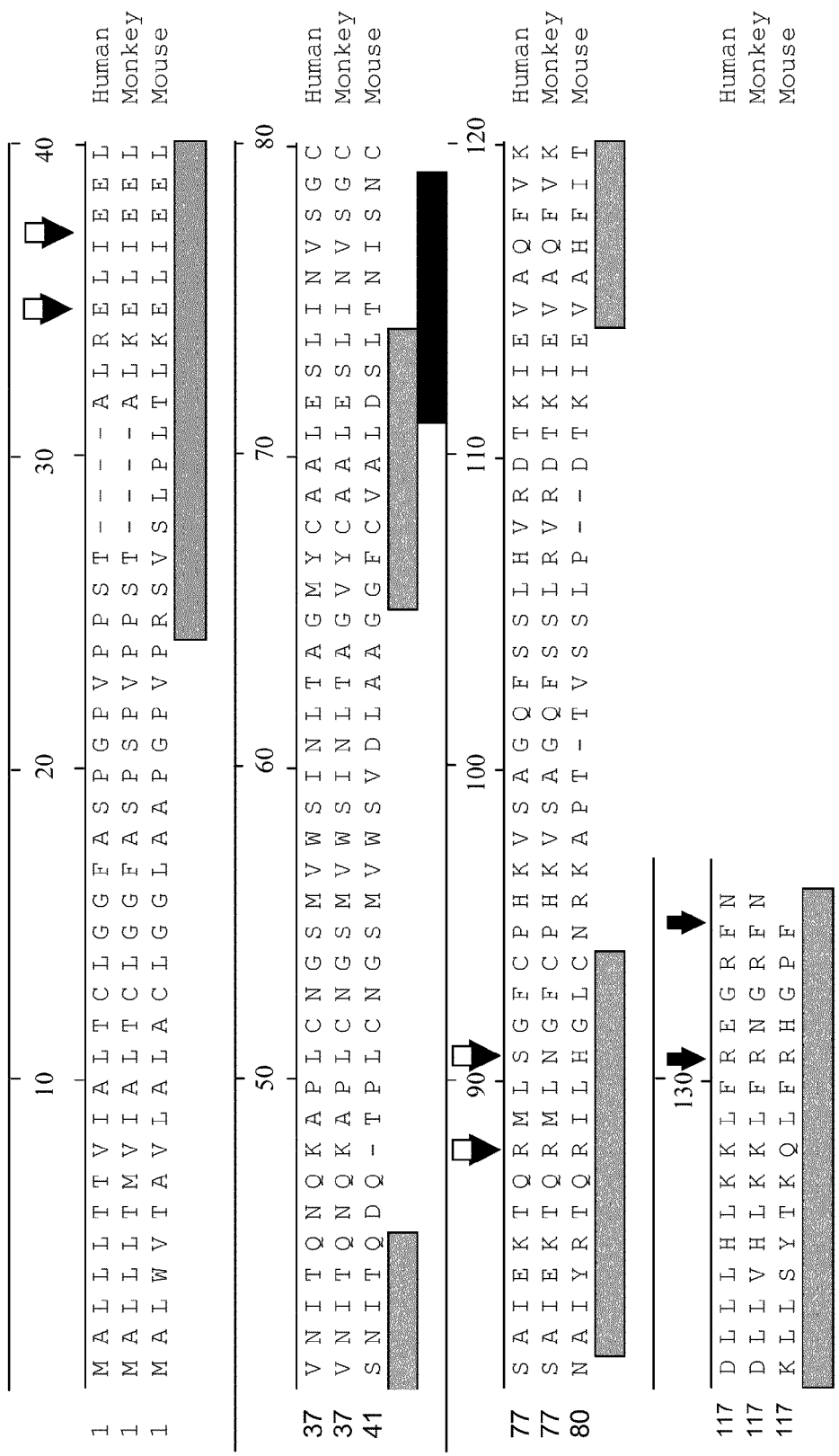

FIGURE 20

|   | CDR-L1 |   |   | CDR-H1 |   |
|---|---|---|---|---|---|
| P | RASKSVDSYGNSFMH | SEQ ID NO 99 | P | AYSVN | SEQ ID NO 117 |
| V1 | RASKSVDSYGQSFMH | SEQ ID NO 100 | V1 | AKSVN | SEQ ID NO 118 |
| V2 | RASKSVDSYGQSFLH | SEQ ID NO 101 | V2 | ANSVN | SEQ ID NO 119 |
| V3 | RASKSVDSYGNSYMH | SEQ ID NO 102 | V3 | GYSVN | SEQ ID NO 120 |
| V4 | RASKSVDSYGNSFLH | SEQ ID NO 103 | V4 | AHSVN | SEQ ID NO 121 |
|   |   |   | V5 | ARSVN | SEQ ID NO 122 |
|   | CDR-L2 |   |   | CDR-H2 |   |
| P | LASNLES | SEQ ID NO 104 | P | MIWGDGKIVYNSALKS | SEQ ID NO 123 |
| V1 | LASNLNS | SEQ ID NO 105 | V1 | MIWGDGKISYNSALKS | SEQ ID NO 124 |
| V2 | LASNLQS | SEQ ID NO 106 | V2 | MIWGDGKIVYNSALES | SEQ ID NO 125 |
| V3 | LATNLES | SEQ ID NO 107 | V3 | MIWGDGKIVYNSALKS | SEQ ID NO 126 |
| V4 | LASNLKS | SEQ ID NO 108 | V4 | MIWGDGKIVYNSDLKS | SEQ ID NO 127 |
| V5 | LASNLEK | SEQ ID NO 109 | V5 | MIWGDGKVVYNSALKS | SEQ ID NO 128 |
| V6 | LASRLES | SEQ ID NO 110 | V6 | MIWGDGKIVYNSELKS | SEQ ID NO 129 |
| V7 | LASNLHS | SEQ ID NO 111 | V7 | MIWGDGKIAYNSALKS | SEQ ID NO 130 |
| V8 | LASNLSS | SEQ ID NO 112 | V8 | MIWGDGKIVYNSALKE | SEQ ID NO 131 |
| V9 | LASFLES | SEQ ID NO 113 | V9 | MVWGDGKIVYNSALKS | SEQ ID NO 132 |
| V10 | LANNLES | SEQ ID NO 114 | V10 | MIWGDGKIVYNSALAS | SEQ ID NO 133 |
|   |   |   | V11 | MIWGDGKKVYNSALKS | SEQ ID NO 134 |
|   | CDR-L3 |   |   | CDR-H3 |   |
| P | QQNEDPRT | SEQ ID NO 115 | P | DGYYPYAMDN | SEQ ID NO 135 |
| V1 | QQNAEDPRT | SEQ ID NO 116 | V1 | DGRYPYAMDN | SEQ ID NO 136 |
|   |   |   | V2 | DGYYPYAMKN | SEQ ID NO 137 |
|   |   |   | V3 | DGRYPYAMKN | SEQ ID NO 138 |
|   |   |   | V4 | DGYYPYAMSN | SEQ ID NO 139 |
|   |   |   | V5 | DGYYPYAMAN | SEQ ID NO 140 |
|   |   |   | V6 | DGYYPYALDN | SEQ ID NO 141 |

FIGURE 21A: Variable Region Amino Acid Sequences for certain anti-IL13 Candidates:

CL-89 Vk (SEQ ID NO: 142):

DIVMTQSPDSLSVSLGERATINCRASKSVDSYGNSFMHWYQQKPGQPPKLLIYLASNLESGVPDRFSGSGSGT
DFTLTISSLQAEDVAVYYCQQNNEDPRTFGGGTKVEIKR

CL-276G Vh (SEQ ID NO: 143):

QVTLRESGPALVKPTQTLTLTCTVSGFSLSAYSVNWIRQPPGKALEWLAMIWGDGKIVYNSALKSRLTISKDTS
KNQVVLTMTNMDPVDTATYYCAGDGYYPYAMDNWGQGSLVTVSS

RL-36 (Random Library Candidate) Vk (SEQ ID NO 144):

DIVMTQSPDSLSVSLGERATINCRASKSVDSYGNSFMHWYQQKPGQPPKLLIYLASNLESGVPDRFSGSGSGT
DFTLTISSLQAEDVAVYYCQQNNEDPRTFGGGTKVEIKR

RL-36 (Random Library Candidate) Vh (SEQ ID NO 145):

QVTLRESGPALVKPTQTLTLTCTGSSGFSLSAYSVNWIRQPPGKALEWLAMIWGDGKIVYNSALKSRLTISKDTS
KNQVVLTMTNMDPVDTATYYCAVDGYYPYAMDNWGQGSLVTV

RL-19 (Random Library Candidate) Vh (SEQ ID NO 146):

QVTLRESGPALVKPTQTLTLTCTSSGFSLSAYSVNWIRQPPGKALEWLAMIWGDGKIVYNSALKSRLTISKDTS
KNQVVLTMTNMDPVDTATYYCALDGYYPYAMDNWGQGSLVTV
SS

FIGURE 21B: Variable Region Amino Acid Sequences for certain anti-IL13 Candidates:

RL-11 (Random Library Candidate) Vh (SEQ ID NO 147):

QVTLRESGPALVKPTQTLTLTCTTSGFSLSAYSVNWIRQPPGKALEWLAMIWGDGKIVYNSALKSRLTISKDTS
KNQVVLTMTNMDPVDTATYYCAVDGYYPYAMDNWGQGSLVTV
SS

RL-8 (Random Library Candidate) Vh (SEQ ID NO 148):

QVTLRESGPALVKPTQTLTLTCTLSGFSLSAYSVNWIRQPPGKALEWLAMIWGDGKIVYNSALKSRLTISKDTSK
NQVVLTMTNMDPVDTATYYCASDGYYPYAMDNWGQGSLVTV
SS

RL-45 (Random Library Candidate) Vh (SEQ ID NO 149):

QVTLRESGPALVKPTQTLTLTCTTSGFSLSAYSVNWIRQPPGKALEWLAMIWGDGKIVYNSALKSRLTISKDTS
KNQVVLTMTNMDPVDTATYYCATDGYYPYAMDNWGQGSLVTV
SS

RL36-L1.59 (L1 Affinity Matured Candidate) Vk (SEQ ID NO 150):

DIVMTQSPDSLSVSLGERATINCRASKSVDSYGQSFMHWYQQKPGQPPKLLIYLASNLESGVPDRFGGGTKVEIKR
DFTLTISSLQAEDVAVYYCQQNNEDPRTFGGGTKVEIKR

RL36-L1.59 (L1 Affinity Matured Candidate) Vh (SEQ ID NO 151):

QVTLRESGPALVKPTQTLTLTCTGSGFSLSAYSVNWIRQPPGKALEWLAMIWGDGKIVYNSALKSRLTISKDTS
KNQVVLTMTNMDPVDTATYYCAVDGYYPYAMDNWGQGSLVTVSS scFV Candidate #212 (SEQ ID NO 152):

QVTLRESGPALVKPTQTLTLTCTVSGFSLSAYSVNWIRQPPGKALEWLAMIWGDGKIVYNSALKSRLTISKDTS
KNQVVLTMTNMDPVDTATYYCAGDGYYPYAMDNWGQGSLVTV
SSGGGSRSSSGGGGSGGGGDIVMTQSPDSLSVSLGERATINCRASKSVDSYGNSFMHWYQQKPGQPPKLLI
YLASNLESGVPDRFSGSGSGTDFTLTISSVQAEDVAVYYCQQN
NEDPRTFGGGTKVEIKR

SEQUENCE LISTING

```
<160> NUMBER OF SEQ ID NOS: 193

<210> SEQ ID NO 1
<211> LENGTH: 114
<212> TYPE: PRT
<213> ORGANISM: Homo sapiens

<400> SEQUENCE: 1

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn

<210> SEQ ID NO 2
<211> LENGTH: 114
<212> TYPE: PRT
<213> ORGANISM: Homo sapiens
<220> FEATURE:
<221> NAME/KEY: misc_feature
<222> LOCATION: (13)..(13)
<223> OTHER INFORMATION: Xaa can be any naturally occurring amino acid

<400> SEQUENCE: 2
```

-continued

```
Ser Pro Gly Pro Val Pro Ser Thr Ala Leu Arg Xaa Leu Ile Glu
1               5                   10                  15

Glu Leu Val Asn Ile Thr Gln Asn Gln Lys Ala Pro Leu Cys Asn Gly
                20                  25                  30

Ser Met Val Trp Ser Ile Asn Leu Thr Ala Gly Met Tyr Cys Ala Ala
            35                  40                  45

Leu Glu Ser Leu Ile Asn Val Ser Gly Cys Ser Ala Ile Glu Lys Thr
        50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
                100                 105                 110

Phe Asn

<210> SEQ ID NO 3
<211> LENGTH: 113
<212> TYPE: PRT
<213> ORGANISM: Murinae gen. sp.
<220> FEATURE:
<221> NAME/KEY: CHAIN
<222> LOCATION: (1)..(113)
<223> OTHER INFORMATION: VARIABLE REGION OF LIGHT CHAIN OF MONOCLONAL
      ANTIBODY 228B/C

<400> SEQUENCE: 3

Asn Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Ser Tyr Tyr Cys Gln Gln Asn Asn
                85                  90                  95

Glu Asp Pro Arg Thr Phe Gly Gly Gly Thr Lys Leu Glu Ile Lys Arg
                100                 105                 110

Ala

<210> SEQ ID NO 4
<211> LENGTH: 118
<212> TYPE: PRT
<213> ORGANISM: Murinae gen. sp.
<220> FEATURE:
<221> NAME/KEY: CHAIN
<222> LOCATION: (1)..(118)
<223> OTHER INFORMATION: VARIABLE REGION OF HEAVY CHAIN OF MONOCLONAL
      ANTIBODY 228B/C

<400> SEQUENCE: 4

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Asn Ala Tyr
                20                  25                  30

Ser Val Asn Trp Val Arg Gln Pro Pro Gly Lys Gly Leu Glu Trp Leu
            35                  40                  45
```

```
Gly Met Ile Trp Gly Asp Gly Lys Ile Val Tyr Asn Ser Ala Leu Lys
        50                  55                  60

Ser Arg Leu Asn Ile Ser Lys Asp Ser Ser Lys Ser Gln Val Phe Leu
65                  70                  75                  80

Lys Met Ser Ser Leu Gln Ser Asp Asp Thr Ala Arg Tyr Tyr Cys Ala
                85                  90                  95

Gly Asp Gly Tyr Tyr Pro Tyr Ala Met Asp Asn Trp Gly His Gly Thr
            100                 105                 110

Ser Val Thr Val Ser Ser
        115

<210> SEQ ID NO 5
<211> LENGTH: 118
<212> TYPE: PRT
<213> ORGANISM: Murinae gen. sp.
<220> FEATURE:
<221> NAME/KEY: CHAIN
<222> LOCATION: (1)..(118)
<223> OTHER INFORMATION: VARIABLE REGION OF LIGHT CHAIN OF MONOCLONAL
      ANTIBODY 228A-4

<400> SEQUENCE: 5

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
                20                  25                  30

Asn Ile Asn Trp Ile Arg Gln Pro Pro Gly Lys Gly Leu Glu Trp Leu
            35                  40                  45

Gly Met Ile Trp Gly Asp Gly Ser Thr Ala Tyr Asn Ser Ala Leu Lys
        50                  55                  60

Ser Arg Leu Ser Ile Ser Lys Asp Asn Ser Lys Ser Gln Ile Phe Leu
65                  70                  75                  80

Lys Met Asn Ser Leu Gln Thr Glu Asp Thr Ala Arg Tyr Tyr Cys Ala
                85                  90                  95

Arg Asp Gly Tyr Phe Pro Tyr Ala Met Ala Tyr Trp Gly Gln Gly Thr
            100                 105                 110

Ser Val Thr Val Ser Ser
        115

<210> SEQ ID NO 6
<211> LENGTH: 118
<212> TYPE: PRT
<213> ORGANISM: Murinae gen. sp.
<220> FEATURE:
<221> NAME/KEY: CHAIN
<222> LOCATION: (1)..(118)
<223> OTHER INFORMATION: VARIABLE REGION OF HEAVY CHAIN OF MONOCLONAL
      ANTIBODY 228A-4

<400> SEQUENCE: 6

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
                20                  25                  30

Asn Ile Asn Trp Ile Arg Gln Pro Pro Gly Lys Gly Leu Glu Trp Leu
            35                  40                  45

Gly Met Ile Trp Gly Asp Gly Ser Thr Ala Tyr Asn Ser Ala Leu Lys
        50                  55                  60

Ser Arg Leu Ser Ile Ser Lys Asp Asn Ser Lys Ser Gln Ile Phe Leu
65                  70                  75                  80
```

```
Lys Met Asn Ser Leu Gln Thr Glu Asp Thr Ala Arg Tyr Tyr Cys Ala
                85                  90                  95

Arg Asp Gly Tyr Phe Pro Tyr Ala Met Ala Tyr Trp Gly Gln Gly Thr
            100                 105                 110

Ser Val Thr Val Ser Ser
        115

<210> SEQ ID NO 7
<211> LENGTH: 114
<212> TYPE: PRT
<213> ORGANISM: Murinae gen. sp.
<220> FEATURE:
<221> NAME/KEY: CHAIN
<222> LOCATION: (1)..(114)
<223> OTHER INFORMATION: VARIABLE REGION OF LIGHT CHAIN OF MONOCLONAL
      ANTIBODY 227-26
<220> FEATURE:
<221> NAME/KEY: CHAIN
<222> LOCATION: (1)..(114)
<223> OTHER INFORMATION: VARIABLE REGION OF LIGHT CHAIN OF MONOCLONAL
      ANTIBODY 227-26-1

<400> SEQUENCE: 7

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala

<210> SEQ ID NO 8
<211> LENGTH: 120
<212> TYPE: PRT
<213> ORGANISM: Murinae gen. sp.
<220> FEATURE:
<221> NAME/KEY: CHAIN
<222> LOCATION: (1)..(120)
<223> OTHER INFORMATION: VARIABLE REGION OF HEAVY CHAIN OF MONOCLONAL
      ANTIBODY 227-26-1

<400> SEQUENCE: 8

Gln Val Gln Leu Gln Gln Ser Gly Asp Asp Leu Val Leu Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Lys Gln Arg Pro Gly Gln Gly Leu Glu Trp Ile
        35                  40                  45

Gly His Ile Ala Pro Gly Ser Gly Ser Thr Tyr Phe Asn Glu Met Phe
    50                  55                  60

Lys Gly Lys Ala Thr Leu Thr Val Asp Thr Ser Ser Ser Thr Ala Tyr
65                  70                  75                  80

Ile Gln Leu Ser Ser Leu Ser Ser Glu Asp Ser Ala Val Tyr Phe Cys
```

```
                    85                  90                  95
Ala Arg Ser Asp Ile Phe Leu Ser Tyr Ala Met Asp Tyr Trp Gly Gln
                100                 105                 110

Gly Thr Ser Val Thr Val Ser Ser
        115                 120

<210> SEQ ID NO 9
<211> LENGTH: 50
<212> TYPE: DNA
<213> ORGANISM: ARTIFICIAL SEQUENCE
<220> FEATURE:
<223> OTHER INFORMATION: Forward oligonucleotide primer for a mutant
      IL13 sequence

<400> SEQUENCE: 9
aagctttccc caggccctgt gcctccctct acagccctca ggaagctcat         50

<210> SEQ ID NO 10
<211> LENGTH: 30
<212> TYPE: DNA
<213> ORGANISM: ARTIFICIAL SEQUENCE
<220> FEATURE:
<223> OTHER INFORMATION: Reverse Oligo nucleotide primer of a mutant
      IL13 sequence

<400> SEQUENCE: 10
ctcgaggttg aaccgtccct cgcgaaaaag                               30

<210> SEQ ID NO 11
<211> LENGTH: 22
<212> TYPE: DNA
<213> ORGANISM: ARTIFICIAL SEQUENCE
<220> FEATURE:
<223> OTHER INFORMATION: Forward degenerate oligonucleotide primer for
      monkey IL13

<400> SEQUENCE: 11
gyyctrggcy ycatggcgct yt                                       22

<210> SEQ ID NO 12
<211> LENGTH: 25
<212> TYPE: DNA
<213> ORGANISM: ARTIFICIAL SEQUENCE
<220> FEATURE:
<223> OTHER INFORMATION: Reverse degenerate oligonucleotide primer for
      monkey IL13

<400> SEQUENCE: 12
tttcagttga accgtccyty gcgaa                                    25

<210> SEQ ID NO 13
<211> LENGTH: 399
<212> TYPE: DNA
<213> ORGANISM: Macaca fascicularis

<400> SEQUENCE: 13
atggcgctct tgttgaccat ggtcattgct ctcacttgcc tcggcggctt tgcctcccca    60
agccctgtgc ctccctctac agccctcaag gagctcattg aggagctggt caacatcacc   120
cagaaccaga aggccccgct ctgcaatggc agcatggtgt ggagcatcaa cctgacagct   180
ggcgtgtact gtgcagccct ggaatccctg atcaacgtgt caggctgcag tgccatcgag   240
aagacccaga ggatgctgaa cggattctgc ccgcacaagg tctcagctgg gcagtttccc   300
agcttgcgtg tccgagacac caaaatcgag gtggcccagt ttgtaaagga cctgctcgta   360
```

-continued

```
catttaaaga aacttttcg caatggacgg ttcaactga                    399
```

<210> SEQ ID NO 14
<211> LENGTH: 34
<212> TYPE: DNA
<213> ORGANISM: ARTIFICIAL SEQUENCE
<220> FEATURE:
<223> OTHER INFORMATION: Forward oligonucleotide primer for cynomologus
      monkey IL13

<400> SEQUENCE: 14

```
aagcttcacc atggcgctct tgttgaccat ggtc                        34
```

<210> SEQ ID NO 15
<211> LENGTH: 40
<212> TYPE: DNA
<213> ORGANISM: ARTIFICIAL SEQUENCE
<220> FEATURE:
<223> OTHER INFORMATION: Reverse oligonucleotide primer for cynomologus
      monkey IL13

<400> SEQUENCE: 15

```
tcacaagatc tgggctcctc gaggttgaac cgtccattgc                  40
```

<210> SEQ ID NO 16
<211> LENGTH: 23
<212> TYPE: DNA
<213> ORGANISM: ARTIFICIAL SEQUENCE
<220> FEATURE:
<223> OTHER INFORMATION: Forward oligonucleotide primer for Fc gamma1

<400> SEQUENCE: 16

```
ctcgaggagc ccagatcttg tga                                    23
```

<210> SEQ ID NO 17
<211> LENGTH: 35
<212> TYPE: DNA
<213> ORGANISM: ARTIFICIAL SEQUENCE
<220> FEATURE:
<223> OTHER INFORMATION: Reverse oligonucleotide primer for Fc gamma 1

<400> SEQUENCE: 17

```
gctctagagc ctcatttacc cggagacagg gagag                       35
```

<210> SEQ ID NO 18
<211> LENGTH: 8
<212> TYPE: PRT
<213> ORGANISM: ARTIFICIAL SEQUENCE
<220> FEATURE:
<223> OTHER INFORMATION: EPITOPE BINDING SITE

<400> SEQUENCE: 18

Glu Ser Leu Ile Asn Val Ser Gly
1               5

<210> SEQ ID NO 19
<211> LENGTH: 12
<212> TYPE: PRT
<213> ORGANISM: ARTIFICIAL SEQUENCE
<220> FEATURE:
<223> OTHER INFORMATION: EPITOPE BINDING SITE

<400> SEQUENCE: 19

Tyr Cys Ala Ala Leu Glu Ser Leu Ile Asn Val Ser
1               5                   10

<210> SEQ ID NO 20

```
<211> LENGTH: 23
<212> TYPE: PRT
<213> ORGANISM: ARTIFICIAL SEQUENCE
<220> FEATURE:
<223> OTHER INFORMATION: FRL1 228B/C-1

<400> SEQUENCE: 20

Asn Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 21
<211> LENGTH: 23
<212> TYPE: PRT
<213> ORGANISM: ARTIFICIAL SEQUENCE
<220> FEATURE:
<223> OTHER INFORMATION: FRL1 TEMPLATE HT2

<400> SEQUENCE: 21

Asp Ile Val Met Thr Gln Ser Pro Asp Ser Leu Ser Val Ser Leu Gly
1               5                   10                  15

Glu Arg Ala Thr Ile Asn Cys
            20

<210> SEQ ID NO 22
<211> LENGTH: 23
<212> TYPE: PRT
<213> ORGANISM: ARTIFICIAL SEQUENCE
<220> FEATURE:
<223> OTHER INFORMATION: FRL1 VARIANT B

<400> SEQUENCE: 22

Asp Ile Val Met Thr Gln Ser Pro Ala Ser Leu Ala Val Ser Leu Gly
1               5                   10                  15

Glu Arg Ala Thr Ile Asn Cys
            20

<210> SEQ ID NO 23
<211> LENGTH: 23
<212> TYPE: PRT
<213> ORGANISM: ARTIFICIAL SEQUENCE
<220> FEATURE:
<223> OTHER INFORMATION: FRL1 VARIANT J

<400> SEQUENCE: 23

Asp Ile Val Leu Thr Gln Ser Pro Asp Ser Leu Ala Val Ser Leu Gly
1               5                   10                  15

Glu Arg Ala Thr Ile Asn Cys
            20

<210> SEQ ID NO 24
<211> LENGTH: 23
<212> TYPE: PRT
<213> ORGANISM: ARTIFICIAL SEQUENCE
<220> FEATURE:
<223> OTHER INFORMATION: FRL1 VARIANT L

<400> SEQUENCE: 24

Asp Ile Val Leu Thr Gln Ser Pro Ala Ser Leu Ser Val Ser Leu Gly
1               5                   10                  15

Glu Arg Ala Thr Ile Asn Cys
            20

<210> SEQ ID NO 25
```

```
<211> LENGTH: 23
<212> TYPE: PRT
<213> ORGANISM: ARTIFICIAL SEQUENCE
<220> FEATURE:
<223> OTHER INFORMATION: FRL1 VARIANT HT-NEW #300

<400> SEQUENCE: 25

Asp Ile Val Leu Thr Gln Ser Pro Asp Ser Leu Ser Val Ser Leu Gly
 1               5                  10                  15

Glu Arg Ala Thr Ile Asn Cys
            20

<210> SEQ ID NO 26
<211> LENGTH: 23
<212> TYPE: PRT
<213> ORGANISM: ARTIFICIAL SEQUENCE
<220> FEATURE:
<223> OTHER INFORMATION: FRL1 VARIANT HT2-DP27 #29

<400> SEQUENCE: 26

Asp Ile Val Leu Thr Gln Ser Pro Val Ser Leu Ala Val Ser Leu Gly
 1               5                  10                  15

Glu Arg Ala Thr Ile Asn Cys
            20

<210> SEQ ID NO 27
<211> LENGTH: 23
<212> TYPE: PRT
<213> ORGANISM: ARTIFICIAL SEQUENCE
<220> FEATURE:
<223> OTHER INFORMATION: FRL1 VARIANT HT2-DP27 #53

<400> SEQUENCE: 27

Asp Ile Val Met Thr Gln Ser Pro Ala Ser Leu Ser Val Ser Leu Gly
 1               5                  10                  15

Glu Arg Ala Thr Ile Asn Cys
            20

<210> SEQ ID NO 28
<211> LENGTH: 23
<212> TYPE: PRT
<213> ORGANISM: ARTIFICIAL SEQUENCE
<220> FEATURE:
<223> OTHER INFORMATION: FRL1 VARIANT HT2-DP27 #66

<400> SEQUENCE: 28

Asp Ile Val Met Thr Gln Ser Pro Asp Ser Leu Ala Val Ser Leu Gly
 1               5                  10                  15

Glu Arg Ala Thr Ile Asn Cys
            20

<210> SEQ ID NO 29
<211> LENGTH: 15
<212> TYPE: PRT
<213> ORGANISM: ARTIFICIAL SEQUENCE
<220> FEATURE:
<223> OTHER INFORMATION: FRL2 228B/C

<400> SEQUENCE: 29

Trp Tyr Gln Gln Lys Pro Gly Gln Pro Pro Lys Leu Leu Ile Tyr
 1               5                  10                  15

<210> SEQ ID NO 30
<211> LENGTH: 32
<212> TYPE: PRT
<213> ORGANISM: ARTIFICIAL SEQUENCE
```

```
<220> FEATURE:
<223> OTHER INFORMATION: FRL3 288 B/C

<400> SEQUENCE: 30

Gly Val Pro Ala Arg Phe Ser Gly Ser Gly Ser Arg Thr Asp Phe Thr
1               5                   10                  15

Leu Thr Ile Asp Pro Val Glu Ala Asp Ala Ala Ser Tyr Tyr Cys
            20                  25                  30

<210> SEQ ID NO 31
<211> LENGTH: 32
<212> TYPE: PRT
<213> ORGANISM: ARTIFICIAL SEQUENCE
<220> FEATURE:
<223> OTHER INFORMATION: FRL3 HT2

<400> SEQUENCE: 31

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 32
<211> LENGTH: 32
<212> TYPE: PRT
<213> ORGANISM: ARTIFICIAL SEQUENCE
<220> FEATURE:
<223> OTHER INFORMATION: FRL3 VARIANT B

<400> SEQUENCE: 32

Gly Val Pro Asp Arg Phe Ser Gly Ser Gly Ser Gly Thr Asp Phe Thr
1               5                   10                  15

Leu Thr Ile Asp Pro Leu Gln Ala Glu Asp Val Ala Val Tyr Tyr Cys
            20                  25                  30

<210> SEQ ID NO 33
<211> LENGTH: 32
<212> TYPE: PRT
<213> ORGANISM: ARTIFICIAL SEQUENCE
<220> FEATURE:
<223> OTHER INFORMATION: FRL3 VARIANT J

<400> SEQUENCE: 33

Gly Val Pro Asp Arg Phe Ser Gly Ser Gly Ser Gly Thr Asp Phe Thr
1               5                   10                  15

Leu Thr Ile Asp Ser Leu Gln Ala Glu Asp Val Ala Val Tyr Tyr Cys
            20                  25                  30

<210> SEQ ID NO 34
<211> LENGTH: 32
<212> TYPE: PRT
<213> ORGANISM: ARTIFICIAL SEQUENCE
<220> FEATURE:
<223> OTHER INFORMATION: FRL3 VARIANT L

<400> SEQUENCE: 34

Gly Val Pro Asp Arg Phe Ser Gly Ser Gly Ser Arg Thr Asp Phe Thr
1               5                   10                  15

Leu Thr Ile Asp Pro Leu Gln Ala Glu Asp Val Ala Val Tyr Tyr Cys
            20                  25                  30

<210> SEQ ID NO 35
<211> LENGTH: 32
<212> TYPE: PRT
<213> ORGANISM: ARTIFICIAL SEQUENCE
```

```
<220> FEATURE:
<223> OTHER INFORMATION: FRL3 VARIANT N

<400> SEQUENCE: 35

Gly Val Pro Asp Arg Phe Ser Gly Ser Gly Ser Arg Thr Asp Phe Thr
1               5                   10                  15

Leu Thr Ile Asp Pro Val Gln Ala Glu Asp Val Ala Val Tyr Tyr Cys
            20                  25                  30

<210> SEQ ID NO 36
<211> LENGTH: 32
<212> TYPE: PRT
<213> ORGANISM: ARTIFICIAL SEQUENCE
<220> FEATURE:
<223> OTHER INFORMATION: FRL3 VARIANT P

<400> SEQUENCE: 36

Gly Val Pro Asp Arg Phe Ser Gly Ser Gly Ser Arg Thr Asp Phe Thr
1               5                   10                  15

Leu Thr Ile Asp Ser Val Gln Ala Glu Asp Val Ala Val Tyr Tyr Cys
            20                  25                  30

<210> SEQ ID NO 37
<211> LENGTH: 32
<212> TYPE: PRT
<213> ORGANISM: ARTIFICIAL SEQUENCE
<220> FEATURE:
<223> OTHER INFORMATION: FRL3 VARIANT R

<400> SEQUENCE: 37

Gly Val Pro Asp Arg Phe Ser Gly Ser Gly Ser Arg Thr Asp Phe Thr
1               5                   10                  15

Leu Thr Ile Ser Ser Val Gln Ala Glu Asp Val Ala Val Tyr Tyr Cys
            20                  25                  30

<210> SEQ ID NO 38
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-NEW #1

<400> SEQUENCE: 38

Gly Val Pro Asp Arg Phe Ser Gly Ser Gly Ser Arg Thr Asp Phe Thr
1               5                   10                  15

Leu Thr Ile Ser Pro Val Gln Ala Glu Asp Val Ala Val Tyr Tyr Cys
            20                  25                  30

<210> SEQ ID NO 39
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-NEW #9

<400> SEQUENCE: 39

Gly Val Pro Asp Arg Phe Ser Gly Ser Gly Ser Gly Thr Asp Phe Thr
1               5                   10                  15

Leu Thr Ile Ser Ser Val Glu Ala Glu Asp Val Ala Val Tyr Tyr Cys
            20                  25                  30

<210> SEQ ID NO 40
<211> LENGTH: 32
<212> TYPE: PRT
<213> ORGANISM: ARTIFICIAL SEQUENCE
```

-continued

```
<220> FEATURE:
<223> OTHER INFORMATION: FRL3 VARIANT HT2-NEW #14

<400> SEQUENCE: 40

Gly Val Pro Asp Arg Phe Ser Gly Ser Gly Ser Arg Thr Asp Phe Thr
1               5                   10                  15

Leu Thr Ile Ser Pro Val Glu Ala Glu Asp Val Ala Val Tyr Tyr Cys
            20                  25                  30

<210> SEQ ID NO 41
<211> LENGTH: 32
<212> TYPE: PRT
<213> ORGANISM: ARTIFICIAL SEQUENCE
<220> FEATURE:
<223> OTHER INFORMATION: FRL3 HT2-NEW #21

<400> SEQUENCE: 41

Gly Val Pro Asp Arg Phe Ser Gly Ser Gly Ser Gly Thr Asp Phe Thr
1               5                   10                  15

Leu Thr Ile Ser Ser Val Glu Ala Glu Asp Val Ala Val Tyr Tyr Cys
            20                  25                  30

<210> SEQ ID NO 42
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-NEW # 67

<400> SEQUENCE: 42

Gly Val Pro Asp Arg Phe Ser Gly Ser Gly Ser Gly Thr Asp Phe Thr
1               5                   10                  15

Leu Thr Ile Asp Pro Leu Glu Ala Glu Asp Val Ala Val Tyr Tyr Cys
            20                  25                  30

<210> SEQ ID NO 43
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-NEW #74

<400> SEQUENCE: 43

Gly Val Pro Asp Arg Phe Ser Gly Ser Gly Ser Gly Thr Asp Phe Thr
1               5                   10                  15

Leu Thr Ile Ser Pro Val Gln Ala Glu Asp Val Ala Val Tyr Tyr Cys
            20                  25                  30

<210> SEQ ID NO 44
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-NEW #78

<400> SEQUENCE: 44

Gly Val Pro Asp Arg Phe Ser Gly Ser Gly Ser Gly Thr Asp Phe Thr
1               5                   10                  15

Leu Thr Ile Asp Ser Val Glu Ala Glu Asp Val Ala Val Tyr Tyr Cys
            20                  25                  30

<210> SEQ ID NO 45
<211> LENGTH: 32
<212> TYPE: PRT
<213> ORGANISM: ARTIFICIAL SEQUENCE
```

```
<220> FEATURE:
<223> OTHER INFORMATION: FRL3 VARIANT HT2-NEW #322

<400> SEQUENCE: 45

Gly Val Pro Asp Arg Phe Ser Gly Ser Gly Ser Arg Thr Asp Phe Thr
1               5                   10                  15

Leu Thr Ile Asp Ser Leu Glu Ala Glu Asp Val Ala Val Tyr Tyr Cys
            20                  25                  30

<210> SEQ ID NO 46
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-NEW #162

<400> SEQUENCE: 46

Gly Val Pro Asp Arg Phe Ser Gly Ser Gly Ser Gly Thr Asp Phe Thr
1               5                   10                  15

Leu Thr Ile Asp Pro Val Gln Ala Glu Asp Val Ala Val Tyr Tyr Cys
            20                  25                  30

<210> SEQ ID NO 47
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-DP27 # 7

<400> SEQUENCE: 47

Gly Val Pro Asp Arg Phe Ser Gly Ser Gly Ser Gly Thr Asp Phe Thr
1               5                   10                  15

Leu Thr Ile Asp Ser Val Gln Ala Glu Asp Val Ala Val Tyr Tyr Cys
            20                  25                  30

<210> SEQ ID NO 48
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-DP27 #57

<400> SEQUENCE: 48

Gly Val Pro Asp Arg Phe Ser Gly Ser Gly Ser Gly Thr Asp Phe Thr
1               5                   10                  15

Leu Thr Ile Ser Pro Val Glu Ala Glu Asp Val Ala Val Tyr Tyr Cys
            20                  25                  30

<210> SEQ ID NO 49
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-DP27 #73

<400> SEQUENCE: 49

Gly Val Pro Asp Arg Phe Ser Gly Ser Gly Ser Gly Thr Asp Phe Thr
1               5                   10                  15

Leu Thr Ile Asp Pro Val Glu Ala Glu Asp Val Ala Val Tyr Tyr Cys
            20                  25                  30

<210> SEQ ID NO 50
<211> LENGTH: 32
<212> TYPE: PRT
<213> ORGANISM: ARTIFICIAL SEQUENCE
```

-continued

```
<220> FEATURE:
<223> OTHER INFORMATION: FRL3 VARIANT HT2-DP27 #92

<400> SEQUENCE: 50

Gly Val Pro Asp Arg Phe Ser Gly Ser Gly Ser Gly Thr Asp Phe Thr
1               5                   10                  15

Leu Thr Ile Asp Thr Val Gln Ala Glu Asp Val Ala Val Tyr Tyr Cys
            20                  25                  30

<210> SEQ ID NO 51
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-DP27 #118

<400> SEQUENCE: 51

Gly Val Pro Asp Arg Phe Ser Gly Ser Gly Ser Arg Thr Asp Phe Thr
1               5                   10                  15

Leu Thr Ile Ser Pro Leu Gln Ala Glu Asp Val Ala Val Tyr Tyr Cys
            20                  25                  30

<210> SEQ ID NO 52
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-DP27 #123

<400> SEQUENCE: 52

Gly Val Pro Asp Arg Phe Ser Gly Ser Gly Ser Arg Thr Asp Phe Thr
1               5                   10                  15

Leu Thr Ile Ser Ser Leu Glu Ala Glu Asp Val Ala Val Tyr Tyr Cys
            20                  25                  30

<210> SEQ ID NO 53
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-DP27 #83

<400> SEQUENCE: 53

Gly Val Pro Asp Arg Phe Ser Gly Ser Gly Ser Arg Thr Asp Phe Thr
1               5                   10                  15

Leu Thr Ile Asp Pro Leu Glu Ala Glu Asp Val Ala Val Tyr Tyr Cys
            20                  25                  30

<210> SEQ ID NO 54
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-DP27 #135

<400> SEQUENCE: 54

Gly Val Pro Asp Arg Phe Ser Gly Ser Gly Ser Gly Thr Asp Phe Thr
1               5                   10                  15

Leu Thr Ile Ser Ser Leu Glu Ala Glu Asp Val Ala Val Tyr Tyr Cys
            20                  25                  30

<210> SEQ ID NO 55
<211> LENGTH: 32
<212> TYPE: PRT
<213> ORGANISM: ARTIFICIAL SEQUENCE
```

```
<220> FEATURE:
<223> OTHER INFORMATION: FRL3 VARIANT HT2-DP27 #273

<400> SEQUENCE: 55

Gly Val Pro Asp Arg Phe Ser Gly Ser Gly Ser Gly Thr Asp Phe Thr
1               5                   10                  15

Leu Thr Ile Ser Ser Val Gln Ala Glu Asp Val Ala Val Tyr Tyr Cys
            20                  25                  30

<210> SEQ ID NO 56
<211> LENGTH: 32
<212> TYPE: PRT
<213> ORGANISM: ARTIFICIAL SEQUENCE
<220> FEATURE:
<223> OTHER INFORMATION: FRL3 VARIANT HT2-DP27 #301

<400> SEQUENCE: 56

Gly Val Pro Asp Arg Phe Ser Gly Ser Gly Ser Gly Thr Asp Phe Thr
1               5                   10                  15

Leu Thr Ile Ser Pro Leu Gln Ala Glu Asp Val Ala Val Tyr Tyr Cys
            20                  25                  30

<210> SEQ ID NO 57
<211> LENGTH: 12
<212> TYPE: PRT
<213> ORGANISM: ARTIFICIAL SEQUENCE
<220> FEATURE:
<223> OTHER INFORMATION: FRL4 228 B/C

<400> SEQUENCE: 57

Phe Gly Gly Gly Thr Lys Leu Glu Ile Lys Arg Ala
1               5                   10

<210> SEQ ID NO 58
<211> LENGTH: 11
<212> TYPE: PRT
<213> ORGANISM: ARTIFICIAL SEQUENCE
<220> FEATURE:
<223> OTHER INFORMATION: FRL4 HT2

<400> SEQUENCE: 58

Phe Gly Gly Gly Thr Lys Val Glu Ile Lys Arg
1               5                   10

<210> SEQ ID NO 59
<211> LENGTH: 11
<212> TYPE: PRT
<213> ORGANISM: ARTIFICIAL SEQUENCE
<220> FEATURE:
<223> OTHER INFORMATION: FRL4 VARIANT B

<400> SEQUENCE: 59

Phe Gly Gly Gly Thr Lys Leu Glu Ile Lys Arg
1               5                   10

<210> SEQ ID NO 60
<211> LENGTH: 30
<212> TYPE: PRT
<213> ORGANISM: ARTIFICIAL SEQUENCE
<220> FEATURE:
<223> OTHER INFORMATION: FRH1 228 B/C

<400> SEQUENCE: 60

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Asn
```

<210> SEQ ID NO 61
<211> LENGTH: 30
<212> TYPE: PRT
<213> ORGANISM: ARTIFICIAL SEQUENCE
<220> FEATURE:
<223> OTHER INFORMATION: FRH1 DP27

<400> SEQUENCE: 61

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 62
<211> LENGTH: 30
<212> TYPE: PRT
<213> ORGANISM: ARTIFICIAL SEQUENCE
<220> FEATURE:
<223> OTHER INFORMATION: FRH1 NEW

<400> SEQUENCE: 62

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser
            20                  25                  30

<210> SEQ ID NO 63
<211> LENGTH: 30
<212> TYPE: PRT
<213> ORGANISM: ARTIFICIAL SEQUENCE
<220> FEATURE:
<223> OTHER INFORMATION: FRH1 VARIANT HT2-NEW #73

<400> SEQUENCE: 63

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser
            20                  25                  30

<210> SEQ ID NO 64
<211> LENGTH: 30
<212> TYPE: PRT
<213> ORGANISM: ARTIFICIAL SEQUENCE
<220> FEATURE:
<223> OTHER INFORMATION: FRH1 HT2-DP27 #7

<400> SEQUENCE: 64

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Asn
            20                  25                  30

<210> SEQ ID NO 65
<211> LENGTH: 30
<212> TYPE: PRT
<213> ORGANISM: ARTIFICIAL SEQUENCE
<220> FEATURE:
<223> OTHER INFORMATION: FRH1 VARIANT HT2-DP27 #40

<400> SEQUENCE: 65

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser 20                  25                  30

<210> SEQ ID NO 66
<211> LENGTH: 30
<212> TYPE: PRT
<213> ORGANISM: ARTIFICIAL SEQUENCE
<220> FEATURE:
<223> OTHER INFORMATION: FRH1 VARIANT HT2-DP27 #268

<400> SEQUENCE: 66

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Asn
            20                  25                  30

<210> SEQ ID NO 67
<211> LENGTH: 14
<212> TYPE: PRT
<213> ORGANISM: ARTIFICIAL SEQUENCE
<220> FEATURE:
<223> OTHER INFORMATION: FRH2 228 B/C

<400> SEQUENCE: 67

Trp Val Arg Gln Pro Pro Gly Lys Gly Leu Glu Trp Leu Gly
1               5                   10

<210> SEQ ID NO 68
<211> LENGTH: 14
<212> TYPE: PRT
<213> ORGANISM: ARTIFICIAL SEQUENCE
<220> FEATURE:
<223> OTHER INFORMATION: FRH2 DP27

<400> SEQUENCE: 68

Trp Ile Arg Gln Pro Pro Gly Lys Ala Leu Glu Trp Leu Ala
1               5                   10

<210> SEQ ID NO 69
<211> LENGTH: 14
<212> TYPE: PRT
<213> ORGANISM: ARTIFICIAL SEQUENCE
<220> FEATURE:
<223> OTHER INFORMATION: FRH2 NEW

<400> SEQUENCE: 69

Trp Val Arg Gln Pro Pro Gly Arg Gly Leu Glu Trp Ile Gly
1               5                   10

<210> SEQ ID NO 70
<211> LENGTH: 14
<212> TYPE: PRT
<213> ORGANISM: ARTIFICIAL SEQUENCE
<220> FEATURE:
<223> OTHER INFORMATION: FRH2 VARIANT 1

<400> SEQUENCE: 70

Trp Val Arg Gln Pro Pro Gly Lys Ala Leu Glu Trp Leu Gly
1               5                   10

<210> SEQ ID NO 71
<211> LENGTH: 14
<212> TYPE: PRT
<213> ORGANISM: ARTIFICIAL SEQUENCE
<220> FEATURE:
<223> OTHER INFORMATION: FRH2 VARIANT 3

<400> SEQUENCE: 71

Trp Ile Arg Gln Pro Pro Gly Lys Gly Leu Glu Trp Leu Gly
1               5                   10

<210> SEQ ID NO 72
<211> LENGTH: 14
<212> TYPE: PRT
<213> ORGANISM: ARTIFICIAL SEQUENCE
<220> FEATURE:
<223> OTHER INFORMATION: FRH2 VARIANT HT2-DP27 #7

<400> SEQUENCE: 72

Trp Ile Arg Gln Pro Pro Gly Lys Ala Leu Glu Trp Leu Gly
1               5                   10

<210> SEQ ID NO 73
<211> LENGTH: 14
<212> TYPE: PRT
<213> ORGANISM: ARTIFICIAL SEQUENCE
<220> FEATURE:
<223> OTHER INFORMATION: FRH2 VARIANT HT2-DP27 # 43

<400> SEQUENCE: 73

Trp Ile Arg Gln Pro Pro Gly Lys Gly Leu Glu Trp Leu Ala
1               5                   10

<210> SEQ ID NO 74
<211> LENGTH: 14
<212> TYPE: PRT
<213> ORGANISM: ARTIFICIAL SEQUENCE
<220> FEATURE:
<223> OTHER INFORMATION: FRH2 VARIANT HT2-DP27 #50

<400> SEQUENCE: 74

Trp Val Arg Gln Pro Pro Gly Lys Gly Leu Glu Trp Leu Ala
1               5                   10

<210> SEQ ID NO 75
<211> LENGTH: 14
<212> TYPE: PRT
<213> ORGANISM: ARTIFICIAL SEQUENCE
<220> FEATURE:
<223> OTHER INFORMATION: FRH2 VARIANT HT2-DP27 #100

<400> SEQUENCE: 75

Trp Val Arg Gln Pro Pro Gly Lys Ala Leu Glu Trp Leu Ala
1               5                   10

<210> SEQ ID NO 76
<211> LENGTH: 32
<212> TYPE: PRT
<213> ORGANISM: ARTIFICIAL SEQUENCE
<220> FEATURE:
<223> OTHER INFORMATION: FRH3 228 B/C

<400> SEQUENCE: 76

Arg Leu Asn Ile Ser Lys Asp Ser Ser Lys Ser Gln Val Phe Leu Lys
1               5                   10                  15

Met Ser Ser Leu Gln Ser Asp Asp Thr Ala Arg Tyr Tyr Cys Ala Gly
            20                  25                  30

<210> SEQ ID NO 77
<211> LENGTH: 32
<212> TYPE: PRT
<213> ORGANISM: ARTIFICIAL SEQUENCE
<220> FEATURE:
<223> OTHER INFORMATION: FRH3 DP27

<400> SEQUENCE: 77

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 78
<211> LENGTH: 32
<212> TYPE: PRT
<213> ORGANISM: ARTIFICIAL SEQUENCE
<220> FEATURE:
<223> OTHER INFORMATION: FRH3 NEW

<400> SEQUENCE: 78

Arg Val Thr Met Leu Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Arg
            20                  25                  30

<210> SEQ ID NO 79
<211> LENGTH: 32
<212> TYPE: PRT
<213> ORGANISM: ARTIFICIAL SEQUENCE
<220> FEATURE:
<223> OTHER INFORMATION: FRH3 VARIANT 1

<400> SEQUENCE: 79

Arg Leu Thr Ile Ser Lys Asp Ser Ser Lys Asn Gln Val Val Leu Thr
1               5                   10                  15

Met Thr Asn Met Asp Pro Val Asp Thr Ala Thr Tyr Tyr Cys Ala Gly
            20                  25                  30

<210> SEQ ID NO 80
<211> LENGTH: 32
<212> TYPE: PRT
<213> ORGANISM: ARTIFICIAL SEQUENCE
<220> FEATURE:
<223> OTHER INFORMATION: FRH3 VARIANT 3

<400> SEQUENCE: 80

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Gly
            20                  25                  30

<210> SEQ ID NO 81
<211> LENGTH: 32
<212> TYPE: PRT
<213> ORGANISM: ARTIFICIAL SEQUENCE
<220> FEATURE:
<223> OTHER INFORMATION: FRH3 VARIANT 4

<400> SEQUENCE: 81

Arg Leu Thr Ile Ser Lys Asp Thr Ser Lys Asn Gln Val Val Leu Thr
1               5                   10                  15

Met Thr Asn Met Asp Pro Val Asp Thr Ala Arg Tyr Tyr Cys Ala Gly
            20                  25                  30

<210> SEQ ID NO 82
<211> LENGTH: 32
<212> TYPE: PRT
<213> ORGANISM: ARTIFICIAL SEQUENCE
<220> FEATURE:
<223> OTHER INFORMATION: FRH3 HT2-NEW #1

<400> SEQUENCE: 82

-continued

Arg Leu Asn Met Ser Lys Asp Thr Ser Lys Asn Gln Phe Phe Leu Arg
1               5                   10                  15

Leu Ser Ser Val Thr Ala Ala Asp Thr Ala Val Tyr Tyr Cys Ala Gly
            20                  25                  30

<210> SEQ ID NO 83
<211> LENGTH: 32
<212> TYPE: PRT
<213> ORGANISM: ARTIFICIAL SEQUENCE
<220> FEATURE:
<223> OTHER INFORMATION: FRH3 VARIANT HT2-NEW #9

<400> SEQUENCE: 83

Arg Leu Asn Met Ser Lys Asp Thr Ser Lys Asn Gln Phe Phe Leu Arg
1               5                   10                  15

Leu Ser Ser Val Thr Ala Ala Asp Thr Ala Arg Tyr Tyr Cys Ala Gly
            20                  25                  30

<210> SEQ ID NO 84
<211> LENGTH: 32
<212> TYPE: PRT
<213> ORGANISM: ARTIFICIAL SEQUENCE
<220> FEATURE:
<223> OTHER INFORMATION: FRH3 VARIANT HT2-NEW #14

<400> SEQUENCE: 84

Arg Val Asn Met Ser Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Arg
            20                  25                  30

<210> SEQ ID NO 85
<211> LENGTH: 32
<212> TYPE: PRT
<213> ORGANISM: ARTIFICIAL SEQUENCE
<220> FEATURE:
<223> OTHER INFORMATION: FRH3 VARIANT HT2-DP27 #26

<400> SEQUENCE: 85

Arg Leu Asn Ile Ser Lys Asp Thr Ser Lys Asn Gln Val Val Leu Thr
1               5                   10                  15

Met Thr Asn Met Asp Pro Val Asp Thr Ala Arg Tyr Tyr Cys Ala Arg
            20                  25                  30

<210> SEQ ID NO 86
<211> LENGTH: 32
<212> TYPE: PRT
<213> ORGANISM: ARTIFICIAL SEQUENCE
<220> FEATURE:
<223> OTHER INFORMATION: FRH3 VARIANT HT2-DP27 #275

<400> SEQUENCE: 86

Arg Leu Thr Ile Ser Lys Asp Ile Ser Lys Asn Gln Val Val Leu Thr
1               5                   10                  15

Met Thr Asn Met Asp Pro Val Asp Thr Ala Arg Tyr Tyr Cys Ala Gly
            20                  25                  30

<210> SEQ ID NO 87
<211> LENGTH: 32
<212> TYPE: PRT
<213> ORGANISM: ARTIFICIAL SEQUENCE
<220> FEATURE:
<223> OTHER INFORMATION: FRH3 VARIANT HT2-DP27 #301

<400> SEQUENCE: 87

```
Arg Leu Asn Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Gly
            20                  25                  30
```

<210> SEQ ID NO 88
<211> LENGTH: 32
<212> TYPE: PRT
<213> ORGANISM: ARTIFICIAL SEQUENCE
<220> FEATURE:
<223> OTHER INFORMATION: FRH3 VARIANT HT2-DP27 #580

<400> SEQUENCE: 88

```
Arg Leu Asn Ile Ser Lys Asp Ser Ser Lys Asn Gln Val Val Leu Thr
1               5                   10                  15

Met Thr Asn Met Asp Pro Val Asp Thr Ala Thr Tyr Tyr Cys Ala Gly
            20                  25                  30
```

<210> SEQ ID NO 89
<211> LENGTH: 32
<212> TYPE: PRT
<213> ORGANISM: ARTIFICIAL SEQUENCE
<220> FEATURE:
<223> OTHER INFORMATION: FRH3 VARIANT HT2-DP27 #345

<400> SEQUENCE: 89

```
Arg Leu Asn Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30
```

<210> SEQ ID NO 90
<211> LENGTH: 32
<212> TYPE: PRT
<213> ORGANISM: ARTIFICIAL SEQUENCE
<220> FEATURE:
<223> OTHER INFORMATION: FRH3 VARIANT HT2-DP27 #634

<400> SEQUENCE: 90

```
Arg Leu Thr Ile Ser Lys Asp Ser Ser Lys Asn Gln Val Val Leu Thr
1               5                   10                  15

Met Thr Asn Met Asp Pro Val Asp Thr Ala Arg Tyr Tyr Cys Ala Gly
            20                  25                  30
```

<210> SEQ ID NO 91
<211> LENGTH: 11
<212> TYPE: PRT
<213> ORGANISM: ARTIFICIAL SEQUENCE
<220> FEATURE:
<223> OTHER INFORMATION: FRH4 228B/C

<400> SEQUENCE: 91

```
Trp Gly His Gly Thr Ser Val Thr Val Ser Ser
1               5                   10
```

<210> SEQ ID NO 92
<211> LENGTH: 11
<212> TYPE: PRT
<213> ORGANISM: ARTIFICIAL
<220> FEATURE:
<223> OTHER INFORMATION: FRH4 DP27

<400> SEQUENCE: 92

```
Trp Gly Gln Gly Ser Leu Val Thr Val Ser Ser
1               5                   10
```

<210> SEQ ID NO 93
<211> LENGTH: 112
<212> TYPE: PRT
<213> ORGANISM: ARTIFICIAL SEQUENCE
<220> FEATURE:
<223> OTHER INFORMATION: VARIABLE LIGHT CHAIN OF CL5

<400> SEQUENCE: 93

```
Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Gln Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Ala
                85                  90                  95

Glu Asp Pro Arg Thr Phe Gly Gly Gly Thr Lys Val Glu Ile Lys Arg
            100                 105                 110
```

<210> SEQ ID NO 94
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN OF CL5

<400> SEQUENCE: 94

```
Gln Val Thr Leu Arg Glu Ser Gly Pro Ala Leu Val Lys Pro Thr Gln
1               5                   10                  15

Thr Leu Thr Leu Thr Cys Thr Gly Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Val Asp Gly Tyr Tyr Pro Tyr Ala Met Lys Asn Trp Gly Gln Gly Ser
            100                 105                 110

Leu Val Thr Val Ser Ser
        115
```

<210> SEQ ID NO 95
<211> LENGTH: 112
<212> TYPE: PRT
<213> ORGANISM: ARTIFICIAL SEQUENCE
<220> FEATURE:
<223> OTHER INFORMATION: VARIABLE LIGHT CHAIN OF CL-13

<400> SEQUENCE: 95

```
Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30
```

```
                20                  25                  30
Gly Gln Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

<210> SEQ ID NO 96
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN OF CL-13

<400> SEQUENCE: 96

Gln Val Thr Leu Arg Glu Ser Gly Pro Ala Leu Val Lys Pro Thr Gln
1               5                   10                  15

Thr Leu Thr Leu Thr Cys Thr Gly Ser Gly Phe Ser Leu Ser Ala Lys
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Val Asp Gly Tyr Tyr Pro Tyr Ala Met Ser Asn Trp Gly Gln Gly Ser
            100                 105                 110

Leu Val Thr Val Ser Ser
        115

<210> SEQ ID NO 97
<211> LENGTH: 112
<212> TYPE: PRT
<213> ORGANISM: ARTIFICIAL SEQUENCE
<220> FEATURE:
<223> OTHER INFORMATION: VARIABLE LIGHT CHAIN OF CL-50

<400> SEQUENCE: 97

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Gln Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Ala
                85                  90                  95

Glu Asp Pro Arg Thr Phe Gly Gly Gly Thr Lys Val Glu Ile Lys Arg
```

<210> SEQ ID NO 98
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN OF CL-50

<400> SEQUENCE: 98

Gln Val Thr Leu Arg Glu Ser Gly Pro Ala Leu Val Lys Pro Thr Gln
1               5                   10                  15

Thr Leu Thr Leu Thr Cys Thr Gly Ser Gly Phe Ser Leu Ser Ala Lys
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Val Asp Gly Tyr Tyr Pro Tyr Ala Met Lys Asn Trp Gly Gln Gly Ser
            100                 105                 110

Leu Val Thr Val Ser Ser
        115

<210> SEQ ID NO 99
<211> LENGTH: 15
<212> TYPE: PRT
<213> ORGANISM: ARTIFICIAL SEQUENCE
<220> FEATURE:
<223> OTHER INFORMATION: CDR-L1 228B/C

<400> SEQUENCE: 99

Arg Ala Ser Lys Ser Val Asp Ser Tyr Gly Asn Ser Phe Met His
1               5                   10                  15

<210> SEQ ID NO 100
<211> LENGTH: 15
<212> TYPE: PRT
<213> ORGANISM: ARTIFICIAL SEQUENCE
<220> FEATURE:
<223> OTHER INFORMATION: CDR-L1 VARIANT 1

<400> SEQUENCE: 100

Arg Ala Ser Lys Ser Val Asp Ser Tyr Gly Gln Ser Phe Met His
1               5                   10                  15

<210> SEQ ID NO 101
<211> LENGTH: 15
<212> TYPE: PRT
<213> ORGANISM: ARTIFICIAL SEQUENCE
<220> FEATURE:
<223> OTHER INFORMATION: CDR-L1 VARIANT 2

<400> SEQUENCE: 101

Arg Ala Ser Lys Ser Val Asp Ser Tyr Gly Gln Ser Phe Leu His
1               5                   10                  15

<210> SEQ ID NO 102
<211> LENGTH: 15
<212> TYPE: PRT
<213> ORGANISM: ARTIFICIAL SEQUENCE

```
<220> FEATURE:
<223> OTHER INFORMATION: CDR-L1 VARIANT 3

<400> SEQUENCE: 102

Arg Ala Ser Lys Ser Val Asp Ser Tyr Gly Asn Ser Tyr Met His
1               5                   10                  15

<210> SEQ ID NO 103
<211> LENGTH: 15
<212> TYPE: PRT
<213> ORGANISM: ARTIFICIAL SEQUENCE
<220> FEATURE:
<223> OTHER INFORMATION: CDR-L1 VARIANT 4

<400> SEQUENCE: 103

Arg Ala Ser Lys Ser Val Asp Ser Tyr Gly Asn Ser Phe Leu His
1               5                   10                  15

<210> SEQ ID NO 104
<211> LENGTH: 7
<212> TYPE: PRT
<213> ORGANISM: ARTIFICIAL SEQUENCE
<220> FEATURE:
<223> OTHER INFORMATION: CDR-L2 228B/C

<400> SEQUENCE: 104

Leu Ala Ser Asn Leu Glu Ser
1               5

<210> SEQ ID NO 105
<211> LENGTH: 7
<212> TYPE: PRT
<213> ORGANISM: ARTIFICIAL SEQUENCE
<220> FEATURE:
<223> OTHER INFORMATION: CDR-L2 VARIANT 1

<400> SEQUENCE: 105

Leu Ala Ser Asn Leu Asn Ser
1               5

<210> SEQ ID NO 106
<211> LENGTH: 7
<212> TYPE: PRT
<213> ORGANISM: ARTIFICIAL SEQUENCE
<220> FEATURE:
<223> OTHER INFORMATION: CDR-L2 VARIANT 2

<400> SEQUENCE: 106

Leu Ala Ser Asn Leu Gln Ser
1               5

<210> SEQ ID NO 107
<211> LENGTH: 7
<212> TYPE: PRT
<213> ORGANISM: ARTIFICIAL SEQUENCE
<220> FEATURE:
<223> OTHER INFORMATION: CDR-L2 VARIANT 3

<400> SEQUENCE: 107

Leu Ala Thr Asn Leu Glu Ser
1               5

<210> SEQ ID NO 108
<211> LENGTH: 7
<212> TYPE: PRT
<213> ORGANISM: ARTIFICIAL SEQUENCE
<220> FEATURE:
<223> OTHER INFORMATION: CDR-L2 VARIANT 4
```

```
<400> SEQUENCE: 108

Leu Ala Ser Asn Leu Lys Ser
1               5

<210> SEQ ID NO 109
<211> LENGTH: 7
<212> TYPE: PRT
<213> ORGANISM: ARTIFICIAL SEQUENCE
<220> FEATURE:
<223> OTHER INFORMATION: CDR-L2 VARIANT 5

<400> SEQUENCE: 109

Leu Ala Ser Asn Leu Glu Lys
1               5

<210> SEQ ID NO 110
<211> LENGTH: 7
<212> TYPE: PRT
<213> ORGANISM: ARTIFICIAL SEQUENCE
<220> FEATURE:
<223> OTHER INFORMATION: CDR-L2 VARIANT 6

<400> SEQUENCE: 110

Leu Ala Ser Arg Leu Glu Ser
1               5

<210> SEQ ID NO 111
<211> LENGTH: 7
<212> TYPE: PRT
<213> ORGANISM: ARTIFICIAL SEQUENCE
<220> FEATURE:
<223> OTHER INFORMATION: CDR-L2 VARIANT 7

<400> SEQUENCE: 111

Leu Ala Ser Asn Leu His Ser
1               5

<210> SEQ ID NO 112
<211> LENGTH: 7
<212> TYPE: PRT
<213> ORGANISM: ARTIFICIAL SEQUENCE
<220> FEATURE:
<223> OTHER INFORMATION: CDR-L2 VARIANT 8

<400> SEQUENCE: 112

Leu Ala Ser Asn Leu Ser Ser
1               5

<210> SEQ ID NO 113
<211> LENGTH: 7
<212> TYPE: PRT
<213> ORGANISM: ARTIFICIAL SEQUENCE
<220> FEATURE:
<223> OTHER INFORMATION: CDR-L2 VARIANT 9

<400> SEQUENCE: 113

Leu Ala Ser Phe Leu Glu Ser
1               5

<210> SEQ ID NO 114
<211> LENGTH: 7
<212> TYPE: PRT
<213> ORGANISM: ARTIFICIAL SEQUENCE
<220> FEATURE:
<223> OTHER INFORMATION: CDR-L2 VARIANT 10

<400> SEQUENCE: 114
```

Leu Ala Asn Asn Leu Glu Ser
1               5

<210> SEQ ID NO 115
<211> LENGTH: 9
<212> TYPE: PRT
<213> ORGANISM: ARTIFICIAL SEQUENCE
<220> FEATURE:
<223> OTHER INFORMATION: CDR-L3 228B/C

<400> SEQUENCE: 115

Gln Gln Asn Asn Glu Asp Pro Arg Thr
1               5

<210> SEQ ID NO 116
<211> LENGTH: 9
<212> TYPE: PRT
<213> ORGANISM: ARTIFICIAL SEQUENCE
<220> FEATURE:
<223> OTHER INFORMATION: CDR-L3 VARIANT 1

<400> SEQUENCE: 116

Gln Gln Asn Ala Glu Asp Pro Arg Thr
1               5

<210> SEQ ID NO 117
<211> LENGTH: 5
<212> TYPE: PRT
<213> ORGANISM: ARTIFICIAL SEQUENCE
<220> FEATURE:
<223> OTHER INFORMATION: CDR-H1 228B/C

<400> SEQUENCE: 117

Ala Tyr Ser Val Asn
1               5

<210> SEQ ID NO 118
<211> LENGTH: 5
<212> TYPE: PRT
<213> ORGANISM: ARTIFICIAL SEQUENCE
<220> FEATURE:
<223> OTHER INFORMATION: CDR-H1 VARIANT 1

<400> SEQUENCE: 118

Ala Lys Ser Val Asn
1               5

<210> SEQ ID NO 119
<211> LENGTH: 5
<212> TYPE: PRT
<213> ORGANISM: ARTIFICIAL SEQUENCE
<220> FEATURE:
<223> OTHER INFORMATION: CDR-H1 VARIANT 2

<400> SEQUENCE: 119

Ala Asn Ser Val Asn
1               5

<210> SEQ ID NO 120
<211> LENGTH: 5
<212> TYPE: PRT
<213> ORGANISM: ARTIFICIAL SEQUENCE
<220> FEATURE:
<223> OTHER INFORMATION: CDR-H1 VARIANT 3

<400> SEQUENCE: 120

Gly Tyr Ser Val Asn

```
1               5

<210> SEQ ID NO 121
<211> LENGTH: 5
<212> TYPE: PRT
<213> ORGANISM: ARTIFICIAL SEQUENCE
<220> FEATURE:
<223> OTHER INFORMATION: CDR-H1 VARIANT 4

<400> SEQUENCE: 121

Ala His Ser Val Asn
1               5

<210> SEQ ID NO 122
<211> LENGTH: 5
<212> TYPE: PRT
<213> ORGANISM: ARTIFICIAL SEQUENCE
<220> FEATURE:
<223> OTHER INFORMATION: CDR-H1 VARIANT 5

<400> SEQUENCE: 122

Ala Arg Ser Val Asn
1               5

<210> SEQ ID NO 123
<211> LENGTH: 16
<212> TYPE: PRT
<213> ORGANISM: ARTIFICIAL SEQUENCE
<220> FEATURE:
<223> OTHER INFORMATION: CDR-H2 228B/C

<400> SEQUENCE: 123

Met Ile Trp Gly Asp Gly Lys Ile Val Tyr Asn Ser Ala Leu Lys Ser
1               5                   10                  15

<210> SEQ ID NO 124
<211> LENGTH: 16
<212> TYPE: PRT
<213> ORGANISM: ARTIFICIAL SEQUENCE
<220> FEATURE:
<223> OTHER INFORMATION: CDR-H2 VARIANT 1

<400> SEQUENCE: 124

Met Ile Trp Gly Asp Gly Lys Ile Ser Tyr Asn Ser Ala Leu Lys Ser
1               5                   10                  15

<210> SEQ ID NO 125
<211> LENGTH: 16
<212> TYPE: PRT
<213> ORGANISM: ARTIFICIAL SEQUENCE
<220> FEATURE:
<223> OTHER INFORMATION: CDR-H2 VARIANT 2

<400> SEQUENCE: 125

Met Ile Trp Gly Asp Gly Lys Ile Val Tyr Asn Ser Ala Leu Glu Ser
1               5                   10                  15

<210> SEQ ID NO 126
<211> LENGTH: 16
<212> TYPE: PRT
<213> ORGANISM: ARTIFICIAL SEQUENCE
<220> FEATURE:
<223> OTHER INFORMATION: CDR-H2 VARIANT 3

<400> SEQUENCE: 126

Met Ile Trp Gly Asp Gly Lys Ile Val Tyr Asn Ser Ala Leu Lys Ser
1               5                   10                  15
```

```
<210> SEQ ID NO 127
<211> LENGTH: 16
<212> TYPE: PRT
<213> ORGANISM: ARTIFICIAL SEQUENCE
<220> FEATURE:
<223> OTHER INFORMATION: CDR-H2 VARIANT 4

<400> SEQUENCE: 127

Met Ile Trp Gly Asp Gly Lys Ile Val Tyr Asn Ser Asp Leu Lys Ser
1               5                   10                  15

<210> SEQ ID NO 128
<211> LENGTH: 16
<212> TYPE: PRT
<213> ORGANISM: ARTIFICIAL SEQUENCE
<220> FEATURE:
<223> OTHER INFORMATION: CDR-H2 VARIANT 5

<400> SEQUENCE: 128

Met Ile Trp Gly Asp Gly Lys Val Val Tyr Asn Ser Ala Leu Lys Ser
1               5                   10                  15

<210> SEQ ID NO 129
<211> LENGTH: 16
<212> TYPE: PRT
<213> ORGANISM: ARTIFICIAL SEQUENCE
<220> FEATURE:
<223> OTHER INFORMATION: CDR-H2 VARIANT 6

<400> SEQUENCE: 129

Met Ile Trp Gly Asp Gly Lys Ile Val Tyr Asn Ser Glu Leu Lys Ser
1               5                   10                  15

<210> SEQ ID NO 130
<211> LENGTH: 16
<212> TYPE: PRT
<213> ORGANISM: ARTIFICIAL SEQUENCE
<220> FEATURE:
<223> OTHER INFORMATION: CDR-H2 VARIANT 7

<400> SEQUENCE: 130

Met Ile Trp Gly Asp Gly Lys Ile Ala Tyr Asn Ser Ala Leu Lys Ser
1               5                   10                  15

<210> SEQ ID NO 131
<211> LENGTH: 16
<212> TYPE: PRT
<213> ORGANISM: ARTIFICIAL SEQUENCE
<220> FEATURE:
<223> OTHER INFORMATION: CDR-H2 VARIANT 8

<400> SEQUENCE: 131

Met Ile Trp Gly Asp Gly Lys Ile Val Tyr Asn Ser Ala Leu Lys Glu
1               5                   10                  15

<210> SEQ ID NO 132
<211> LENGTH: 16
<212> TYPE: PRT
<213> ORGANISM: ARTIFICIAL SEQUENCE
<220> FEATURE:
<223> OTHER INFORMATION: CDR-H2 VARIANT 9

<400> SEQUENCE: 132

Met Val Trp Gly Asp Gly Lys Ile Val Tyr Asn Ser Ala Leu Lys Ser
1               5                   10                  15

<210> SEQ ID NO 133
```

```
<211> LENGTH: 16
<212> TYPE: PRT
<213> ORGANISM: ARTIFICIAL SEQUENCE
<220> FEATURE:
<223> OTHER INFORMATION: CDR-H2 VARIANT 10

<400> SEQUENCE: 133

Met Ile Trp Gly Asp Gly Lys Ile Val Tyr Asn Ser Ala Leu Ala Ser
1               5                   10                  15

<210> SEQ ID NO 134
<211> LENGTH: 16
<212> TYPE: PRT
<213> ORGANISM: ARTIFICIAL SEQUENCE
<220> FEATURE:
<223> OTHER INFORMATION: CDR-H2 VARIANT 11

<400> SEQUENCE: 134

Met Ile Trp Gly Asp Gly Lys Lys Val Tyr Asn Ser Ala Leu Lys Ser
1               5                   10                  15

<210> SEQ ID NO 135
<211> LENGTH: 10
<212> TYPE: PRT
<213> ORGANISM: ARTIFICIAL SEQUENCE
<220> FEATURE:
<223> OTHER INFORMATION: CDR-H3 228B/C

<400> SEQUENCE: 135

Asp Gly Tyr Tyr Pro Tyr Ala Met Asp Asn
1               5                   10

<210> SEQ ID NO 136
<211> LENGTH: 10
<212> TYPE: PRT
<213> ORGANISM: ARTIFICIAL SEQUENCE
<220> FEATURE:
<223> OTHER INFORMATION: CDR-H3 VARIANT 1

<400> SEQUENCE: 136

Asp Gly Arg Tyr Pro Tyr Ala Met Asp Asn
1               5                   10

<210> SEQ ID NO 137
<211> LENGTH: 10
<212> TYPE: PRT
<213> ORGANISM: ARTIFICIAL SEQUENCE
<220> FEATURE:
<223> OTHER INFORMATION: CDR-H3 VARIANT 2

<400> SEQUENCE: 137

Asp Gly Tyr Tyr Pro Tyr Ala Met Lys Asn
1               5                   10

<210> SEQ ID NO 138
<211> LENGTH: 10
<212> TYPE: PRT
<213> ORGANISM: ARTIFICIAL SEQUENCE
<220> FEATURE:
<223> OTHER INFORMATION: CDR-H3 VARIANT 3

<400> SEQUENCE: 138

Asp Gly Arg Tyr Pro Tyr Ala Met Lys Asn
1               5                   10

<210> SEQ ID NO 139
<211> LENGTH: 10
<212> TYPE: PRT
```

```
<213> ORGANISM: ARTIFICIAL SEQUENCE
<220> FEATURE:
<223> OTHER INFORMATION: CDR-H3 VARIANT 4

<400> SEQUENCE: 139

Asp Gly Tyr Tyr Pro Tyr Ala Met Ser Asn
1               5                   10

<210> SEQ ID NO 140
<211> LENGTH: 10
<212> TYPE: PRT
<213> ORGANISM: ARTIFICIAL SEQUENCE
<220> FEATURE:
<223> OTHER INFORMATION: CDR-H3 VARIANT 5

<400> SEQUENCE: 140

Asp Gly Tyr Tyr Pro Tyr Ala Met Ala Asn
1               5                   10

<210> SEQ ID NO 141
<211> LENGTH: 10
<212> TYPE: PRT
<213> ORGANISM: ARTIFICIAL SEQUENCE
<220> FEATURE:
<223> OTHER INFORMATION: CDR-H3 VARIANT 6

<400> SEQUENCE: 141

Asp Gly Tyr Tyr Pro Tyr Ala Leu Asp Asn
1               5                   10

<210> SEQ ID NO 142
<211> LENGTH: 112
<212> TYPE: PRT
<213> ORGANISM: ARTIFICIAL SEQUENCE
<220> FEATURE:
<223> OTHER INFORMATION: VARIABLE LIGHT CHAIN OF CL-89

<400> SEQUENCE: 142

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

<210> SEQ ID NO 143
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN CL-276G

<400> SEQUENCE: 143

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
```

-continued

```
                20                  25                  30
Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
        50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser
            115

<210> SEQ ID NO 144
<211> LENGTH: 112
<212> TYPE: PRT
<213> ORGANISM: ARTIFICIAL SEQUENCE
<220> FEATURE:
<223> OTHER INFORMATION: VARIABLE LIGHT CHAIN OF RL-36

<400> SEQUENCE: 144

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

<210> SEQ ID NO 145
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN RL-36

<400> SEQUENCE: 145

Gln Val Thr Leu Arg Glu Ser Gly Pro Ala Leu Val Lys Pro Thr Gln
1               5                   10                  15

Thr Leu Thr Leu Thr Cys Thr Gly Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Val Asp Gly Tyr Tyr Pro Tyr Ala Met Asp Asn Trp Gly Gln Gly Ser
```

-continued

<210> SEQ ID NO 146
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN RL-19

<400> SEQUENCE: 146

```
Gln Val Thr Leu Arg Glu Ser Gly Pro Ala Leu Val Lys Pro Thr Gln
1               5                   10                  15

Thr Leu Thr Leu Thr Cys Thr Ser Gly Phe Ser Leu Ser Ala Tyr
            20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
        50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Leu Asp Gly Tyr Tyr Pro Tyr Ala Met Asp Asn Trp Gly Gln Gly Ser
            100                 105                 110

Leu Val Thr Val Ser Ser
        115
```

<210> SEQ ID NO 147
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN RL-11

<400> SEQUENCE: 147

```
Gln Val Thr Leu Arg Glu Ser Gly Pro Ala Leu Val Lys Pro Thr Gln
1               5                   10                  15

Thr Leu Thr Leu Thr Cys Thr Ser Gly Phe Ser Leu Ser Ala Tyr
            20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
        50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Val Asp Gly Tyr Tyr Pro Tyr Ala Met Asp Asn Trp Gly Gln Gly Ser
            100                 105                 110

Leu Val Thr Val Ser Ser
        115
```

<210> SEQ ID NO 148
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN RL-8

-continued

```
<400> SEQUENCE: 148

Gln Val Thr Leu Arg Glu Ser Gly Pro Ala Leu Val Lys Pro Thr Gln
1               5                   10                  15

Thr Leu Thr Leu Thr Cys Thr Leu Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Ser Asp Gly Tyr Tyr Pro Tyr Ala Met Asp Asn Trp Gly Gln Gly Ser
            100                 105                 110

Leu Val Thr Val Ser Ser
        115

<210> SEQ ID NO 149
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN RL-45

<400> SEQUENCE: 149

Gln Val Thr Leu Arg Glu Ser Gly Pro Ala Leu Val Lys Pro Thr Gln
1               5                   10                  15

Thr Leu Thr Leu Thr Cys Thr Thr Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Thr Asp Gly Tyr Tyr Pro Tyr Ala Met Asp Asn Trp Gly Gln Gly Ser
            100                 105                 110

Leu Val Thr Val Ser Ser
        115

<210> SEQ ID NO 150
<211> LENGTH: 112
<212> TYPE: PRT
<213> ORGANISM: ARTIFICIAL SEQUENCE
<220> FEATURE:
<223> OTHER INFORMATION: VARIABLE LIGHT CHAIN RL-36-L1,59

<400> SEQUENCE: 150

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Gln Ser Phe Met His Trp Tyr Gln Gln Lys Pro Gly Gln Pro Pro
        35                  40                  45
```

```
Lys Leu Leu Ile Tyr Leu Ala Ser Asn Leu Glu Ser Gly Val Pro Asp
         50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                 85                  90                  95

Glu Asp Pro Arg Thr Phe Gly Gly Thr Lys Val Glu Ile Lys Arg
            100                 105                 110

<210> SEQ ID NO 151
<211> LENGTH: 118
<212> TYPE: PRT
<213> ORGANISM: ARTIFICIAL SEQUENCE
<220> FEATURE:
<223> OTHER INFORMATION: VARIABLE HEAVY CHAIN RL36-L1,59

<400> SEQUENCE: 151

Gln Val Thr Leu Arg Glu Ser Gly Pro Ala Leu Val Lys Pro Thr Gln
 1               5                  10                  15

Thr Leu Thr Leu Thr Cys Thr Gly Ser Gly Phe Ser Leu Ser Ala Tyr
             20                  25                  30

Ser Val Asn Trp Ile Arg Gln Pro Pro Gly Lys Ala Leu Glu Trp Leu
         35                  40                  45

Ala Met Ile Trp Gly Asp Gly Lys Ile Val Tyr Asn Ser Ala Leu Lys
     50                  55                  60

Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Val Asp Gly Tyr Tyr Pro Tyr Ala Met Asp Asn Trp Gly Gln Gly Ser
            100                 105                 110

Leu Val Thr Val Ser Ser
            115

<210> SEQ ID NO 152
<211> LENGTH: 248
<212> TYPE: PRT
<213> ORGANISM: ARTIFICIAL SEQUENCE
<220> FEATURE:
<223> OTHER INFORMATION: SINGLE CHAIN FV

<400> SEQUENCE: 152

Gln Val Thr Leu Arg Glu Ser Gly Pro Ala Leu Val Lys Pro Thr Gln
 1               5                  10                  15

Thr Leu Thr Leu Thr Cys Thr Val Ser Gly Phe Ser Leu Ser Ala Tyr
             20                  25                  30

Ser Val Asn Trp Ile Arg Gln Pro Pro Gly Lys Ala Leu Glu Trp Leu
         35                  40                  45

Ala Met Ile Trp Gly Asp Gly Lys Ile Val Tyr Asn Ser Ala Leu Lys
     50                  55                  60

Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Gly Asp Gly Tyr Tyr Pro Tyr Ala Met Asp Asn Trp Gly Gln Gly Ser
            100                 105                 110

Leu Val Thr Val Ser Ser Gly Gly Ser Ser Arg Ser Ser Ser Ser Gly
            115                 120                 125
```

```
Gly Gly Gly Ser Gly Gly Gly Asp Ile Val Met Thr Gln Ser Pro
        130             135             140
Asp Ser Leu Ser Val Ser Leu Gly Glu Arg Ala Thr Ile Asn Cys Arg
145             150                 155                 160
Ala Ser Lys Ser Val Asp Ser Tyr Gly Asn Ser Phe Met His Trp Tyr
                165                 170                 175
Gln Gln Lys Pro Gly Gln Pro Pro Lys Leu Leu Ile Tyr Leu Ala Ser
            180                 185                 190
Asn Leu Glu Ser Gly Val Pro Asp Arg Phe Ser Gly Ser Gly Ser Gly
            195                 200                 205
Thr Asp Phe Thr Leu Thr Ile Ser Ser Val Gln Ala Glu Asp Val Ala
        210                 215                 220
Val Tyr Tyr Cys Gln Gln Asn Asn Glu Asp Pro Arg Thr Phe Gly Gly
225             230                 235                 240
Gly Thr Lys Val Glu Ile Lys Arg
                245
```

```
<210> SEQ ID NO 153
<211> LENGTH: 23
<212> TYPE: PRT
<213> ORGANISM: Artificial Sequence
<220> FEATURE:
<223> OTHER INFORMATION: FRL1 VARIANT N

<400> SEQUENCE: 153

Asp Ile Val Leu Thr Gln Ser Pro Ala Ser Leu Ala Val Ser Leu Gly
1               5                   10                  15
Glu Arg Ala Thr Ile Asn Cys
            20
```

```
<210> SEQ ID NO 154
<211> LENGTH: 23
<212> TYPE: PRT
<213> ORGANISM: Artificial Sequence
<220> FEATURE:
<223> OTHER INFORMATION: FRL1 VARIANT HT2-DP27 #118

<400> SEQUENCE: 154

Asp Ile Val Leu Thr Gln Ser Pro Ala Ser Leu Ala Val Ser Leu Gly
1               5                   10                  15
Glu Arg Ala Thr Ile Asn Cys
            20
```

```
<210> SEQ ID NO 155
<211> LENGTH: 32
<212> TYPE: PRT
<213> ORGANISM: Artificial Sequence
<220> FEATURE:
<223> OTHER INFORMATION: FRL3 VARIANT HT2-dp27 #40

<400> SEQUENCE: 155

Gly Val Pro Asp Arg Phe Ser Gly Ser Gly Ser Arg Thr Asp Phe Thr
1               5                   10                  15
Leu Thr Ile Asp Ser Val Glu Ala Glu Asp Val Ala Val Tyr Tyr Cys
            20                  25                  30
```

```
<210> SEQ ID NO 156
<211> LENGTH: 32
<212> TYPE: PRT
<213> ORGANISM: Artificial Sequence
<220> FEATURE:
<223> OTHER INFORMATION: FRL3 VARIANT HT2-dp27 #26
```

-continued

```
<400> SEQUENCE: 156

Gly Val Pro Asp Arg Phe Ser Gly Ser Gly Ser Arg Thr Asp Phe Thr
1               5                   10                  15

Leu Thr Ile Asp Pro Val Glu Ala Glu Asp Val Ala Val Tyr Tyr Cys
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: FRL3 VARIANT HT2-dp27 #164

<400> SEQUENCE: 157

Gly Val Pro Asp Arg Phe Ser Gly Ser Gly Ser Arg Thr Asp Phe Thr
1               5                   10                  15

Leu Thr Ile Ser Pro Leu Glu Ala Glu Asp Val Ala Val Tyr Tyr Cys
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: FRL3 VARIANT HT2-dp27 #304

<400> SEQUENCE: 158

Gly Val Pro Asp Arg Phe Ser Gly Ser Gly Ser Arg Thr Asp Phe Thr
1               5                   10                  15

Leu Thr Ile Asp Ser Val Glu Ala Glu Asp Val Ala Val Tyr Tyr Cys
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: FRL3 VARIANT HT2-dp27 #274

<400> SEQUENCE: 159

Gly Val Pro Asp Arg Phe Ser Gly Ser Gly Ser Arg Thr Asp Phe Thr
1               5                   10                  15

Leu Thr Ile Asp Pro Val Gln Ala Glu Asp Val Ala Val Tyr Tyr Cys
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: FRL3 VARIANT HT2-dp27 #530

<400> SEQUENCE: 160

Gly Val Pro Asp Arg Phe Ser Gly Ser Gly Ser Arg Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: FRL3 VARIANT HT2-dp27 #374
```

<400> SEQUENCE: 161

Gly Val Pro Asp Arg Phe Ser Gly Ser Gly Ser Arg Thr Asp Phe Thr
1               5                   10                  15

Leu Thr Ile Asp Ser Leu Gln Ala Glu Asp Val Ala Val Tyr Tyr Cys
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: FRL3 VARIANT HT2-dp27 #610

<400> SEQUENCE: 162

Gly Val Pro Asp Arg Phe Ser Gly Ser Gly Ser Gly Thr Asp Phe Thr
1               5                   10                  15

Leu Thr Ile Asp Ser Leu Glu Ala Glu Asp Val Ala Val Tyr Tyr Cys
            20                  25                  30

<210> SEQ ID NO 163
<211> LENGTH: 14
<212> TYPE: PRT
<213> ORGANISM: Artificial Sequence
<220> FEATURE:
<223> OTHER INFORMATION: FRH2 Variant HT2-NEW #14

<400> SEQUENCE: 163

Trp Val Arg Gln Pro Pro Gly Lys Gly Leu Glu Trp Ile Gly
1               5                   10

<210> SEQ ID NO 164
<211> LENGTH: 14
<212> TYPE: PRT
<213> ORGANISM: Artificial Sequence
<220> FEATURE:
<223> OTHER INFORMATION: FRH2 Variant HT2-NEW #67

<400> SEQUENCE: 164

Trp Val Arg Gln Pro Pro Gly Arg Gly Leu Glu Trp Leu Gly
1               5                   10

<210> SEQ ID NO 165
<211> LENGTH: 32
<212> TYPE: PRT
<213> ORGANISM: Artificial Sequence
<220> FEATURE:
<223> OTHER INFORMATION: FRH3 Variant HT2-NEW #17

<400> SEQUENCE: 165

Arg Leu Asn Met Ser Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Gly
            20                  25                  30

<210> SEQ ID NO 166
<211> LENGTH: 32
<212> TYPE: PRT
<213> ORGANISM: Artificial Sequence
<220> FEATURE:
<223> OTHER INFORMATION: FRH3 Variant HT2-NEW #65

<400> SEQUENCE: 166

Arg Leu Thr Ile Ser Lys Asp Thr Ser Lys Asn Gln Phe Ser Leu Arg
1               5                   10                  15

Leu Ser Ser Val Thr Ala Ala Asp Thr Ala Arg Tyr Tyr Cys Ala Gly

<210> SEQ ID NO 167
<211> LENGTH: 32
<212> TYPE: PRT
<213> ORGANISM: Artificial Sequence
<220> FEATURE:
<223> OTHER INFORMATION: FRH3 Variant HT2-NEW #67

<400> SEQUENCE: 167

Arg Val Asn Met Ser Lys Asp Thr Ser Lys Asn Gln Phe Ser Leu Arg
1               5                   10                  15

Leu Ser Ser Val Thr Ala Ala Asp Thr Ala Arg Tyr Tyr Cys Ala Gly
            20                  25                  30

<210> SEQ ID NO 168
<211> LENGTH: 32
<212> TYPE: PRT
<213> ORGANISM: Artificial Sequence
<220> FEATURE:
<223> OTHER INFORMATION: FRH3 Variant HT2-NEW #73

<400> SEQUENCE: 168

Arg Val Thr Met Leu Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Gly
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: FRH3 Variant HT2-NEW #74

<400> SEQUENCE: 169

Arg Val Thr Ile Leu Lys Asp Thr Ser Lys Asn Gln Phe Ser Leu Arg
1               5                   10                  15

Leu Ser Ser Val Thr Ala Ala Asp Thr Ala Arg Tyr Tyr Cys Ala Gly
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: FRH3 Variant HT2-NEW #78

<400> SEQUENCE: 170

Arg Val Asn Ile Leu Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Gly
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: FRH3 Variant HT2-NEW #275

<400> SEQUENCE: 171

Arg Val Asn Ile Leu Lys Asp Thr Ser Lys Asn Gln Phe Phe Leu Arg
1               5                   10                  15

Leu Ser Ser Val Thr Ala Ala Asp Thr Ala Arg Tyr Tyr Cys Ala Gly

```
                        20                  25                  30

<210> SEQ ID NO 172
<211> LENGTH: 32
<212> TYPE: PRT
<213> ORGANISM: Artificial Sequence
<220> FEATURE:
<223> OTHER INFORMATION: FRH3 Variant HT2-NEW #284

<400> SEQUENCE: 172

Arg Leu Ile Ile Ser Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Gly
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: FRH3 Variant HT2-NEW #291

<400> SEQUENCE: 173

Arg Leu Thr Ile Leu Lys Asp Thr Ser Lys Asn Gln Phe Phe Leu Arg
1               5                   10                  15

Leu Ser Ser Val Thr Ala Ala Asp Thr Ala Val Tyr Tyr Cys Ala Gly
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: FRH3 Variant HT2-NEW #300

<400> SEQUENCE: 174

Arg Val Thr Ile Ser Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Gly
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: FRH3 Variant HT2-NEW #302

<400> SEQUENCE: 175

Arg Val Asn Met Ser Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Gly
            20                  25                  30

<210> SEQ ID NO 176
<211> LENGTH: 32
<212> TYPE: PRT
<213> ORGANISM: Artificial Sequence
<220> FEATURE:
<223> OTHER INFORMATION: FRH3 Variant HT2-NEW #322

<400> SEQUENCE: 176

Arg Val Asn Ile Ser Lys Asp Thr Ser Lys Asn Gln Phe Phe Leu Arg
1               5                   10                  15

Leu Ser Ser Val Thr Ala Ala Asp Thr Ala Arg Tyr Tyr Cys Ala Gly
```

<210> SEQ ID NO 177
<211> LENGTH: 32
<212> TYPE: PRT
<213> ORGANISM: Artificial Sequence
<220> FEATURE:
<223> OTHER INFORMATION: FRH3 Variant HT2-NEW #111

<400> SEQUENCE: 177

Arg Leu Thr Ile Ser Lys Asp Thr Ser Lys Asn Gln Phe Phe Leu Arg
1               5                   10                  15

Leu Ser Ser Val Thr Ala Ala Asp Thr Ala Arg Tyr Tyr Cys Ala Gly
            20                  25                  30

<210> SEQ ID NO 178
<211> LENGTH: 32
<212> TYPE: PRT
<213> ORGANISM: Artificial Sequence
<220> FEATURE:
<223> OTHER INFORMATION: FRH3 Variant HT2-NEW #162

<400> SEQUENCE: 178

Arg Leu Thr Met Ser Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Gly
            20                  25                  30

<210> SEQ ID NO 179
<211> LENGTH: 32
<212> TYPE: PRT
<213> ORGANISM: Artificial Sequence
<220> FEATURE:
<223> OTHER INFORMATION: FRH3 Variant HT2-NEW #139

<400> SEQUENCE: 179

Arg Val Thr Met Ser Lys Asp Thr Ser Lys Asn Gln Phe Phe Leu Arg
1               5                   10                  15

Leu Ser Ser Val Thr Ala Ala Asp Thr Ala Arg Tyr Tyr Cys Ala Gly
            20                  25                  30

<210> SEQ ID NO 180
<211> LENGTH: 32
<212> TYPE: PRT
<213> ORGANISM: Artificial Sequence
<220> FEATURE:
<223> OTHER INFORMATION: FRH3 Variant HT2-NEW #177

<400> SEQUENCE: 180

Arg Val Thr Met Ser Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Gly
            20                  25                  30

<210> SEQ ID NO 181
<211> LENGTH: 11
<212> TYPE: PRT
<213> ORGANISM: Artificial Sequence
<220> FEATURE:
<223> OTHER INFORMATION: FRH4 variant HT2-dp27 #19

<400> SEQUENCE: 181

Trp Gly His Gly Ser Leu Val Thr Val Ser Ser
1               5                   10

```
<210> SEQ ID NO 182
<211> LENGTH: 32
<212> TYPE: PRT
<213> ORGANISM: Artificial Sequence
<220> FEATURE:
<223> OTHER INFORMATION: FRH3 variant HT2-dp27 #19

<400> SEQUENCE: 182

Arg Leu Asn Ile Ser Lys Asp Ser Ser Lys Asn Gln Val Val Leu Thr
1               5                   10                  15

Met Thr Asn Met Asp Pro Val Asp Thr Ala Arg Tyr Tyr Cys Ala Gly
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: FRH3 variant HT2-dp27 #43

<400> SEQUENCE: 183

Arg Leu Asn Ile Ser Lys Asp Thr Ser Lys Asn Gln Val Val Leu Thr
1               5                   10                  15

Met Thr Asn Met Asp Pro Val Asp Thr Ala Arg Tyr Tyr Cys Ala Gly
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: FRH3 variant HT2-dp27 #118

<400> SEQUENCE: 184

Arg Leu Thr Ile Ser Lys Asp Ile Ser Lys Asn Gln Val Val Leu Thr
1               5                   10                  15

Met Thr Asn Met Asp Pro Val Asp Thr Ala Arg Tyr Tyr Cys Ala Gly
            20                  25                  30

<210> SEQ ID NO 185
<211> LENGTH: 5
<212> TYPE: PRT
<213> ORGANISM: Artificial Sequence
<220> FEATURE:
<223> OTHER INFORMATION: CDR-H1 Cl-65 Variant

<400> SEQUENCE: 185

Ala Ser Ser Val Asn
1               5

<210> SEQ ID NO 186
<211> LENGTH: 131
<212> TYPE: PRT
<213> ORGANISM: Artificial Sequence
<220> FEATURE:
<223> OTHER INFORMATION: Majority sequence of aligned IL-13 of various
      species

<400> SEQUENCE: 186

Met Ala Leu Trp Leu Thr Ala Val Ile Ala Leu Ala Cys Leu Gly Gly
1               5                   10                  15

Leu Ala Ser Pro Gly Pro Val Pro Pro Ser Thr Ala Leu Lys Glu Leu
            20                  25                  30

Ile Glu Glu Leu Val Asn Ile Thr Gln Asn Gln Lys Ala Pro Leu Cys
        35                  40                  45
```

```
Asn Gly Ser Met Val Trp Ser Val Asn Leu Thr Ala Gly Gly Tyr Cys
    50                  55                  60

Ala Ala Leu Glu Ser Leu Ile Asn Ile Ser Gly Cys Ser Ala Ile Gln
65                  70                  75                  80

Arg Thr Gln Arg Met Leu Asn Gly Leu Cys Pro His Lys Ala Ser Ala
                85                  90                  95

Gly Gln Ser Ser Ser Arg Val Arg Asp Thr Lys Ile Glu Val Ala Gln
                100                 105                 110

Phe Val Lys Asp Leu Leu Asn Tyr Ser Lys Gln Leu Phe Arg Asn Gly
            115                 120                 125

Arg Phe Asn
    130

<210> SEQ ID NO 187
<211> LENGTH: 132
<212> TYPE: PRT
<213> ORGANISM: Homo sapiens
<220> FEATURE:
<223> OTHER INFORMATION: Human interleukin-13 sequence

<400> SEQUENCE: 187

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
            35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
                100                 105                 110

Gln Phe Val Lys Asp Leu Leu Leu His Leu Lys Lys Leu Phe Arg Glu
            115                 120                 125

Gly Arg Phe Asn
    130

<210> SEQ ID NO 188
<211> LENGTH: 132
<212> TYPE: PRT
<213> ORGANISM: Macaque
<220> FEATURE:
<223> OTHER INFORMATION: Monkey interleukin-13 sequence

<400> SEQUENCE: 188

Met Ala Leu Leu Leu Thr Met Val Ile Ala Leu Thr Cys Leu Gly Gly
1               5                   10                  15

Phe Ala Ser Pro Ser Pro Val Pro Ser Thr Ala Leu Lys Glu Leu
            20                  25                  30

Ile Glu Glu Leu Val Asn Ile Thr Gln Asn Gln Lys Ala Pro Leu Cys
            35                  40                  45

Asn Gly Ser Met Val Trp Ser Ile Asn Leu Thr Ala Gly Val Tyr Cys
    50                  55                  60

Ala Ala Leu Glu Ser Leu Ile Asn Val Ser Gly Cys Ser Ala Ile Glu
65                  70                  75                  80
```

```
Lys Thr Gln Arg Met Leu Asn Gly Phe Cys Pro His Lys Val Ser Ala
                85                  90                  95

Gly Gln Phe Ser Ser Leu Arg Val Arg Asp Thr Lys Ile Glu Val Ala
            100                 105                 110

Gln Phe Val Lys Asp Leu Leu Val His Leu Lys Lys Leu Phe Arg Asn
        115                 120                 125

Gly Arg Phe Asn
        130

<210> SEQ ID NO 189
<211> LENGTH: 132
<212> TYPE: PRT
<213> ORGANISM: Bovine
<220> FEATURE:
<223> OTHER INFORMATION: Cow interleukin-13 sequence

<400> SEQUENCE: 189

Met Ala Leu Leu Leu Thr Ala Val Ile Val Leu Ile Cys Phe Gly Gly
1               5                   10                  15

Leu Thr Ser Pro Ser Pro Val Pro Ser Ala Thr Ala Leu Lys Glu Leu
            20                  25                  30

Ile Glu Glu Leu Val Asn Ile Thr Gln Asn Gln Lys Val Pro Leu Cys
        35                  40                  45

Asn Gly Ser Met Val Trp Ser Leu Asn Leu Thr Ser Ser Met Tyr Cys
50                  55                  60

Ala Ala Leu Asp Ser Leu Ile Ser Ile Ser Asn Cys Ser Val Ile Gln
65                  70                  75                  80

Arg Thr Lys Lys Met Leu Asn Ala Leu Cys Pro His Lys Pro Ser Ala
                85                  90                  95

Lys Gln Val Ser Ser Glu Tyr Val Arg Asp Thr Lys Ile Glu Val Ala
            100                 105                 110

Gln Phe Leu Lys Asp Leu Leu Arg His Ser Arg Ile Val Phe Arg Asn
        115                 120                 125

Glu Arg Phe Asn
        130

<210> SEQ ID NO 190
<211> LENGTH: 131
<212> TYPE: PRT
<213> ORGANISM: Canis C. lupus
<220> FEATURE:
<223> OTHER INFORMATION: Dog interleukin-13 sequence

<400> SEQUENCE: 190

Met Ala Leu Trp Leu Thr Val Val Ile Ala Leu Thr Cys Leu Gly Gly
1               5                   10                  15

Leu Ala Ser Pro Ser Pro Val Thr Pro Ser Pro Thr Leu Lys Glu Leu
            20                  25                  30

Ile Glu Glu Leu Val Asn Ile Thr Gln Asn Gln Ala Ser Leu Cys Asn
        35                  40                  45

Gly Ser Met Val Trp Ser Val Asn Leu Thr Ala Gly Met Tyr Cys Ala
50                  55                  60

Ala Leu Glu Ser Leu Ile Asn Val Ser Asp Cys Ser Ala Ile Gln Arg
65                  70                  75                  80

Thr Gln Arg Met Leu Lys Ala Leu Cys Ser Gln Lys Pro Ala Ala Gly
                85                  90                  95

Gln Ile Ser Ser Glu Arg Ser Arg Asp Thr Lys Ile Glu Val Ile Gln
            100                 105                 110
```

```
Leu Val Lys Asn Leu Leu Thr Tyr Val Arg Gly Val Tyr Arg His Gly
        115                 120                 125

Asn Phe Arg
    130

<210> SEQ ID NO 191
<211> LENGTH: 131
<212> TYPE: PRT
<213> ORGANISM: Rat
<220> FEATURE:
<223> OTHER INFORMATION: Rat interleukin-13 sequence

<400> SEQUENCE: 191

Met Ala Leu Trp Val Thr Ala Val Leu Ala Leu Ala Cys Leu Gly Gly
1               5                   10                  15

Leu Ala Thr Pro Gly Pro Val Arg Arg Ser Thr Ser Pro Val Ala
            20                  25                  30

Leu Arg Glu Leu Ile Glu Glu Leu Ser Asn Ile Thr Gln Asp Gln Lys
        35                  40                  45

Thr Ser Leu Cys Asn Ser Ser Met Val Trp Ser Val Asp Leu Thr Ala
    50                  55                  60

Gly Gly Phe Cys Ala Ala Leu Glu Ser Leu Thr Asn Ile Ser Ser Cys
65                  70                  75                  80

Asn Ala Ile His Arg Thr Gln Arg Ile Leu Asn Gly Leu Cys Asn Gln
                85                  90                  95

Lys Ala Ser Asp Val Ala Ser Ser Pro Pro Asp Thr Lys Ile Glu Val
            100                 105                 110

Ala Gln Phe Ile Ser Lys Leu Leu Asn Tyr Ser Lys Gln Leu Phe Arg
        115                 120                 125

Tyr Gly His
    130

<210> SEQ ID NO 192
<211> LENGTH: 131
<212> TYPE: PRT
<213> ORGANISM: Mus Musculus
<220> FEATURE:
<223> OTHER INFORMATION: Mouse interleukin-13 sequence

<400> SEQUENCE: 192

Met Ala Leu Trp Val Thr Ala Val Leu Ala Leu Ala Cys Leu Gly Gly
1               5                   10                  15

Leu Ala Ala Pro Gly Pro Val Pro Arg Ser Val Ser Leu Pro Leu Thr
            20                  25                  30

Leu Lys Glu Leu Ile Glu Glu Leu Ser Asn Ile Thr Gln Asp Gln Thr
        35                  40                  45

Pro Leu Cys Asn Gly Ser Met Val Trp Ser Val Asp Leu Ala Ala Gly
    50                  55                  60

Gly Phe Cys Val Ala Leu Asp Ser Leu Thr Asn Ile Ser Asn Cys Asn
65                  70                  75                  80

Ala Ile Tyr Arg Thr Gln Arg Ile Leu His Gly Leu Cys Asn Arg Lys
                85                  90                  95

Ala Pro Thr Thr Val Ser Ser Leu Pro Asp Thr Lys Ile Glu Val Ala
            100                 105                 110

His Phe Ile Thr Lys Leu Leu Ser Tyr Thr Lys Gln Leu Phe Arg His
        115                 120                 125

Gly Pro Phe
    130
```

```
<210> SEQ ID NO 193
<211> LENGTH: 125
<212> TYPE: PRT
<213> ORGANISM: Meriones (rodent)
<220> FEATURE:
<223> OTHER INFORMATION: Gerbil interleukin-13 sequence

<400> SEQUENCE: 193

Met Ala Leu Trp Leu Thr Ala Val Leu Ala Leu Ala Cys Leu Ser Gly
1               5                   10                  15

Leu Ala Val Pro Gly Pro Val Gly Arg Ser Val Ser Pro Pro Val Ala
            20                  25                  30

Leu Lys Glu Leu Ile Glu Glu Leu Ser Asn Ile Thr Gln Asp Gln Arg
        35                  40                  45

Thr Pro Leu Cys Asn Gly Ser Met Val Trp Ser Val Asp Leu Ala Ala
    50                  55                  60

Gly Gly Phe Cys Ala Ala Leu Asp Ser Leu Thr Asn Ile Ser Ser Cys
65                  70                  75                  80

Asn Thr Ile Gln Lys Thr Gln Arg Ile Leu Asn Gly Leu Cys Ala Arg
                85                  90                  95

Lys Ala Pro Ala Val Val Ser Arg Val Pro Asp Thr Lys Ile Glu Ala
            100                 105                 110

Ala Gln Phe Ile Lys Asn Leu Leu Asn Tyr Ser Lys Gln
            115                 120                 125
```

ANTI-IL 13 ANTIBODIES AND USES THEREOF

This application is a divisional of U.S. application Ser. No. 10/583,927 which is a national stage of International Application No. PCT/US2004/043501 filed Dec. 23, 2004, which claims the benefit of U.S. Provisional Application No. 60/532,130 filed Dec. 23, 2003.

BACKGROUND OF INVENTION

The interleukin (IL)-13 is a pleiotropic T helper cell subclass 2 (Th2) cytokine. Like IL4, IL13 belongs to the family of type I cytokines sharing the tertiary structure defined by a 4α-helical hydrophobic bundle core. IL13 has approximately 30% amino acid sequence homology with IL4 and shares many of the properties of IL4 (Wynn, Ann. Rev. Immunol., 21: 425 (2003)). The functional similarity of IL4 and IL13 is attributed to the fact that IL13 can bind IL4 receptor alpha chain (IL4R-α) subsequent to its binding to IL13 receptor alpha chain-1 (IL13Rα1) (Hershey, J. Allergy Clin. Immunol., 111: 677 (2003)). IL4Rα is activated by IL4 and IL13 resulting in Jak1-dependent STAT6 phosphorylation. Both IL4 and IL13 promote B-cell proliferation and induce class switching to IgG4 and IgE in combination with CD40/CD40L costimulation (Punnonen et al., Proc. Nat. Acad. Sci. USA, 90: 3730 (1993), Oettgen et al., J. Allergy Clin. Immunol., 107: 429 (2001)).

However, unlike IL4, IL13 is not involved in the differentiation of naïve T cells into Th2 cells (Zurawski et al., Immunol. Today, 15: 19 (1994)). IL13 up-regulates FcεRI and thus helps in IgE priming of mast cells (de Vries, Allergy Clin. Immunol. 102: 165 (1998). In monocytes/macrophages, IL13 up-regulates expression of CD23 and MHC class I and class II antigens, down-regulate the expression of Fcγ and CD14, and inhibit antibody-dependent cytotoxicity (de Waal Malefyt et al., J. Immunol., 151: 6370 (1993), Chomarat et al., Int. Rev. Immunol., 17: 1 (1998)). IL13, but not IL4, promotes eosinophil survival, activation, and recruitment (Horle et al., Intern. Med., 36: 179 (1997), Luttmann et al., J. Immunol. 157: 1678 (1996), Pope et al., J. Allergy Clin. Immunol., 108: 594 (2001). IL13 also manifests important functions on non-hematopoietic cells, such as smooth muscle cells, epithelial cells, endothelial cells and fibroblast cells. IL13 enhances proliferation and cholinergic-induced contractions of smooth muscles (Wills-Karp, J. Allergy Clin. Immunol., 107: 9 (2001). In epithelial cells IL13 is a potent inducer of chemokine production (Li et al., J. Immunol., 162: 2477 (1999), alters mucociliary differentiation (Laoukili et al., J. Clin. Invest., 108: 1817 (2001), decreases ciliary beat frequency of ciliated epithelial cells (Laoukili et al., J. Clin. Invest., 108: 1817 (2001), and results in goblet cell metaplasia (Zhu et al., J. Clin. Invest., 103: 779 (1999), Grunig et al., Science, 282: 2261 (1998)). In endothelial cells IL13 is a potent inducer of vascular cell adhesion molecule 1 (VCAM-1) which is important for recruitment of eosinophils (Bochner et al., J. Immunol., 154: 799 (1995)). In human dermal fibroblasts IL13 induces type 1 collagen synthesis in human dermal fibroblasts (Roux et al., J. Invest. Dermatol., 103: 444 (1994)).

Although IL13 and IL4 share certain functional similarities, studies in animal models of disease and gene-knockout mice demonstrated that IL13 possesses unique effector functions distinct from IL4 and provides compelling evidence that IL13, independent of other Th2 cytokines, is necessary and sufficient to induce all features of allergic asthma (Wills-Karp et al. Science, 282: 2258 (1998), Walter et al. J. Immunol. 167: 4668 (2001)). IL13 may play a more significant role than other Th2 cytokines in effector functions associated with the symptoms of asthma (Corry, Curr. Opin. Immunol., 11: 610 (1999)).This contention is supported in human disease by a strong association between IL13 levels and genetic polymorphisms in the IL13 gene and disease correlates (Wills-Karp. et al. Respir. Res. 1: 19 (2000); Vercelli et al., Curr. Opin. Allergy Clin. Immunol., 2: 389 (2002); He et al., Genes Immunol., 4: 385 (2003), Arima et al, J. Allergy Clin. Immunol., 109: 980 (2003), Liu et al., J. Clin. Allergy Immunol., 112: 382 (2003)). Emerging data suggest that IL13 induces features of the allergic response via its actions on mucosal epithelium and smooth muscle cells, rather than through the traditional pathways involving eosinophils and IgE-mediated events (Wills-Karp et al., Sci., 282: 2258 (1998)).

Asthma is described as a chronic pulmonary disease that involves airway inflammation, hyperresponsiveness and obstruction. Physiologically, airway hyperresponsiveness is documented by decreased bronchial airflow after bronchoprovocation with methacholine or histamine. Other triggers that provoke airway obstruction include cold air, exercise, viral upper respiratory infection, cigarette smoke, and respiratory allergens. Bronchial provocation with allergen induces a prompt early phase immunoglobulin E (IgE)-mediated decrease in bronchial airflow followed in many patients by a late-phase IgE-mediated reaction with a decrease in bronchial airflow for 4-8 hours. The early response is caused by acute release of inflammatory substances, such as histamine, $PGD_2$, leukotriene, tryptase and platelet activating factor (PAF), whereas the late response is caused by de novo synthesized pro-inflammatory cytokines (e.g. TNFα, IL4, IL13) and chemokines (e.g. MCP-1 and MIP-1α) (Busse et al. In: Allergy: Principles and Practice, Ed. Middleston, 1173 (1998)). In chronic asthmatic patients, persistent pulmonary symptoms are mediated by the heightened response of Th2 cells. Th2 cytokines are believed to play a vital role in the disease (Larche et al., J. Allergy Clin. Immunol., 111: 450 (2003)), in particular, IL13 and IL4 produced by Th2 cells with NK phenotype (NKT) in the airway as indicated in a model of asthma in rodents (Akbari et al., Nature Med., 9: 582 (2003)). The gross pathology of asthmatic airways displays lung hyperinflation, smooth muscle hypertrophy, lamina reticularis thickening, mucosal edema, epithelial cell sloughing, cilia cell disruption, and mucus gland hypersecretion. Microscopically, asthma is characterized by the presence of increased numbers of eosinophils, neutrophils, lymphocytes, and plasma cells in the bronchial tissues, bronchial secretions, and mucus. Initially, there is recruitment of leukocytes from the bloodstream to the airway by activated CD4+ T-lymphocytes. The activated T-lymphocytes also direct the release of inflammatory mediators from eosinophils, mast cells, and lymphocytes. In addition, the Th2 cells produce IL4, IL5, IL9 and IL13. IL4, in conjunction with IL13, signals the switch from IgM to IgE antibodies.

Cross-linking of membrane-bound IgE molecules by allergen causes mast cells to degranulate, releasing histamine, leukotrienes, and other mediators that perpetuate the airway inflammation. IL5 activates the recruitment and activation of eosinophils. The activated mast cells and eosinophils also generate their cytokines that help to perpetuate the inflammation. These repeated cycles of inflammation in the lungs with injury to the pulmonary tissues followed by repair may produce long-term structural changes ("remodeling") of the airways.

Moderate asthma is currently treated with a daily inhaled anti-inflammatory-corticosteroid or mast cell inhibitor such as cromolyn sodium or nedocromil plus an inhaled beta2-agonist as needed (3-4 times per day) to relieve breakthrough symptoms or allergen- or exercise-induced asthma. Cromolyn sodium and nedocromil block bronchospasm and inflammation, but are usually effective only for asthma that is associated with allergens or exercise and typically, only for juvenile asthmatics. Inhaled corticosteroids improve inflammation, airways hyperreactivity, and obstruction, and reduce the number of acute exacerbations. However, it takes at least a month before effects are apparent and up to a year for marked improvement to occur. The most frequent side effects are hoarseness and oral fungal infection, i.e., candidiasis. More serious side effects have been reported, e.g., partial adrenal suppression, growth inhibition, and reduced bone formation, but only with the use of higher doses. Beclomethasone, triamcinolone, and flunisolide probably have a similar potency; whereas budesonide and fluticasone are more potent and reportedly have fewer systemic side effects.

Even patients with mild disease show airway inflammation, including infiltration of the mucosa and epithelium with activated T cells, mast cells, and eosinophils. T cells and mast cells release cytokines that promote eosinophil growth and maturation and the production of IgE antibodies, and these, in turn, increase microvascular permeability, disrupt the epithelium, and stimulate neural reflexes and mucus-secreting glands. The result is airways hyperreactivity, bronchoconstriction, and hypersecretion, manifested by wheezing, coughing, and dyspnea.

Traditionally, asthma has been treated with oral and inhaled bronchodilators. These agents help the symptoms of asthma, but do nothing for the underlying inflammation. Recognition during the last 10 years of the importance of inflammation in the etiology of asthma has led to the increased use of corticosteroids, but many patients continue to suffer from uncontrolled asthma.

Because of the importance of treating inflammatory diseases in humans, particularly asthma, new bioactive compounds having fewer side effects are continually being sought. The development of potent and specific inhibitors of IL13, which remain active when administered long term to asthmatic airways, offers a novel approach to the treatment of asthma, as well as in other IL13- and IgE-mediated diseases.

SUMMARY OF INVENTION

The present invention relates at least in part to antibodies that bind specifically and with high affinity to both glycosylated and non-glycosylated human IL13; does not bind mouse IL13, and neutralize human IL13 activity at an approximate molar ratio of 1:2 (MAb:IL13). Also included in the present invention are antibodies comprising the antigen binding regions derived from the light and/or heavy chain variable regions of said antibodies. The antibodies of the invention may be monoclonal, and a monoclonal antibody may be a human antibody, a chimeric antibody, or a humanized antibody.

Examples of these antibodies are 228B/C-1, 228A-4, 227-26, and 227-43. The hybridomas that produce these antibodies were deposited on Nov. 20, 2003, with the American Type Culture Collection, 10801 University Blvd., Manassas, Va. 20110-2209, under Accession Numbers PTA-5657, PTA-5656, PTA-5654, and PTA-5655, respectively.

The present invention includes antibodies which have a VL sequence at least 95% homologous to that set forth in SEQ ID NO: 3, and a VH sequence at least 95% homologous to that set forth in SEQ ID NO: 4; antibodies which have a VL sequence at least 95% homologous to that set forth in SEQ ID NO: 5, and a VH sequence at least 95% homologous to that set forth in SEQ ID NO: 6; and antibodies which have a VL sequence at least 95% homologous to that set forth in SEQ ID NO: 7, and a VH sequence at least 95% homologous to that set forth in SEQ ID NO: 8. The present invention also includes a recombinant antibody molecule, or an IL13-binding fragment thereof, comprising at least one antibody heavy chain, or an IL13-binding fragment thereof, comprising non-human CDRs at positions 31-35 (CDR1), 50-65 (CDR2) and 95-102 (CDR3) (Kabat numbering) from a mouse anti-IL13 antibody, wherein positions 27-30 have the amino acid Gly 26, Phe 27, Ser 28, Leu 29, Asn 30, (SEQ ID NO: 18); and at least one antibody light chain, or an IL13-binding fragment thereof, comprising non-human CDRs at positions 24-34 (CDR1), 50-56 (CDR2) and 89-97 (CDR3) from a mouse anti-IL13 antibody, and framework regions from a human monoclonal antibody.

The present invention includes human antigen-binding antibody fragments of the antibodies of the present invention including, but are not limited to, Fab, Fab' and F(ab')$_2$, Fd, single-chain Fvs (scFv), single-chain antibodies, disulfide-linked Fvs (sdFv). The invention also includes single-domain antibodies comprising either a VL or VH domain. On example of an scFv is depicted in FIG. 21, having the sequence of SEQ ID NO 152.

The present invention includes humanized sequences of monoclonal antibody 228B/C-1. These humanized recombinant antibody molecules comprise a variable light chain region comprising an amino acid sequence having the formula: FRL1-CDRL1-FRL2-CDRL2-FRL3-CDRL3-FRL4, wherein FRL1 consists of any one of SEQ ID Nos: 20-25; CDRL1 consists of any one of SEQ ID NOs: 99-103; FRL2 consists of SEQ ID NO: 29; CDRL2 consists of any one of SEQ ID NOs: 104-114; FRL3 consists of any one of SEQ ID NOs: 30-56; CDRL3 consists of any of SEQ ID NOs: 115-116; and FRL4 consists of SEQ ID NO: 57-59; and comprising a variable heavy chain region comprising an amino acid sequence having the formula: FRH1-CDRH1-FRH2-CDRH2-FRH3-CDRH3-FRH4, wherein FRH1 consists of any one of SEQ ID NOs: 60-66; CDRH1 consists of any one of SEQ ID NOs: 117-122; FRH2 consists of any one of SEQ ID NOs: 67-75; CDRH2 consists of any one of SEQ ID NOs: 123-134; FRH3 consists of any one of SEQ ID NOs: 76-90; CDRH3 consists of any of SEQ ID NOs: 135-141; and FRH4 consists of SEQ ID NO: 91-92. The variable heavy chain region may further comprise at least the CH1 domain of a constant region or the CH1, CH2 and CH3 domains of a constant region. The heavy chain constant region may comprise an IgG antibody. wherein the IgG antibody is an IgG1 antibody, an IgG2 antibody, an IgG3 antibody, or an IgG4 antibody.

The present invention also includes recombinant antibody molecules wherein the variable light chain is chosen from any one of SEQ ID Nos: 3, 5, 7, 93, 95, 97, 142, 144, and 150, and a variable heavy chain chosen from any one of SEQ ID Nos: 4, 6, 8, 94, 96, 98, 143, 145, 146, 147, 148, and 149. One particular antibody comprises the variable light chain having the sequence set forth in SEQ ID NO:142, and a variable heavy chain having the sequence set forth in SEQ ID NO:143.

The present invention includes the hybridoma cell lines that produce the monoclonal antibodies 228B/C-1, 228A-4, 227-26, and 227-43. The present invention includes nucleic acids encoding the monoclonal antibodies 228B/C-1, 228A-4, 227-26, and 227-43, cell lines comprising a nucleic acid encoding these antibodies or chains thereof, and vectors comprising the nucleic acid encoding these antibodies or chains thereof.

The present invention also includes antibodies that bind the same epitope as 228B/C-1. Exemplary polypeptides comprise all or a portion of SEQ ID NO. 1 or variants thereof, or SEQ ID NO. 2, wherein amino acid 13 is changed from glutamic acid to lysine. The invention also relates to the epitope recognized by the antibodies of the present invention. Epitope peptides include a peptide comprising essentially or consisting of ESLINVSG (SEQ ID NO: 18) or YCAALE-SLINVS (SEQ ID NO:19).

The present invention includes a composition comprising the antibodies according to the claimed invention in combination with a pharmaceutically acceptable carrier, diluent, excipient, or stabilizer.

The present invention includes a method of treating a subject suffering from asthmatic symptoms comprising administering to a subject, e.g. a subject in need thereof, an amount of an antibody according to the claimed invention effective to reduce the asthmatic symptoms, wherein the antibody may down-regulate the activity of IL13 in the patient, reduce bronchial hyperresponsiveness in the patient, and/or reduce eosinophilia in the lungs of the subject. The present invention also includes a method of inhibiting the infection of respiratory syncytial virus (RSV) comprising administering to a subject, e.g. a subject in need thereof, an inhibiting amount of the antibody of the claimed invention.

The antibody of the present invention may be administered by one or more of the routes including intravenous, intraperitoneal, inhalation, intramuscular, subcutaneous and oral routes. The present invention includes an inhalation device that delivers to a patient a therapeutically effective amount of an antibody according to the claimed invention.

The present invention includes a method for detecting interleukin-13 protein in a subject, e.g., a patient suffering from an allergic disease, comprising, e.g., the steps of allowing the antibody of the claimed invention to contact a sample; and detecting the interleukin-13 through the occurrence of immunoreaction. Also described are and methods for diagnosing overexpression of IL13 in a subject, comprising the steps of (a) obtaining a sample from the subject; (b) combining the sample with an antibody according to the claimed invention under conditions which would allow immunoreaction with IL13; and (c) determining whether or not IL13 is overexpressed relative to a normal level of expression of IL13.

The present invention includes a method for producing the antibodies of the claimed invention, comprising the steps of a) producing an immunogenic compound comprising a glycosylated IL13 moiety and an immunogenic moiety; b) preparing an injectable solution comprising said immunogenic compound in phosphate buffered saline (PBS) and an adjuvant; c) immunizing a mouse with said injectable solution by a combination of intravenous and intraperitoneal injections, d) producing a hybridoma by fusing a spleen cell from said immunized mouse with a myeloma cell; e) selecting a hybridoma producing an antibody having the characteristics of the antibody of the claimed invention; and f) isolating said antibody.

The present invention includes a method for inhibiting IgE antibody production in a patient, which comprises administrating to the patient an effective amount of an IgE antibody production inhibiting effective amount of an antibody according to the claimed invention. The inhibition of IgE antibody production may prevent bronchial asthma, allergic rhinitis, allergic dermatitis, and anaphylaxis, and also treat bronchial asthma, allergic rhinitis, uticaria, and atopic dermatitis.

The present invention includes a method of treating an IL13-mediated disorder in a patient, comprising administering to the patient an effective amount of an antibody or antigen-binding fragment thereof according to the claimed invention, wherein said antibody or antigen-binding fragment thereof inhibits binding of IL13 to its receptor and inhibits one or more functions associated with binding of the interleukin to said receptor.

The present invention includes a method of treating an IgE-mediated disorder in a patient, comprising administering to the patient an effective amount of an antibody or antigen-binding fragment thereof according to the claimed invention, wherein said antibody or antigen-binding fragment thereof inhibits binding of IL13 to its receptor and inhibits one or more functions associated with binding of the interleukin to said receptor.

The present invention includes a method for reducing the severity of asthma in a mammal comprising administering to the mammal a therapeutically effective amount of an anti-IL13 monoclonal antibody having at least one of the following characteristics: the ability to bind human IL13 with a $K_D$ between about $1 \times 10^{10}$ to about $1 \times 10^{12}$ M; the ability to inhibit one or more functions associated with binding of the interleukin IL13 to the IL13 receptor; and the inability of the antibody does to bind to mouse IL13.

Diseases and/or conditions mediated by IL13 that are contemplated by the invention include, but are not limited to, allergic asthma, non-allergic (intrinsic) asthma, allergic rhinitis, atopic dermatitis, allergic conjunctivitis, eczema, urticaria, food allergies, chronic obstructive pulmonary disease, ulcerative colitis, RSV infection, uveitis, scleroderma, and osteoporosis.

BRIEF DESCRIPTION OF THE DRAWINGS

FIG. 1 depicts the binding of anti-IL13 monoclonal antibodies to human IL13.

FIG. 2 depicts the binding of anti-IL13 monoclonal antibodies mutant IL13-Fc.

FIG. 3 illustrates that there is no inhibition of MAb 228B/C-1 binding to human IL13 by MAb JES10-5A2 (Pharmingen).

FIG. 4 illustrates the effect of anti-IL13 monoclonal antibodies on the proliferation of Hodgkin Lymphoma L-1236 cells.

FIG. 5 illustrates the effect of anti-IL13 monoclonal antibodies on IL13-induced suppression of CD14 expression in human monocytes.

FIG. 6 illustrates the effect of anti-IL13 monoclonal antibodies on IL13-induced up-regulation of CD23 expression in human monocytes.

FIG. 7 illustrates the effect of anti-IL13 monoclonal antibodies on IL13-induced STAT6 phosphorylation in THP-1 cells.

FIG. 8 depicts the amino acid sequence of the VH and VL regions of monoclonal antibody 228B/C-1.

FIG. 9 depicts the amino acid sequence of the VH and VL regions of monoclonal antibody 228A-4.

FIG. 10 depicts the amino acid sequence of the VH and VL regions of monoclonal antibody 227-26.

FIGS. 11A-1, 11A-2, 11B-1, 11B-2, 11C-1, 11C-2, 11D-1, and 11D-2 depict the sequences of the light chain variable regions (VK) for humanization of monoclonal antibody 228B/C-1. Clones B to R represent clones tested with a human template 2 for VK and a murine VH. HT2-NEW and HT2-DP27 clones were constructed with human frameworks for both VK and VH. The amino acid sequences of framework region (FR) 1 (FIGS. 11A-1 and 11C-1), FR2 (FIGS. 11A-2 and 11C-2), FR3 (FIGS. 11B-1 and 11D-1), and FR4 (FIGS. 11B-2 and 11D-2) of the VK of the indicated clones are depicted.

FIGS. 12A-1, 12A-2, 12B-1, 12B-2, 12C-1, 12C-2, 12C-3, 12C-4, 12D-1, 12D-2, 12D-3, and 12D-4 depict the corresponding heavy chain variable region sequences of clones in FIG. 11 (i.e., 11A-1, 11A-1, 11B-1, 11B-2, 11C-1, 11C-2, 11D-1, and 11D-2). The amino acid sequences of FR1 (FIGS. 12A-1, 12C-1, and 12C-2), FR2 (FIGS. 12A-2, 12C-3, and 12C-4), FR3 (FIGS. 12B-1, 12D-1 and 12D-2), and FR4 (FIGS. 12B-2, 12D-3 and 12D-4) of the VH of the indicated clones are depicted.

FIG. 15 depicts the sequences of combinatorial library candidates.

FIG. 17 depicts the sequences of three affinity matured candidates.

FIG. 18 shows the alignment of IL 13 protein sequences. The amino acid sequence for the following species of IL-13 protein are aligned: human (SEQ ID NO: 187), monkey (SEQ ID NO: 188), bovine (SEQ ID NO: 189), dog (SEQ ID NO: 190), rat (SEQ ID NO: 191), mouse (SEQ ID NO: 192), and gerbil (SEQ ID NO: 193). The majority sequence (SEQ ID NO: 186) based on the alignment is depicted.

FIG. 19 depicts the binding epitope of Mab 228B/C-1. The human (SEQ ID NO: 187), monkey (SEQ ID NO: 188) and mouse (SEQ ID NO: 192) IL-13 amino acid sequences are depicted.

FIG. 20 depicts the CDR variants and their respective SEQ ID Nos.

FIGS. 21A and 21B depict the variable light chain and variable heavy chain sequences for select candidate recombinant antibodies.

DETAILED DESCRIPTION

Figure 13A:
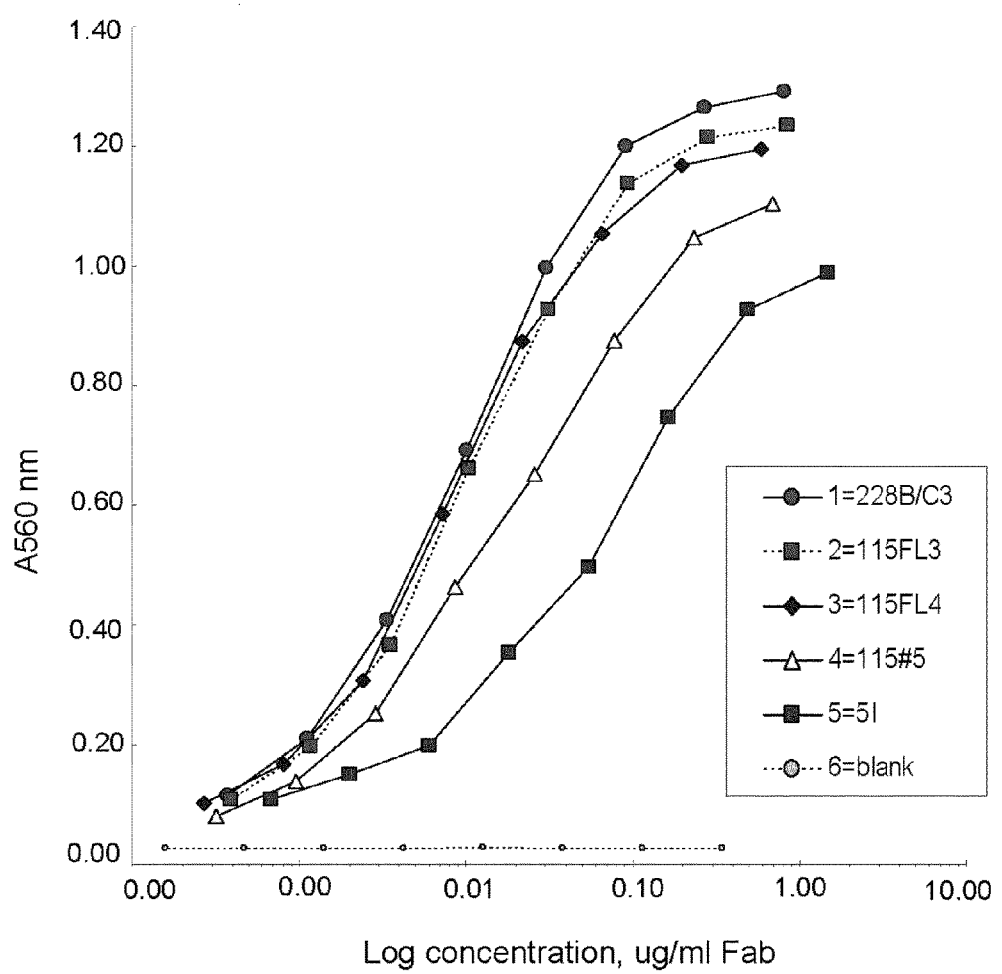
FIG. 13 A-D depict ELISA profiles for combinatorial humanized candidates.

This invention is not limited to the particular methodology, protocols, cell lines, vectors, or reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise, e.g., reference to "a host cell" includes a plurality of such host cells.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by virtue of prior invention.

Immunogen

Recombinant IL13 was used to immunize mice to generate the hybridomas that produce the monoclonal antibodies of the present invention. Recombinant IL13 is commercially available from a number of sources (see, e.g. R & D Systems, Minneapolis, Minn., PeproTech, Inc., NJ, and Sanofi Bio-Industries, Inc., Tervose, Pa.). Alternatively, a gene or a cDNA encoding IL13 may be cloned into a plasmid or other expression vector and expressed in any of a number of expression systems according to methods well known to those of skill in the art. Methods of cloning and expressing IL13 and the nucleic acid sequence for IL13 are well known (see, for example, U.S. Pat. No. 5,652,123). Because of the degeneracy of the genetic code, a multitude of nucleotide sequences encoding IL13 polypeptides may be produced. One may vary the nucleotide sequence by selecting combinations based on possible codon choices. These combinations are made in accordance with the standard triplet genetic code as applied to the nucleotide sequence that codes for naturally occurring IL13 polypeptide and all such variations are to be considered. Any one of these polypeptides may be used in the immunization of an animal to generate antibodies that bind to IL13.

The immunogen IL13 polypeptide may, when beneficial, be expressed as a fusion protein that has the IL13 polypeptide attached to a fusion segment. The fusion segment often aids in protein purification, e.g., by permitting the fusion protein to be isolated and purified by affinity chromatography. Fusion proteins can be produced by culturing a recombinant cell transformed with a fusion nucleic acid sequence that encodes a protein including the fusion segment attached to either the carboxyl and/or amino terminal end of the protein. Fusion segments may include, but are not limited to, immunoglobulin Fc regions, glutathione-S-transferase, β-galactosidase, a poly-histidine segment capable of binding to a divalent metal ion, and maltose binding protein.

Exemplary polypeptides comprise all or a portion of SEQ ID NO.1 or variants thereof, or SEQ ID NO. 2 wherein amino acid 13 is Xaa and may be changed from the wt, e.g, glutamic acid to lysine.

A fusion protein comprising a mutant form of human IL13 was used to generate the antibodies of the present invention. This mutant form of IL13 contained a single mutation resulting in an inactive form of the protein (Thompson et al., J. Biol. Chem. 274: 2994 (1999)). In order to generate neutralizing antibodies with high affinity, the fusion protein comprised the mutant IL13 protein fused to an immunoglobulin Fc, specifically IgG1, and was expressed in a mammalian cell line such that the recombinant protein was naturally glycosylated. The Fc portion of the fusion protein may have provided a conformational structure that exposed a key epitope. The glycosylation may have increased the immunogenicity of the epitope, allowing the generation of antibodies to this particular epitope.

IL13 polypeptides expressed in *E. coli* lack glycosylation and the commercially available antibodies tested were generated using this protein. We tested these antibodies, e.g., R&D Systems and Pharmingen, and found that antibodies generated with an immunogen produced in *E. coli* do not cross react with the epitope bound by the antibodies of the present invention.

Antibody Generation

The antibodies of the present invention may be generated by any suitable method known in the art. The antibodies of the present invention may comprise polyclonal antibodies. Methods of preparing polyclonal antibodies are known to the skilled artisan (Harlow, et al., Antibodies: a Laboratory Manual, (Cold spring Harbor Laboratory Press, 2nd ed. (1988), which is hereby incorporated herein by reference in its entirety).

For example, an immunogen as described above may be administered to various host animals including, but not limited to, rabbits, mice, rats, etc., to induce the production of sera containing polyclonal antibodies specific for the antigen. The administration of the immunogen may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Additional examples of adjuvants which may be employed include the MPL-TDM adjuvant (monophosphoryl lipid A, synthetic trehalose dicorynomycolate). Immunization protocols are well known in the art in the art and may be performed by any method that elicits an immune response in the animal host chosen. Adjuvants are also well known in the art.

Typically, the immunogen (with or without adjuvant) is injected into the mammal by multiple subcutaneous or intraperitoneal injections, or intramuscularly or through IV. The immunogen may include an IL13 polypeptide, a fusion protein or variants thereof. Depending upon the nature of the polypeptides (i.e., percent hydrophobicity, percent hydrophilicity, stability, net charge, isoelectric point etc.), it may be useful to conjugate the immunogen to a protein known to be immunogenic in the mammal being immunized. Such conjugation includes either chemical conjugation by derivatizing active chemical functional groups to both the immunogen and the immunogenic protein to be conjugated such that a covalent bond is formed, or through fusion-protein based methodology, or other methods known to the skilled artisan. Examples of such immunogenic proteins include, but are not limited to, keyhole limpet hemocyanin, ovalbumin, serum albumin, bovine thyroglobulin, soybean trypsin inhibitor, and promiscuous T helper peptides. Various adjuvants may be used to increase the immunological response as described above.

The antibodies of the present invention comprise monoclonal antibodies. Monoclonal antibodies may be prepared using hybridoma technology, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, 2.sup.nd ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies include, but are not limited to, the human B-cell hybridoma technique (Kosbor et al., 1983, Immunology Today 4:72; Cole et at., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the MAb of this invention may be cultivated in vitro or in vivo.

Using typical hybridoma techniques, a host such as a mouse, a humanized mouse, a mouse with a human immune system, hamster, rabbit, camel or any other appropriate host animal, is typically immunized with an immunogen to elicit lymphocytes that produce or are capable of producing antibodies that will specifically bind to IL13. Alternatively, lymphocytes may be immunized in vitro with the antigen.

Generally, in making antibody-producing hybridomas, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), substances that prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines may also be used for the production of human monoclonal antibodies (Kozbor, J. Immunol., 133: 3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the IL13. The binding specificity of monoclonal antibodies produced by the hybridoma cells is determined by, e.g., immunoprecipitation or by an in vitro binding assay, such as radioimmunoassay (RIA) or enzyme-linked immunoadsorbant assay (ELISA). Such techniques are known in the art and within the skill of the artisan. The binding affinity of the monoclonal antibody to IL13 can, for example, be determined by a Scatchard analysis (Munson et al., Anal. Biochem., 107:220 (1980)).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. The monoclonal antibodies secreted by the subclones may be isolated or purified from the culture medium by conventional immunoglobulin purification procedures such as, e.g., protein A-sepharose, hydroxyapatite chromatography, gel exclusion chromatography, gel electrophoresis, dialysis, or affinity chromatography.

A variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as NS0 cells, Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety.

Humanized antibodies are antibody molecules generated in a non-human species that bind the desired antigen having one or more complementarity determining regions (CDRs) from the non-human species and framework (FR) regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties). Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(415):489-498 (1991); Studnicka et al., Protein Engineering 7(6):805-814 (1994); Roguska. et al., PNAS 91:969-973 (1994)), and chain shuffling (U.S. Pat. No. 5,565,332).

Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human MAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards IL13, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are well known. Traditionally, the recombinant production of bispecific antibodies is based on the co-expression of two immunoglobulin heavy-chain/light-chain pairs, where the two heavy chains have different specificities (Milstein and Cuello, Nature, 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It may have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

In addition, one can generate single-domain antibodies to IL-13. Examples of this technology have been described in WO9425591 for antibodies derived from Camelidae heavy chain Ig, as well in US20030130496 describing the isolation of single domain fully human antibodies from phage libraries.

Identification of Anti-IL13 Antibodies

The present invention provides antagonist monoclonal antibodies that inhibit and neutralize the action of IL13. In particular, the antibodies of the present invention bind to IL13 and inhibit the activation of the IL13 receptor alpha chain-1 (IL13Rα1). The antibodies of the present invention include the antibodies designated 228B/C-1, 228A-4, 227-26, and 227-43, and humanized clones of 228B/C-1 are disclosed. The present invention also includes antibodies that bind to the same epitope as one of these antibodies, e.g., that of monoclonal antibody 228B/C-1.

Candidate anti-IL13 antibodies were tested by enzyme linked immunosorbent assay (ELISA), Western immunoblotting, or other immunochemical techniques. Assays performed to characterize the individual antibodies included: (1) Inhibition of IL13-autocrine proliferation of Hodgkin's lymphoma cell lines HDLM-2 and L-1236; (2) Inhibition of IL13-induced STAT6 phosphorylation in THP-1 cells; and (3) Inhibition of IL13-induced suppression of CD14 expression in primary human monocytes; and (4) Inhibition of IL13-induced up-regulation of CD23 expression on primary human monocytes. Experimental details are described in the Examples.

Antibodies of the invention include, but are not limited to, polyclonal, monoclonal, monovalent, bispecific, heteroconjugate, multispecific, human, humanized or chimeric antibodies, single chain antibodies, single-domain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above.

The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (MAb) is meant to include intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal or plant, and may have less non-specific tissue binding than an intact antibody (Wahl et al., J. Nucl. Med. 24:316-325 (1983)).

The antibodies may be human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and single-domain antibodies comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments comprising any combination of variable region(s) with a hinge region, CH1, CH2, and CH3 domains. The antibodies of the invention may be from any animal origin including birds and mammals. Preferably, the antibodies are from human, non-human primates, rodents (e.g., mouse and rat), donkey, sheep, rabbit, goat, guinea pig, camel, horse, or chicken.

As used herein, "human" antibodies" include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of IL13 or may be specific for both IL13 as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of IL13 which they recognize or specifically bind. The epitope(s) or polypeptide portion(s) may be specified as described herein, e.g., by N-terminal and C-terminal positions, by size in contiguous amino acid residues, or listed in the Tables and Figures.

Antibodies of the present invention may also be described or specified in terms of their cross-reactivity. Antibodies that bind IL13 polypeptides, which have at least 95%, at least 90%, at least 85%, at least 80%, at least 75%, at least 70%, at least 65%, at least 60%, at least 55%, and at least 50% identity (as calculated using methods known in the art and described herein) to IL-13 are also included in the present invention. Anti-IL-13 antibodies may also bind with a $K_D$ of less than about $10^{-7}$ M, less than about $10^{-6}$ M, or less than about $10^{-5}$ M to other proteins, such as IL-13 antibodies from species other than that against which the anti-IL-13 antibody is directed.

In specific embodiments, antibodies of the present invention cross-react with monkey homologues of human IL13 and the corresponding epitopes thereof. In a specific embodiment, the above-described cross-reactivity is with respect to any single specific antigenic or immunogenic polypeptide, or combination(s) of the specific antigenic and/or immunogenic polypeptides disclosed herein.

Further included in the present invention are antibodies which bind polypeptides encoded by polynucleotides which hybridize to a polynucleotide encoding IL13 under stringent hybridization conditions. Antibodies of the present invention may also be described or specified in terms of their binding affinity to a polypeptide of the invention. Preferred binding affinities include those with an equilibrium dissociation constant or $K_D$ from $10^{-8}$ to $10^{-15}$ M, $10^{-8}$ to $10^{-12}$ M, $10^{-8}$ to $10^{-10}$ M, or $10^{-10}$ to $10^{-12}$ M. The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Vectors and Host Cells

In another aspect, the present invention provides vector constructs comprising a nucleotide sequence encoding the antibodies of the present invention and a host cell comprising such a vector. Standard techniques for cloning and transformation may be used in the preparation of cell lines expressing the antibodies of the present invention.

Recombinant expression vectors containing a nucleotide sequence encoding the antibodies of the present invention can be prepared using well known techniques. The expression vectors include a nucleotide sequence operably linked to suitable transcriptional or translational regulatory nucleotide sequences such as those derived from mammalian, microbial, viral, or insect genes. Examples of regulatory sequences include transcriptional promoters, operators, enhancers, mRNA ribosomal binding sites, and/or other appropriate sequences which control transcription and translation initiation and termination. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of the appropriate nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody. The signal peptide may be cleaved from the polypeptide upon secretion of antibody from the cell. Examples of such secretory signals are well known and include, e.g., those described in U.S. Pat. Nos. 5,698,435, 5,698,417, and 6,204,023.

Host cells useful in the present invention include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

The vector may be a plasmid vector, a single or double-stranded phage vector, or a single or double-stranded RNA or DNA viral vector. Such vectors may be introduced into cells as polynucleotides by well known techniques for introducing DNA and RNA into cells. The vectors, in the case of phage and viral vectors also may be introduced into cells as packaged or encapsulated virus by well known techniques for infection and transduction. Viral vectors may be replication competent or replication defective. In the latter case, viral propagation generally will occur only in complementing host cells. Cell-free translation systems may also be employed to produce the protein using RNAs derived from the present DNA constructs. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

Prokaryotes useful as host cells in the present invention include gram negative or gram positive organisms such as *E. coli*, and *B. subtilis*. Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the pKK223-3 (Pharmacia Fine Chemicals, Uppsala, Sweden), pGEM1 (Promega Biotec, Madison, Wis., USA), and the pET (Novagen, Madison, Wis., USA) and pRSET (Invitrogen Corporation, Carlsbad, Calif., USA) series of vectors (Studier, F. W., J. Mol. Biol. 219: 37 (1991); Schoepfer, R. Gene 124: 83 (1993)). Promoter sequences commonly used for recombinant prokaryotic host cell expression vectors include T7, (Rosenberg, et al. Gene 56, 125-135 (1987)), β-lactamase (penicillinase), lactose promoter system (Chang et al., Nature 275:615, (1978); and Goeddel et al., Nature 281:544, (1979)), tryptophan (trp) promoter system (Goeddel et al., Nucl. Acids Res. 8:4057, (1980)), and tac promoter (Sambrook et al., 1990, Molecular Cloning, A Laboratory Manual, 2d Ed., Cold Spring Harbor Laboratory, Cold Spring Harbor, N.Y.)

Yeasts useful in the present invention include those from the genus *Saccharomyces, Pichia, Actinomycetes* and *Kluyveromyces*. Yeast vectors will often contain an origin of replication sequence from a 2µ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991). Other suitable promoters and vectors for yeast and yeast transformation protocols are well known in the art. Yeast transformation protocols are well known. One such protocol is described by Hinnen et al., Proc. Natl. Acad. Sci., 75:1929 (1978). The Hinnen protocol selects for Trp$^+$ transformants in a selective medium.

Mammalian or insect host cell culture systems may also be employed to express recombinant antibodies, e.g., Baculovirus systems for production of heterologous proteins. In an insect system,—*Autographa californica* nuclear polyhedrosis virus (AcNPV) may be used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

NS0 or Chinese hamster ovary (CHO) cells for mammalian expression of the antibodies of the present invention may be used. Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are commercially available.

Polynucleotides Encoding Antibodies

The invention further provides polynucleotides or nucleic acids, e.g., DNA, comprising a nucleotide sequence encoding an antibody of the invention and fragments thereof. Exemplary polynucleotides include those encoding antibody chains comprising one or more of the amino acid sequences described herein. The invention also encompasses polynucleotides that hybridize under stringent or lower stringency hybridization conditions to polynucleotides that encode an antibody of the present invention.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A$^+$ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine MAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

Methods of Producing Anti-IL13 Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody molecules of the invention as described above. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as E. coli, and eukaryotic cells are commonly used for the expression of a recombinant antibody molecule, especially for the expression of whole recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk, hgprt or aprt-cells, respectively. Also, antimetabolite resistance can be used as the basis of selection for the following genes: dhfr, which confers resistance to methotrexate (Wigler et al., Proc. Natl. Acad. Sci., USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu, Biotherapy 3:87-95 (1991)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" (DNA Cloning, Vol.3. Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See e.g., Harbor et al., supra, and PCT publication WO 93/21232; EP 439,095; Naramura et al., Immunol. Lett. 39:91-99 (1994); U.S. Pat. No. 5,474,981; Gillies et al., Proc. Natl. Acad. Sci. 89:1428-1432 (1992); Fell et al., J. Immunol. 146:2446-2452(1991), which are incorporated by reference in their entireties.

Moreover, the antibodies or fragments thereof of the present invention can be fused to marker sequences, such as a peptide to facilitate purification in preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Diagnostic Uses for Anti-IL13 Antibodies

The antibodies of the invention include derivatives that are modified, i.e., by the covalent attachment of any type of molecule to the antibody, such that covalent attachment does not interfere with binding to IL13. For example, but not by way of limitation, the antibody derivatives include antibodies that have been modified, e.g., by biotinylation, HRP, or any other detectable moiety.

Antibodies of the present invention may be used, for example, but not limited to, to purify or detect IL13, including both in vitro and in vivo diagnostic methods. For example, the antibodies have use in immunoassays for qualitatively and quantitatively measuring levels of IL13 in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalently conjugations) to polypeptides or other compositions. For example, antibodies of the present invention may be recombinantly fused or conjugated to molecules useful as labels in detection assays.

The present invention further encompasses antibodies or fragments thereof conjugated to a diagnostic agent. The antibodies can be used diagnostically to, for example, monitor the development or progression of an allergic response as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotrianylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Labeled antibodies, and derivatives and analogs thereof, which specifically bind to IL13 can be used for diagnostic purposes to detect, diagnose, or monitor diseases, disorders, and/or conditions associated with the aberrant expression and/or activity of IL13. The invention provides for the detection of aberrant expression of IL13, comprising (a) assaying the expression of IL13 in cells or body fluid of an individual using one or more antibodies of the present invention specific to IL13 and (b) comparing the level of gene expression with a standard gene expression level, whereby an increase or decrease in the assayed IL13 expression level compared to the standard expression level is indicative of aberrant expression.

Antibodies may be used for detecting the presence and/or levels of IL13 in a sample, e.g., a bodily fluid or tissue sample. The detecting method may comprise contacting the sample with an IL13 antibody and determining the amount of antibody that is bound to the sample.

The invention provides a diagnostic assay for diagnosing a disorder, comprising (a) assaying the expression of IL13 in cells or body fluid of an individual using one or more antibodies of the present invention and (b) comparing the level of gene expression with a standard gene expression level, whereby an increase or decrease in the assayed gene expression level compared to the standard expression level is indicative of a particular disorder.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of IL13 in an animal, preferably a mammal and most preferably a human. In one embodiment, diagnosis comprises: a) administering (for example, parenterally, subcutaneously, or intraperitoneally) to a subject an effective amount of a labeled molecule which specifically binds to IL13; b) waiting for a time interval following the administration permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of IL13. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

In another aspect, the present invention provides a method for diagnosing the predisposition of a patient to develop diseases caused by the unregulated expression of cytokines. Increased amounts of IL13 in certain patient cells, tissues, or body fluids may indicate that the patient is predisposed to certain immune diseases. In one embodiment, the method comprises collecting a cell, tissue, or body fluid sample a subject known to have low or normal levels of IL13, analyzing the tissue or body fluid for the presence of IL13 in the tissue, and predicting the predisposition of the patient to certain immune diseases based upon the level of expression of IL13 in the tissue or body fluid. In another embodiment, the method comprises collecting a cell, tissue, or body fluid sample known to contain a defined level of IL13 from a patient, analyzing the tissue or body fluid for the amount of IL13, and predicting the predisposition of the patient to certain immune diseases based upon the change in the amount of IL13 compared to a defined or tested level established for normal cell, tissue, or bodily fluid. The defined level of IL13 may be a known amount based upon literature values or may be determined in advance by measuring the amount in normal cell, tissue, or body fluids. Specifically, determination of IL13 levels in certain tissues or body fluids permits specific and early, preferably before disease occurs, detection of immune diseases in the patient. Immune diseases that can be diagnosed using the present method include, but are not limited to, the immune diseases described herein. In the preferred embodiment, the tissue or body fluid is peripheral blood, peripheral blood leukocytes, biopsy tissues such as lung or skin biopsies, and tissue.

Therapeutic Uses of Anti-IL13 Antibodies

An antibody, with or without a therapeutic moiety conjugated to it, administered alone or in combination with cytotoxic factor(s) can be used as a therapeutic. The present invention is directed to antibody-based therapies which involve administering antibodies of the invention to an animal, a mammal, or a human, for treating an IL13-mediated disease, disorder, or condition. The animal or subject may be an animal in need of a particular treatment, such as an animal having been diagnosed with a particular disorder, e.g., one relating to IL13. Antibodies directed against IL13 are useful for inhibiting allergic reactions in animals, including but not limited to cows, pigs, horses, chickens, cats, dogs, non-human primates etc., as well as humans. For example, by administering a therapeutically acceptable dose of an antibody, or antibodies, of the present invention, or a cocktail of the present antibodies, or in combination with other antibodies of varying sources, an allergic response to antigens may be reduced or eliminated in the treated mammal.

Therapeutic compounds of the invention include, but are not limited to, antibodies of the invention (including fragments, analogs and derivatives thereof as described herein) and nucleic acids encoding antibodies of the invention as described below (including fragments, analogs and derivatives thereof and anti-idiotypic antibodies as described herein). The antibodies of the invention can be used to treat, inhibit or prevent diseases, disorders or conditions associated with aberrant expression and/or activity of IL13, including, but not limited to, any one or more of the diseases, disorders, or conditions described herein. The treatment and/or prevention of diseases, disorders, or conditions associated with aberrant expression and/or activity of IL13 includes, but is not limited to, alleviating at least one symptoms associated with those diseases, disorders or conditions. Antibodies of the invention may be provided in pharmaceutically acceptable compositions as known in the art or as described herein.

Anti-IL13 antibodies of the present invention may be used therapeutically in a variety of diseases. The present invention provides a method for preventing or treating IL13-mediated diseases in a mammal. The method comprises administering a disease preventing or treating amount of anti-IL13 antibody to the mammal. The anti-IL13 antibody binds to IL13 and regulates cytokine and cellular receptor expression resulting in cytokine levels characteristic of non-disease states. Thus, diseases for treatment include allergy, asthma, autoimmune disease, or other inflammatory diseases. Other allergic diseases include allergic rhinitis, atopic dermatitis, food hypersensitivity and urticaria; immune-mediated skin diseases include bullous skin diseases, erythema multiform and contact dermatitis; autoimmune disease include psoriasis, rheumatoid arthritis, juvenile chronic arthritis; inflammatory bowel disease (i.e., ulcerative colitis, Crohn's disease); other diseases associated with IL13 include idiopathic interstitial pneumonia, goblet cell metaplasia, inflammatory and fibrotic lung diseases such as cystic fibrosis, gluten-sensitive enteropathy, and Whipple's disease; immunologic diseases of the lung such as eosinophilic pneumonia, idiopathic pulmonary fibrosis and hypersensitivity pneumonitis; chronic obstructive pulmonary disease, RSV infection, uveitis, scleroderma, osteoporosis, and Hodgkin's lymphoma.

The amount of the antibody which will be effective in the treatment, inhibition and prevention of a disease or disorder associated with aberrant expression and/or activity of IL13 can be determined by standard clinical techniques. The antibody can be administered in treatment regimes consistent with the disease, e.g., a single or a few doses over one to several days to ameliorate a disease state or periodic doses over an extended time to prevent allergy or asthma. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The antibodies of this invention may be advantageously utilized in combination with other monoclonal or chimeric antibodies, or with lymphokines or hematopoietic growth factors (such as, e.g., IL-2, IL-3 IL-7, IFN), for example, which serve to increase the number or activity of effector cells which interact with the antibodies.

The antibodies of the invention may be administered alone or in combination with other types of treatments, such as immunotherapy, bronchodilators, anti-IgE molecules, antihistamines, or anti-leukotrienes.

In a preferred aspect, the antibody is substantially purified (e.g., substantially free from substances that limit its effect or produce undesired side-effects).

Various delivery systems are known and can be used to administer an antibody of the present invention, including injection, e.g., encapsulation in liposomes, microparticles, microcapsules, recombinant cells capable of expressing the compound, receptor-mediated endocytosis (see, e.g., Wu et al., J. Biol. Chem. 262:4429-4432 (1987)), construction of a nucleic acid as part of a retroviral or other vector, etc.

The anti-IL13 antibody can be administered to the mammal in any acceptable manner. Methods of introduction include but are not limited to intradermal, intramuscular, intraperitoneal, intravenous, subcutaneous, intranasal, epidural, inhalation and oral routes. The antibodies or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the therapeutic antibodies or compositions of the invention into the central nervous system by any suitable route, including intraventricular and intrathecal injection; intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent. The antibody may also be administered into the lungs of a patient in the form of a dry powder composition (See e.g., U.S. Pat. No. 6,514,496).

In a specific embodiment, it may be desirable to administer the therapeutic antibodies or compositions of the invention locally to the area in need of treatment; this may be achieved by, for example, and not by way of limitation, local infusion, topical application, by injection, by means of a catheter, by means of a suppository, or by means of an implant, said implant being of a porous, non-porous, or gelatinous material, including membranes, such as sialastic membranes, or fibers. Preferably, when administering an antibody of the invention, care must be taken to use materials to which the protein does not absorb.

In another embodiment, the antibody can be delivered in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.).

In yet another embodiment, the antibody can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target.

The present invention also provides pharmaceutical compositions. Such compositions comprise a therapeutically effective amount of the antibody, and a physiologically acceptable carrier. In a specific embodiment, the term "physiologically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable carriers are described in "Remington's Pharmaceutical Sciences" by E. W. Martin. Such compositions will contain an effective amount of the antibody, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In addition, the antibodies of the present invention may be conjugated to various effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387. An antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982). Alternatively, an antibody can be conjugated to a second antibody to form an antibody heteroconjugate. (See, e.g., Segal in U.S. Pat. No. 4,676,980.)

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or *diphtheria* toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibody-Based Gene Therapy

In a another aspect of the invention, nucleic acids comprising sequences encoding antibodies or functional derivatives thereof, are administered to treat, inhibit or prevent a disease or disorder associated with aberrant expression and/or activity of IL13, by way of gene therapy. Gene therapy refers to therapy performed by the administration to a subject of an expressed or expressible nucleic acid. In this embodiment of the invention, the nucleic acids produce their encoded protein that mediates a therapeutic effect. Any of the methods for gene therapy available can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993).

In a one aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific.

In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates the delivery of the gene into a patient. More detail about retroviral vectors can be found in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. Gen. and Dev. 3:110-114 (1993).

Adenoviruses may also be used in the present invention. Adenoviruses are especially attractive vehicles in the present invention for delivering antibodies to respiratory epithelia. Adenoviruses naturally infect respiratory epithelia. Other targets for adenovirus-based delivery systems are liver, the central nervous system, endothelial cells, and muscle. Adenoviruses have the advantage of being capable of infecting non-dividing cells. Kozarsky and Wilson, Curr. Opin. Gen. Dev. 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). Adeno-associated virus (AAV) has also been proposed for use in gene therapy (Walsh et al., Proc. Soc. Exp. Biol. Med. 204:289-300 (1993); U.S. Pat. Nos. 5,436,146; 6,632,670; 6,642,051).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a one embodiment, the cell used for gene therapy is autologous to the patient. Nucleic acid sequences encoding an antibody of the present invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

EXAMPLES

Example 1

Preparation of IL13 Immunogen: a Mutated, Inactive Human IL13/Fc (MT-IL13/Fc)

A. Cloning and Construction of an Expression Plasmid for MT-IL13/Fc

It was reported that human IL13 with a mutation (glutamic acid to lysine) at amino acid residue #13 bound IL13Rα1 with equal or higher affinity but had lost the ability to activate IL13Rα1-bearing cells (Thompson et al., J. Biol. Chem., 274: 29944 (1999)). This mutated, inactive IL13, designated MT-IL13, was expressed in human embryonic kidney cells 293-T. The purified recombinant protein was used as the immunogen in the present invention to generate anti-IL13 monoclonal antibodies. Two oligonucleotide primers:

```
5' AAGCTTTCCCCAGGCCCTGTGCCTCCCTCTACAGCCCTCAGGAAGCTCAT 3' (SEQ ID NO 9)

5' CTCGAGGTTGAACCGTCCCTCGCGAAAAAG 3'                     (SEQ ID NO 10)
``` corresponding to the oligonucleotide sequence of MT-IL13 gene were synthesized and used as templates in polymerase chain reactions (PCR) to clone the IL13 gene from human testis cDNA library (BD Biosciences Clontech, Palo Alto, Calif.). The PCR fragment (342 base pairs) which lacked the predicted signal peptide sequence of IL13 was ligated into the pSecTag/FRT vector (Invitrogen, Carlsbad, Calif.) that contained a secretion signal peptide sequence at the 5' end and a human Fcγ1 (hinge and constant regions CH2 and CH3) sequence at the 3' end. The construct's composition was confirmed by sequencing.

B. Production of MT-IL13/Fc from Transfected 293T Cells

For transient expression of MT-IL13/Fc, purified plasmid DNA was transfected into 293T cells by Lipofectamine 2000 (Invitrogen), according to the manufacturer's protocol. At 72 hours post-transfection, culture supernatants from transfected cells were collected for purification. For stable expression of MT-IL13/Fc, cell lines were established using a Flp-In 293T cell line (Invitrogen). To confirm expression, culture supernatants were analyzed by sodium dodecyl sulfate polyacrylamide gel electrophoresis (SDS-PAGE). The separated proteins were transferred to nitrocellulose membrane and detected by reaction with horseradish peroxidase (HRP) conjugated mouse anti-human IgG (Fc) monoclonal antibody (Sigma, St. Louis, Mo.) or polyclonal goat anti-IL13 antibodies (R&D Systems, Minneapolis, Minn.), which were then detected with HRP-donkey anti-goat IgG (Jackson ImmunoResearch Laboratories, West Grove, Pa.). The immunoreactive proteins were identified on film, using enhanced chemi-luminescence detection (Supersignal West Pico Chemiluminescent Substrate, Pierce, Rockford, Ill.).

C. Purification of MTIL13/Fc

MT-IL13/Fc was purified with a hyper-D protein A affinity column (Invitrogen) equilibrated with phosphate-buffered saline (PBS). After applying the cell culture supernatant to the column, the resin was washed with more than 20 column volumes of PBS. Then, the resin was washed with SCC buffer (0.05 M sodium citrate, 0.5 M sodium chloride, pH 6.0) to remove unbound proteins. The IL13 fusion proteins were then eluted (0.05 M sodium citrate, 0.15 M sodium chloride, pH 3.0) and dialyzed in PBS.

Fractions from the affinity column containing MT-IL13/Fc were analyzed by SDS-PAGE. The purity of the proteins were analyzed by Coomassie Blue staining and the identity of the proteins by Western immunoblotting using goat anti-human IgG (Fc) antibody (Sigma) and goat anti-human IL13 antibody (R&D Systems) as described above.

Example 2

Generation of Anti-IL13 Monoclonal Antibodies

Male A/J mice (Harlan, Indianapolis, Ind.), 8-12 weeks old, were injected subcutaneously with 20 µg MT-IL13/Fc in complete Freund's adjuvant (Difco Laboratories, Detroit, Mich.) in 200 µL of PBS pH 7,4. At two-week intervals the mice were twice injected subcutaneously with 20 µg MT-IL13/Fc in incomplete Freund's adjuvant. Then, two weeks later and three days prior to sacrifice, the mice were again injected intraperitoneally with 20 µg of the same immunogen in PBS. Spleen cells isolated from one or more antigen-immunized mouse were used for fusion. Similar procedures of immunization and fusion were also used with *E. coli* expressed human IL13 (R&D Systems) as immunogen.

In the fusion leading to the generation of the anti-IL13 MAb 228B/C-1, $26.4 \times 10^6$ spleen cells and $58.8 \times 10^6$ spleen cells from two immunized mice were combined. For each fusion, single cell suspensions were prepared from the spleen of immunized mice and used for fusion with Sp2/0 myeloma cells. Sp2/0 and spleen cells at a ratio of 1:1 were fused in a medium containing 50% polyethylene glycol (M.W. 1450) (Kodak, Rochester, N.Y.) and 5% dimethylsulfoxide (Sigma). The cells were then adjusted to a concentration of $1.5 \times 10^5$ spleen cells per 250 µL of the suspension in DMEM medium (Invitrogen, CA), supplemented with 10% fetal bovine serum, 100 units/mL of penicillin, 100 µg/mL of streptomycin, 0.1 mM hypoxanthine, 0.4 µM aminopterin, and 16 µM thymidine. Two hundred and fifty microliters of the cell suspension were added to each well of about fifty 96-well microculture plates. After about ten days culture supernatants were withdrawn for screening for reactivity with MT-IL13/Fc in ELISA.

Wells of Immulon 2 (Dynatech Laboratories, Chantilly, Va.) microtest plates were coated by adding purified MT-IL13/Fc (0.1 µg/mL) overnight at room temperature. After the coating solution was removed by flicking of the plate, 200 µL of a blocking/diluting buffer (PBS containing 2% bovine serum albumin and 0.05% TWEEN® 20) was added to each well for one hour to block the non-specific sites. One hour later, the wells were then washed with PBST buffer (PBS containing 0.05% TWEEN® 20). Fifty microliters of culture supernatant was collected from each fusion well, mixed with 50 µL of the blocking/diluting buffer and then added to the individual wells of the microtest plates. After one hour of incubation, the wells were washed with PBST. The bound murine antibodies were then detected by reaction with HRP-conjugated goat anti-mouse IgG (Fc specific) (Jackson ImmunoResearch Lab, West Grove, Pa.) and diluted at 1:2,000 with the blocking/diluting buffer. Peroxidase substrate solution containing 0.1% 3,3,5,5 tetramethyl benzidine (Sigma, St. Louis, Mo.) and 0.003% hydrogen peroxide (Sigma) was added to the wells for color development for 30 minutes. The reaction was terminated by the addition of 50 µL of 2 M $H_2SO_4$ per well. The $OD_{450}$ of the reaction mixture was measured with a BioTek ELISA Reader (BioTek Instruments, Winooski, Vt.).

The culture supernatants from the positive wells of MT-IL13/Fc screening were then tested for negative binding to an irrelevant Fγ1 fusion protein. Final positive wells were then selected for single-cell cloning by limiting dilution. Culture supernatants from monoclonal antibodies were re-tested to confirm their reactivity by ELISA. Selected hybridomas were grown in spinner flasks and the spent culture supernatant collected for antibody purification by protein A affinity chromatography.

The purified antibodies were tested by four assays: i) Cross-reactivity with 293T cell expressed MT-IL13/Fc and *E. coli* expressed mouse IL13; ii) Inhibition of IL13-autocrine proliferation of HDLM-2 and L-1236 cells; iii) Inhibition of IL13-induced STAT6 phosphorylation in THP-1 cells; and iv) Inhibition of IL13-regulated CD14 and CD23 expression on human monocytes.

Seventy-three anti-IL13 MAbs were obtained from the fusions performed on MT-IL13/Fc and IL13 immunized mice. Thirty-nine of these MAbs were purified for characterization by ELISA and cell-based assays. Thirteen of these 39 MAbs inhibited autocrine IL13-induced proliferation of HDLM-2 and L-1236 cells (see assay description and results in Example 5). Four of the MAbs were found to be very strongly reactive with human IL13 in ELISA and were neutralizing against human IL13 in functional cell-based assays. These MAbs were designated 228B/C-1, 228A-4, 227-26, and 227-43. These antibodies were all generated using the glycosylated MT-IL13/Fc as immunogen.

Example 3

Reactivity of Anti-IL13 Monoclonal Antibodies with Human and Mouse IL13 in ELISA The reactivity of various anti-IL13 monoclonal antibodies was tested by ELISA. Different wells of 96-well microtest plates were coated with either *E. coli* expressed non-glycosylated human IL13 (R&D Systems), 293T cell expressed glycosylated MT-IL13/Fc, or *E. coli* expressed mouse IL13 (R&D Systems) by the addition of 100 µL of IL13 protein at 0.1 µg/mL in PBS. After overnight incubation at room temperature, the wells were treated with PBSTB (PBST containing 2% BSA) to saturate the remaining binding sites. The wells were then washed with PBST.

One hundred microliters of two-fold serially diluted anti-IL13 MAbs (0.5 µg/mL (3.33 nM) to 0.05 ng/mL (0.00033 nM)) were added to the wells for 1 hour at room temperature. An anti-IL13 MAb JES-5A2 from (BD Biosciences-Pharmingen, San Diego, Calif.) was also tested as a positive control. This antibody was generated by using *E. coli* expressed human IL13 as immunogen. An isotype-matched mouse anti-HIV-1 gp120 MAb was used as irrelevant negative control. The wells were then washed with PBST. Bound antibody was detected by incubation with diluted HRP-goat anti-mouse IgG (Fc) (Jackson ImmunoResearch) for 1 hour at room temperature. Peroxidase substrate solution was then added for color development as described above. The $OD_{450}$ was measured using an ELISA reader.

FIG. 1 shows the dose-dependent binding of anti-IL13 MAbs 228B/C-1, 228A-4, 227-26, 227-43, and the negative control in ELISA. Among these MAbs, 228B/C-1 showed the strongest reactivity. FIG. 2 shows the dose-dependent binding of the anti-IL13 MAbs to MT-IL13/Fc in ELISA. 228B/C-1 and 228A-4 showed the strongest reactivity with MT-IL13/Fc, whereas 227-26 and 227-43 showed moderate reactivity.

FIGS. 1 and 2 show that 228B/C-1 has highest affinity for both glycosylated and non-glycosylated human IL13 among all the anti-IL13 MAbs tested. All these anti-IL13 MAbs did not cross-react with mouse IL13 in ELISA (data no shown).

Example 4

Lack of Competition of 228B/C-1-Hrp Binding to Human IL13 by JES10-5A2

To address whether JES10-5A2 and 228B/C-1 bind to the same epitope on human IL13, a competition ELISA was used to examine the effect of JES10-5A2 on 228B/C-1-HRP binding to *E. coli* expressed human IL13. Each well of 96-well microtest plates were incubated with 100 µL of IL13 protein at 0.1 µg/mL in PBS. After overnight incubation at room temperature, the wells were treated with PBSTB (PBST containing 2% BSA) to saturate the remaining binding sites. The wells were then washed with PBST. Fifty microliters of two fold serially diluted 228B/C-1 and JES10-5A2 (from a final concentration of 20 µg/mL to 9.76 ng/mL) were mixed with 50 µL of pre-titrated 228B/C-1-HRP (at 1:6,400 dilution). The mixtures were then added to the wells and incubated for 1 hour at room temperature. Peroxidase substrate solution was then added for color development as described above. The $OD_{450}$ was measured using an ELISA reader.

FIG. 3 demonstrates that JES10-5A2 does not compete with the binding of 228B/C-1-HRP to human IL13, indicating that 228B/C-1 and JES10-5A2 bind to different sites on human IL13.

Example 5

Screening for Anti-IL13 Neutralizing Monoclonal Antibodies by an IL-13-Autocrine Dependent Proliferation Assay Using L-1236 and HDLM-2 Cells L-1236 and HDLM-2 are Hodgkin lymphoma cell lines obtained from the German Collection of Microorganisms and Cell Cultures (DSMZ, Braunschweig, Germany). These cell lines produce IL13 which in turn activates their cell proliferation in an autocrine fashion (Kapp U et. al., J. Exp. Med. 189:1939 (1999)).

Cells were cultured (25,000 cells/well) in the presence or absence of different anti-IL13 MAb (0.2, 0.02 and 0.002 µg/mL) in 5% $CO_2$ at 37° C. for 3-5 days. Cell proliferation was then measured either by an assay using the tetrazolium compound MTS (Promega, Madison, Wis.) (readouts at $OD_{490}$) or by the incorporation of $^3$H-thymidine (Amersham Biosciences, Piscataway, N.J.).

The addition of an anti-IL13 neutralizing MAb to the culture of these cell lines was expected to inhibit their proliferation by the binding and inactivation of the IL13 produced by these cells. The results illustrated in FIG. 4 shows the effect of anti-IL13 MAb of the present invention on the proliferation of L-1235 cells. MAb 228B/C-1 displays the highest potency of inhibition of L-1236 cell proliferation in a dose-dependent manner among the neutralizing antibodies tested. TA1-37 (an anti-IL13 MAb generated by using *E. coli* expressed human IL13 as immunogen) did not have any inhibitory activity even at a dose as high as 0.2 µg/mL. Similar results were obtained with HDLM-2 cells.

Example 6

Assay for IL13-Regulated CD14 and CD23 Expression on Primary Human Monocytes

IL13 induces suppression of CD14 expression and the up-regulation of CD23 expression in the human monocytes (de Waal Malefyt et al., J. Immunol., 151: 6370 (1993), Chomarat et al., Int. Rev. Immunol., 17: 1 (1998)). Peripheral blood leukocytes (PBLs) were isolated from freshly collected, heparinized whole blood of healthy human donors by density-gradient centrifugation in Histopaque-1077 (Sigma). PBLs ($1.5 \times 10^6$) suspended in RPMI-1640 medium (Invitrogen) with 5% fetal bovine serum were added to each well of a 96-well tissue culture plate containing recombinant IL13 (final 10 ng/mL=0.813 nM) and an anti-IL13 monoclonal antibody or an irrelevant antibody (three-fold serial dilutions, from a final 12 µg/mL=80 nM). CD14 expression or CD23 expression on monocytes was suppressed or up-regulated, respectively, by the addition of 0.813 nM human IL13 to the incubating medium. The medium control contained RPMI-1640/FBS medium without recombinant IL13.

The cells were incubated in 5% $CO_2$ at 37° C. for 2 days. The cells were harvested for staining with anti-CD14-FITC or anti-CD23-PE (BD Biosciences-Pharmingen). The expression levels of CD14 and CD23 in the monocyte population were measured by flow cytometry and represented by Median Fluorescence Intensity (MFI).

The effects of anti-IL13 MAbs on IL13-suppressed CD14 expression on human monocytes are depicted in FIG. 5. Among all the anti-IL13 MAbs tested, 228B/C-1 had the highest potency in inhibiting the effect of IL13 on CD14 expression. Complete inhibition of the effect of IL13 was achieved at 0.33 nM. The inhibitory activities of MAbs 227-26 and 228A-4 were moderate, whereas that of JES10-5A2 was weak. The effect of IL13 could not be completely inhibited by JES10-5A2 even at 80 nM.

The effects of anti-IL13 MAbs on IL13-induced CD23 up-regulation on human monocytes are depicted in FIG. 6. Similar to the results on CD14 expression (FIG. 5), 228B/C-1 was most potent in inhibiting the effect of IL13 on CD23 expression among the anti-IL13 MAbs tested. Complete inhibition by 228B/C-1 was achieved at 0.33 nM. The inhibitory potency of JES10-5A2 was weak.

Based on the results presented in FIGS. 5 and 6, complete inhibition of IL13 by 228B/C-1 can be achieved at a molar stoichiometric ratio of 1:2 (MAb:IL13), and, therefore, 228B/C-1 is a very high affinity neutralizing MAb against human IL13.

Example 7

IL13-Induced STAT6 Phosphorylation Assay in THP-1 Cells

IL13 can activate the myeloid cell line THP-1(ATCC, Manassas, Va.) to induce phosphorylation of STAT6 which is a critical step in the signal transduction pathway of IL13 (Murata T et al., Int. Immunol. 10: 1103-1110 (1998). The anti-IL13 MAbs were tested for inhibition of IL13 in this assay.

THP-1 cells were maintained in Dulbecco's Modified Eagle Medium (DMEM) (lnvitrogen) supplemented with 5% fetal bovine serum. On the day of experiments, the cells were washed and incubated in serum-free DMEM at 37° C. in 5% $CO_2$ for 2 hours. $0.3 \times 10^6$ cells in 80 µL of the serum-free medium were then added to each well of a 96-well round-bottom plate. One hundred and twenty microliters of medium containing human IL13 (final concentration of 10 ng/mL=0.813 nM) and anti-IL13 MAbs (5 fold serial dilutions, from final concentration of 0.5 µg/mL=3.333 nM). Negative control wells containing either no IL13 or IL13 and an isotype-matched irrelevant mouse MAb.

The mixtures were incubated at 37° C. under 5% $CO_2$ for 10 min. The plates were then centrifuged at 300×g for 3 minutes at 4° C. After discarding the supernatant, the cell pellets were resuspended in 100 µL of Laemmli non-reducing sample buffer (SDS-PAGE loading buffer, BioRad, CA) and then transferred to microcentrifuge tubes. The tubes were heated at 95° C. for 5 minutes and then centrifuged at 10,000×g for 10 minutes at room temperature. The supernatants were collected and analyzed by 4-20% gradient SDS-PAGE. The separated proteins were transferred to PVDF membrane which was then incubated with diluted mouse anti-human Stat6 (Y641, phospho-specific) MAb (BD Biosciences Pharmingen).

The bound antibody was detected by HRP conjugated goat anti-mouse IgG (Fc) antibodies (Jackson ImmunoResearch Laboratories). The immunoreactive proteins were identified on film, using enhanced chemiluminescence detection (Supersignal West Pico Chemiluminescent Substrate, Pierce) FIG. 7 depicts the results of the effect of anti-IL13 MAbs on IL13-induced phosphorylation of Stat6 in THP-1 cells. Stat6 is phosphorylated in THP-1 cells treated with 0.813 nM human IL13. Dose-dependent inhibition of Stat6 phosphorylation was found when the cells were treated with MAbs 228B/C-1, 228A-4, 227-26, 227-43 and JES10-5A2. MAb 228B/C-1 is the most potent neutralizing antibodies among the anti-IL13 MAbs tested. Complete inhibition by 228B/C-1 was achieved at a concentration between 0.667 nM and 0.133 nM. The approximate molar stoichiometric ratio between 228B/C-1 and IL13 for complete inhibition was 1:2. It is consistent with the data shown in FIGS. 5 and 6.

Example 8

Molecular Cloning of Heavy and Light Chain Genes Encoding Anti-IL13 Monoclonal Antibodies Total RNA was isolated from hybridoma cells using a QIAGEN kit (Valencia, Calif.). Reverse transcription (first strand cDNA) reaction was carried out as follows: 1-1.5 mg of total RNA was mixed with 1 ml 10 mM dNTPs, 50 ng random Hexamers, and RNase free water in a final volume of 12 mL.

The reaction mixture was incubated at 65° C. for 5 minutes and placed on ice immediately for 1 minute. After a brief centrifugation, the following reagents were added: 4 mL of 5× first strand buffer (250 mM Tris-HCl, pH 8.3, 375 mM KCl, 15 mM $MgCl_2$), 2 mL of 0.1 mM DTT, and 1 mL of RNase-OUT RNase inhibitor (40 U/mL). After mixing, the reaction was incubated at room temperature for 2 minutes. One milliliter of Superscript II RT (50 U/ml) was then added to the mixture for incubation at 25° C. for 10 minutes followed by 50 minutes at 42° C. After a brief centrifugation, the reaction was incubated for 15 minutes at 70° C. to inactivate the reverse transcriptase. One microliter of RNase H (2 U/ml) was then added and the reaction was incubated for 20 minutes at 37° C. to destroy RNA.

To amplify the variable regions of the heavy and light chains, a method described by O'Brien and Jones (O'Brien S. and Jones T., "Humanizing antibodies by CDR grafting", Antibody Engineering, Springer Lab manual, Eds. Kontermann and Duble, S (2001)) was used. Briefly, 5' primers were selected from the signal peptide region (11 sets for light chain and 12 sets of degenerate primers for heavy chain) and 3' primers were selected from the constant region of either the light or heavy chain. 5' and 3' primers (1.5 mL of 10 mM) were mixed with 5 mL of 10× PCR buffer (250 mM Tris-HCl, pH 8.8, 20 mM $MgSO_4$, 100 mM KCl, 100 mM $(NH_4)_2 SO_4$, 1% Triton X-100, 1 mg/mL nuclease free BSA), 1 mL cDNA as prepared previously, 1 mL of Turbo pfu (Stratagene) and water to adjust the total volume of the reaction to 50 mL. PCR was performed as follows: 1 cycle at 94° C. for 4 minutes; 25 cycles at 94° C. for 30 seconds, at 53° C. for 30 seconds, and at 72° C. for 45 seconds; and 1 cycle at 72° C. for 7 minutes. Reaction mixtures were resolved by electrophoresis in a 1% agarose gel.

Amplified DNA fragment was purified and cloned into a pcDNA3.1 vector. Cloning was carried out using the Invitrogen TOPO cloning kit following the manufacturer's suggested protocol (Invitrogen). Fifteen to twenty colonies of transformed *E. coli* were used for plasmid purification. Plasmids were sequenced using a T7 primer. The predominant sequences for the heavy and light chains were cloned into an M13 Fab expression vector by hybridization mutagenesis (Glaser S. et al. Antibody Engineering (Oxford University Press, New York(1995)), Near R I, BioTechniques 12: 88 (1992)). Binding properties of the expressed Fab were confirmed by ELISA. FIGS. 8-10 depict the VH and VL chain amino acid sequences for 228B/C, 228A-4, and 227-26, respectively.

Example 9

Humanization of Clone 228B/C

A. General Protocol

The variable regions of murine antibody 228B/C were cloned and sequenced as described in Example 8. A chimeric Fab in a phage vector was constructed as a control which combined the variable regions of the murine 228B/C and the constant region of the human kappa chain and the CH1 part of human IgG.

To begin the humanization process, a suitable v gene sequence selected from known human germ line gene sequences was selected to provide the framework regions one to three (FM1-FM3), and a suitable J gene sequence was selected to provide framework 4 (FM4) according to the criteria described in WO04/070010 (incorporated herein by reference). This template may be chosen based on, e.g., its comparative overall length, the size of the CDRs, the amino acid residues located at the junction between the framework and the CDRs, overall homology, etc. The template chosen can be a mixture of more than one sequence or may be a consensus template.

Constructing an expression vector comprising the heavy and/or light chain variants generated comprised the formulas:

FRH1-CDRH1-FRH2-CDRH2-FRH3-CDRH3-FRH4　　(i) and

FRL1-CDRL1-FRL2-CDRL2-FRL3-CDRL3-FRL4　　(ii), wherein FRH1, FRH2, FRH3, FRH4, FRL1, FRL2, FRL3 and FRL4 represent the variants of the framework template heavy chain and light chain sequences chosen from the germ line templates and the CDRs represent those of the parent antibody. The differences between the murine parent antibody and the selected human template sequences were determined to serve as a basis for generating a library of antibody Fabs. This library can be generated for the light chain individually, and then the heavy chain or simultaneously. Affinity maturation of the CDR regions may also be analyzed simultaneously or sequentially with the humanization of the framework.

The library of variant Fabs was generated containing (1) the murine amino acid residue, (2) the amino acid residue from the chosen human germ line gene, or optionally, (3) a randomly selected amino acid, at each of the selected positions found to differ from the murine framework sequence. The desired variants were generated by annealing overlapping oligonucleotides and then incorporating the chosen residue at the framework positions that were of interest. An amplification of the annealed product was done using two primers, one of which was biotin-labeled. The biotin tag was used for the purification of a single-strand of the primer and this was used as a mutagenic oligo in a Kunkel-based mutagenesis reaction using the vector of interest in a U-template format (Rosok, M. J., at al., (1996) *Journal of Biological Chemistry* 271: 22611-22618). After annealing and elongating the plasmid, the reaction underwent digestion with a unique restriction enzyme, XbaI, which cleaves the original template but not the newly synthesized mutated strand. The plasmid was electroporated into competent cells for amplification and mixed with a phage-competent *E. coli* cell-type for generation of phage particles. The plasmid constructs are able to synthesize a Fab which is secreted into the supernatant. Individual plaques were selected and the antibody eluted for analysis.

The library was analyzed for quality and completeness. Upon sequencing a random sampling of the library, the number of candidates selected that had the correct insertion of the Vk (or Vh) region was determined. This number was used to determine the overall efficiency of the library. Once the library was established, the candidates were screened using a functional ELISA-based assay to determine which candidates produced functional Fabs specific for IL-13. Those candidates demonstrating activity for IL-13 comparable to the chimeric clone were assayed further for reproducibility. Several of the candidates were sequenced to determine how tolerant the targeted framework positions were for humanization.

After the libraries were found to be representative, variants were analyzed for binding affinity, and those found to have comparable or greater binding affinity than the chimeric control antibody were sequenced. If the isolates analyzed did not contain a residue from human germ line gene at a chosen position in the framework, it was concluded that the human amino acid residue was not tolerated at that position. At this point, if only the murine and human amino acids were tested, another Fab library could be made randomizing the amino acids at the positions where human template residues were not found. Fabs with suitable replacement residues (non murine) would then be selected and converted into whole MAbs. In addition, consensus templates may be used as the starting framework.

B. IL-13 Monoclonal Antibody Vk Humanization

Humanization of the variable region of the light chain (Vk) was performed first. However, one can begin with either chain or humanize both chains simultaneously. The human template chosen was Human Template 2 and involved studying the effects on 9 residues close to the CDRs within the light chain to determine if they could be humanized without a loss of functional activity. The positions that were studied on the light chain for the second round of screening were 4, 9, 12, 73, 81, 82, 83, 84, and 109.

A library was generated varying each of these positions with either the murine or the human template residue. Approximately 860 variants were screened using a functional ELISA assay. Only 18 candidates demonstrated comparable function to the chimeric clone. These candidates were assayed further. Six candidates of the 18 demonstrated a greater affinity for antigen compared to the chimeric clone, and these 6 were sequenced. The sequencing results are presented in FIGS. 11A and B, and from these results, positions 4, 12 and 81 favor the murine residue.

C. Vh Humanization

In order to assess the contribution of the heavy chain framework residues to the overall function of the candidate antibody, a library was established varying 10 positions within the human DP27 template framework that differed from the murine parent, while maintaining the murine light chain. The library was generated using synthesized overlapping oligonucleotides for the Vh, and generation of the murine Vk using PCR. The Vk and Vh were then inserted into the Fab expression vector using mutagenesis and the library was then screened for functional Fabs. The complexity of the library was $(2^{10}/70\%) \times 3 = 3840$.

A total of 1056 candidates were screened, using a 96-well format ELISA assay. The candidates from this library that were chosen for sequencing were those that yielded the highest values from the screen results. Five of these high activity candidates were sequenced to determine their level of humanization and their sequences are presented in FIGS. 12A and B. From these results, three of the framework residues on the heavy chain favored the murine residue (#24, 68 and 94).

The second framework studied was the human template NEW. A combinatorial library was generated in which both the Vk and Vh were humanized concurrently. Nine residues on the Vk were varied between the murine and the human residues and nine residues were also chosen for the Vh. Approximately 5200 candidates (55 96-well plates) were screened from this library. From the screen, approximately 300 candidates yielded results comparable to the chimeric clone. From this group, thirty candidates were sequenced to determine the humanization level of these functional clones.

The sequencing results for the light chains are presented in FIGS. 11A and B. The heavy chain sequences are presented in FIGS. 12 A & B. Position 83 on the Vk had a high incidence for retaining the murine residue, whereas several positions in the Vh template favored the murine residue. In particular, position 94 retained the murine residue in 29 out of 30 candidates screened. Although no candidates appear to have completely humanized frameworks, several variable regions which were highly humanized in either the Vk or Vh will be used for further humanization. The most humanized Vk was combined with the most humanized Vh to assay functional activity. (See FIG. 13.)

A second library which combined the framework residues of the Vk and Vh of interest was generated using DP27 as the heavy chain template and HT2 as the light chain template. As described above, overlapping oligonucleotides were synthesized which contained the human framework with either human or murine residues at each position in question. These oligos were mixed and then annealed to generate the complete variable regions. The regions were amplified through PCR and then made into single-stranded fragments. The fragments were phosphorylated and then used in a mutagenesis reaction to incorporate the variable regions into the M13-based vector.

The library was then screened for functional Fabs that were specific for IL-13 in an ELISA-based assay. The sequences for the light chain and heavy chains are shown in FIGS. 11C&D and 12C&D, respectively.

From the sequencing results, the Vk chain was able to tolerate human residues throughout, and thus this chain was fully humanized. For the heavy chain, two positions were intolerant of the human residues: position 24 and 94. Thus, the heavy chain variable region was ~98% humanized.

D. Generation of Combinatorial Humanized Candidates

Since no candidate picked up from the screening of either of the libraries was fully humanized, the humanization was engineered. A series of candidates were generated in which the desired humanization levels were obtained. The most humanized Vk from the HT2 library was combined with the most humanized Vh from either the NEW or the DP27 libraries. These combinatorial candidates were then assayed to determine which maintained the specific function while carrying the highest humanization level. The candidates chosen from HT2-NEW were HT2-NEW #73 for heavy chain and HT2-NEW #115 for the light chain. The candidates chosen from HT2-DP27 light chain were HT2-DP27 #89 and HT2-DP27 #144, and the candidates for heavy chain were HT2-DP27 #123 and HT2-DP27 #276. For HT2-DP27, constructs were made as follows: #89 Vk with #276 Vh and #89 Vk with #123 Vh; #144 Vk with #276 Vh and #144 Vk with #123 Vh. In addition, one construct was made with #144 Vk DP27 with #73 Vh NEW to determine whether NEW and DP27 interactions with the HT2 light chain differed.

These combinations were tested by ELISA to determine if there was any further loss of function upon further humanization. For these assays, the antigen IL-13 was captured on the plate in a limiting amount. The anti-IL 13 Fabs were then added to the plate at a known concentration and titrated down the plate at a 1:3 dilution. Binding was detected with a secondary antibody that is specific for Fab. FIG. 13 depicts the functional assay results. FIG. 13A —115Vk/73Vh; FIG. 13B—89Vk/276Vh; FIG. 13C—144Vk/276Vh; and FIG. 13D —144Vk/73Vh. From these data, the observed results suggested that the engineered combinations of humanized variable regions did not adversely affect the binding of the Fabs to the antigen.

Figure 14A:
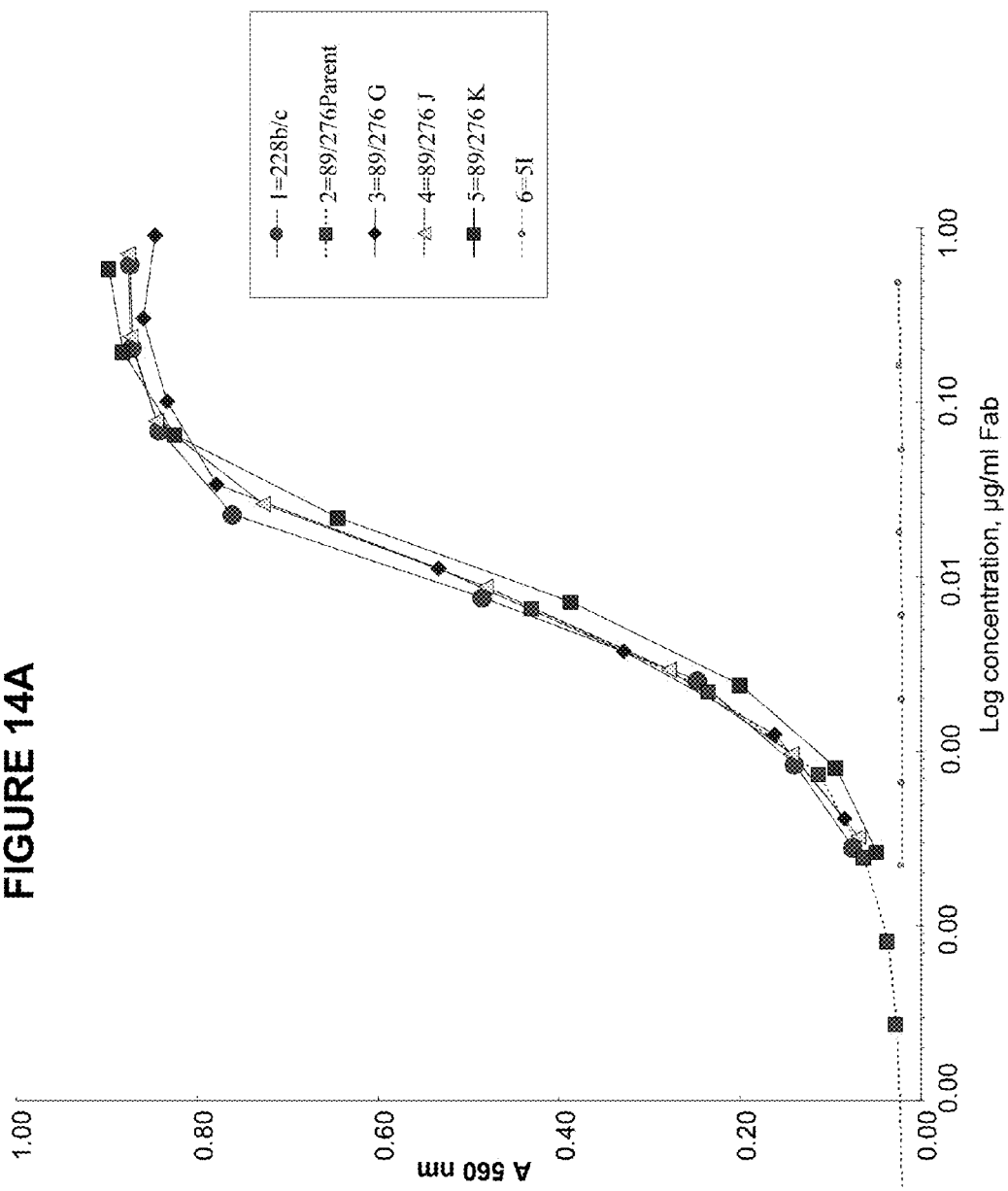
FIG. 14A depicts ELISA profiles for 89 Vk/276G.
Figure 14B:
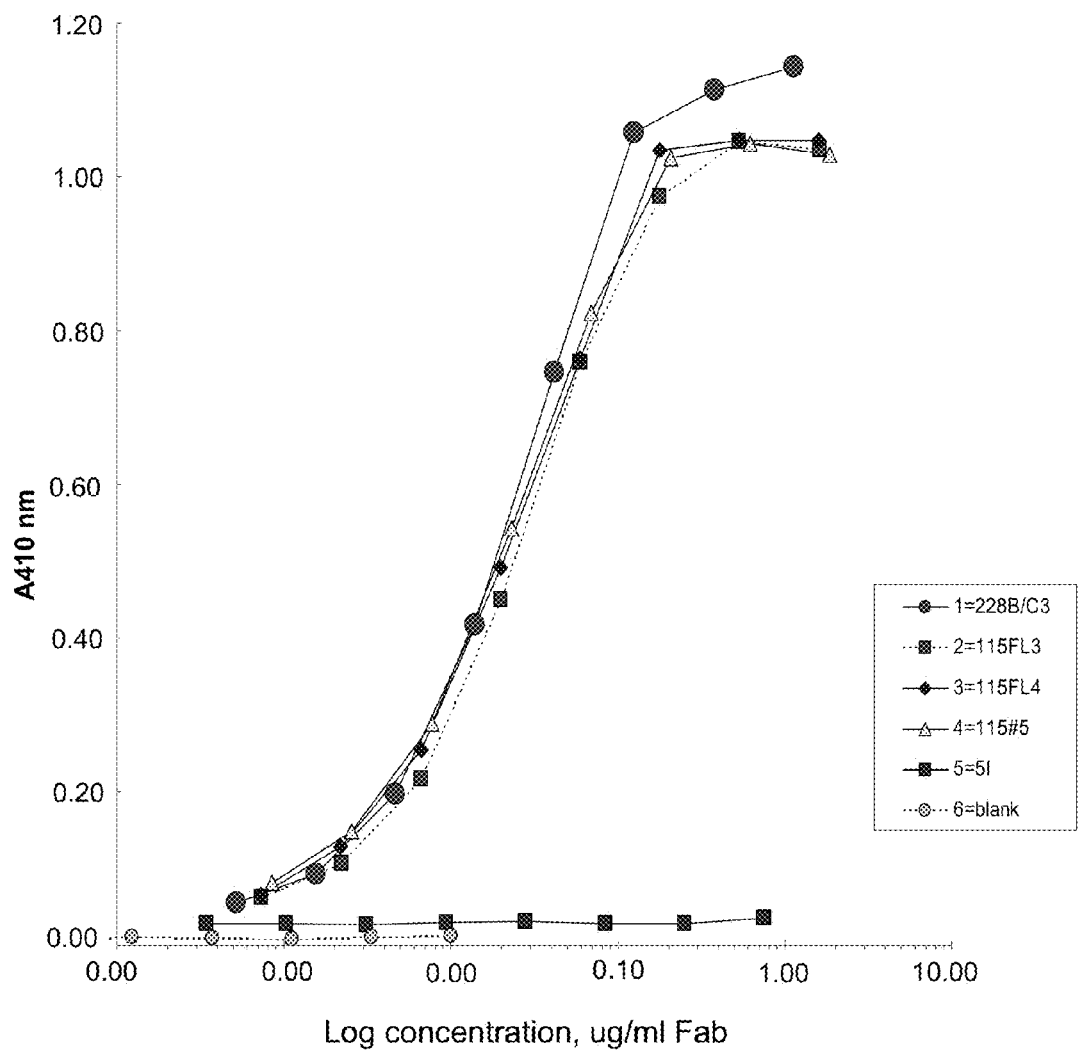
FIG. 14B depicts the ELISA results for construct 115Vk/73Vh FL.

Because the results in FIGS. 11 and 12 suggested that the HT2 light chain could be fully humanized and all but 2 positions in DP27 (24 and 94) could be humanized, the ideal humanized candidate was engineered in which the only 2 murine residues remained. Upon generation of this particular candidate, the clone was assayed in comparison with its parent as well as the other candidates to determine if there was any loss of function. From the data presented in FIG. 14A, this humanized candidate shows no significant loss of function with this high degree of humanization (89 Vk/276G). Humanization was also done for the HT2-NEW framework candidate. This candidate has a final humanization level of 98%, as there are two murine residues that remain on the heavy chain. FIG. 14B depicts the ELISA results for this construct (115Vk/73Vh FL).

An attempt was made to further humanize 89Vk/276G by replacing the two remaining murine residues. Upon mutating the positions to the human residues, the candidate clones were assayed by ELISA and compared to the parent. However, a significant loss of function was observed upon replacing the murine residues with those of the chosen template. Therefore, another library was generated in which the two positions on the Vh were randomized to allow for all possible amino acids at these two positions. The candidates were screened using a functional ELISA assay and thirty candidates that yielded comparable results to the parent clone (89Vk/276G) were sequenced to determine which amino acids were present at the targeted positions. A list of the candidates and the amino acids at the two positions is shown below.

| Candidate | 24 | 94 | Candidate | 24 | 94 | Candidate | 24 | 94 | Candidate | 24 | 94 |
|---|---|---|---|---|---|---|---|---|---|---|---|
| 228B/C | V | G | RL49 | A | T | RL19 | S | L | RL84 | L | T |
| DP27 | F | R | RL59 | I | M | RL27 | G | V | RL88 | L | S |
| 89/276G | V | G | RL61 | S | T | RL32 | G | G | RL89 | L | S |
| RL7 | A | S | RL62 | T | T | RL35 | S | L | RL91 | G | L |
| RL8 | L | S | RL70 | S | L | RL36 | G | V | RL95 | I | L |
| RL11 | T | V | RL72 | V | T | RL40 | L | S | RL97 | T | T |
| RL12 | I | I | RL78 | I | M | RL45 | T | T | RL18 | S | R |
| RL15 | L | L | RL79 | V | T | | | | | | |

Thus, from this screen, there are several amino acids which apparently are tolerated at the designated positions and yet do not result in significant loss of function. Thus, by changing the framework residues to amino acids that are not found in the murine sequence nor in the human framework, a fully functional Fab was generated without detrimental effect on binding to the target antigen. The candidates that were further tested from this random library were RL-19 and RL-36.

Example 10

CDR Optimization

Upon determining the optimal framework sequence for the candidate anti-IL-13 antibody, optimization of the CDRs was performed. For this process, the CDR amino acid sequence was randomized and then the libraries were screened to identify those candidates which had equal or better functional activity than the parent clone. For this library, the parent candidate was RL-36 (see above). The six CDRs were randomized, one position at a time and the libraries were screened using a functional ELISA. Strongly reactive candidates were sequenced for comparison with the parent CDR. It is noted that all unique sequences listed in the tables below also appear in FIG. 20 with appropriate SEQ ID NO identifiers.

A. CDR-L1 Optimization

CDR-L1 comprised 15 amino acids. Each of these positions was randomized using synthesized oligonucleotides which were the mixed in equimolar amounts to be used in a mutagenesis reaction. The efficiency of incorporation of the mutagenic oligonucleotides was determined to be 40%. Using this percentage, the number of candidates which needed to be screened was 3600. The clones were assayed using a functional ELISA and those clones that yielded comparable functional activity were sequenced. From the number of candidates that were screened, 166 positive candidates were identified. From this group, 10 candidates were sequenced to determine the changes within the CDR. From the sequencing results shown below results, the positions 11 and IL4 lead to improved affinity are N to Q and M to L.

|        | 1 | 2 | 3 | 4 | 5 | 6 | 7 | 8 | 9 | 10 | 11 | 12 | 13 | 14 | 15 |
|--------|---|---|---|---|---|---|---|---|---|----|----|----|----|----|----|
| CDR-L1 | R | A | S | K | S | V | D | S | Y | G  | N  | S  | F  | M  | H  |
| L1-21  | R | A | S | K | S | V | D | S | Y | G  | N  | S  | F  | L  | H  |
| L1-39  | R | A | S | K | S | V | D | S | Y | G  | Q  | S  | F  | M  | H  |
| L1-47  | K | A | S | K | S | V | D | S | Y | G  | N  | S  | F  | M  | H  |
| L1-50  | R | A | S | K | S | V | D | S | Y | G  | N  | S  | Y  | M  | H  |
| L1-59  | R | A | S | K | S | V | D | S | Y | G  | Q  | S  | F  | M  | H  |
| L1-61  | R | A | S | K | S | V | D | S | Y | G  | N  | S  | F  | M  | H  |
| L1-62  | R | A | S | K | S | V | D | S | Y | G  | N  | S  | F  | L  | H  |
| L1-63  | R | A | S | K | S | V | D | S | Y | G  | N  | S  | F  | L  | H  |
| L1-117 | N | A | S | K | S | V | D | S | Y | G  | N  | S  | F  | M  | H  |
| L1-125 | R | A | S | K | S | V | D | S | Y | G  | N  | S  | F  | M  | H  |

B. CDR2-L2 Optimization

CDR-L2 comprised 7 amino acids. This library was prepared as described above. The efficiency of this library was 80% and 840 clones were assayed. The number of positive clones identified from the assay was 75 and 11 were sequenced. From the results shown below, several positions within this CDR yielded improved activity, although the positions and replacement amino acids appeared random. This result supports the observation that CDR-L2 is farthest from the antigen binding site and as such should exert the least influence upon antigen binding.

|        | 1 | 2 | 3 | 4 | 5 | 6 | 7 |
|--------|---|---|---|---|---|---|---|
| CDR-L2 | L | A | S | N | L | E | S |
| L2-10  | L | A | S | N | L | N | S |
| L2-13  | L | A | S | N | L | E | S |
| L2-25  | L | A | S | N | L | Q | S |
| L2-37  | L | A | T | N | L | E | S |
| L2-41  | L | A | S | N | L | K | S |
| L2-44  | L | A | S | N | L | E | K |
| L2-45  | L | A | S | R | L | E | S |
| L2-53  | L | A | S | N | L | H | S |
| L2-58  | L | A | S | N | L | S | S |
| L2-65  | L | A | S | F | L | E | S |
| L2-70  | L | A | N | N | L | E | S |

C. CDR-L3 Optimization

CDR-L3 was composed of 9 amino acids. This library upon generation yielded an efficiency of 50%, requiring ~1700 clones be screened. From this screen, 257 positive candidates were identified and ten were sequenced. From these results, only one position yielded a change from the parent sequence. Several candidates demonstrated the same sequence which suggested that this positional change was highly favored (N to A).

|        | 1 | 2 | 3 | 4 | 5 | 6 | 7 | 8 | 9 |
|--------|---|---|---|---|---|---|---|---|---|
| CDR-L3 | Q | Q | N | N | E | D | P | R | T |
| L3-1   | Q | Q | N | N | E | D | P | R | T |
| L3-32  | Q | Q | N | A | E | D | P | R | T |
| L3-90  | Q | Q | N | N | E | D | P | R | T |
| L3-100 | Q | Q | N | N | E | D | P | R | T |
| L3-150 | Q | Q | N | N | E | D | P | R | T |
| L3-170 | Q | Q | N | A | E | D | P | R | T |
| L3-185 | Q | Q | N | A | E | D | P | R | T |
| L3-207 | Q | Q | N | A | E | D | P | R | T |
| L3-225 | Q | Q | N | N | E | D | P | R | T |

D. CDR-H1 Optimization

CDR-H1 comprised 5 amino acids. The efficiency of this library was 80%, requiring only about 600 candidates be screened. From the screen, there were 138 positive clones and eleven of the clones were sequenced. From the results are listed below, the second position within this CDR seemed to offer the greatest chance of improvement of antigen binding. However, several amino acids favorably affect binding.

|        | 1 | 2 | 3 | 4 | 5 |
|--------|---|---|---|---|---|
| CDR-H1 | A | Y | S | V | N |
| H1-2   | A | K | S | V | N |
| H1-12  | G | Y | S | V | N |
| H1-18  | A | K | S | V | N |
| H1-24  | A | K | S | V | N |
| H1-31  | A | H | S | V | N |
| H1-89  | A | Y | S | V | N |
| H1-90  | G | Y | S | V | N |
| H1-114 | A | S | S | V | N |
| H1-115 | A | H | S | V | N |
| H1-123 | A | R | S | V | N |
| H1-126 | A | R | S | V | N |

E. CDR-H2 Optimization

CDR-H2 comprised 16 amino acids. The efficiency of this library was 70%, which meant that over 2100 candidates needed to be screened. From the screen, 192 positive candidates were identified and thirteen were sequenced to determine the changes that occurred within the CDR. From the sequencing results listed below, several positions improved binding affinity but none of the amino acid changes appeared significantly different from the parent.

|         | 1 | 2 | 3 | 4 | 5 | 6 | 7 | 8 | 9 | 10 | 11 | 12 | 13 | 14 | 15 | 16 |
|---------|---|---|---|---|---|---|---|---|---|----|----|----|----|----|----|----|
| CDR-H2  | M | I | W | G | D | G | K | I | V | Y  | N  | S  | A  | L  | K  | S  |
| H2-38   | M | I | W | G | D | G | K | I | S | Y  | N  | S  | A  | L  | K  | S  |
| H2-43   | M | I | W | G | D | G | K | I | V | Y  | N  | S  | A  | L  | E | S  |
| H2-51   | M | I | W | G | D | G | K | I | V | Y  | N  | S  | A  | L  | K  | S  |
| H2-66   | M | I | W | G | D | G | K | I | S | Y  | N  | S  | A  | L  | K  | S  |
| H2-79   | M | I | W | G | D | G | K | I | V | Y  | N  | S  | D | L  | K  | S  |
| H2-86   | M | I | W | G | D | G | K | V | V | Y  | N  | S  | A  | L  | K  | S  |
| H2-101  | M | I | W | G | D | G | K | I | V | Y  | N  | S  | E | L  | K  | S  |
| H2-109  | M | I | W | G | D | G | K | I | A | Y  | N  | S  | A  | L  | K  | S  |
| H2-119  | M | I | W | G | D | G | K | I | V | Y  | N  | S  | A  | L  | K  | E |
| H2-121  | M | V | W | G | D | G | K | I | V | Y  | N  | S  | A  | L  | K  | S  |
| H2-129  | M | I | W | G | D | G | K | I | V | Y  | N  | S  | A  | L  | K  | S  |
| H2-169  | M | I | W | G | D | G | K | I | V | Y  | N  | S  | A  | L  | A | S  |
| H2-176  | M | I | W | G | D | G | K | K | V | Y  | N  | S  | A  | L  | K  | S  |

F. CDR-H3 Optimization

CDR-H3 comprised 10 amino acids. This CDR in general is believed to be the one that imposes the greatest influence on antigen binding, because this loop is generally in the middle of the binding site. This library had an efficiency of 40%, and so 2400 candidates needed to be screened. Of these, 174 positive candidates were identified and ten were sequenced to determine the changes within the CDR. The results listed below indicated that the change from Y to R in the third position may be an important one for improvement in binding.

|         | 1 | 2 | 3 | 4 | 5 | 6 | 7 | 8 | 9 | 10 |
|---------|---|---|---|---|---|---|---|---|---|----|
| H3      | D | G | Y | Y | P | Y | A | M | D | N  |
| H3-1    | D | G | R | Y | P | Y | A | M | D | N  |
| H3-30   | D | G | Y | Y | P | Y | A | M | S | N  |
| H3-73,  | D | G | Y | Y | P | Y | A | M | A | N  |
| H3-89   | D | G | Y | Y | P | Y | A | M | A | N  |
| H3-130  | D | G | R | V | P | V | A | M | D | N  |
| H3-131  | D | G | R | Y | P | V | A | M | D | N  |
| H3-133  | D | G | Y | V | P | Y | A | L | D | N  |
| H3-135  | D | G | R | V | P | Y | A | M | D | N  |
| H3-161  | D | G | Y | Y | P | Y | A | M | D | N  |
| H3-162  | D | G | Y | Y | P | V | A | M | K | N  |

G. Combinatorial Library

Once the changes within the CDRs which yielded the greatest overall improvement in antigen binding were determined, the best candidates were then combined to see if these changes improved binding. Thus, a candidate was engineered to combine all favorable amino acid substitutions.

To generate the combinatorial library, the initial clone was the one that incorporated the alteration in CDR-L1-59 (N to Q). To this clone, the other changes were made for CDR-L3, N to A (position 4), for CDR-H1, Y to either R, H, K or S (position 2), for CDR-H3, Y to R (position 3) and D to either K or S (position 9). No changes were made to CDR-L2 or CDR-H2. Over 1100 candidates from this library were screened using a functional ELISA assay. A total of 120 candidates were identified as having activity greater than the parent clone. The sequences of those clones are shown in FIG. 15.

To confirm that these combinatorial candidates maintained function, a competition assay was performed. For this assay, IL-13 was captured on an ELISA plate. The candidates, which are purified Fabs, were pre-mixed in varying concentrations to a constant concentration of labeled chimeric anti-IL-13 Fab. This mixture was added to the ELISA plate. The labeled chimeric anti-IL-13 capable of binding to the plate-bound IL-13 were detected.

Figure 16:
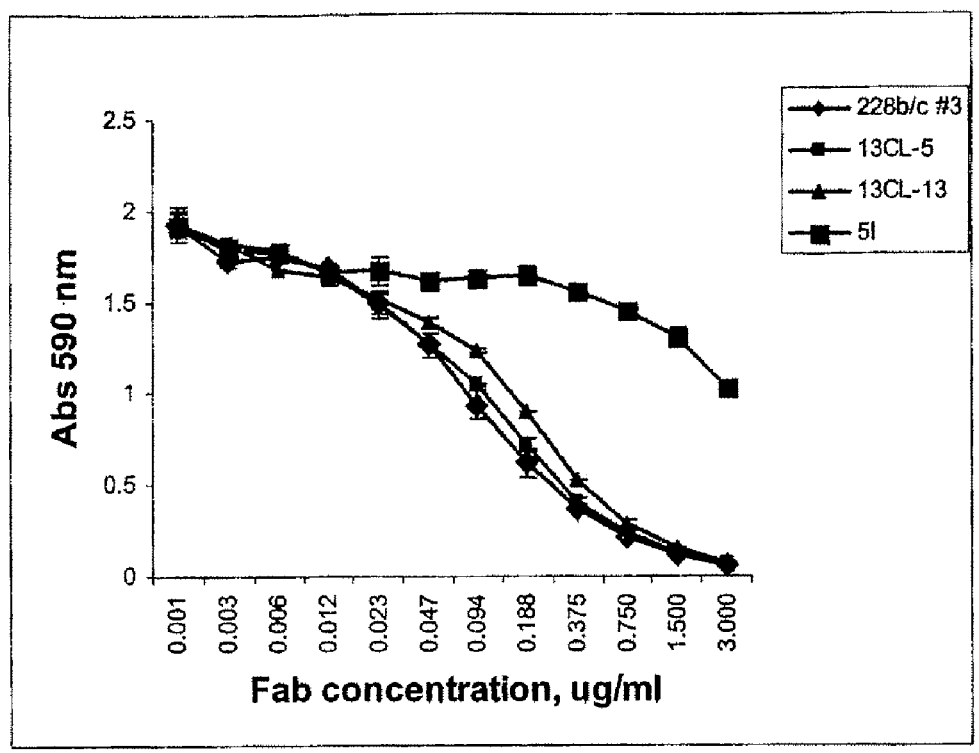
FIG. 16 depicts a competition profile for two candidates (CL5 and CL-13) assayed demonstrated as compared with the chimeric candidate (228 B/C #3) for binding to IL-13. The irrelevant Fab is 5I, which demonstrates no ability to compete.

From the results of this competition, the two candidates assayed demonstrated equivalent ability to compete with the chimeric candidate (228 B/C #3) for binding to IL-13 (FIG. 16). The irrelevant Fab is 5I, which demonstrates no ability to compete. FIG. 17 depicts the sequences of three affinity matured candidates.

Example 11

Epitope Mapping

Anti-IL13 MAb 228B/C-1 binds to a conformational epitope and binds to cynomologous monkey IL13 with the same high affinity as it does to human IL13. However, 228B/C does not bind to murine IL13. So, the strategy devised for epitope mapping was to exchange small portions of the monkey IL13 with the corresponding mouse IL13 sequence. Overlapping oligonucleotides were synthesized as shown in FIG. 18. Two rounds of PCR were performed to assemble the IL13 hybrid constructs so that part of monkey IL13 was replaced by the corresponding sequence from mouse IL13 (FIG. 18). The final PCR amplified IL13 coding regions were cloned into pcDNA3.1 vector in frame with a V5 tag using TOPO cloning kit (Invitrogen). All PCR amplified region were confirmed by sequencing to contain only the desired domain swapping mutations and not additional unwanted mutation in the expression vectors.

The anti-IL13 MAb binding epitope was identified as a 8-mer peptide from amino acid #49 to 56, ESLINVSG (SEQ ID NO 18). This epitope is located in Helix-B and loop-BC in human IL13. When the epitope peptide derived from cyno-IL13 was used to swap the corresponding sequence in murine IL13, the resulting hybrid IL13 molecule can bind to 228B/C with affinity similar to that of the original cyno IL13, further validated that 228B/C MAb binding to cyno or human IL13 at this peptide between residual #49-56. Sequence comparison between human, cyno, and murine IL13 reveals only three residues Ile52, Val54, Gly56 in human IL13 are not conserved, suggesting the critical residues for IL13 and anti-IL13 MAb interaction through this 8-mer peptide is determined by one or combination of some of these three residues.

This epitope was further confirmed by peptide spot analysis. The entire human IL13 peptide was scanned with a series of overlapping 12-mer peptides synthesized via SPOT on cellulose membrane. The only anti-IL13 MAb reactive peptide was identified as a 12-mer peptide of amino acid #44-56, YCAALESLINVS (SEQ ID NO 19), which is overlapping with the region identified through domain swapping experiments.

Deposits

The following cultures have been deposited with the American Type Culture Collection, 10801 University Boulevard, Manassas, Va. 20110-2209 USA (ATCC):

| Hybridoma | ATCC NO. | Deposit Date |
|---|---|---|
| Anti-IL13 228B/C-1 | PTA-5657 | Nov. 20, 2003 |
| Anti-IL13 228A-4 | PTA-5656 | Nov. 20, 2003 |
| Anti-IL13 227-26 | PTA-5654 | Nov. 20, 2003 |
| Anti-IL13 227-43 | PTA-5655 | Nov. 20, 2003 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, which assures permanent and unrestricted availability of the progeny of the culture to the public upon issuance of the pertinent U.S. patent.

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as illustration of one aspect of the invention and any culture that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

Those skilled in the art will recognize, or be able to ascertain using no more than routine experimentation, many equivalents to the specific embodiments of the invention described herein. Such equivalents are intended to be encompassed by the following claims.

---

The invention claimed is:

1. A monoclonal antibody that specifically binds human interleukin-13 ("IL-13"), wherein said antibody comprises a variable heavy chain region comprising complementarity determining regions CDRH 1, CDRH2 and CDRH3 having the amino acid sequences of SEQ ID NO: 117, SEQ ID NO: 123, and SEQ ID NO: 135, respectively; and wherein said antibody comprises a variable light chain region comprising complementarity determining regions CDRL1, CDRL2 and CDRL3 having the amino acid sequences of SEQ ID NO: 99, SEQ ID NO: 104, and SEQ ID NO: 115, respectively.

2. The antibody of claim 1, wherein said antibody comprises the amino acid sequence of SEQ ID NO: 4, and the amino acid sequence of SEQ ID NO: 3.

3. The antibody of claim 1, wherein said antibody comprises the amino acid sequence of SEQ ID NO: 142, and the amino acid sequence of SEQ ID NO: 143.

4. The antibody of claim 1, wherein the antibody is an IgG antibody.

5. The antibody of claim 4, wherein the antibody is an IgG1, an IgG2, an IgG3 or an IgG4 antibody.

6. The antibody of claim 1, wherein the antibody is humanized.

7. The antibody of claim 1, wherein the antibody is an antibody fragment.

8. The antibody of claim 1, wherein the antibody is a monovalent antibody, a multispecific antibody, a chimeric antibody, a single chain antibody, a Fab fragment or a F(ab') fragment.

9. A pharmaceutical composition comprising the antibody of claim 1, 2, 3, 4, 5, 6, or 8.

10. A pharmaceutical composition comprising the antibody of claim 7.

11. A hybridoma cell line that produces the antibody of claim 1.

12. A monoclonal antibody that specifically binds human IL-13, wherein said antibody comprises the amino acid sequence of an antibody produced by a hybridoma designated with American Type Culture Collection ("ATCC") accession number PTA-5657.

13. A monoclonal antibody that specifically binds human IL-13, wherein said antibody is produced by a method comprising the step of expressing the antibody from a host cell, wherein said antibody is the antibody of claim 1, 3, or 6.

14. The monoclonal antibody of claim 13, wherein said method further comprises purifying the antibody from said host cell.

15. The monoclonal antibody of claim 13, wherein the host cell is a mammalian cell.

16. The monoclonal antibody of claim 14, wherein the mammalian cell is a Chinese hamster ovary (CHO) cell.

17. The monoclonal antibody of claim 1, 3, or 6, wherein said antibody is conjugated to a molecule.

18. The monoclonal antibody of claim 17, wherein the molecule is a polypeptide or a detectable substance.

19. The monoclonal antibody of claim 12, wherein the antibody is an IgG antibody.

20. The monoclonal antibody of claim 13, wherein the antibody is an IgG antibody.

21. The monoclonal antibody of claim 19, wherein the antibody is an IgG1, an IgG2, an IgG3 or an IgG4 antibody.

22. The monoclonal antibody of claim 20, wherein the antibody is an IgG1, an IgG2, an IgG3 or an IgG4 antibody.

23. The monoclonal antibody of claim 3, wherein the antibody is a monovalent antibody, a multispecific antibody, a single chain antibody, a Fab fragment, is a F(ab') fragment.

24. The monoclonal antibody of claim 13, wherein the antibody is a monovalent antibody, a multispecific antibody, a chimeric antibody, a humanized antibody, a single chain antibody, a Fab fragment, or a F(ab') fragment.

25. The monoclonal antibody of claim 23, wherein the antibody is a multispecific antibody that is a bispecific antibody.

26. The monoclonal antibody of claim 24, wherein the antibody is a multispecific antibody that is a bispecific antibody.

27. The monoclonal antibody of claim 8, wherein the antibody is a multispecific antibody that is a bispecific antibody.

28. A pharmaceutical composition comprising the monoclonal antibody of claim 13.

29. A pharmaceutical composition comprising the monoclonal antibody of claim 19.

30. A pharmaceutical composition comprising the monoclonal antibody of claim 20.

31. A pharmaceutical composition comprising the monoclonal antibody of claim 21, 23, or 25.

32. A pharmaceutical composition comprising the monoclonal antibody of claim 22.

33. A pharmaceutical composition comprising the monoclonal antibody of claim 24.

34. A pharmaceutical composition comprising the monoclonal antibody of claim 26.

35. A pharmaceutical composition comprising the monoclonal antibody of claim 27.

36. The hybridoma cell line of claim 11, which comprises a hybridoma designated with ATCC accession number PTA-5657.

37. The monoclonal antibody of claim 1, further comprising human framework regions.

* * * * *

UNITED STATES PATENT AND TRADEMARK OFFICE
CERTIFICATE OF CORRECTION

| | | |
|---|---|---|
| PATENT NO. | : 8,088,618 B2 | Page 1 of 1 |
| APPLICATION NO. | : 12/240604 | |
| DATED | : January 3, 2012 | |
| INVENTOR(S) | : Fung et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 441 days.

Signed and Sealed this
Seventeenth Day of April, 2012

David J. Kappos
*Director of the United States Patent and Trademark Office*